(12) United States Patent
Petkovic et al.

(10) Patent No.: US 7,595,175 B2
(45) Date of Patent: Sep. 29, 2009

(54) POLYKETIDES AND THEIR SYNTHESIS

(75) Inventors: Hrvoje Petkovic, Cambridge (GB); Steven Gary Kendrew, Cambridge (GB); Peter Francis Leadlay, Cambridge (GB)

(73) Assignee: Biotica Technology Limited, Cambridgeshire (GB)

( * ) Notice: Subject to any disclaimer, the term of this patent is extended or adjusted under 35 U.S.C. 154(b) by 383 days.

(21) Appl. No.: 10/344,738

(22) PCT Filed: Aug. 14, 2001

(86) PCT No.: PCT/GB01/03642

§ 371 (c)(1), (2), (4) Date: Jul. 31, 2003

(87) PCT Pub. No.: WO02/14482

PCT Pub. Date: Feb. 21, 2002

(65) Prior Publication Data

US 2004/0023342 A1    Feb. 5, 2004

(30) Foreign Application Priority Data

Aug. 14, 2000  (GB)  ................................. 0019986.9

(51) Int. Cl.
*C12P 19/60* (2006.01)
*C07K 19/00* (2006.01)
*C12N 15/52* (2006.01)

(52) U.S. Cl. ..................... 435/75; 435/69.1; 435/320.1; 435/252.3; 536/23.2

(58) Field of Classification Search .................. 435/75, 435/69.1, 320.1, 252.3; 536/23.2
See application file for complete search history.

(56) References Cited

FOREIGN PATENT DOCUMENTS

WO    WO 00/01838    1/2000
WO    WO03/014312    2/2003

OTHER PUBLICATIONS

Aparicio, J.F. et al. (1996) "Organization of the biosynthetic gene cluster for rapamycin in *Streptomyces hygroscopicus*: analysis of the enzymatic domains in the modular polyketide synthase" *Gene* 169:9-16, by Elsevier Science B.V.
Haydock, S.F. et al. (1995) "Divergent sequence motifs correlated with the substrate specificity of (methyl) malonyl-CoA:acyl carrier protein transacylase domains in modular polyketide synthases" *FEBS Letters* 374:246-248.
Katz, Leonard (1997) "Manipulation of modular polyketide synthases" *Chem. Rev.* 97:2557-2575 by American Chemical Society.
Khosla C. et al. (1999) "Tolerance and specificity of polyketide synthases" *Annu. Rev. Biochem* 68:219-253 by Annual Reviews.
Lau, J. et al. (1999) "Dissecting the role of acyltransferase domains of modular polyketide synthases in the choice and stereochemical fate of extender units" *Biochemistry* 38:1643-1651 by American Chemical Society.
Oliynyk, M. et al. (1996) "A hybrid modular polyketide synthase obtained by domain swapping" *Chemistry & Biology* vol. 3 No. 10 833-839.
Reeves, C.D. et al. (2001) "Alteration of the substrate specificity of a modular polyketide synthase acyltransferase domain through site-specific mutations" *Biochemistry* 40:15464-15470 by American Chemical Society.
Ruan, X., et al. (1997) Acyltransferase domain substitutions in erythromycin polyketide synthase yield novel erythromycin derivatives *Journal of Bacteriology*, Oct. 1997:6416-6425 by American Society for Microbiology.
Reeves et.al., "Alteration of the Substrate Specificity of a Modular Polyketide Synthase Acyltransferase Domain through Site-Specific Mutations", American Chemical Society—Biochemistry(Oct. 17, 2001); A-G.

*Primary Examiner*—Chih-Min Kam
(74) *Attorney, Agent, or Firm*—Weaver Austin Villeneuve & Sampson LLP; Emily M. Haliday

(57) ABSTRACT

Biosyntheses of compounds whereof at least portions are polyketides produced by means of polyketide synthase (PKS) enzyme complexes are carried out after specific alterations have been made within the acyltransferase (AT) domains of the PKSs. Particular motifs in or near the substrate binding pocket are disclosed, such that alterations therein affect substrate specificity.

25 Claims, 26 Drawing Sheets

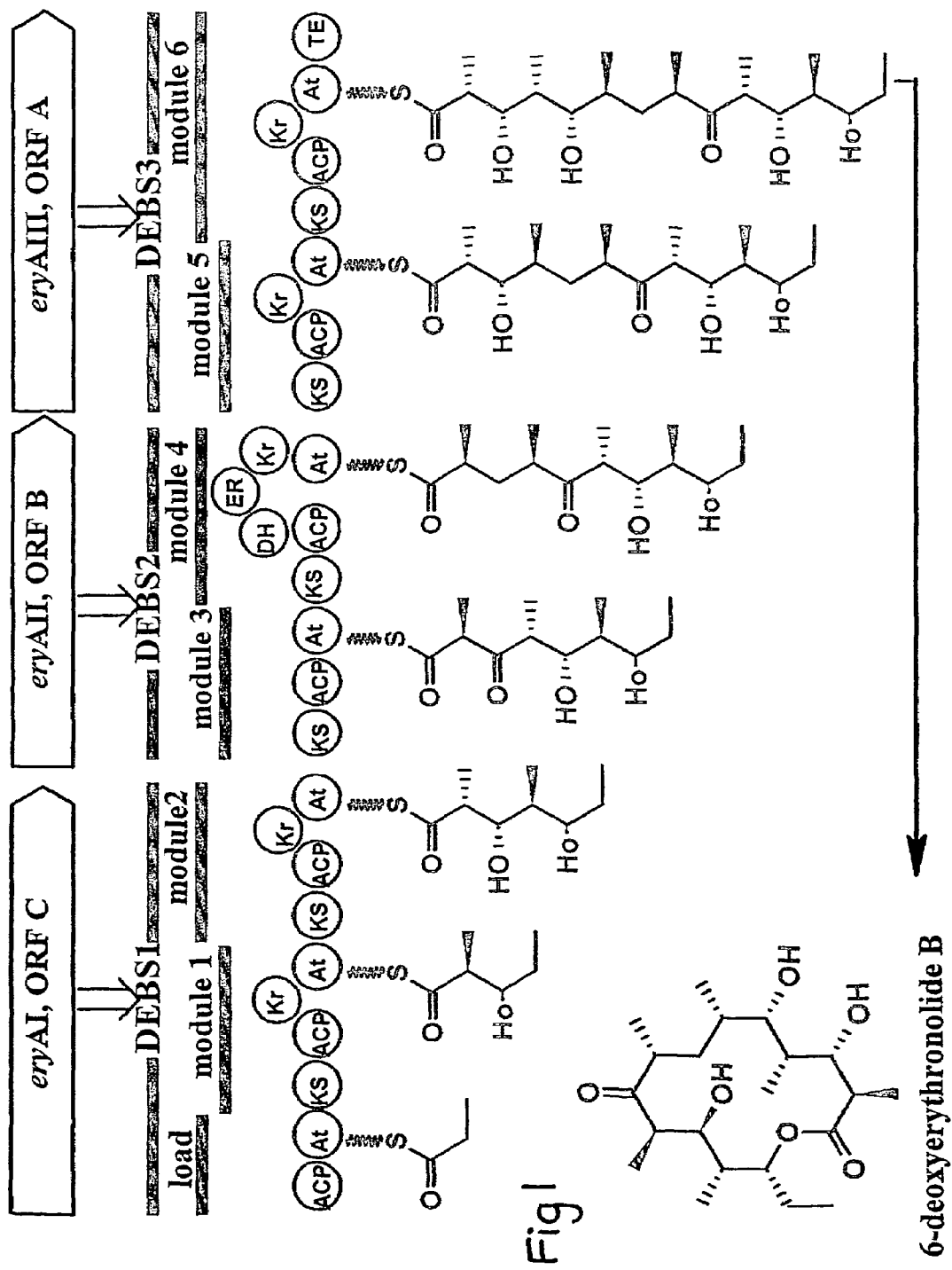

```
                  1                                                      50
    atave00x   ~~~~~~~~~~ ~~~~~~~~~~ ~~~~~~~~~~ ~~~~~~~~~~ ~~~~~~~~~~
    atdebs00p  ~~~~~~~~~~ ~~~~~~~~~~ ~~~~~~~~~~ ~~~~~~~~~~ ~~~~~~~~~~
    atepo06p   ~~~~~~~~~~ ~~~~~~~~~~ ~~~~~~~~~~ ~~~~~~~~~~ ~~~~~~~~~~
    atepo07p   ~~~~~~~~~~ ~~~~~~~~~~ ~~~~~~~~~~ ~~~~~~~~~~ ~~~~~~~~~~
    atepo01p   ~~~~~~~~~~ ~~~~~~~~~~ ~~~~~~~~~~ ~~~~~~~~~~ ~~~~~~~~~~
    atepo05p   ~~~~~~~~~~ ~~~~~~~~~~ ~~~~~~~~~~ ~~~~~~~~~~ ~~~~~~~~~~
    atsora1x   ~~~~~~~~~~ ~~~~~~~~~~ ~~~~~~~~~~ ~~~~~~~~~~ ~~~~~~~~~~
    atfkb01p   ~~~~~~~~~~ ~~~~~~~~~~ ~~~~~~~~~~ ~~~~~~~~~~ ~~~~~~~~~~
    atfkb09p   ~~~~~~~~~~ ~~~~~~~~~~ ~~~~~~~~~~ ~~~~~~~~~~ ~~~~~~~~~~
    atrap03p   ~~~~~~~~~~ ~~~~~~~~~~ ~~~~~~~~~~ ~~~~~~~~~~ ~~~~~~~~~~
    atrap06p   ~~~~~~~~~~ ~~~~~~~~~~ ~~~~~~~~~~ ~~~~~~~~~~ ~~~~~~~~~~
    atrap04p   ~~~~~~~~~~ ~~~~~~~~~~ ~~~~~~~~~~ ~~~~~~~~~~ ~~~~~~PLVI
    atrap13p   ~~~~~~~~~~ ~~~~~~~~~~ ~~~~~~~~~A EEAQPVETPV VASDVLPLVI
    atrap01p   ~~~~~~~~~~ ~~~~~~~~~~ ~~~~~~~~~~ ~~~~~~~~~~ ~~~~~~~~~~
    atrap07p   ~~~~~~~~~~ ~~~~~~~~~~ ~~~~~~~~~~ ~~~~~~~~PV VASELVPLVI
    atrap10p   ~~~~~~~~~~ ~~~~~~~~~~ ~~~~~~~~~~ ~~~~~~~~~~ ~~~~~~~~~~
    atfkb04x   ~~~~~~~~~~ ~~~~~~~~~~ ~~~~~~~~~~ ~~~~~~~~~~ ~~~~~~~~~~
    atty104p   ~~~~~~~~~~ ~~~~~~~~VV REAAGRLAEV VEAGGVGLAD VAVTMAGRSR
    atty106p   ~~~~~~~~~~ ~~~~~~~~~~ ~~~~GRLAEV VEAGGVGLAD VAVTMAGRSR
    atty101p   ~~~~~~~~~~ ~~~~~~~~~~ ~~~~~~~~~~ ~~~~~~~~~~ ~~~~MAGRSR
    atty102p   ~~~~~~~~~~ ~~~~~~~~~~ ~~~~~~~~~~ ~~~~~~~~~~ ~~~~~~~~~~
    atty100p   ~~~~~~~~~~ ~~~~~~~~~~ ~~~~~~~~~~ ~~~~~~~~~D VAVTMADRSR
    atnid05b   ~~~~~~~~~~ ~~~~~~~~~~ ~~~~~~~~~~ ~~~~~~~~~~ ~~~~~~~~~~
    atty105b   ~~~~~~~~~~ ~~~~~~~~~~ ~~~~~~~~~~ ~~~~~~~AAL REQSTRLLND
    atnid06x   ~~~~~~~~~~ ~~~~~~~~~~ ~~~~~~~~~~ ~~~~~~~~~~ ~~~~~~~~~~
    atdebs01p  ~~~~~~~~~~ ~~~~~~~~~~ ~~~~~~~~~~ ~~~~~~~~~~ ~~~~~~~~~~
    atmon02p   ~~~~~~~~~~ ~~~~~~~~~~ ~~~~~~~~~~ ~~~~~~~~~~ ~~~~~~~~~~
    atmon10p   ~~~~~~~~~~ ~~~~~~~~~~ ~~~~~~~~~~ ~~~~~~~~~~ ~~~~~~~~~~
    atmon04p   ~~~~~~~~~~ ~~~~~~~~~~ ~~~~~~~~~~ ~~~~~~~~~~ ~~~~~~~~~~
    atmon07p   ~~~~~~~~~~ ~~~~~~~~~~ ~~~~~~~~~~ ~~~~~~~~~~ ~~~~~~~~~~
    atmon11p   ~~~~~~~~~~ ~~~~~~~~~~ ~~~~~~~~~~ ~~~~~~~~~~ ~~~~~~~~~~
    atmon12p   ~~~~~~~~~~ ~~~~~~~~~~ ~~~~~~~~~~ ~~~~~~~~~~ ~~~~~~~~~~
    atmon05b   ~~~~~~~~~~ ~~~~~~~~~~ ~~~~~~~~~~ ~~~~~~~~~~ ~~~~~~~~~~
    atmon01p   ~~~~~~~~~~ ~~~~~~~~~~ ~~~~~~~~~~ ~~~~~~~~~~ ~~~~~~~~~~
    atdebs02p  ~~~~~~~~~~ ~~~~~~~~~~ ~~~~~~~~~~ ~~~~~~~~~~ ~~~~~~~~~~
    atdebs06p  ~~~~~~~~~~ ~~~~~~~~~~ ~~~~~~~~~~ ~~~~~~~~~~ ~~~~~~~~~~
    atave01p   ~~~~~~~~~~ ~~~~~~~~~~ ~~~~~~~~~~ ~~~~~~~~~~ ~~~~~~~~~~
    atave07p   ~~~~~~~~~~ ~~~~~~~~~~ ~~~~~~~~~~ ~~~~~~~~~~ ~~~~~~~~~~
    atave06p   ~~~~~~~~~~ ~~~~~~~~~~ ~~~~~~~~~~ ~~~~~~~~~~ ~~~~~~~~~~
    atave09p   ~~~~~~~~~~ ~~~~~~~~~~ ~~~~~~~~~~ ~~~~~~~~~~ ~~~~~~~~~~
    atnys01p   ~~~~~~~~~~ ~~~~~~~~~~ ~~~~~~~~~~ ~~~~~~~~~~ ~~~~~~~~~~
    atnys11p   ~~~~~~~~~~ ~~~~~~~~~~ ~~~~~~~~~~ ~~~~~~~~~~ ~~~~~~~~~~
    atrif05p   ~~~~~~~~~~ ~~~~~~~~~~ ~~~~~~~~~~ ~~~~~~~~~~ ~~~~~~~~~~
    atrif07p   ~~~~~~~~~~ ~~~~~~~~~~ ~~~~~~~~~~ ~~~~~~~~~~ ~~~~~~~~~~
    atrif08p   ~~~~~~~~~~ ~~~~~~~~~~ ~~~~~~~~~~ ~~~~~~~~~~ ~~~~~~~~~~
    atrif10p   ~~~~~~~~~~ ~~~~~~~~~~ ~~~~~~~~~~ ~~~~~~~~~~ ~~~~~~~~~~
    atrif03p   ~~~~~~~~~~ ~~~~~~~~~~ ~~~~~~~~~~ ~~~~~~~~~~ ~~~~~~~~~~
    atrif06p   ~~~~~~~~~~ ~~~~~~~~~~ ~~~~~~~~~~ ~~~~~~~~~~ ~~~~~~~~~~
    atrif04p   ~~~~~~~~~~ ~~~~~~~~~~ ~~~~~~~~~~ ~~~~~~~~~~ ~~~~~~~~~~
    atrif01p   ~~~~~~~~~~ ~~~~~~~~~~ ~~~~~~~~~~ ~~~~~~~~~~ ~~~~~~~~~~
    atnys02p   ~~~~~~~~~~ ~~~~~~~~~~ ~~~~~~~~~~ ~~~~~~~~~~ ~~~~~~~~~~
    atfkb02p   ~~~~~~~~~~ ~~~~~~~~~~ ~~~~~~~~~~ ~~~~~~~~~~ ~~~~~~~~~~
    atave11p   ~~~~~~~~~~ ~~~~~~~~~~ ~~~~~~~~~~ ~~~~~~~~~~ ~~~~~~~~~~
    atdebs03p  ~~~~~~~~~~ ~~~~~~~~~~ ~~~~~~~~~~ ~~~~~~~~~~ ~~~~~~~~~~
    atnid04p   ~~~~~~~~~~ ~~~~~~~~~~ ~~~~~~~~~~ ~~~~~~~~~~ ~~~~~~~~~~
    atdebs05p  ~~~~~~~~~~ ~~~~~~~~~~ ~~~~~~~~~~ ~~~~~~~~~~ ~~~~~~~~~~
    atdebs04p  ~~~~~~~~~~ ~~~~~~~~~~ ~~~~~~~~~~ ~~~~~~~~~~ ~~~~~~~~~~
```

Fig 2a

| | | | | | |
|---|---|---|---|---|---|
| atave02a | ~~~~~~~~~~ | ~~~~~~~~~~ | ~~~~~~~~~~ | ~~~~~~~~~~ | ~~~~~~~~~~ |
| atave05a | ~~~~~~~~~~ | ~~~~~~~~~~ | ~~~~~~~~~~ | ~~~~~~~~~~ | ~~~~~~~~~~ |
| atave04a | ~~~~~~~~~~ | ~~~~~~~~~~ | ~~~~~~~~~~ | ~~~~~~~~~~ | ~~~~~~~~~~ |
| atave08a | ~~~~~~~~~~ | ~~~~~~~~~~ | ~~~~~~~~~~ | ~~~~~~~~~~ | ~~~~~~~~~~ |
| atave03a | ~~~~~~~~~~ | ~~~~~~~~~~ | ~~~~~~~~~~ | ~~~~~~~~~~ | ~~~~~~~~~~ |
| atrap02a | ~~~~~~~~~~ | ~~~~~~~~~~ | ~~~~~~~~~~ | ~~~~~~~~~~ | ~~~~~~~~~~ |
| atrap11a | ~~~~~~~~~~ | ~~~~~~~~~~ | ~~~~~~~~~~ | ~~~~~~~~~~ | ~~~~~~~~~~ |
| atrap08a | ~~~~~~~~~~ | ~~~~~~~~~~ | ~~~~~~~~~~ | ~PPTQPADNA | VIERAPEWLP |
| atrap12a | ~~~~~~~~~~ | ~~~~~~~~~~ | ~~~~~~~~~~ | ~~~~~~~~~~ | ~~~~~~~~~~ |
| atrap05a | ~~~~~~~~~~ | ~~~~~~~~~~ | ~~~~~~~~~~ | ~~~~~~~~~~ | ~~~~~~~~~~ |
| atrap09a | ~~~~~~~~~~ | ~~~~~~~~~~ | ~~~~~~~~~D | DVRPADAPVV | ASVMASELVP |
| atfkb03a | ~~~~~~~~~~ | ~~~~~~~~~~ | ~~~~~~~~~~ | ~~~~~~~~~~ | ~~~~~~~~~~ |
| atfkb07x | ~~~~~~~~~~ | ~~~~~~~~~~ | ~~~~~~~~~~ | ~~~~~~~~~~ | ~~~~~~~~~~ |
| atfkb08x | ~~~~~~~~~~ | ~~~~~~~~~~ | ~~~~~~~~~~ | ~~~~~~~~~~ | ~~~~~~~~~~ |
| atnid01a | ~~~~~~~~~~ | ~~~~~~~~~~ | ~~~~~~~~~~ | ~~~~~~~~~~ | ~~~~~~~~~~ |
| atnid03a | ~~~~~~~~~~ | ~~~~~~~~~~ | ~~~~~~~~~~ | ~~~~~~~~~~ | ~~~~~~~~~~ |
| atnid02a | ~~~~~~~~~~ | ~~~~~~~~~~ | ~~~~~~~~~~ | ~~~~~~~~~~ | ~~~~~~~~~~ |
| atnid00a | ~~~~~~~~~~ | ~~~~~~~~~~ | ~~~~~~~~~~ | ~~~~~~~~~~ | ~~~~~~~~~~ |
| atfkb10a | ~~~~~~~~~~ | ~~~~~~~~~~ | ~~~~~~~~~~ | ~~~~~~~~~~ | ~~~~~~~~~~ |
| atrap14a | ~~~~~~~~~~ | ~~~~~~~~~~ | ~~~~~~~~~~ | ~~~~~~~~~~ | ~~~~~~~~~~ |
| atmon06a | ~~~~~~~~~~ | ~~~~~~~~~~ | ~~~~~~~~~~ | ~~~~~~~~~~ | ~~~~~~~~~~ |
| atmon08a | ~~~~~~~~~~ | ~~~~~~~~~~ | ~~~~~~~~~~ | ~~~~~~~~~~ | ~~~~~~~~~~ |
| atmon09a | ~~~~~~~~~~ | ~~~~~~~~~~ | ~~~~~~~~~~ | ~~~~~~~~~~ | ~~~~~~~~~~ |
| atepo02a | ~~~~~~~~~~ | ~~~~~~~~~~ | ~~~~~~~~~~ | ~~~~~~~~~~ | ~~~~~~~~~~ |
| atepo03x | ~~~~~~~~~~ | ~~~~~~~~~~ | ~~~~~~~~~~ | ~~~~~~~~~~ | ~~~~~~~~~~ |
| atepo08a | ~~~~~~~~~~ | ~~~~~~~~~~ | ~~~~~~~~~~ | ~~~~~~~~~~ | ~~~~~~~~~~ |
| atepo00a | ~~~~~~~~~~ | ~~~~~~~~~~ | ~~~~~~~~~~ | ~~~~~~~~~~ | ~~~~~~~~~~ |
| atepo04a | ~~~~~~~~~~ | ~~~~~~~~~~ | ~~~~~~~~~~ | ~~~~~~~~~~ | ~~~~~~~~~~ |
| atnid07a | ~~~~~~~~~~ | ~~~~~~~~~~ | ~~~~~~~~~~ | ~~~~~~~~LR | DHLSRTPGAR |
| attyl07a | ~~~~~~~~~~ | ~~~~~~~~~~ | ~~~~~~~~~~ | ~~~~~~~~~~ | ~~~~~~~~~~ |
| atsor02a | ~~~~~~~~~~ | ~~~~~~~~~~ | ~~~~~~~~~~ | ~~~~~~~~~~ | ~~~~~~~~~~ |
| atsorb1a | ~~~~~~~~~~ | ~~~~~~~~~~ | ~~~~~~~~~~ | ~~~~~~~~~~ | ~~~~~~~~~~ |
| atnys09a | ~~~~~~~~~~ | ~~~~~~~~~~ | ~~~~~~~~~~ | ~~~~~~~~~~ | ~~~~~~~~~~ |
| atnys12a | ~~~~~~~~~~ | ~~~~~~~~~~ | ~~~~~~~~~~ | ~~~~~~~~~~ | ~~~~~~~~~~ |
| atnys16a | ~~~~~~~~~~ | ~~~~~~~~~~ | ~~~~~~~~~~ | ~~~~~~~~~~ | ~~~~~~~~~~ |
| atnys17a | ~~~~~~~~~~ | ~~~~~~~~~~ | ~~~~~~~~~~ | ~~~~~~~~~~ | ~~~~~~~~~~ |
| atnys03a | ~~~~~~~~~~ | ~~~~~~~~~~ | ~~~~~~~~~~ | ~~~~~~~~~~ | ~~~~~~~~~~ |
| atnys15a | ~~~~~~~~~~ | ~~~~~~~~~~ | ~~~~~~~~~~ | ~~~~~~~~~~ | ~~~~~~~~~~ |
| atnys07a | ~~~~~~~~~~ | ~~~~~~~~~~ | ~~~~~~~~~~ | ~~~~~~~~~~ | ~~~~~~~~~~ |
| atnys08a | ~~~~~~~~~~ | ~~~~~~~~~~ | ~~~~~~~~~~ | ~~~~~~~~~~ | ~~~~~~~~~~ |
| atnys05a | ~~~~~~~~~~ | ~~~~~~~~~~ | ~~~~~~~~~~ | ~~~~~~~~~~ | ~~~~~~~~~~ |
| atnys06a | ~~~~~~~~~~ | ~~~~~~~~~~ | ~~~~~~~~~~ | ~~~~~~~~~~ | ~~~~~~~~~~ |
| atnys04a | ~~~~~~~~~~ | ~~~~~~~~~~ | ~~~~~~~~~~ | ~~~~~~~~~~ | ~~~~~~~~~~ |
| atnys14a | ~~~~~~~~~~ | ~~~~~~~~~~ | ~~~~~~~~~~ | ~~~~~~~~~~ | ~~~~~~~~~~ |
| atnys00a | ~~~~~~~~~~ | ~~~~~~~~~~ | ~~~~~~~~~~ | ~~~~~~~~~~ | ~~~~~~~~~~ |
| atnys10a | ~~~~~~~~~~ | ~~~~~~~~~~ | ~~~~~~~~~~ | ~~~~~~~~~~ | ~~~~~~~~~~ |
| atnys18a | ~~~~~~~~~~ | ~~~~~~~~~~ | ~~~~~~~~~~ | ~~~~~~~~~~ | ~~~~~~~~~~ |
| atnys13a | ~~~~~~~~~~ | ~~~~~~~~~~ | ~~~~~~~~~~ | ~~~~~~~~~~ | ~~~~~~~~~~ |
| atave10a | ~~~~~~~~~~ | ~~~~~~~~~~ | ~~~~~~~~~~ | ~~~~~~~~~~ | ~~~~~~~~~~ |
| atrif02a | ~~~~~~~~~~ | ~~~~~~~~~~ | ~~~~~~~~~~ | ~~~~~~~~~~ | ~~~~~~~~~~ |
| atmon03a | ~~~~~~~~~~ | ~~~~~~~~~~ | ~~~~~~~~~~ | ~~~~~~~~~~ | ~~~~~~~~~~ |
| atave12a | ~~~~~~~~~~ | ~~~~~~~~~~ | ~~~~~~~~~~ | ~~~~~~~~~~ | ~~~~~~~~~~ |
| atrif09a | ~~~~~~~~~~ | ~~~~~~~~~~ | ~~~~~~~~~~ | ~~~~~~~~~~ | ~~~~~~~~~~ |
| atmon00a | ~~~~~~~~~~ | ~~~~~~~~~~ | ~~~~~~~~~~ | ~~~~~~~~~~ | ~~~~~~~~~~ |
| attyl03a | SVPAGEPPAA | GRPEDTGGAW | TVSGRGPAAL | RAQAARLYDA | LTGTGTGTGQ |

Fig 2b

```
                          51                                                    100
ataveOOx     ~~~~~~~~~~  ~~~~~~~~~~  ~~~~~~~~~~  ~~~~~~~VQR  MDGGEEPRPA
atdebs00p    ~~~~~~~~~~  ~~~~~~~~~~  ~~~~~~~~~~  ~~~~~~~~~~  ~~~VADGRPH
atepo06p     ~~~~~~~~~~  ~~~~~~~~~~  ~~~~~~~~~~  ~~~~~~~~~~  ~~AAAQGHTP
atepo07p     ~~~~~~~~~~  ~~~~~~~~~~  ~~~~~~~~~~  ~SSREALRGA  LSAAAQGHTP
atepo01p     ~~~~~~~~~~  ~~~~~~~~~~  ~~~~~~~~~~  ~~~~~~~REG  LDAAARGQTP
atepo05p     ~~~~~~~~~~  ~~~~~~~~~~  ~~~~~~~~~~  ~~~~~~~~~~  ~~~~~~~~~P
atsoralx     ~~~~~~~~~~  ~~~~~~~~~~  ~~~~~~~~~~  ~~~~~~~~~~  ~~~~~~~~~~
atfkb01p     ~~~~~~~~~~  ~~~~~~~~~~  ~~~~~~~~~~  ~~~~~~~~~~  ~~~~~~~~~~
atfkb09p     ~~~~~~~~~~  ~~~~~~~~~~  ~~~~~~~~~~  ~~~~~~~~~~  ~~~~~~~~~~
atrap03p     SAKTQPALTE  HEDRLRAYLA  ASPGADTRAV  ASTLAVTRSV  FEHRAVLLGD
atrap06p     ~~~TQPALTE  HEDRLRAYLA  ASPGVDTRAV  ASTLAVTRSV  FEHRAVLLGD
atrap04p     SAKTQPALTE  HEDRLRAYLA  ASPGADTRAV  ASTLAVTRSV  FEHRAVLLGD
atrap13p     SAKTQPALTE  HEDRLRAYLA  ASPGADIRAV  ASTLAVTRSV  FEHRAVLLGD
atrap01p     ~~~~~~~~~~  ~~~~~~~~~~  ~~~~~~~~~~  ~~~LAVTRSL  FEHRAVLLGD
atrap07p     SAKTLPALTE  HEDRLRAYLA  ASPGADMRAV  GSTLALTRSV  FEHRAVLLGH
atrap10p     ~~~~~~~~~~  ~~~~~~~~~~  ~~~~~~~~AV  ASTLAVTRSV  FEHRAVLLGD
atfkb04x     ~~~~~~~~~~  ~~~~~~~~~~  ~~~~~~~~~~  ~~~~~~~~~~  ~~~~~~~~~~
atty104p     FGYRAVVLAR  GEAELAGRLR  ALAGGDPDAG  VVTGAVVD..  ..........
atty106p     FGYRAVVLAR  GEAELAGRLR  ALAGGDPDAG  VVTGAVVD..  ..........
atty101p     FGYRAVVLAR  GEAELAGRLR  ALAGGDPDAG  VVTGAVVD..  ..........
atty102p     ~~~~~~~~~~  ~~~~~~~RLR  ALAGGDPDAG  VVTGAVVD..  ..........
atty100p     FGYRAVVLAR  GEAELAGRLR  ALAGGDPDAG  VVTGAVLDGG  VVVGAAPGGA
atnid05b     ~~~~~~~~~~  ~~~~~LLSTR  ARFPRRAAVV  GESMTELAEA  LDAVAEGGPH
atty105b     LLEHPDEHPA  DVGYTLITGR  AHFGHRAAVI  GESREELLDA  LKALAEGREH
atnid06x     ~~~~~~~~~~  ~~~~~~~~~~  ~~~~~~~~~~  ~~~~~~~~~~  ~RSVAEERPE
atdebs01p    ~~~~~~~~~~  ~~~~~~~~~~  ~~~~~~~~~~  ~~~~~~~~~~  ~~GLATGNAD
atmon02p     ~~~~~~~~~~  ~~~~~~~~~~  ~~~~~~~~~~  ~~~~~~~~~~  ~GALAAGEAS
atmon10p     ~~~~~~~~~~  ~~~~~~~~~~  ~~~~~~~~~~  ~~~~~~~~~~  LGALAAGEAS
atmon04p     ~~~~~~~~~~  ~~~~~~~~~~  ~~~~~~~~~~  ~~~~~~~~~~  ~~~LAAGETP
atmon07p     ~~~~~~~~~~  ~~~~~~~~~~  ~~~~~~~~~~  ~~~~~~~~~~  ~~ALAAGEES
atmon11p     ~~~~~~~~~~  ~~~~~~~~~~  ~~~~~~~~~~  ~~~~~~~~~~  ~~ALAAGEAS
atmon12p     ~~~~~~~~~~  ~~~~~~~~~~  ~~~~~~~~~~  ~~~~~~~~~~  ~~~LAAGEPS
atmon05b     ~~~~~~~~~~  ~~~~~~~~~~  ~~~~~~~~~~  ~~~~~~~~~~  ~~SLAAGEAS
atmon01p     ~~~~~~~~~~  ~~~~~~~~~~  ~~~~~~~~~~  ~~~~~~~~~~  ~EALAAGDAS
atdebs02p    ~~~~~~~~~~  ~~~~~~~~~~  ~~~~~~~~~~  ~~~~~~~~~~  ~~~~~ADGAVV
atdebs06p    ~~~~~~~~~~  ~~~~~~~~~~  ~~~~~~~~~~  ~~~~~~~~~~  ~RAVAEGVAA
atave01p     ~~~~~~~~~~  ~~~~~~~~~~  ~~~~~~~~~~  ~~~~~~~~~G  LGALAAGEPD
atave07p     ~~~~~~~~~~  ~~~~~~~~~~  ~~~~~~~~~~  ~~~~~~~~~G  LGALAAGEPD
atave06p     ~~~~~~~~~~  ~~~~~~~~~~  ~~~~~~~~~~  ~~~~~~~~QA  LTALAAGEPH
atave09p     ~~~~~~~~~~  ~~~~~~~~~~  ~~~~~~~~~~  ~~~~~~~~~~  LTALAAGEPH
atnys01p     ~~~~~~~~~~  ~~~~~~~~~~  ~~~~~~~~~~  ~~~~~~~~~~  ~~~~~~~~~~
atnys11p     ~~~~~~~~~~  ~~~~~~~~~~  ~~~~~~~~~~  ~~~~~~~~~~  ~~~~AVATDG
atrif05p     ~~~~~~~~~~  ~~~~~~~~~~  ~~~~~~~~~~  ~~~~~~~~~~  ~TALARGESA
atrif07p     ~~~~~~~~~~  ~~~~~~~~~~  ~~~~~~~~~~  ~~~~~~~~~G  LGALARGEAA
atrif08p     ~~~~~~~~~~  ~~~~~~~~~~  ~~~~~~~~~~  ~~~~~~~~AG  LAALARGESA
atrif10p     ~~~~~~~~~~  ~~~~~~~~~~  ~~~~~~~~~~  ADSAEEARAG  LGALARGEDA
atrif03p     ~~~~~~~~~~  ~~~~~~~~~~  ~~~~~~~~~~  ~~~~~~~QDG  LQALARGENA
atrif06p     ~~~~~~~~~~  ~~~~~~~~~~  ~~~~~~~~~~  ~~SREEAVTN  LEALARGEDP
atrif04p     ~~~~~~~~~~  ~~~~~~~~~~  ~~~~~~~~~~  ~~~~~~~~~~  ~RALARGESA
atrif01p     ~~~~~~~~~~  ~~~~~~~~~~  ~~~~~~~~~~  ~~~~~~~~~V  VVAGSREEAV
atnys02p     ~~~~~~~~~~  ~~~~~~~~~~  ~~~~~~AVVV  GERREDFLRG  LAALSTGAST
atfkb02p     ~~~~~~~~~~  ~~~~~~~~~~  ~~~~~~~~~~  ~~~~~~~~~~  ~~~~~~GEEV
atave11p     ~~~~~~~~~~  ~~~~~~~~~~  ~~~~~~~~~~  ~~~~~~~LHA  LDALAEGAPT
atdebs03p    ~~~~~~~~~~  ~~~~~~~~~~  ~~~~~~~~~~  ~~~~~~~~~~  ~~~~~~AATA
atnid04p     ~~~~~SLADS  AGIGHGLAVG  RAALPHRAVL  LGDGAAPLDA  LAALASGEVS
atdebs05p    ~~~~~~~~~~  ~~~~~~~~~~  ~~~~~~~~~~  ~~~~~~~~~~  ~~~~ADRRIA
atdebs04p    ~~~~~~~~~~  ~~~~~~~~~~  ~~~~~~~~~~  ~~~~~~~~~~  ~~ALAEGRPS
```

Fig 2c

```
atave02a   ~~~~~~~~~~ ~~~~~~~~~~ ~~~~~~~~~~ ~~~~~~~~~~ ~~~~~~~~~~
atave05a   ~~~~~~~~~~ ~~~~~~~~~~ ~~~~~~~~~~ ~~~~~QALQAL AAGEPHPAVI
atave04a   ~~~~~~~~~~ ~~~~~~~~~~ ~~~~~~~~~~ ~~~~~QALQAL AAGEPHPAVI
atave08a   ~~~~~~~~~~ ~~~~~~~~~~ ~~~~~~~~~~ ~~~~~QALQAL AAGEPHPAVI
atave03a   ~~~~~~~~~~ ~~~~~~~~~~ ~~~~~~~~~~ ~~~~~QALQAL AAGEPHPAVI
atrap02a   ~~~~~~~~~~ ~~~~~~~~~~ ~~~~~~~~DT RAVASTLAMT RSVFEYRAVL
atrap11a   ~~~~~~~~~~ ~~~~~~~~~~ ~~~~~~~~~~ ~AVASTLAMT RSMFEHRGVL
atrap08a   MVISARTQSA LTEHEGRLRA YLAASPGVDM RAVASTLAIT RSVFEHRAVL
atrap12a   ~~~~~~~~~~ LTEHEGRLRA YLAASPGVDM RAVASTLAMT RSVFEHRAVL
atrap05a   ~~~~~~~~~~ ~~~~~~~~~~ ~~~~~~~~~~ ~~~ASTLAVT RSVFEHRAVL
atrap09a   LVISAKTQSA LAEYEGRLRA YLAASPGVDM RAVASTLAMT RSVFEHRAVI
atfkb03a   ~~~~~~~~~~ ~~~~~~~~~~ ~~~~~~~~~~ ~~~~~~~~~~ ~~~~~~HRAAL
atfkb07x   ~~~~~~~~~~ ~~~~~~~~~~ ~~~~~~~~~~ ~~~~~~~~~~ ~~~~~~~~~L
atfkb08x   ~~~~~~~~~~ ~~~~~~~~~~ ~~~~~~~~~~ ~~~~~~~~~~ ~~~~~~~~~~
atnid01a   ~~~~~~~~~~ ~~~~~~~~~~ ~~~~~~KHRA VITGRTRTEL HTKLHTLDAI
atnid03a   ~~~~~~~~TQA DPQDIAHALA TTRTHFKHRA VITGRTRTEL HTKLHTLDAI
atnid02a   ~~~~~~~~~~ ~~~~~~HALA TTCTHFKHRA VITGRTRTEL HTKLHTLDAI
atnid00a   ~~~~~~~~~~ ~~~~~~~~~~ ~~~~~~~~~~ ~~~~~~~~~~ SSALAALAAG
atfkb10a   ~~~~~~~~~~ ~~~~~~~~~~ ~~~~~~~~~~ ~~~~~~~~~~ ~~~~~~~~~~
atrap14a   ~~~~~~~~~~ ~~~~~~~~~~ ~~~~~~~~~~ ~~~~~DFLRA LSKLADGAPW
atmon06a   ~~~~~~~~~~ ~~~~~~~~~~ ~~~~~~~~~~ ~~~~~~~~~~ ~~~~TGEPHA
atmon08a   ~~~~~~~~~~ ~~~~~~~~~~ ~~~~~~~~~~ ~~~~~~~~~~ ~~~~AGEEHP
atmon09a   ~~~~~~~~~~ ~~~~~~~~~~ ~~~~~~~~~~ ~~~~~~~~~~ ~~~~~GEEHP
atepo02a   ~~~~~~~~~~ ~~~~~~~~~~ ~~~~~~~~~~ ~~~~~~~~~~ AALSAVAQGQ
atepo03x   ~~~~~~~~~~ ~~~~~~~~~~ ~~~~~~~~~A VAVTSREGLL AALSAVAQGQ
atepo08a   ~~~~~~~~~~ ~~~~~~~~~~ ~~~~~~~~~~ ~~~~~~~~~~ ~~~~VAAQGQ
atepo00a   ~~~~~~~~~~ ~~~~~~~~~~ ~~~~~~~~~~ ~~~~SREGLR AALDAAAQGQ
atepo04a   ~~~~~~~~~~ ~~~~~~~~~~ ~~~~~~~~~~ ~~~~~~~~LR GALDAAAQQK
atnid07a   ~~~~~~~~~~ ~~~~~~~~~~ ~~~~~~~~~A AAHDALLAVA DGRPSDAVVT
attyl07a   PRDIAFSLAA TRAAFDHRAV LIGSDGAELA AALDAL...A EGRDGPAVVR
atsor02a   ~~~~~~~~~~ ~~~~~~~~~~ ~~~~~~~~~~ ~~~~~~~~~~ ~~~~~~~~~~
atsorb1a   ~~~~~~~~~~ ~~~~~~~~~~ ~~~~~~~~~~ ~~~~~~~~~~ ~~~~~~~~~~
atnys09a   ~~~~~~~~~~ ~~~~~~~~~~ ~~~~~~~~~~ ~~~~~~~~AD DPAAAPAWIT
atnys12a   ~~~~~~~~~~ ~~~~~~~~~~ ~~~~~~~~~~ ~~~~~~~~~S DGRPDPGLVQ
atnys16a   ~~~~~~~~~~ ~~~~~~~~~~ ~~~~~~~~~~ ~~~~~~~~~~ ~PD.LPEVAR
atnys17a   ~~~~~~~~~~ ~~~~~~~~~~ ~~~~~~~~~~ ~~~~~~~~~~ APDGITAAAR
atnys03a   ~~~~~~~~~~ ~~~~~~~~~~ ~~~GYALADGR ATFEHRAVLL PDGTELA..H
atnys15a   ~~~~~~~~~~ ~~~~~~~~~~ ~~~~~~~~~~ ~~~~~~~~~~ PDAHE.G..H
atnys07a   ~~~~~~~~~~ ~~~~~~~~~~ ~~~~~~~~~~ ~~~~~~~IAA DEA.DAAAAT
atnys08a   ~~~~~~~~~~ ~~~~~~~~~~ ~~~~~~~~~~ ~~~ALAALAS GVA.DPAVVS
atnys05a   ~~~~~~~~~~ ~~~~~~~~~~ ~~~~~~~~~~ AVRALTALAA ADA.DLSAVV
atnys06a   ~~~~~~~~~~ ~~~~~~~~~~ ~~~~~~~~~~ ATRALSALAT TAASDPSALT
atnys04a   ~~~~~~~~~~ ~~~~~~~~HR AVVLGTDRAE ALRALTALAA GE.TDPAALT
atnys14a   ~~~~~~~~~~ ~~~~~~~~~~ ~~~~~~~~DG LRTGLTAVAE GTTAPHTAEH
atnys00a   ~~~~~~~~~~ ~~~~~~~~~~ ~~~~~~~~~~ ~~~~~~~~~~ ~~ADAVEHAR
atnys10a   ~~~~~~~~~~ ~~~~~~~~~~ ~~VVAQDRDQ LIASLGALAA DRPDPAVVEG
atnys18a   ~~~~~~~~~~ ~~~~~~~~~~ ~~~~~~~~~~ ~~~~~~~~~~ EGGAVTEVAR
atnys13a   ~~~~~~~~~~ ~~~~~~~~~~ ~~~~~~~~~~ ~~~~~~~LLA GPDGVREAAR
atave10a   ~~~~~~~~~~ ~~~~~~~~~~ ~~~~~~~~~~ ~~~LHALDALA GGRPVPGVVE
atrif02a   ~~~~~~~~~~ ~~~~~~~~~~ ~~~~~~~~~~R AVVLASDRAQ LCADLAAFGS
atmon03a   ~~~~~~~~~~ ~~~~~~~~~~ ~~~~~~~~~~ ~~~~~~~~~A LAAGRAHPAL
atave12a   ~~~~~~~~~~ ~~~~~~~~~~ ~~~~~~~~~~ ~~~QALDALA EGRSADGLIE
atrif09a   ~~~~~~~~~~ ~~~~~~~~~~ ~~GRALLGDR AVVVAGTDED AVAGLRALAR
atmon00a   ~~~~~~~~~~ ~~~~~~~~~~ ~~~~~~~~~~ ~~~~~~~~~~ ~~~~~~LAEG
attyl03a   GAGQGAGPGT AEVAGALAHA RTAFRHRAVV LGGNRAELLA GLRELAEEEH
```

Fig 2d

```
                     101                                                        150
atave00x    AGEVLGVADE  ADGG..VVFV  FPGQGPQWPG  MGRELLDASD  VFRESVRACE
atdebs00p   ASVVRGVA.R  PSAP..VVFV  FPGQGAQWAG  MAGELLGESR  VFAAAMDACA
atepo06p    PGAVRGRASG  GSAP.KVVFV  FPGQGSQWVG  MGRKLMAEEP  VFRAALEGCD
atepo07p    PGAVRGRASG  GSAP.KVVFV  FPGQGSQWVG  MGRKLMAEEP  VFRAALEGCD
atepo01p    PGAVRGRCSP  GNVP.KVVFV  FPGQGSQWVG  MGRQLLAEEP  VFHAALSACD
atepo05p    PAAARGHAST  GSAP.KVVFV  FPGQGSQWLG  MGQKLLSEEP  VFRDALSACD
atsora1x    ~~~~~~~~~~  ~~~~~~~VFV  FAGQGAQWFG  MGRALLQREP  VFRTTIEQCS
atfkb01p    ~~~~SAVAGV  AVEGARTVFV  FPGQGSQWVG  MGRELMGASE  VFAARMRECA
atfkb09p    ~~~~~~~~~~  ~~~~~~~VFV  FPGQGSQWVG  MGRELMGCSE  VFAARMRECA
atrap03p    D..TV..TGT  AVSDPRVVFV  FPGQGWQWLG  MGSALRDSSV  VFAERMAECA
atrap06p    D..TV..TGT  AVSDPRVVFV  FPGQGWQWLG  MGSALRDSSI  VFAERMAECA
atrap04p    D..AV..TGT  AVTDPRVVFV  FPGQGWQWLG  MGSALRDSSV  VFAERMAECA
atrap13p    D..TV..TGT  AVTDPRIVFV  FPGQGWQWLG  MGSALRDSSV  VFAERMAECA
atrap01p    D..SVTGTGT  AVSDPRVVFV  FPGQGWQWLG  MGSALRTSSM  VFAERMAECA
atrap07p    DTVTVTGTGT  AVSNPRVVFV  FPGQGWQWLG  MGSALRGSSV  VFAERMAECA
atrap10p    ETV....TGT  AVSDPRIVFV  FPGQGWQWLG  MGSALRDSSV  VFAERMAECA
atfkb04x    ~~~~~VVTGT  ALTAPRTVFV  FPGQGSQWLG  MGRELMAESP  VFAARMRQCA
attyl04p    .......PET  GSGGGGVVLV  FPGQGTQWVG  MGAGLLGSSE  VFAASMRECA
attyl06p    .......PET  GSGGGGVVLV  FPGQGTQWVG  MGAGLLGSSE  VFAASMRECA
attyl01p    .......PET  GSGGGGVVLV  FPGQGTQWVG  MGAGLLGSSE  VFAASMRECA
attyl02p    .......PET  GSGGGGVVLV  FPGQGTQWVG  MGAGLLGSSE  VFAASMRECA
attyl00p    GAAGGAGAAG  GAGGGGVVLV  FPGQGTQWVG  MGAGLLGSSE  VFAASMRECA
atnid05b    ..PLAATGT.  AGTADRVVFV  FPGQGSQWAG  MAEGLLERSG  AFRSAADSCD
attyl05b    HTVVRGDGT.  AHPDRRVVFV  FPGQGSQWPS  MARDLLDRAP  AFRETAKACD
atnid06x    PDVVL..GE.  AGSDRAPAFV  FPGQGAQWAG  LGARLLADSP  VFRARAEACA
atdebs01p   GAAV...GT.  SRAQQRAVFV  FPGQGWQWAG  MAVDLLDTSP  VFAAALRECA
atmon02p    AGVVAG.VAG  DVGPGP.VLV  FPGQGAQWVG  MGAQLLDESA  VFAARIAECE
atmon10p    AGVVAG.VAG  DVGPGP.VLV  FPGQGSQWVG  MGAQLLDESP  VFAARIAECE
atmon04p    TDVVSG.AAA  SSGAGP.VLV  FPGQGSQWVG  MGAQLLDESP  VFAARIAECE
atmon07p    ADVVAG.VAG  DVGPGP.VLV  FPGQGSQWVG  MGAQLLDESP  VFAARIAECE
atmon11p    ADVVAG.VAG  DVGPGP.VLV  FPGQGSQWVG  MGAQLLDESP  VFAARIAECE
atmon12p    PDVVEGAVQG  ASGAGP.VLV  FPGQGSQWVG  MGAQLLDESP  VFAARIAECE
atmon05b    PDVVSGAV.G  PTGPGP.VMV  FPGQGGQWVG  MGARLLDESP  VFAARIAECE
atmon01p    PDVVCG.VAG  DVGPGP.VLV  FPGQGSQWVG  MGAQLLGESA  VFAARIDACE
atdebs02p   PGVVTGSASD  ....GGSVFV  FPGQGAQWEG  MARELL.PVP  VFAESIAECD
atdebs06p   PGATTGTASA  ....GGVVFV  FPGQGAQWEG  MARGLL.SVP  VFAESIAECD
atave01p    RRVTTGHAPG  GDRGG.VVFV  FPGQGGQWAG  MGVRLLASSP  VFARRMQACE
atave07p    RRVTTGHAPG  GDRGG.VVFV  FPGQGGQWAG  MGVRLLASSP  VFARRMQACE
atave06p    PHITTGHTRG  GDRGG.VVFV  FPGQGGQWAG  MGLTLLTSSP  VFAEHIDACE
atave09p    PHITTGHTRG  SDRGG.VVFV  FPGQGGQWAG  MGLTLLTSSP  VFAEHIDACE
atnys01p    ~~~~~~~~L.  ADVEGRTVFV  FPGQGSQWVG  MGAQLLDESA  VFAERIAECA
atnys11p    PSPVVARGV.  ADVEGRTVFV  FPGQGSQWVG  MGSQLLDESA  VFAERIAECA
atrif05p    SGLVTGT...  AGMPGKTVWV  FPGQGTQWAG  MGRELLEASP  VFAERIEECA
atrif07p    PGVVTGT...  AGKPGKVVWV  FPGQGTQWVG  MGRELLDASP  VFAERIKECA
atrif08p    ADVVTGTVAA  SGVPGKLVWV  FPGQGSQWVG  MGRELLEASP  VFAARIAECA
atrif10p    PGLVRGRVPA  SGLPGKLVWV  FPGQGTQWVG  MGRELLEESP  VFAERIAECA
atrif03p    PGVVTGT...  AGKPGKVVWV  FPGQGSQWMG  MGRDLLDSSP  VFAARIKECA
atrif06p    AAVVTGR...  AGSPGKLVWV  FPGQGSQWIG  MGRELLDSSP  VFAERVAECA
atrif04p    PGLLSGR..G  SGVPGKVVWV  FPGQGTQWAG  MGRELLDSSE  VFAARIAECE
atrif01p    TGLRALNTAG  SGTPGKVVWV  FPGQGTQWAG  MGRELLAESP  VFAERIAECA
atnys02p    AGLVSG..IA  GPDPEGAVFV  FPGQGSQWWG  MGRELLATSE  VFRTAIDDCA
atfkb02p    PGVVRGTADV  TDT..RAVFV  FPGQGSQWDG  MAELLATEP   VFARRLGECA
atave11p    AGVVQGVAGP  AA.DGKIAML  FGGQGTHWEG  MAQELLGSSP  VFAQQMSDCA
atdebs03p   DAVVEGV.TE  VD.GRNVVFL  FPGQGSQWAG  MGAELLSSSP  VFAGKIRACD
atnid04p    PDVVTG..SA  AD.VRRVAFV  FPGQGAQWAG  MGAELLDSSP  VFAAELARCE
atdebs05p   DRTATGQ.GP  NS.PRRVAMV  FPGQGAQWQG  MARDLLRESQ  VFADSIRDCE
atdebs04p   ADAVAPVTSA  ...PRKPVLV  FPGQGAQWVG  MARDLLESSE  VFAESMSRCA
```

Fig 2e

```
atave02a   HSSAPGGTGT  GEAAGKTAFI  CSGQGTQRPG  MAHGLYHTHP  VFAAALNDIC
atave05a   HSSAPGGTGT  GEAAGKTAFI  CSGQGTQRPG  MAHGLYHTHP  VFAAALNDIC
atave04a   HSSAPGGTGT  GEAAGKTAFI  CSGQGTQRPG  MAHGLYHTHP  VFAAALNDIC
atave08a   HSSAPGGTGT  GEAAGKTAFI  CSGQGTQRPG  MAHGLYHTHP  VFAAALNDIC
atave03a   HSSAPGGTGT  GEAAGKTAFI  CSGQGTQRPG  MAHGLYHTHP  VFAAALNDIC
atrap02a   IGDDTVTG.T  AATDPRVVFV  FPGQGSQRAG  MGEELAAAFP  VFARIHQQVW
atrap11a   LGDGTVSG.T  AVSDPRVVFV  FPGQGSQRAG  MGEELAAAFP  VFARIHQQVW
atrap08a   LGDDTVTG.T  AATDPRVVFV  FPGQGSQRAG  MGEELAAAFP  VFARIHQQVW
atrap12a   LGDDTVTG.T  AVSDPRAVFV  FPGQGSQRAG  MGEELAAAFP  VFARIHQQVW
atrap05a   LGDDTVTG.T  TVSDPRVVFV  FPGQGSQRAG  MGEELAAAFP  VFARIHQQVW
atrap09a   VGDDTVSG.T  AATDPRVVFV  FPGQGSQRAG  MGAELAAAFP  VFARIHQQVW
atfkb03a   IGTDLITG.T  AEPDRRLVWL  FSGQGSQRPG  MGDELAAAYD  VFARTRRDVL
atfkb07x   LGDTLITADP  NAGSGPVVFV  YSGQSTLHPH  TGHQLAATYS  VFADAWGEVL
atfkb08x   ~~~~~IGAPP  ADQADELVFV  YSGQGTQHPA  MGEQLAAAFP  VFADAWHDAL
atnid01a   Q.......GT  AHPHPRLTLL  FTGQGAQHRG  MGQELYATDP  HFAAALDEVC
atnid03a   Q.......GT  AHPHPRLTLL  FTGQGAQHPG  MGQELYTTDP  HFAAALDEVC
atnid02a   Q.......GT  AHPHPRLTLL  FTGQGAQHPG  MGQELYTTDP  HFAAALDEIC
atnid00a   QTPRGVRIGS  TDADGRLALL  FTGQGAQHPG  MGQELYTTDP  HFAAALDEVC
atfkb10a   ~~~EAPESSA  EPPRSARRFL  FDGQGAQRVG  MGRELHGRFP  VFAAAWDEVS
atrap14a   PGLTTATATA  KARRVA..FL  FDGQGTQRLG  MGKELYDSYP  AFARAWDTVS
atmon06a   ALVGPACSQA  RVGGDDVVWL  FSGQGSQLVG  MGAGLYERFP  VFAAAFDEVC
atmon08a   AVTRSREDGV  AASG.AVVWL  FSGQGSQLVG  MGAGLYERFP  VFAAAFDEVC
atmon09a   AVTRSREEAA  VAASGDVVWL  FSGQGSQLVG  MGAGLYERFP  VFAAAFDEVC
atepo02a   TPAGAARCIA  SSSRGKLAFL  FTGQGAQTPG  MGRGLCAAWP  AFREAFDRCV
atepo03x   TPPGAARCIA  SSSRGKLAFL  FTGQGAQTPG  MGRGLCAAWP  AFREAFDRCV
atepo08a   TPAGAARGRA  ASSPGKLAFL  FAGQGAQVPG  MGRGLWEAWP  AFRETFDRCV
atepo00a   TSPGAVRSIA  DSSRGKLAFL  FTGQGAQTLG  MGRGLYDVWS  AFREAFDLCV
atepo04a   TPQGAVRGKA  VSSRGKLAFL  FTGQGAQMPG  MGRGLYETWP  AFREAFDRCV
atnid07a   GIAR......  ..RGRDVAFL  FSGQGAQRAG  AGRELYASFP  VFAQALDEVA
attyl07a   GVRD......  ..RDGRMAFL  FTGQGSQRAG  MAHDLHAAHT  FFASALDEVT
atsor02a   ~~~~~~~~~~  ~~~~~~~~AVL  FTGQGSQRPT  MGRALYDAFP  VFRDALDTVA
atsor01a   ~~~~~~~~~~  ~~~~~~~~AIL  FTGQGSQRPT  MGRALYDAFP  VFRGALDAAA
atnys09a   GTT.R.....  ..AETRLAVL  FTGQGAQRLG  AGRELAARFP  AFATALDAAL
atnys12a   GTA.......  ..GRGRTAFL  FTGQGSQRPG  MGRELHDRYP  VFADALDEVL
atnys16a   GAA.TPH...  ..RT...AFL  FSGQGAQRSG  MGRELHAAFP  VFAAAFDEVV
atnys17a   AEA.RER...  ..ST...AFL  FSGQGAQRSG  MGRELHAAFP  VFAAAFDEVV
atnys03a   GTA.GEG...  ..PC...AVL  FSGQGSQRPG  MGRELHARFP  VFAAAFDEIT
atnys15a   .AA.GRT...  ..RC...AAL  FSGQGAQRLG  MGRELHARFP  VFARALDTAV
atnys07a   GRV.GAG...  ..RH...AVL  FSGQGAQRLG  MGRELYERFP  VFAEALDVVV
atnys08a   DAV.STG...  ..GS...AVL  FTGQGAQRLG  MGRELYGRFP  VFAEALDVVV
atnys05a   GDT.RTG...  ..RH...AVL  FSGQGSQRLG  MGRELYERFP  VFAEALDVAI
atnys06a   GTV.TMG...  ..RC...AVL  FSGQGSQRLG  MGRELYERFP  VFAEALDVVI
atnys04a   GTV.RTG...  ..RT...AFL  FSGQGSQRLG  MGRVLYERFP  AFAEALDTVL
atnys14a   HLQ.GTG...  ..KR...AVL  FSGQGSQRLG  MGRELHERHP  VFAEAFDSVL
atnys00a   GAA.HQR...  ..RT...AVL  FSGQGSQRPG  MGRELAARFP  VFADALDDAL
atnys10a   EAA.GRG...  ..RT...AVL  FTGQGSQRAA  MGRELHEVQP  EFAAAFDAVC
atnys18a   GAV.PTG...  ..DRGGLAVL  FSGQGSQRPG  MGRELHARYP  VFAAAFDETV
atnys13a   AAA.PRT...  ..P.GRTAFL  FSGQGAQHAL  MGHDLYQRFP  VYADALDTVL
atave10a   GRT.TSG...  .....ELAVL  FAGQGTQRAG  MGRELYEAYP  VFAQAIDEIC
atrif02a   GVVTGTP...  ..VDGKLAVL  FTGQGSQWAG  MGRELAETFP  VFRDAFEAAC
atmon03a   TRAAGPA...  ..RNGGTAFL  FTGQGSQRPG  MGRQLYDTFD  VFAESLDETC
atave12a   GSVGPRGGHS  GRRRGKTAML  FAGQGTQRVG  MGRQLYAAHP  AYADALDQVL
atrif09a   GDRAPGVLTG  SAKHGKVVYV  FPGQGSQRLG  MGRELYDRYP  VFATAFDEAC
atmon00a   AETASIVRGE  AYTEGRTAFL  FSGQGAQRLG  MGRELYAVFP  VFADALDEAF
attyl03a   PGPRVVTGTA  PATERRTAFL  FSGQGSQRAG  SGRGLYRRHP  VFARALDEVC
                                      ***                              GQG
```

Fig 2f

```
                  151                                                       200
ataveOOx    AAFAPYVDWS VEQVLRDSPD A.......... ........PG LDRVDVVQPT
atdebs00p   RAFEPVTDWT LAQVL.DSPE Q.......... ........S. .RRVEVVQPA
atepo06p    RAIEAEAGWS LLGEL..... .SA........ ....DEAASQ LGRIDVVQPV
atepo07p    RAIEAEAGWS LLGEL..... .SA........ ....DEAASQ LGRIDVVQPV
atepo01p    RAIQAEAGWS LLAEL..... .AA........ ....DEGSSQ LERIDVVQPV
atepo05p    RAIQAEAGWS LLAEL..... .AA........ ....DETTSQ LGRIDVVQPA
atsoralx    SFIQQNLGWS LLDEL..... .MT........ ....DRESSR LDEIDVSLPA
atfkb01p    AVLEPHTGWD LLDVL..... ........... .....GEAVV VDRVEVLQPA
atfkb09p    AVLEPYTGWD LLDVL..... ........... .....GEAVV AERVEVLQPA
atrap03p    AALSEFVDWD L.TVL..... ........... .....DDPAV VDRVDVVQPA
atrap06p    PALREFVDWD LFTVL..... ........... .....DDPAV VDRVDVVQPA
atrap04p    AALSEFVDWD LFAVL..... ........... .....DDPAV VDRVDVVQPA
atrap13p    AALREFVDWD LFTVL..... ........... .....DDPAV VDRVDVVQPA
atrap01p    AALSEFVDWD LFAVL..... ........... .....DDPAV VDRVDVVQPA
atrap07p    AALSEFVDWD LFAVL..... ........... .....DDPAV VARVDVVQPA
atrap10p    AALSEFVDWD LFAVL..... ........... .....DDPAV VDRVDVVQPA
atfkb04x    DALAEHTGRD LIAML..... ........... .....DDPAV KSRVDVVHPV
attyl04p    RALSVHVGWD LLEVVSG... ........... ......GAG LERVDVVQPV
attyl06p    RALSVHVGWD LLEVVSG... ........... ......GAG LERVDVVQPV
attyl01p    RALSVHVEWD LLEVVSG... ........... ......GAG LERVDVVQPV
attyl02p    RALSVHVEWD LLEVVSG... ........... ......GAG LERVDVVQPV
attyl00p    RALSVHVGWD LLEVVSG... ........... ......GAG LERVDVVQPV
atnid05b    AALRPYLGWS VLSVLRGEPD ........... .......APS LDRVDVVQPV
attyl05b    AALSVHLDWS VLDVLQEKPD ........... .......APP LSRVDVVQPV
atnid06x    RALEPHLDWS VLDVLAGAPG ........... .......TPP IDRADVVQPV
atdebs01p   DALEPHLDFE VIPFLRAEAA RRE........ ....QDAALS TERVDVVQPV
atmon02p    RALSAHVDWS LSAVLRG..D ........... .......GSE LSRVEVVQPV
atmon10p    RALSAYVDWS LSAVLRG..D ........... .......GSE LSRVEVVQPV
atmon04p    QALSAYVDWS LSDVLRG..D ........... .......GSE LSRVEVVQPV
atmon07p    QALSAYVDWS LSAVLRG..D ........... .......GSE LSRVEVVQPV
atmon11p    QALSAHVDWS LSDVLRG..D ........... .......GSE LSRVEVVQPV
atmon12p    RALSAHVDWS LSAVLRG..D ........... .......GSE LSRVEVVQPV
atmon05b    QALSAYVDWS LTDVLRG..D ........... .......GSE LARIDVVQPV
atmon01p    QALSPYVDWS LTEVLRG..D ........... .......GRE LSRVDVVQPV
atdebs02p   AVLSEVAGFS VSEVLEPRPD ........... .......APS LERVDVVQPV
atdebs06p   AVLSEVAGFS ASEVLEQRPD ........... .......APS LERVDVVQPV
atave01p    EALAPWVDWS VVDILRRDAG ........... .......DAV WERADVVQPV
atave07p    EALAPWVDWS VVDILRRDAG ........... .......DAV WERADVVQPV
atave06p    KALTPWVPWS LTDILHRDPD ........... .......DPA WQQADVVQPV
atave09p    KALTPWVPWS LTDILHRDPD ........... .......DPA WQQADVVQPV
atnys01p    AALAEFTDWS LVDVLRGVVG ........... .......APS LERVDVVQPA
atnys11p    AALAEFTDWS LVDVLRGVVG ........... .......APS LERVDVVQPA
atrif05p    AALQPWIDWS LLDVLRG..E ........... .......GE. LDRVDVLQPA
atrif07p    AALDQWTDWS LLDVLRG..D ........... .......GD. LDSVEVLQPA
atrif08p    AALEPWIDWS LLDVLRG..E ........... .......GD. LDRVDVVQPA
atrif10p    AALEPWIGWS LFDVLRG..D ........... .......GD. LDRVDVLQPA
atrif03p    AALEQWTDWS LLDVLRG..D ........... .......ADL LDRVDVVQPA
atrif06p    AALEPWIDWS LLDVLRG..E ........... .......SDL LDRVDVVQPA
atrif04p    TALGRWVDWS LTDVLRG..E ........... .......ADL LDRVDVVQPA
atrif01p    AALAPWIDWS LVDVLRG..E ........... .......GD. LGRVDVLQPA
atnys02p    TALAPYVDWS LHDVLAGEGD ........... .......PAL LERVDVVQPA
atfkb02p    EALAPYTGWD LLDVIARRPG ........... .......APE LDRVDVVQPA
atave11p    QALEPYLDWS LLDVLRGAPD ........... .......APP LQRVDVVQPV
atdebs03p   ESMAPMQDWK VSDVLRQAPG ........... .......APG LDRVDVVQPV
atnid04p    AALEPFVDWS LTDVLRGAPG ........... .......APG LDRVDVVQPV
atdebs05p   RALAPHVDWS LTDLL...SG ........... .......ARP LDRVDVVQPA
atdebs04p   EALSPHTDWK LLDVVRGDGG ........... .......PDP HERVDVLQPV
```

Fig 2g

```
atave02a  THLDPHLDHP  LLPLLTQ..N  DNDN......  ....EDAAAL  LQQTRYAQPA
atave05a  THLDPHLDHP  LLPLLTQNDN  DNDN......  ....EDAAAL  LQQTPYAQPA
atave04a  THLDPHLDHP  LLPLLTQDPN  TQDT......  .TTLEEAAAL  LQQTPYAQPA
atave08a  THLDPHLDHP  LLPLLTQDPN  TQDT......  .TTLEEAAAL  LQQTPYAQPA
atave03a  THLDPHLDHP  LLPLLTQDPN  TQDT......  .TTLEEAAAL  LQQTRYAQPA
atrap02a  DLLDVP.DLD  ..........  ..........  ..........  VNETGYAQPA
atrap11a  DLLDVP.DLD  ..........  ..........  ..........  VNETGYAQPA
atrap08a  DLLDVP.DLE  ..........  ..........  ..........  VNETGYAQPA
atrap12a  DLLDVP.DLE  ..........  ..........  ..........  VNETGYAQPA
atrap05a  GLLDVP.DLE  ..........  ..........  ..........  VNETGYAQPA
atrap09a  DLLDVP.DLE  ..........  ..........  ..........  VNETGYAQPA
atfkb03a  DALQVPAGLD  ..........  ..........  ..........  VHDTGYAQPA
atfkb07x  GHLN..ADQG  ..........  ..........  ..........  P.......AT
atfkb08x  RRLD...DPD  ..........  ..........  ..........  PHDPTRSQHT
atnid01a  EELQR.....  ........C   GTQNLREVMF  TPD...QPDL  LDRTEYTQPA
atnid03a  EELQR.....  ........C   GTQNLREVMF  TPD...QPDL  LDRTEYTQPA
atnid02a  EELQR.....  ........C   GTQNLREVMF  TPD...QPDL  LDRTEYTQPA
atnid00a  EELQR.....  ........C   GTQNLREVMF  TPD...QPDL  LDRTEYTQPA
atfkb10a  DAFGKHLE..  ..........  ..HSPTDVFH  GEHGD....L  AHDTLYAQVG
atrap14a  AGFDKHLD..  ..........  ..HSLTDVCF  GEGGSTTAGL  VDDTLYAQAG
atmon06a  GLLEGPL...  ........GV  EAGGLREVVF  RGPR....ER  LDHTVWAQAG
atmon08a  GLLEGPL...  ........GV  EAGGLREVVF  RGPR....ER  LDHTMWAQAG
atmon09a  GLLEGEL...  ........GV  GSGGLREVVF  WGPR....ER  LDHTVWAQAG
atepo02a  ALFDRELDRP  ..........  ....LREVMW  AEAGSAESLL  LDQTAFTQPA
atepo03x  ALFDRELDRP  ..........  ....LREVMW  AEPGSAESLL  LDQTAFTQPA
atepo08a  TLFDRELHQP  ..........  ....LCEVMW  AEPGSSRSSL  LDQTAFTQPA
atepo00a  RLFNQELDRP  ..........  ....LREVMW  AEPASVDAAL  LDQTAFTQPA
atepo04a  ALFDREIDQP  ..........  ....LREVMW  AAPGLAQAAR  LDQTAYAQPA
atnid07a  GGFDAHLERP  ..........  ....LLQVMF  AEPGTADAAL  LDRTAYAQPA
attyl07a  DRLDPLLGRP  ..........  ....LGALLD  ARPGSPEAAL  LDRTEYTQPA
atsor02a  AHLDRDLDRP  ..........  ....LRDVLF  APDGSEQAAR  LDQTAFTQPA
atsor01a  AHLDRDLDRP  ..........  ....LRDVLF  APDGSEQAAR  LDQTAFTQPA
atnys09a  DAFTPHLDRP  ..........  ....LREVLW  ....GTDAAL  LDRTAYAQPA
atnys12a  ARLDDGPDRP  ..........  ....LREVLF  AAPDSAEAAL  LDRTGYAQPA
atnys16a  AVLDAELGSD  ........AD  GGVSLREVMW  GGG....SEL  LDRTRFTQPA
atnys17a  AVLDAELATG  ........SG  GGVSLREVMW  GGG....SEL  LDRTRFTQPA
atnys03a  ALLDTHLDRP  ..........  ....LREVVW  GTD....ADL  LNDTGWAQPA
atnys15a  DLLDAELGGT  ..........  ....LREVIW  GTD....DAP  LNETGFTQPA
atnys07a  DHLDAALPAQ  ........AG  ....LREVMW  GDD....AEL  LNETGWTQPA
atnys08a  DHLDAALPAQ  ........AG  ....LREVMW  GDD....VEL  LNETGWTQPA
atnys05a  DHLDAALPAQ  ........AS  ....LREVMW  GDD....VEL  LDETGWTQPA
atnys06a  DHLDAALPAQ  ........AG  ....LREVMW  GDD....VEL  LNETGWTQPA
atnys04a  TALDAELGHP  ..........  ....LRDIIW  GED....AQL  VDRTGYTQPA
atnys14a  ARLDDRLDTP  ..........  ....LRDVVW  GTD....EEA  LHATGNTQPA
atnys00a  RALDRHLDGP  ..........  ....VREVMW  GTD....AAL  LDRTGWTQPA
atnys10a  AVFDPLLDRP  ..........  ....LREVVF  AEDGSDEAAL  LDETGWTQPA
atnys18a  ALLDARL...  ..........  .GTSLRDIVW  DQDRTR....  LDDTRHTQPA
atnys13a  AQFDTVLDVP  ..........  ....LRAALF  AAPGTPEAAL  LDQTGFTQPA
atave10a  AEADTARTDP  ........GA  PG..LRDVLF  APQDSPEGRL  IEDTGFAQPA
atrif02a  EAVDTHL...  ..........  RERPLREVVF  .....DDSAL  LDQTMYTQGA
atmon03a  ARLDPLLEQP  ..........  ....LKPVLF  APADTAQAAV  LHGTGMTQAA
atave12a  AELDGHLDQP  ........LR  PLIHASADL.  .ADVADAADV  LDRTRYAQPA
atrif09a  EQLDVCL..A  ........GR  AGHRVRDVVL  GE.VPAETGL  LNQTVFTQAG
atmon00a  AALDVHLDRP  LREIVLGETD  SGGNVSGENV  IGEGADHQAL  LDQTAYTQPA
attyl03a  AALEPHLHRP  ..........  ....LRDLMF  AEPGSPEAEP  LDRTEFTQPA
```

Fig 2h

```
                  201                                                                    250
ataveOOx   LFAVMISLAA L.WRSQGVEP CAVLGHSLGE IAAAHVSGGL SLADAARVVT
atdebs00p  LFAVQTSLAA L.WRSFGVTP DAVVGHSIGE LAAAHVCGAA GAADAARAAA
atepo06p   LFAMEVALSA L.WRSWGVEP EAVVGHSMGE VAAAHVAGAL SLEDAVAIIC
atepo07p   LFAMEVALSA L.WRSWGVEP EAVVGHSMGE VAAAHVAGAL SLEDAVAIIC
atepo01p   LFALAVAFAA L.WRSWGVAP DVVIGHSMGE VAAAHVAGAL SLEDAVAIIC
atepo05p   LFAIEVALSA L.WRSWGVEP DAVVGHSMGE VAAAHVAGAL SLEDAVAIIC
atsoralx   IISIEIALAA Q.WRAWGVEP AFVVGHSTGE IAAAHVAGVL SIEDAMRTIC
atfkb01p   SWAVAVSLAA L.WQAHGVVP DAVVGHSQGE IAAACVAGAL SLEDAARVVA
atfkb09p   SWAVAVSLAA L.WQAHGVSP DAVIGHSQGE IAAACVAGAL SLEDAARIVA
atrap03p   SWAVMVSLAA V.WQAAGVRP DAVIGHSQGE IAAACVAGAV SLRDAARIVT
atrap06p   SWRMMVSLAA V.WQAAGVRP DAVIGHSQGE IAAACVAGAV SMRDAARIVT
atrap04p   SWAVMVSLAA V.WQAAGVRP DAVIGHSQGE IAAACVAGAV SLRDAARIVT
atrap13p   SWAMMVSLAA V.WQAAGVRP DAVIGHSQGE IAAACVAGAV SLRDAARIVT
atrap01p   SWAVMVSLAA V.WQAAGVRP DAVVGHSQGE IAAACVAGAV SLRDAARVVT
atrap07p   SWAVMVSLAA V.WQADGVRP DAVIGHSQGE IAAACVAGAV SLRDAARSVT
atrap10p   SWAVMVSLAA V.WQAAGVRP DAVIGHSQGE IAAACVAGAV SMRDAARIVT
atfkb04x   CWAVMVSLAA V.WEAAGVRP DAVVGHSQGE IAAACVAGAI SLEDGARLVA
attyl04p   TWAVMVSLAR Y.WQAMGVDV AAVVGHSQGE IAAATVAGAL SLEDAAAVVA
attyl06p   TWAVMVSLAR Y.WQAMGVDV AAVVGHSQGE IAAATVAGAL SLEDAAAVVA
attyl01p   TWAVMVSLAR Y.WQAMGVDV AAVVGHSQGE IAAATVAGAL SLEDAAAVVA
attyl02p   TWAVMVSLAR Y.WQAMGVDV AAVVGHSQGE IAAATVAGAL SLEDAAAVVA
attyl00p   TWAVMVSLAR Y.WQAMGVDV AAVVGHSQGE IAAATVAGAL SLEDAAAVVA
atnid05b   LFTMMVSLAA V.WRALGVEP AAVVGHSQGE IAAAHVAGAL SLDDSARIVA
attyl05b   LFTMMLSLAA C.WRDLGVHP AAVVGHSQGE IAAACVAGAL SLEDAARIVA
atnid06x   LFTTMVSLAA L.WEAHGVRP AAVVGHSQGE VAAACVAGAL SLDDAALVIA
atdebs01p  MFAVMVSLAS M.WRAHGVEP AAVIGHSQGE IAAACVAGAL SLDDAARVVA
atmon02p   LWAVMVSLAA V.WADYGVTP AAVIGHSQGE MAAACVAGAL SLEDAARIVA
atmon10p   LWAVMVSLAA V.WADYGVTP AAVIGHSQGE MAAACVAGAL SLEDAARIVA
atmon04p   LWAVMVSLAA V.WADYGVTP AAVVGHSQGE MAAACVAGAL SLEDAARIVA
atmon07p   LWAVMVSLAA V.WADYGVTP AAVIGHSQGE MAAACVAGAL SLEDAARVVA
atmon11p   LWAVMVSLAA V.WADYGITP AAVIGHSQGE MAAACVAGAL SLEDAARIVA
atmon12p   LWAVMVSLAS V.WADYGITP AAVIGHSQGE MAAACVAGAL SLEDAARIVA
atmon05b   LWAVMVALAA V.WADQGIEP AAVVGHSQGE IAAACVVGAI SLDEAARIVA
atmon01p   LWAVMVSLAA V.WADHGVTP AAVVGHSQGE IAAVVAGAL TLEDGAKIVA
atdebs02p  LFAVMVSLAR L.WRACGAVP SAVIGHSQGE IAAAVVAGAL SLEDGMRVVA
atdebs06p  LFSVMVSLAR L.WGACGVSP SAVIGHSQGE IAAAVVAGVL SLEDGVRVVA
atave01p   LFSVMVSLAA L.WRSYGIEP DAVLGHSQGE IAAAHVCGAL SLKDAAKTVA
atave07p   LFSVMVSLAA L.WRSYGIEP DAVLGHSQGE IAAAHVCGAL SLKDAAKTVA
atave06p   LFSIMVSLAA L.WRSYGIEP DAVLGHSQGE IAAAHICGAL SLKDAAKTVA
atave09p   LFSIMVSLAA L.WRSYGIEP DAVLGHSQGE IAAAHICGAL SLKDAAKTVA
atnys01p   SFAVMVSLAA L.WGSRGVLP DAVVGHSQGE IAAAVVSGAL SLRDGARVVA
atnys11p   SFAVMVSLAA L.WRSRGVLP DAVVGHSQGE IAAAVVSGAL SLRDGARVVA
atrif05p   CFAVMVGLAA V.WASVGVVP DAVLGHSQGE IAAACVSGAL SLEDAAKVVA
atrif07p   CFAVMVGLAA V.WESAGVRP DAVVGHSQGE IAAACVSGAL TLDDAAKVVA
atrif08p   SFAVMVGLAA V.WSSVGVVP DAVLGHSQGE IAAACVSGAL SLQDAAKVVA
atrif10p   CFAVMVGLAA V.WSSAGVVP DAVLGHSQGE IAAACVSGAL SLEDAAKVVA
atrif03p   SFAMMVGLAA V.WTSLGVTP DAVLGHSQGE IAAACVSGAL SLDDAAKVVA
atrif06p   SFAMMVGLAA V.WQSVGVRP DAVVGHSQGE IAAACVSGAL SLQDAAKVVA
atrif04p   SFAMMVGLAA V.WASLGVEP EAVVGHSQGE IAAACVSGAL SLEDAAKVVA
atrif01p   CFAVMVGLAA V.WESVGVRP DAVVGHSQGE IAAACVSGAL SLEDAAKVVA
atnys02p   LFAMMVGLSA L.WRSHGVVP AAVVGHSQGE IAAACVAGAL SLADAARVVA
atfkb02p   SFAMMVALAE L.WRAHGVAP AAVVGHSQGE VAAACVAGVL TLDDAAKVVA
atave11p   LFAVMVSLAA L.WRSYGVHP DAVAGHSQGE IAAAYVAGAL SLDDAARVTA
atdebs03p  LFAVMVSLAE L.WRSYGVEP AAVVGHSQGE IAAAHVAGAL TLEDAAKLVV
atnid04p   TFAVVVALAA M.WRWLGVEP AAVVGHSQGE IAAAHVAGVL SLEDAARVVA
atdebs05p  LFAVMVSLAA L.WRSHGVEP AAVVGHSQGE IAAAHVAGAL TLEDAAKLVA
atdebs04p  LFSIMVSLAE L.WRAHGVTP AAVVGHSQGE IAAAHVAGAL SLEAAAKVVA
```

Fig 2i

```
atave02a  LFAFQVALHR  LLTDGYHITP  HYYAGHSLGE  ITAAHLAGIL  TLTDATTLIT
atave05a  LFAFQVALHR  LLTDGYHITP  HYYAGHSLGE  ITAAHLAGIL  TLTDATTLIT
atave04a  LFAFQVALHR  LLTDGYHITP  HYYAGHSLGE  ITAAHLAGIL  TLTDATTLIT
atave08a  LFAFQVALHR  LLTDGYHITP  HYYAGHSLGE  ITAAHLAGIL  TLTDATTLIT
atave03a  LFAFQVALHR  LLTDGYHITP  HYYAGHSLGE  ITAAHLAGIL  TLTDATTLIT
atrap02a  LFALQVALFG  LL.ESWGVRP  DAVVGHSVGE  LAAGYVSGLW  SLEDACTLVS
atrap11a  LFALQVALFG  LL.ESWGVRP  DAVIGHSVGE  LAAAYVSGVW  SLEDACTLVS
atrap08a  LFALQVALFG  LL.ESWGVRP  DAVVGHSVGE  LAAGYVSGLW  SLEDACTLVS
atrap12a  LFAMQVALFG  LL.ESWGVRP  DAVIGHSVGE  LAAAYVSGVW  SLEDACTLVS
atrap05a  LFALQVALFG  LL.ESWGVRP  DAVVGHSVGE  LAAGYVSGLW  SLEDACTLVS
atrap09a  LFALQVALFG  LL.ESWGVRP  DAVIGHSVGE  LAAAYVSGLW  SLEDACTLVS
atfkb03a  VFALQVALSA  QL.DAWGVRP  DVLVGHSIGE  LAAAYVAGVW  SLDDATELVS
atfkb07x  HFAHQIALTA  LL.RSWGITP  HAVIGHSLGE  ISAACAAGVL  SIGDASALLA
atfkb08x  LFAHQAAFTA  LL.RSWDITP  HAVIGHSLGE  ITAAYAAGIL  SLDDACTLIT
atnid01a  LFALQTALYR  TL.TARGTQA  HLVLGHSVGE  ITAAHIAGVL  DLPDAARLIT
atnid03a  LFALQTALYR  TL.TARGTQA  HLVLGHSVGE  ITAAHIAGVL  DLPDAARLIT
atnid02a  LFALQTALYR  TL.TAHGTQA  HLVLGHSVGE  ITAAHIAGVL  DLPDAARLIT
atnid00a  LFALQTALYR  TL.TARGTQA  HLVLGHSVGE  ITAAHIAGVL  DLPDAARLIT
atfkb10a  LFTLEVALLR  LL.EHWGVRP  DVVVGHSVGE  VTAAYAAGVL  TLADATTLIV
atrap14a  IFAMEAALFG  LL.EDWGVRP  DFVAGHSIGE  ATAAYASGML  SLENVTTLIV
atmon06a  LFALQVGLAR  LW.ESVGVRP  DVVLGHSIGE  IAAAHVAGVF  DLADACRVVG
atmon08a  LFALQVGLAR  LW.ESVGVRP  DVVLGHSIGE  IAAAHVAGVF  DLADACRVVG
atmon09a  LFALQVGLAR  LW.ESVGVRP  DVVLGHSIGE  IAAAHVAGVF  DLADACRVVG
atepo02a  LFAVEYALTA  LW.RSWGVEP  ELLVGHSIGE  LVAACVAGVF  SLEDGVRLVA
atepo03x  LFTVEYALTA  LW.RSWGVEP  ELVAGHSAGE  LVAACVAGVF  SLEDGVRLVA
atepo08a  LFALEYALAA  LF.RSWGVEP  ELVAGHSLGE  LVAACVAGVF  SLEDAVRLVV
atepo00a  LFTFEYALAA  LW.RSWGVEP  ELVAGHSIGE  LVAACVAGVF  SLEDAVFLVA
atepo04a  LFALEYALAA  LW.RSWGVEP  HVLLGHSIGE  LVAACVAGVF  SLEDAVRLVA
atnid07a  LFAVETALFR  LF.ESWGLMP  DVLLGHSIGG  LAAAYAAGVF  SSADAVRLVA
attyl07a  LFAVEVALHR  LL.EHWGMRP  DLLLGHSVGE  LAAAHVAGVL  DLDDACALVA
atsor02a  LFALEVALFQ  LL.QSFGLKP  ALLLGHSIGE  LVAAHVAGVL  SLQDACTLVA
atsorb1a  LFALEVALFE  LL.QSFGLKP  ALLLGHSIGE  LVAAHVAGVL  SLQDACTLVA
atnys09a  LFAVEVALYR  LI.ESFGVRP  DHLAGHSVGE  IVAAHLAGVL  SLADAATLVA
atnys12a  LFAVEVALFR  LL.TSWGLTP  DYLAGHSVGE  LAAAHVAGVL  SLDDACTLVA
atnys16a  LFAVEVALFR  LV.ASWGVGP  EFVAGHSVGE  IAAAHVAGVF  SLVDACRLVV
atnys17a  LFAVEVALFR  LV.ASWGVGP  EFVAGHSVGE  IAAAYVAGVF  SLVDACRLVV
atnys03a  LFAVEVALYR  LV.ASLGVTP  DFVGGHSIGE  LAAAHVAGVL  SLEDACTLVA
atnys15a  LFAVEVALYR  LI.ESWGVAP  DFVAGHSIGE  IAAAHVAGVF  SLEDACTLVA
atnys07a  LFAIEVALFR  LV.ESWGVRP  DFVAGHSIGE  IAAAHVAGVF  SLEDACRLVA
atnys08a  LFAVEVALFR  LV.ERWGVRP  DFVAGHSIGE  IAAAHVAGVF  SLEDACRLVA
atnys05a  LFAVEVALFR  LV.ESWGVRP  DFVAGHSIGE  IAAAHVVGVF  SLEDACRLVA
atnys06a  LFAIEVALFR  LV.ESWGVRP  DFVAGHSIGE  IAAAHVVGVF  SLEDACRLVA
atnys04a  LFAIEVALFR  LL.EAWGITP  DFVAGHSIGE  IAAAHVAGVL  SLGDACRLVV
atnys14a  LFAVEVALYR  LI.ESWGVRP  DFVAGHSVGE  LAAAHVAGVL  SLDDACRLVA
atnys00a  LFAVEVALHR  LV.ASLGVTP  DFVGGHSVGE  IAAAHVAGVL  SLEDACRLVA
atnys10a  LFAVEVALFR  LV.ESWGVRP  DFVAGHSIGE  IAAAHVAGVL  TLEDACRLVA
atnys18a  LFAVEVALYR  LL.ASWGIRP  DHVTGHSIGE  ITAAHVAGVL  TLADACTLVA
atnys13a  LFAVEVALFR  LA.ESWRLTP  DFVAGHSIGE  IAAAHVAGVF  SLEDACTLVA
atave10a  LFAFEVALFR  LL.ETWGLTP  DYVLGHSVGE  LAAAHVAGML  CLADAVALVV
atrif02a  LFAVETALFR  LF.ESWGVRP  GLLAGHSIGE  LAAAHVSGVL  DLADAGELVA
atmon03a  LFALEVALYR  QV.TSFGIAP  SHLTGHSVGE  IAAAHVAGVF  SLADACTLVA
atave12a  LFAVQVALFR  HL.ERLGVRA  DFVAGHSIGE  LAAAHVAGVL  PLAAACRLVA
atrif09a  LFAVESALFR  LA.ESWGVRP  DVVLGHSIGE  ITAAYAAGVF  SLPDAARIVA
atmon00a  LFAIETSLYR  LA.ASFGLKP  DYVLGHSVGE  IAAAHVAGVL  SLPDASALVA
attyl03a  LFALQTALFR  LA.EHHGLRA  EALCGHSVGE  IAAAHAAGVL  TLPDAARLVA
                                   ***                              GHS
```

Fig 2j

```
              251                                                            300
ataveOOx    LWSQAQTT.L  AGTGALVSVA  ATPDELLPRI  APWTEDN.PA  RLAVAAVNGP
atdebs00p   LWSREMIP.L  VGNGDMAAVA  LSADEIEPRI  ARWDDD....  .VVLAGVNGP
atepo06p    RRSRLL.RRI  SGQGEMALVE  LSLEEAEAAL  .....RGHEG  RLSVAVSNSP
atepo07p    RRSRLL.RRI  SGQGEMALVE  LSLEEAEAAL  .....RGHEG  RLSVAVSNSP
atepo01p    RRSRLL.RRI  SGQGEMAVTE  LSLAEAEAAL  .....RGYED  RVSVAVSNSP
atepo05p    RRSLLL.RRI  SGQGEMAVVE  LSLAEAEAAL  .....LGYED  RLSVAVSNSP
atsoralx    AYGRII.RKL  RGKGGMGLVA  LSWEDAGKEL  .....TGYEG  RLFRAIEHSA
atfkb01p    LRSQAIAARL  AGRGAMASIA  VPASAVE...  .......TVE  GVWIAARNGP
atfkb09p    LRSQTIAAHL  AGRGAMASIA  LPATAVE...  .......TVE  GVWVAARNGP
atrap03p    LRSQAIARGL  AGRGAMASVA  LPAQDVE...  .......LVD  GAWIAAHNGP
atrap06p    LRSEAIARGL  AGRGAMASVA  LPAQDVE...  .......LVD  GAWIAAHNGP
atrap04p    LRSQAIARGL  AGRAAMASVA  LPAHEIE...  .......LVD  GAWIAAHNGP
atrap13p    LRSQAIARGL  AGRGAMASVA  LPAQDVE...  .......LVD  GAWIAAHNGP
atrap01p    LRSQVIARGL  AGRGAMASVA  LPAQDVE...  .......LVD  GAWVAARNGP
atrap07p    LRSQAIARGL  AGRGAMASVA  LPAHEIE...  .......LVD  GAWIAAHNGP
atrap10p    LRSQAIARGL  AGRGAMASVA  LPAQDVE...  .......LVD  GAWIAAHNGP
atfkb04x    LRSALLVREL  AGRGAMGSIA  FAA..AA...  .......RID  GVWVAGRNGT
attyl04p    LRAGLIGRYL  AGRGAMAAVP  LPAGEVEAGL  AKWPG.....  .VEVAAVNGP
attyl06p    LRAGLIGRYL  AGRGAMAAVP  LPAGEVEAGL  AKWPG.....  .VEVAAVNGP
attyl01p    LRAGLIGRYL  AGRGAMAAVP  LPAGEVEAGL  AKWPG.....  .VEVAAVNGP
attyl02p    LRAGLIGRYL  AGRGAMAAVP  LPAGEVEAGL  AKWPG.....  .VQVAAVNGP
attyl00p    LRAGLIGRYL  AGRGAMAAVP  LPAGEVEAGL  AKWPG.....  .VEVAAVNGP
atnid05b    LRSRAWLG.L  AGKGGMVAVP  MPAEELRPRL  .....VTWGD  RLAVAAVNSP
attyl05b    LRSRAWLT.L  AGKGGMAAVS  LPEARLRERI  .....ERFGQ  RLSVAAVNSP
atnid06x    GRSRLWGR.L  AGNGGMLAVM  APAERIRELL  .....EPWRQ  RISVAAVNGP
atdebs01p   LRSRVIAT.M  PGNKGMASIA  APAGEVRARI  ........GD  RVEIAAVNGP
atmon02p    VRSDAL.RQL  QGHGDMASLS  TGAEQAAELI  GDRPG.....  .VVVAAVNGP
atmon10p    VRSDAL.RRL  QGHGDMASLS  TGAEQAAELI  GDRPG.....  .VVVAAVNGP
atmon04p    VRSDAL.RQL  QGHGDMASLG  TGAEQAAELI  GDRPG.....  .VVVAAVNGP
atmon07p    VRSDAL.RQL  MGQGDMASLG  ASSEQAAELI  GDRPG.....  .VCIAAVNGP
atmon11p    VRSDAL.RQL  QGHGDMASLS  TGAEQAAELI  GDRPG.....  .VVVAAVNGP
atmon12p    VRSDAL.RQL  MGQGDMASLG  AGSEQVAELI  GDRPG.....  .VCVAAVNGP
atmon05b    VRSVLL.RQL  SGRGGMASLG  MGQEQAADLI  DGHPG.....  .VVVAAVNGP
atmon01p    LRSRAL.RQL  SGGGAMASLG  VGQEQAAELV  EGHPG.....  .VGIAAVNGP
atdebs02p   RRSRAV.RAV  AGRGSMLSVR  GGRSDVEKLL  ADDS...WTG  RLEVAAVNGP
atdebs06p   LRAKAL.RAL  AGKGGMVSLA  APGERARALI  A..P...WED  RISVAAVNSP
atave01p    LRSRALAA.V  RGRGGMASVP  LPAQEVEQLI  ....GERWAG  RLWVAAVNGP
atave07p    LRSRALAA.V  RGRGGMASVP  LPAQEVEQLI  ....GERWAG  RLWVAAVNGP
atave06p    LRSRALAA.V  RGRGAMASLP  LPAQDVQQLI  ....SERWEG  QLWVAALNGP
atave09p    LRSQALAA.V  RGRGAMVSLP  LPAQDVQQLI  ....SERWEG  QLWVAALNGP
atnys01p    LRSQAIGRAL  AGRGGMMSVA  LSVDVLEPRL  VE.....FEG  RVSVAAVNGP
atnys11p    LRSQAIGRAL  AGRGGMMSVA  LSVDVLEPRL  VE.....FEG  RVSVAAVNGP
atrif05p    LRSQAIAAEL  SGRGGMASIQ  LSHDEVAARL  AP.....WAG  RVEIAAVNGP
atrif07p    LRSQAIAARL  SGRGGMASVA  LSEDEANARL  GL.....WDG  RIEVAAVNGP
atrif08p    LRSQAIAAKL  AGRGGMASVA  LSEEDAVARL  RH.....WAD  RVEVAAVNSP
atrif10p    LRSQAIAAKL  SGRGGMASVA  LGEADVVSRL  ........AD  GVEVAAVNGP
atrif03p    LRSQAIAGEL  AGRGGMASVA  LSEEDAVARL  TP.....WAN  RVEVAAVNSP
atrif06p    LRSQAIATRL  AGRGGMASVA  LSEEDATAWL  AP.....WAD  RVQVAAVNSP
atrif04p    LRSQAIAASL  AGRGGMASVA  LSEEDATARL  EP.....WAG  RVEVAAVNGP
atrif01p    LRSQAIAAEL  SGRGGMASVA  LGEDDVVSRL  ........VD  GVEVAAVNGP
atnys02p    LRSQALP.QL  SGRGGMMSVS  APVERVTALL  AP.....WQE  ALSVAAVNGP
atfkb02p    LRSRLVATER  AGHGGMVSVP  PADFDAAA..  .......WAG  RLEVAAVNGP
atave11p    LRSQALA.AL  AGQGAMASVG  LPVEKLEPRL  A......TWGD  RLVIAAVNGA
atdebs03p   GRSRLM.RSL  SGEGGMAAVA  LGEAAVRERL  RPWQ.....D  RLSVAAVNGP
atnid04p    LRSQLIAREL  AGRGSMASVA  LAAADVESRL  AGAEAGGGVR  DVEIAAVNGP
atdebs05p   VRSRVL.RRL  GGQGGMASFG  LGTEQAAERI  .....GRFAG  ALSIASVNGP
atdebs04p   LRSQVL.REL  DDQGGMVSVG  ASRDELETVL  A......RWDG  RVAVAAVNGP
```

Fig 2k

```
atave02a  QRATLMQTMP  P..GTMTTLH  TTPHHIT..H  HLTAHE...N  DLAIAAINTP
atave05a  QRATLMQTMP  P..GTMTTLH  TTPHHIT..H  HLTAHE...N  DLAIAAINTP
atave04a  QRATLMQTMP  P..GTMTTLH  TTPHHIT..H  HLTAHE...N  DLAIAAINTP
atave08a  QRATLMQTMP  P..GTMTTLH  TTPHHIT..H  HITAHE...N  DLAIAAINTP
atave03a  QRATLMQTMP  P..GTMTTLH  TTPHHIT..H  HLTAHE...N  DLAIAAINTP
atrap02a  ARARLMQALP  AG.GVMAAVP  VSEDEARAVL  G........E  GVEIAAVNGP
atrap11a  ARARLMQALP  AG.GVMVAVP  VSEDEARAVL  G........E  GVEIAAVNGP
atrap08a  ARARLMQALP  AG.GVMVAVP  VSEDEARAVL  G........E  GVEIAAVNGP
atrap12a  ARARLMQALP  AG.GVMVAVP  VSEDEARAVL  G........E  GVEIAAVNGP
atrap05a  ARARLMQALP  PG.GVMVAVP  VSEDEARAVL  G........E  GVEIAAVNGP
atrap09a  ARARLMQALP  AG.GVMVAVP  VSEDEARAVL  G........E  GVEIAAVNGP
atfkb03a  ARARLMQALP  PG.GAMAAVS  ASERDALPLL  C........E  GVEIAAVNGP
atfkb07x  ARSRLMDELP  TG.GAMVTVL  TSEENALRAL  R........P  GVEIAAVNGP
atfkb08x  TRARLMHTLP  PP.GAMVTVL  TSEEEARQAL  R........P  GVEIAAVFGP
atnid01a  ARAHLMGQLP  HG.GAMLSVQ  AAEHDLDQLA  ....HT...H  GVEIAAVNGP
atnid03a  ARAHLMGQLP  HG.GAMLSVQ  AAEHDLDQLA  ....HT...H  GVEIAAVNGP
atnid02a  ARAHLMGQLP  HD.GAMLSVQ  AAEHDLDQLA  ....HT...H  GVEIAAVNGP
atnid00a  ARAHVMGQLP  HG.GAMLSVQ  AAEHDLDQLA  ....HT...H  GVEIAAVNGP
atfkb10a  ARGRALRALP  P..GAMTAVE  GSPAEVG..A  FTD....... .LDIAAVNGP
atrap14a  ARGRALRTTP  P..GAMVALR  AGEEEVR..E  FLSRTG...A  ALDLAAVNSP
atmon06a  ARARLMGGLP  EG.GAMCAVQ  ATPAELAA..  ..DVDG...S  AVSVAAVNTP
atmon08a  ARARLMGGLP  EG.GAMCAVQ  ATPAELAA..  ..DVDD...S  GVSVAAVNTP
atmon09a  ARARLMGGLP  EG.GAMCAVQ  ATPAELAA..  ..DVDG...S  SVSVAAVNTP
atepo02a  ARGRLMQGLS  AG.GAMVSLG  APEAEVA..A  AVAPHA...A  SVSIAAVNGP
atepo03x  ARGRLMQGLS  AG.GAMVSLG  APEAEVA..A  AVAPHA...A  SVSIAAVNGP
atepo08a  ARGRLMQALP  AG.GAMVSIA  APEADVA..A  AVAPHA...A  LVSIAAVNGP
atepo00a  ARGRLMQALP  AG.GAMVSIE  APEADVA..A  AVAPHA...A  SVSIAAVNAP
atepo04a  ARGRLMQALP  AG.GAMVAIA  ASEAEVA..A  SVAPHA...A  TVSIAAVNGP
atnid07a  ARGRLMQRLP  EG.GAMVAVR  ATEQEVAELE  WIAGGR.... AV.VAAFNGP
attyl07a  ARGRLMQRLP  PG.GAMVSVR  AGEDEVRAL.  .LAGRE...D  AVCVAAVNGP
atsor02a  ARAKLMQALP  QG.GAMVTLR  ASEEEVRDL.  .LQPYD...G  RASLAALNGP
atsor01a  ARAKLMQALP  QG.GAMVTLQ  ASEQEARDL.  .LQAAE...G  RVSLAAVNGH
atnys09a  ARGRLMQALP  DG.GAMIAVQ  ASEADVAPL.  .LAGHE...D  QVAIAAVNGP
atnys12a  ARGRLMQALP  EG.GAMVALE  AAEDEVLPL.  .LEGLT...D  RVSVAAVNGP
atnys16a  ARASLMDALP  VG.GVMVAVE  AAEAEVVPL.  .L...V...D  GVAIAAVNGP
atnys17a  ARASLMDALP  VG.GVMVAVE  AAEAEVVPL.  .L...V...D  GVAIAAVNGP
atnys03a  ARARLMQALP  RG.GAMLAIR  ATEDEVTPH.  .L...T...D  DVSIAAVNGP
atnys15a  ARAGLMQALP  RG.GAMVAVE  ATEDEVSPL.  .L...T...D  GVAIAAINGP
atnys07a  ARATLMQALP  AG.GAMIAVQ  ATEDEVTPH.  .L...T...D  DVAIAAINGP
atnys08a  ARATLMQALP  TG.GAMIAVQ  ATEDEVTPH.  .L...T...D  EVAIAAVNGP
atnys05a  ARATLMQALP  TG.GAMIAIQ  AAEDEVTQH.  .L...T...D  DVSIAAVNGP
atnys06a  ARATLMQALP  AG.GAMIAVQ  ATEDEVIPH.  .L...T...D  EVAIAAVNGP
atnys04a  ARAVLMQSLP  EG.GAMIAVQ  ATEDEVLPL.  .L...T...D  DVSIAAVNSP
atnys14a  ARAALMQRLP  AG.GAMIAVE  ATEDEVTPL.  .L...T...D  GVSLAAVNGP
atnys00a  ARATLMQALP  AG.GAMAALE  ATEDEVAPL.  .L...G...A  HLALAAVNGP
atnys10a  ARATLMQALP  TG.GAMIAIQ  ATEDEIAAH.  .L...D...D  TVAIAAVNGP
atnys18a  ARATAMSELP  PG.GAMVALE  ATEDEVRPL.  .L...T...D  DLAIAAVNAP
atnys13a  ARASLMQQLP  RD.GAMVALE  ATEDEVAPL.  .L...T...D  GVALAAVNGP
atave10a  ARGRLMQGLP  SG.GAMVAIE  ASEDEILPL.  .PDEYA...S  RVAHAAVNGP
atrif02a  ARGRLMQALP  AG.GAMVAVQ  ATEDEVAPL.  .LDGT..... .VCVAAVNGP
atmon03a  ARGRLMQALP  AG.GAMLAVQ  AAEDDVLPL.  .LAGQE...E  RLSLAAVNGP
atave12a  ARGRLMEQLA  PG.GAMVAVR  ASEAEAR..Q  ALDGRE...A  RVSVAAVNGP
atrif09a  ARGRLMQALA  PG.GAMVAVA  ASEAEVAELL  G........D  GVELAAVNGP
atmon00a  TRGRLMQAVR  AP.GAMAAWQ  ATADEAA..E  QLAGHE...R  HVTVAAVNGP
attyl03a  ARGRLMQALP  AG.GAMAALR  ATAEEIAPL.  .LERRA...G  ELALAAVNGP
          *                                             Arginine
```

Fig 21

```
                 301                                                     350
    atave00x    RSTVVSGARE  AVADLVADLT  AAQVRTRMIP  .VDVPAHSPL  MYAIEERVV.  Load AT
    atdebs00p   RSVLLTGSPE  PVARRVQELS  AEGVRAQVIN  .VSMAAHSAQ  VDDIAEGMR.  Load AT
    atepo06p    RSTVLAGEPA  ALSEVLAALT  AKGVFWRQV.  KVDVASHSPQ  VDPLREEL.I
    atepo07p    RSTVLAGEPA  ALSEVLAALT  AKGVFWRQV.  KVDVASHSPQ  VDPLREEL.I
    atepo01p    RSTVLSGEPA  AIGEVLSSLN  AKGVFCRRV.  KVDVASHSPQ  VDPLREDL.L
    atepo05p    RSTVLAGEPA  ALAEVLAILA  AKGVFCRRV.  KVDVASHSPQ  IDPLRDEL.L
    atsora1x    DSTVLAGEPD  ALDALLQALE  RKNVFCRRV.  AMDVAPHCPQ  VDCLRDEL.F  Benzoate-CoA
    atfkb01p    ESTVVAGDPA  AVERVLARYE  AEGVRVRRI.  AVDYASHTPH  VEAIEAQL.A
    atfkb09p    ESTVVAGDPS  AVERVLARYE  AEGVRVRRI.  AVDYASHTPH  VEAIQEQL.A
    atrap03p    ASTVIAGTPE  AVDHVLTAHE  ARGVRVRRI.  TVDYASHTPH  VELIRDEL.L
    atrap06p    ASTVIAGTPE  AVDHVLTAHE  ARGVRVRRI.  TVDYASHTPH  VELIRDEL.L
    atrap04p    ASTVIAGTPE  AVDHVLTAHE  ARGVRVRRI.  TVDYASHTPH  VELIRDEL.L
    atrap13p    ASTVIAGTPE  AVDHVLTAHE  AQGVRVRRI.  TVDYASHTPH  VELIRDEL.L
    atrap01p    ASTVVAGAPE  AVDRVLAVHE  ARGVRVRRI.  AVDYASHTPH  VELIRDEL.L
    atrap07p    ASTVVAGAPE  AVDRVLAVHE  ARGVRVRRI.  AVDYASHTPH  VELIRDEL.L
    atrap10p    ASTVIAGTPE  AVDHVLTALR  QRGAGAAD..  HVDYASHTPH  VELIRDEL.L
    atfkb04x    ATTIVSGRPD  AVETLIADYE  ARGVWVTRL.  VVDCPTHTPF  VDPLYDEL.Q  C5 unit
    attyl04p    ASTVVSGDRR  AVAGYVAVCQ  AEGVQARLIP  .VDYASHSRH  VEDLKGELE.
    attyl06p    ASTVVSGDRR  AVAGYVAVCQ  AEGVQARLIP  .VDYASHSRH  VEDLKGELE.
    attyl01p    ASTVVSGDRR  AVAGYVAVCQ  AEGVQARLIP  .VDYASHSRH  VEDLKGELE.
    attyl02p    ASTVVSGDRR  AVAGYVAVCQ  AEGVQARLIP  .VDYASHSRH  VEDLKGELE.
    attyl00p    ASTVVSGDRR  AVAGYVAVCQ  AEGVQARLIP  .VDYASHSRH  VEDLKGELE.
    atnid05b    GSCAVAGDPE  ALAELVALLT  GEGVHARPIP  GVDTAGHSPQ  VDALRAHL.L  Etmalonyl-CoA
    attyl05b    GTAAVAGDVD  ALRELLAELT  AEGIRAKPIP  GVDTAGHSAQ  VDGLKEHL.F  Etmalonyl-CoA
    atnid06x    ASVTVSGDAL  ALEEFGARLS  AEGVLRWPLP  GVDFAGHSPQ  VEEFRAEL.L  MeOmalonylCoA
    atdebs01p   RSVVAGDSD   ELDRLVASCT  TECIRAKRL.  AVDYASHSSH  VETIRDALHA
    atmon02p    SSTVISGPPE  HVAAVVADAE  ARGLRARVID  .VGYASHGPQ  IDQLHDLL.T
    atmon10p    SSTVISGPPE  HVAAVVADAE  ARGLRARVID  .VGYASHGPQ  IDQLHDLL.T
    atmon04p    SSTVISGPPE  HVAAVVAEAE  ARGLRARVID  .VGYASHGPQ  IDQLHDLL.T
    atmon07p    SSTVISGPPE  HVAAVVADAE  ERGLRARVID  .VGYASHGPQ  IDQLHDLL.T
    atmon11p    SSTVISGPPE  HVAAVVADAE  AQGLRARVID  .VRYASHGPQ  IDQLHDLL.T
    atmon12p    SSTVISGPPE  HVAAVVADAE  ARGLRARVID  .VGYASHGPQ  IDQLHDLL.T
    atmon05b    SSTVISGPPE  GIAAVVADAQ  ERGLRARAVA  .SDVAGHGPQ  LDAILDQL.T  Et/mal-CoA
    atmon01p    SSTVISGPPE  QVAAVVADAE  ARELRGRVID  .VDYASHSPQ  VDAITDEL.T
    atdebs02p   DAVVVAGDAQ  AAREFLEYCE  GVGIRARAIP  .VDYASHTAH  VEPVRDEL.V
    atdebs06p   SSVVVSGDPE  ALAELVARCE  DEGVRAKTLP  .VDYASHSRH  VEEIRETI.L
    atave01p    RSTAVSGDAE  AVDEVLAYCA  GTGVRARRIP  .VDYASHCPH  VQPLREEL.L
    atave07p    RSTAVSGDAE  AVDEVLAYCA  GTGVRARRIP  .VDYASHCPH  VQPLREEL.L
    atave06p    HSTTVSGDTK  AVDEVLAHCT  DTGLRAKRIP  .VDYASHCPH  VQPLHDEL.L
    atave09p    HSTTVSGDTT  AVEELLTHCA  DTGLRAKRIP  .VDYASHCPH  VQPLHDEL.L
    atnys01p    RSVVVAGEPE  ALDALHARLT  ADDIRARRIA  .VDYASHSHQ  VEDLHEEL.L
    atnys11p    RSVVVAGEPE  ALDALHARLT  ADDIRARRIA  .VDYASHSHQ  VEDLHEEL.L
    atrif05p    ASVVIAGDAE  ALTEAVEVLG  G.....RRVA  .VDYASHTRH  VEDIQDTL.A
    atrif07p    ASVVIAGDAQ  ALDEALEVLA  GDGVRVRQVA  .VDYASHTRH  VEDIRDTL.A
    atrif08p    SSVVIAGDAE  ALDQALEALT  GQDIRVRRVA  .VDYASHTRH  VEDIQEPL.A
    atrif10p    ASVVIAGDAQ  ALDETLEALS  GAGIRARRVA  .VDYASHTRH  VEDIEDTL.A
    atrif03p    SSVVIAGDAQ  ALDEALEALA  GDGVRVRRVA  .VDYASHTRH  VEAIAETL.A
    atrif06p    ASVVIAGEAQ  ALDEVVDALS  GQEVRVRRVA  .VDYGSHTNQ  VEAIEDLL.A
    atrif04p    TSVVIAGDAE  ALDEALDALD  DQGVRIRRVA  .VDYASHTRH  VEAARDAL.A
    atrif01p    SSVVIAGDAH  ALDATLEILS  GEGIRVRRVA  .VDYASHTRH  VEDIRDTL.A
    atnys02p    SSVVVSGDTD  ALDALHTACQ  EQGVRARKVS  .VDYASHGRH  VEAVRDEL.A
    atfkb02p    ASIVVAGAAD  AVEELLAATP  ....HARRIA  .VDYASHTAH  VESIRGAL.L
    atave11p    RSAVVSGEPE  AVDALVEELS  HEDVPARRLM  .VDWASHSPQ  VEAIQGRL.L
    atdebs03p   RSVVVSGEPG  ALRAFSEDCA  AEGIRVRDID  .VDYASHSPQ  IERVREEL.L
    atnid04p    ETTVVCGAPG  AVDSLLGVLQ  GEGVRVRRID  .VDYASHSRH  VEGIRDEL.A
    atdebs05p   RSVVAGESG   PLDELIAECE  AEGITARRIP  .VDYASHSPQ  VESLREEL.L
    atdebs04p   GTSVVAGPTA  ELDEFFAEAE  AREMKPRRIA  .VRYASHSPE  VARIEDRL.A
```

Fig 2m

```
atave02a  TSLVISGTPH  TVQHITTLCQ  QQGIKTKTL.  PTNHAFHSPH  TNPILNQLH.
atave05a  TSLVISGTPH  TVQHITTLCQ  QQGIKTKTL.  PTNHAFHSPH  TNPILNQLH.
atave04a  TSLVISGTPH  TVQHITTLCQ  QQGIKTKTL.  PTKNAFHSPH  TNPILNQLH.
atave08a  TSLVISGTPH  TVQHITTLCQ  QQGIKTKTL.  PTNHAFHSPH  TNPILNQLH.
atave03a  TSLVISGTPH  TVQHITTLCQ  QQGIKTKTL.  PTNHAFHSPH  TNPILNQLH.
atrap02a  SSVVLSGDEA  AVLQAAEGLG  ....KWTRL.  PTSHAFHSAR  MEPMLEEFR.
atrap11a  SSVVLSGDEA  AVLQAAEGLG  ....KWTRL.  ATSHAFHSAR  MEPMLEEFR.
atrap08a  SSVVLSGDEA  AVLQAAEGLG  ....KWTRL.  ATSHAFHSAR  MEPMLEEFR.
atrap12a  SSVVLSGDEA  AVLQAAEGLG  ....KWTRL.  ATSHAFHSAR  MEPMLEEFR.
atrap05a  SSVVLSGDET  AVLQAAAALG  ....KSTRL.  ATSHAFHSAR  MEPMLEEFR.
atrap09a  SSVVLSGDEA  AVLQAAEGLG  ....KWTRL.  ATSHAFHSAR  MEPMLEEFR.
atfkb03a  ASIVLSGDED  AVLDVAARLG  ....RFTRL.  RTSHAFHSAR  MEPMLDEFR.
atfkb07x  HSVVLSGDEG  PVLDVAQQLG  ....IHHRL.  PTRHAGHSAR  MDPLVAPLL.  MeOmalonyl-CoA
atfkb08x  HSVVLSGDED  AVLDVAQRLG  ....IHHRL.  PAPHAGHSAH  MEPVAAELL.  MeOmalonyl-CoA
atnid01a  THCVLSGPRT  ALEETAQQLH  QQGIRHTWL.  KVSHAFHSAL  MDPMLGAFR.
atnid03a  THCVLSGPRT  ALEETAQHLR  EQNVRHTWL.  KVSHAFHSAL  MDPMLGAFR.
atnid02a  THCVLSGPRT  ALEETAQHLR  EQNVRHTWL.  KVSHAFHSAL  MDPMLGAFR.
atnid00a  THCVLSGPRT  ALEETAQHLR  EQNVRHTWL.  KVSHAFHSAL  MDPMLGAFR.
atfkb10a  SAVVLTGAPD  DVAAFEREWA  AAGRRAKRL.  DVGHAFHSRH  VDGALDDFR.
atrap14a  EAVVVSGEPE  PVADFEAAWT  ASGREARKL.  KVRHAFHSRH  VEAVLDEFR.
atmon06a  DSTVISGPSD  EVDRIAGVWR  ERGRKTKAL.  SVSHAFHSAL  MEPMLAEFT.
atmon08a  DSTVISGPSG  EVDRIAGVWR  ERGRKTKAL.  SVSHAFHSAL  MEPMLAEFT.
atmon09a  DSTVISGPSG  EVDRIAGVWR  ERGRKTKAL.  SVSHAFHSAL  MEPMLGEFT.
atepo02a  EQVVIAGVEQ  AVQAIAAGFA  ARGARTKRL.  HVSHAFHSPL  MEPMLEEFG.
atepo03x  EQVVIAGVEQ  AVQAIAAGFA  ARGARTKRL.  HVSHASHSPL  MEPMLEEFG.  Mal/mmal
atepo08a  EQVVIAGAEK  FVQQIAAAFA  ARGARTKPL.  HVSHAFHSPL  MDPMLEAFR.
atepo00a  DQVVIAGAGQ  PVHAIAAAMA  ARGARTKAL.  HVSHAFHSPL  MAPMLEAFG.
atepo04a  DAVVIAGAEV  QVLALGATFA  ARGIRTKRL.  AVSHAFHSPL  MDPMLEDFQ.
atnid07a  DSLVLSGDEQ  AVVSAAGELA  ARGRRTKRL.  SVSHAFHSPH  MDAMLADFR.
attyl07a  RSVVISGAEE  AVAEAAAQLA  GRGRRTRRL.  RVAHAFHSPL  MDGMLAGFR.
atsor02a  LSTVVAGDED  AVVEIARQAE  ALGRKTTRL.  RVSHAFHSPH  MDGMLDDFR.
atsorb1a  LSTVVAGDED  AVLKIARQVE  ALGRKATRL.  RVSHAFHSPH  MDGMLDDFR.
atnys09a  SAVVLSGAEA  TVTALAEQLA  ADGRRTKRL.  RVSHAFHSPL  MEPMLEAFR.
atnys12a  RSVVVAGVEE  DVLLLADLFA  ADGRRTKRL.  RVSHAFHSPL  MDAMLDDFA.
atnys16a  VSVVVSGVEA  AVGQVVDQLV  ERGRRVRRL.  AVSHAFHSPL  MDPMLDAFR.
atnys17a  VSVVVSGVEA  AVGQVVDQLV  ERGRRVRRL.  AVSHAFHSPL  MDPMLDAFR.
atnys03a  TSVVVAGTEE  AVAAIGARFT  AQDRKTTRL.  RVSHAFHSPL  MDPMLAEFR.
atnys15a  TSLVVSGDET  ATLAVAARLA  EQGRRTTRL.  RVSHAFHSPL  MDPMLAEFR.
atnys07a  NALVVSGVED  AAVEIGARFA  AEGRRTTRL.  HVSHAFHSPL  MDPMLAEFR.
atnys08a  TSVVISGAEE  ATQTVAQHFA  DQGRRTTAL.  RVSHAFHSPL  MDPMLAEFR.
atnys05a  TSVVVSGAES  AARTVADRLA  ENGRKTTRL.  RVSHAFHSPL  MDPMLAEFR.
atnys06a  TSVVISGAEE  ATQTVAQHFA  DQGRRTTAL.  RVSHAFHSPL  M..MLAEFR.
atnys04a  TSVVVSGYEN  ATLAVARHFA  DQGRRTTRL.  RVSHAFHSPL  MAPMLDDFR.
atnys14a  TAVVLSGAGD  AVTALGQALA  ERGHRTTRL.  RVSHAFHSHL  MDPMLADFR.
atnys00a  TAVVVAGAED  AVRQLTARFA  DRGRRTSRL.  AVSHAFHSPL  MEPMLDAFR.
atnys10a  QSVVISGDEE  AAETIAATFA  ERGRKTKRL.  RVSHAFHSPR  MDGMLDAFR.
atnys18a  RSVVVAGAED  AALAVRRHFD  DLGRRTTRL.  PVSHAFHSPL  MDPMLDAFR.
atnys13a  RSVVVAGAED  AVRAVADRLA  ADGRRTRRL.  TVSHAFHSPL  MDPMLTDFA.
atave10a  RSIVLSGDED  AVLDLAQQWA  ARGRRTRRL.  RTSHAFHSPH  MDAMLGDFR.
atrif02a  DSVVLSGTEA  AVLAVADELA  GRGRKTRRL.  AVSHAFHSPL  MEPMLDDFR.
atmon03a  TAVVVSGEAA  AVGEVEKALR  GRGLKTKRL.  NVSHAFHSPL  IEPMLDDFR.
atave12a  ASVVFSGAED  EVGNMADWFA  ERGRRVKRL.  RTGHAFHSPL  MDPMLEEFQ.
atrif09a  SAVVLSGDAD  AVVAAAARMR  ERGHKTKQL.  KVSHAFHSAR  MAPMLAEFA.
atmon00a  DSVVVSGDRA  TVDELTAAWR  GRGRKAHHL.  KVSHAFHSPH  MDPILDELR.
attyl03a  SSVVVSGDEA  AVLELLEQWR  AEGREARRL.  AVSHAFHSPR  MDGMLTQFD.
                                               ****  HAFH/YASH/TAGH motif
```

Fig 2n

```
              351                                                          400
atave00x   SGLLPITPRP SRIPFHSSVT G.....GRL. .DTRELDAAY WYRNMSSTVR
atdebs00p  SALAWFAPGG SEVPFYASLT G.....GAV. .DTRELVADY WRRSFRLPVR
atepo06p   AALGAIRPRA AAVPMRSTVT G.....GVI. .AGPELGASY WADNLRQPVR
atepo07p   AALGAIRPRA AAVPMRSTVT G.....GVI. .AGPELGASY WADNLRQPVR
atepo01p   AALGGLRPGA AAVPMRSTVT G.....AMV. .AGPELGANY WMNNLRQPVR
atepo05p   AALGELEPRQ ATVSMRSTVT S.....TIM. .AGPELVASY WADNVRQPVR
atsoralx   DALREVRPNK AQIPIVSEVT G.....TAL. .DGERFDASH WVRNFGDPAL
atfkb01p   DALEGITSST PSVPWWSTVD S.....GWV. ...TEPFGDAY WYRNLRQPVA
atfkb09p   DVLGDITSSA PSVPWWSTVD G.....GWV. ...TEPAGDDY WYRNLRQPVA
atrap03p   DITSDSSSQA PLVPWLSTVD S.....SWV. ...DSPLDGEY WYRNLREPVG
atrap06p   DITSDSSSQA PVVPWLSTVD G.....SWV. ...DSPLDVEY WYRNLREPVG
atrap04p   GITAGIGSQP PVVPWLSTVD G.....SWV. ...DSPLDGEY WYRNLREPVG
atrap13p   DITSDSSSQT PLVPWLSTVD G.....TWV. ...DSPLDGEY WYRNLREPVG
atrap01p   GVIAGVDSRA PVVPWLSTVD G.....TWV. ...EGPLDAEY WYRNLREPVG
atrap07p   DITAGIGSQA PVVPWLSTVD G.....TWV. ...EGPLDVEY WYRNLREPVG
atrap10p   DITSDSSSQD PLVPWLSTVD G.....TWV. ...DSPLDGEY WYRNLREPVG
atfkb04x   RIVAATTSRA PEIPWFSTAD E.....RWI. ...DAPLDDEY WFRNMRNPVG
attyl04p   RVLSGIRPRS PRVPVCSTVA G.....E..Q PGEPVFDAGY WFRNLRNRVE
attyl06p   RVLSGIRPRS PRVPVCSTVA G.....E..Q PGEPVFDAGY WFRNLRNRVE
attyl01p   RVLSGIRPRS PRVPVCSTVA G.....E..Q PGEPVFDAGY WFRNLRNRVE
attyl02p   RVLSGIRPRS PRVPVCSTVA G.....E..Q PGEPVFDAGY WFRNLRNRVE
attyl00p   RVLSGIRPRS PRVPVCSTVA G.....E..Q PGEPVFDAGY WFRNLRNRVE
atnid05b   EVLAPVAPRP ADIPFYSTVT G.....GLL. .DGTELDATY WYRNMREPVE
attyl05b   EVLAPVSPRS SDIPFYSTVT G.....APL. .DTERLDAGY WYRNMREPVE
atnid06x   DLLSGVRPAP SRIPFFSTVT A.....GPC. .GGDQLDGAY WYRNTREPVE
atdebs01p  ELGEDFHPLP GFVPFFSTVT G.....RWT. .QPDELDAGY WYRNLRRTVR
atmon02p   ERLADIRPTN TDVAFYSTVT A.....ERL. TDTTALDTDY WVTNLRQPVR
atmon10p   ERLADIRPAN TDVAFYSTVT A.....ERL. TDTTALDTDY WVTNLRQPVR
atmon04p   EGLADIRPAN TDVAFYSTVT A.....ERL. TDTTALDTDY WVTNLRQPVR
atmon07p   DRLADIRPAT TDVAFYSTVT A.....ERL. TDTTALDTDY WVTNLRQPVR
atmon11p   DRLADIQPTT TDVAFYSTVT A.....ERL. DDTTALDTAY WVTNLRQPVR
atmon12p   ERLADIRPTT TDVAFYSTVT A.....ERL. DDTTTLDTAY WVTNLRQPVR
atmon05b   EGLAGIRPAA TDVAFYSTVT A.....GHL. TDTTELDTAY WVRNVRRTVR
atmon01p   HTLSGVRPTT APVAFYSAVT G.....TRI. .DTAGLDTDY WVTNLRRPVR
atdebs02p  QALAGITPRR AEVPFFSTLT G.....D..F LDGTELDAGY WYRNLRHPVE
atdebs06p  ADLDGISARR AAIPLYSTLH G.....E..R RD...MGPRY WYDNLRSQVR
atave01p   ELLGDISPQP SGVPFFSTVE G.......TW LDTTTLDAAY WYRNLHQPVR
atave07p   ELLGDISPQP SGVPFFSTVE G.......TW LDTTTLDAAY WYRNLHQPVR
atave06p   HLLGDITPQP STVPFFSTVE G.......TW LDTTTLDAAY WYRNLHQPVR
atave09p   HLLGDITPQP STMPFFSTVV G.....HLVW Y.TTTLDAAY WYRNLHQPVR
atnys01p   EVLAELAPRT SEVPFFSTVT G.....DWL. .DTARMDAGY WFRNLRGRVR
atnys11p   EVLAELAPRT SEVPFFSTVT G.....DWL. .DTARMDAGY WFRNLRGRVR
atrif05p   ETLAGIDAQA PVVPFYSTVA G.....EWI. TDAGVVDGGY WYRNLRNQVG
atrif07p   ETLAGITAQA PDVPFRSTVT G.....GWV. RDADVLDGGY WYRNLRNQVR
atrif08p   EALAGIEAHA PTLPFFSTLT G.....DWI. REAGVVDGGY WYRNLRNQVG
atrif10p   EALAGIDARA PLVPFLSTLT G.....EWI. RDEGVVDGGY WYRNLRGRVR
atrif03p   KTLAGIDARV PAIPFYSTVL G.....TWI. EQA.VVDAGY WYRNLRQQVR
atrif06p   ETLAGIEAQA PKVPFYSTLI G.....DWI. RDAGIVDGGY WYRNLRNQVG
atrif04p   EMLGGIRAQA PEVPFYSTVT G.....GWV. EDAGVLDGGY WYRNLRRQVR
atrif01p   ETLAGISAQA PAVPFYSTVT S.....EWV. RDAGVLDGGY WYRNLRNQVR
atnys02p   RVLAPVDPRA PEVPFYSTVT G.....DRV. DDAA.FDGAY WYTNLRQTVR
atfkb02p   DALADLTPGA PEIPFFSTVD E.....AWL. DRPA...DAAY WYDNVRCPVR
atave11p   ELLAPIRART GDVPFYSTVT G.....ERI. .DGTELDADY WYRNLRQVVR
atdebs03p  ETTGDIAPRP ARVTFHSTVE S.....RSM. .DGTELDARY WYRNLRETVR
atnid04p   AVLAGLRPRA GRVPFYSTVE A.....EPL. .DGTALDAGY WYRNLRQRVR
atdebs05p  TELAGISPVS ADVALYSTTT G.....QPI. .DTATMDTAY WYANLREQVR
atdebs04p  AELGTITAVR GSVPLHSTVT G.....EVI. .DTSAMDASY WYRNLRRPVL
```

Fig 2o

```
atave02a   QHTQTLTYHP  PHTPLITANT  ..........  PPDQLLTPHY  WTQQARNTVD
atave05a   QHTQTLTYHP  PHTPLITANT  ..........  PPDQLLTPHY  WTQQARNTVD
atave04a   QHTQTLTYHP  PHTPLITANT  ..........  PPDQLLTPHY  WTQQARNTVD
atave08a   QHTQTLTYHP  PHTPLITANT  ..........  PPDQLLTPHY  WTQQARNTVD
atave03a   QHTQTLTYHP  PHTPLITANT  ..........  PPDQLLTPHY  WTQQARNTVD
atrap02a   AVAEGLTYRT  PQVA......  ........MA  AGDQVMTAEY  WVRQVRDTVR
atrap11a   AVAEGLTYRT  PQVS......  ........MA  VGDQVTTAEY  WVRQVRDTVR
atrap08a   AVAEGLTYRT  PQVS......  ........MA  AGDQLTTTEY  WVRQVRDTVR
atrap12a   AVAEGLTYRT  PQVS......  ........MA  VGDQVTTAEY  WVRQVRDTVR
atrap05a   TVAERLTYQT  PRLA......  ........MA  AGDRVTTAEY  WVRQVRDTVR
atrap09a   AVAQGLTYHA  PGVV......  ........MA  AGDRVMTAEY  WVRQVRDTVR
atfkb03a   DVAERLTYHE  PKLP......  ........MA  AGADCATPEY  WVRQVRDTVR
atfkb07x   EAASGLTYHQ  PHT.......  .........A  IPEDPTTAAY  WARQVRDQVR
atfkb08x   ATTRELRYDR  PHT.......  .........A  IPNDPTTAEY  WAEQVRNPVL
atnid01a   DTLNTLNYQP  PTIPLISNLT  GQIADPNHL.  .....CTPDY  WIDHARHTVR
atnid03a   DTLNTLNYQP  PTIPLISNLT  GQIADPNHL.  .....CTPDY  WIDHARHTVR
atnid02a   DTLNTLNYQP  PTIPLISNLT  GQIADPNHL.  .....CTPDY  WIDHARHTVR
atnid00a   DTLNTLNYQP  PTIPLISNLT  GQIADPNHL.  .....CTPDY  WIDHARHTVR
atfkb10a   GVLESLAFGA  ARLPVVSTTT  GRDAAGD.LA  ......TPEH  WLRHARRPVL
atrap14a   TALESLKFRA  PALPVVSTVT  GRLIDQDEMG  ......TPEY  WLRQVRRPVR
atmon06a   EAIRGVKFRQ  PSIPLMSNVS  GERA......  .GEEITDPEY  WARHVRNAVL
atmon08a   EAIREVKFTR  PKVSLISNVS  GLEA......  .GEEIASPEY  WARHVRQTVL
atmon09a   EAIRGVKFRQ  PSIPLMSNVS  GERA......  .GEEITSPEY  WARHVRQTVL
atepo02a   RVAASVTYRR  PSVSLVSNLS  GKVVT.DEL.  .....SAPGY  WVRHVREAVR
atepo03x   RVAASVTYRR  PSVSLVSNLS  GKVVA.DEL.  .....SAPGY  WVRHVREAVR
atepo08a   RVTESVTYRR  PSIALVSNLS  GKPCT.DEV.  .....SAPGY  WVRHAREAVR
atepo00a   RVAESVSYRR  PSIVLVSNLS  GKACT.DEV.  .....SSPGY  WVRHAREVVR
atepo04a   RVAATIAYRA  PDRPVVSNVT  GHVAG.PEI.  .....ATPEY  WVRHVRSAVR
atnid07a   AVAESVTYRT  PRLPIVSEVT  GRPAPSEL..  .....MDPGY  WTRQIREPVR
attyl07a   EVAAGLRYRE  PELTVVSTVT  GRPARPGEL.  .....TGPDY  WVAQVREPVR
atsor02a   RVAQSLTYHP  ARIPIISNVT  GARATDHEL.  .....ASPDY  WVRHVRHTVR
atsorb1a   RVAQGLTFHP  ARIPIISNVT  GARATDQEL.  .....ASPET  WVRHVRDTVR
atnys09a   AVVEDLTLQP  PLLPVVSNLT  GKPATVQL..  .....TSADY  WVDHVRHAVR
atnys12a   AVARGLTYHP  PTIPFVSNVS  GGLATAEQV.  .....RTPDY  WVGHVRAAVR
atnys16a   AVAEGLEYHQ  PRIPVVSNVT  GEVAAAEEL.  .....CAADY  WVRHVRATVR
atnys17a   AVAEGLEYHQ  PRIPVVSNVT  GEVAAAEEL.  .....CAADY  WVRHVRATVR
atnys03a   AVAAGLTYHE  PRIPVLSNLT  GTVAAVADL.  .....CSADY  WVRHVREAVR
atnys15a   AVAEGLSYGE  PQIPVVSNLT  GAVADGTLL.  .....GTADY  WVRHVREAVR
atnys07a   VVAEGLSYAA  PSLPVVSNLT  GQVATADEL.  .....CSAEY  WVRHVREAVR
atnys08a   AVAEGLSYAT  PSLPVVSNLT  GWLATADEL.  .....CSAEY  WVRHVREAVR
atnys05a   AVAEGLSYAT  PTLPVVSNLT  GRLATADDL.  .....CSAEY  WARHVREAVR
atnys06a   AVAEGLSYAT  PTLPVVSNLT  GQVATADEL.  .....CSAEY  WVRHVREAVR
atnys04a   AVVESLTFTA  PTTPVVSNLT  GELAPAEAL.  .....CSADY  WVRHVREAVR
atnys14a   TVAEGLEYHP  PRIPVVSNLT  GDVADAADL.  .....CSADY  WVRHVRGTVR
atnys00a   DVVSRLTFHQ  PSIPLVSNLT  GELA.GSEI.  .....TSAEY  WVRHVRDTVR
atnys10a   IVAEGLTYRA  PRIPLVSDLT  GRRADDAEV.  .....CTAEY  WVRHVREAVR
atnys18a   TALAPLTFAE  PEIPVVSNLT  GLPATAEEL.  .....ATPHY  WVCHVRQAVR
atnys13a   RVAEGLTYHE  PRIPLVSTLL  GAPAGA.EL.  .....RTPDY  WVRHVRETVR
atave10a   RAAEQVTFSA  PRIPVVSNVT  GAPLPAETM.  .....CTPDY  WVEHARSTVR
atrif02a   AVAERLTYRA  GSLPVVSTLT  GELAA...L.  .....DSPDY  WVGQVRNAVR
atmon03a   EVARGLTFHA  PTLPVVSNLT  GRLADAELM.  .....ADAEY  WVRHVRRPVR
atave12a   QVAASLTYSE  PAIPMVSTLT  GDIVAAGEL.  .....SDPEY  WVRQVRRTVR
atrif09a   AELAGVTWRE  PEIPVVSNVT  GRFAEPGEL.  .....TEPGY  WAEHVRRPVR
atmon00a   AVAAGLTFHE  PVIPVVSNVT  GELVTATATG  SGAGQADPEY  WARHAREPVR
attyl03a   RVARTLTFAP  PTIPLVSTLT  GTPVTEETL.  .....CTADH  WVRQAREPVR
```

Fig 2p

```
              401                                                 450
atave00x    FEPAARLLLQ QGP.KTFVEM SPHPVLTMGL QELAPDLG..  ......DTTG
atdebs00p   FDEAIRSALE VGP.GTFVEA SPHPVLAAAL QQTL......  ......DAEG
atepo06p    FAAAAQALLE GGP.ALFIEM SPHPILVPPL DEIQTA....  ........AE
atepo07p    FAAAAQALLE GGP.ALFIEM SPHPILVPPL DEIQTA....  ........AE
atepo01p    FAEVVQAQLQ GGH.GLFVEM SPHPILTTSV EEMRRA....  ........AQ
atepo05p    FAEAVQSLME DGH.GLFVEM SPHPILTTSV EEIRRA....  ........TK
atsora1x    FSTAIDHLLQ EGP.DIFLEL TPHPLALPAI ESNLRR....  ........SG
atfkb01p    MDTAVSELDG ....SLFIEC SAHPVLLPAL DQ........  ..........
atfkb09p    MDTAIGELDG ....SLFIEC SAHPVLLPAL DQ........  ..........
atrap03p    FHPAVGQLQA QGD.TVFVEV SASPVLLQAM DD........  ..........
atrap06p    FHPAVGQLQA EGD.TVFVEV SASPVLLQAM DD........  ..........
atrap04p    FHPAVSQLQA QGD.AVFVEV SASPVLLQAM DD........  ..........
atrap13p    FHPAVSQLQA QGD.TVFVEV SASPVLLQAM DD........  ..........
atrap01p    FEPAAGQLQA QGD.TVFVEV SASPVLLQAM DD........  ..........
atrap07p    FDSAVGQLRA EGD.TVFVEV SASPVLLQAM DD........  ..........
atrap10p    FHPAVSQLQA QGD.TVFVEV SASPVLMQAM DD........  ..........
atfkb04x    FAAAVAAARE PGD.TVFIEV SAHPVLLPAI NG........  ..........
attyl04p    FSAVVGGLLE EGH.RRFIEV SAHPVLVHAI EQT....A..  ......EAAD
attyl06p    FSAVVGGLLE EGH.RRFIEV SAHPVLVHAI EQT....A..  ......EAAD
attyl01p    FSAVVGGLLE EGH.RRFIEV SAHPVLVHAI EQT....A..  ......EAAD
attyl02p    FSAVVGGLLE QGH.RRFIEV SAHPVLVHAI EQT....A..  ......EAAD
attyl00p    FSAVVGGLLE EGH.RRFIEV SAHPVLVHAI EQT....A..  ......EAAD
atnid05b    FERATRALIA DGH.DVFLET SPHPMLAVAL EQT....V..  ......TDAG
attyl05b    FEKAVRALIA DGY.DLFLEC NPHPMLAMSL DET....L..  ......TDSG
atnid06x    FDATVRALLR AGH.HTFIEV GPHPLLNAAI DEI....A..  ......ADEG
atdebs01p   FADAVRALAE QGY.RTFLEV SAHPILTAAI EEI....G..  ......DGSG
atmon02p    FADTIEALLA DGY.RLFIEA SAHPVLGLGM EETIEQ....  .........AD
atmon10p    FADTIEALLA DGY.RLFIEA SAHPVLGLGM EETIEQ....  .........AD
atmon04p    FADTIEALLA DGY.RLFIEA SAHPVLGLGM EETIEQ....  .........AD
atmon07p    FADTIDALLA DGY.RLFIEA SAHPVLGLGM EETIEQ....  .........AD
atmon11p    FADTIEALLA DGY.RLFIEA SPHPVLNLGI QETIEQQA..  ........GAA
atmon12p    FADTIEALLA DGY.RLFIEA SPHPVLNLGM EETIER....  .........AD
atmon05b    FADTIDALLA DGY.RLFIEV SPHPVLNLAL EGLIER....  .........AA
atmon01p    FADAVTALLA DGH.RVFIEA SSHPVLTLGL QETFEE....  .........AG
atdebs02p   FHSAVQALTD QGY.ATFIEV SPHPVLASSV QETL......  ......DDAE
atdebs06p   FDEAVSAQSP DGH.ATFVEM SPHPVLTAAV QE........  .........IA
ataveO1p    FSDAVQALAD DGH.RVFVEV SPHPTLVPAI EDTTEDTA..  .......ED..
ataveO7p    FSDAVQALAD DGH.RVFVEV SPHPTLVPAI EDTTEDTA..  .......ED..
ataveO6p    FSHAIQTLTD DGH.RAFIEI SPHPTLVPAI EDTTENTT..  .......EN..
ataveO9p    FSHAIQTLTD DGH.RPFIEI SPHPTLVPAI EDTTENTT..  .......EN..
atnys01p    FADAVADLLA AEY.RAFVEV SSHPVLTMAV LD....LI..  ......EEAG
atnys11p    FADAVADLLA AEY.RAFVEV SSHPVLSMAV QE....AI..  ......DEAG
atrif05p    FGPAVAELIE QGH.GVFVEV SAHPVLVQPI SE....LT..  ......D...
atrif07p    FGPAVAELLE QGH.GVFVEV SAHPVLVQPI SE....LT..  ......D...
atrif08p    FGPAVAELLG LGH.RVFVEV SAHPVLVQAI SA....IA..  ......DD..
atrif10p    FGPAVEALLA QGH.GVFVEL SAHPVLVQPI TE....LT..  ......DE..
atrif03p    FGPSVADLAG LGH.TVFVEI SAHPVLVQPL SE....IS..  ......DD..
atrif06p    FGPAVAELVR QGH.GVFVEV SAHPVLVQPL SE....LS..  ......DD..
atrif04p    FGPAVAELIE QGH.RVFVEV SAHPVLVQPI NE....LV..  ......DD..
atrif01p    FGAAATALLE QGH.TVFVEV SAHPVTVQPL SE....LT..  ......GD..
atnys02p    MEEATRALLA AGH.RVFIEV SPHPVLAAPI QETQEAVA..  ......EATG
atfkb02p    FGAAAARLAE LGH.RVFVEA SPHPVLTTAL ADTLAG....  ..........H
atave11p    FRDATQALVR AGH.TVFIEA CPHPAVAVGV QETLDE.M..  ........GD
atdebs03p   FADAVTRLAE SGY.DAFIEV SPHPVVVQAV EEAVEE.A..  ......DGAE
atnid04p    FESALRAMLA DGV.DAFVEC SPHPVLTVPV RQTLED.A..  ........GA.
atdebs05p   FQDATRQLAE AGF.DAFVEV SPHPVLTVGI EATLDS.A..  ......LPAD
atdebs04p   FEQAVRGLVE QGF.DTFVEV SPHPVLLMAV EET....A..  ......EHAG
```

Fig 2q

```
atave02a   YATTTQTLHQ  HG.VTTYIEL   GPDNTLTTLT   HHNLPNPPTT   TLTLTHPHHH
atave05a   YATTTQTLHQ  HG.VTTYIEL   GPDNTLTTLT   HHNLPNTPTT   TLTLTHPHHH
atave04a   YATTTQTLHQ  HG.VTTYIEL   GPDNTLTTLT   HHNLPNTPTT   TLTLTHPHHH
atave08a   IATTTQTLHQ  HG.VTTYIEL   GPDNTLTTLT   HHNLPNTPTT   TLTLTHPHHH
atave03a   YATTTQTLHQ  HG.VTTYIEL   GPDNTLTTLT   HDNLPNTPTT   TLTLTHPHHH
atrap02a   FGEQVASFED  A....VFVEL   GADRSLARLV   DG........   ..........
atrap11a   FGEQVASYED  A....VFVEL   GADRSLARLV   DG........   ..........
atrap08a   FGEQVASYED  A....VFVEL   GADRSLARLV   DG........   ..........
atrap12a   FGEQVASYED  A....VFVEL   GADRSLARLV   DG........   ..........
atrap05a   FGEQVASYED  A....VFIEL   GADRSLARLV   DG........   ..........
atrap09a   FGEQVASYED  A....VFVEL   GADRSLARLV   DG........   ..........
atfkb03a   FAEQVAAYDG  A....ALLEI   GPDRNLARLV   DG........   ..........
atfkb07x   FQAHAERYPG  A....TFLEI   GPNQDLSPVV   DG........   ..........
atfkb08x   FHAHTQRYPD  A....VFVEI   GPGQDLSPLV   DG........   ..........
atnid01a   FADAVQTAHD  QR.TTTYLEI   GAHPTLTTLL   HHTLDNP...   ..........
atnid03a   FADAVQTAHH  QG.TTTYLEI   GPHPTLTTLL   HHTLDNP...   ..........
atnid02a   FADAVQTAHD  QR.TTTYLEI   GPHPTLTTLL   HHTLDNP...   ..........
atnid00a   FADAVQTAHH  QG.TTTYLEI   GPHPTLTTLL   HHTLDNP...   ..........
atfkb10a   YADAVRELAD  LG.VNMFVAV   GPSGALASAA   SENTGGSAGT   YH........
atrap14a   FQDAVRELAE  QG.VGTFVEV   GPSGALASAG   VECLGGDA.S   FH........
atmon06a   FQPAIAQVAD  S..AGVFVEL   GPAPVLTTAA   QHTLDE.SD.   .SQES.....
atmon08a   FQPGIAQVAS  T..AGVFVEL   GPGPVLTTAA   QHTLDDVTDR   HGPEP.....
atmon09a   FQPGVAQVAA  E..ARAFVEL   GPGPVLTAAA   QHTLDHITEP   EGPEP.....
atepo02a   FADGVKALHE  AG.AGTFVEV   GPKPTLLGLL   PACLPEAEP.   ..........
atepo03x   FADGVKALHE  AG.AGTFVEV   GPKPTLLGLL   PACLPEAEP.   ..........
atepo08a   FADGVKALHA  AG.AGLFVEV   GPKPTLLGLV   PACLPDARP.   ..........
atepo00a   FADGVKALHA  AG.AGTFVEV   GPKSTLLGLV   PACMPDARP.   ..........
atepo04a   FGDGAKALHA  AG.AATFVEV   GPKPVLLGLL   PACLGEADA.   ..........
atnid07a   FAAAVRAARA  AG.AATFVEL   GPDAVLSGMA   RECAAG....   ......DTGT
attyl07a   FADAVRTAHR  LG.ARTFLET   GPDGVLCGMA   EECLED....   ......DTVA
atsor02a   FLDGVRALHA  EG.ARVFLEL   GPHAVLSALA   QDALGQ....   ....D.EGTS
atsorb1a   FLDGVRTLHA  EG.ARAFLEL   GPHPVLSALA   QDALGH....   ....D.EGPS
atnys09a   FADGIDWLA.  RHDTTAFLEL   GPDGVLSAMA   QDCLDA....   ....A.DAD.
atnys12a   FADGIDWLAT  QGDVHTFLEL   GPDGVLSAMA   RESLTD....   ....P.SRT.
atnys16a   FADGVRTLAE  RG.ATAFLEI   GPDGVLSALA   RGVL......   ....P.AEA.
atnys17a   FADGVRTLAE  RG.ATAFLEI   GPDGVLSALA   AACL.F....   ....D.TDA.
atnys03a   FADGVTALTD  RG.VTTLVEL   GPDGVLSAMA   QESL......   ....P.DGA.
atnys15a   FADGIRALTD  AG.VGAFLEL   GPDGTLAALA   QQSA......   ....P.D.A.
atnys07a   FADGVTALEA  EG.VRTFLEL   GPDGVLAAMA   GASL......   ....T.ESS.
atnys08a   FADGITTLEA  EG.VRTFLEL   GPDGILSALA   QQSL......   ....A.GEA.
atnys05a   FADGVSTLEN  EG.VTTFLEL   GPDGVLSAMA   QQSL......   ....T.GDA.
atnys06a   FADGVTALEA  EG.VRTFLEL   GPDGVLAAMA   RETV......   ....A.DDT.
atnys04a   FADGIRTLAD  RG.VTTFVEL   GPDSVLSAMA   QESA......   ....P.EGA.
atnys14a   FADGVRTMAD  RG.VHLFLEL   GPDAVLSAMA   RQCA......   ....P.D.A.
atnys00a   FADGITALAK  AG.ADVLIEL   GPGGVLSAMA   RDTL.G....   ....P.DST.
atnys10a   FADCVRTLRD  AG.ATTFLEL   GSDGLLTAMA   EDTL.G....   ....D.DHD.
atnys18a   FGDGVRALAD  RG.VRTFLEL   GPDGVLSALV   RENL......   ....P.EPG.
atnys13a   FADGVRALHD  AG.AGTFVEI   GPDGVLTALT   QQTLDT....   ....V.EAGA
atave10a   FADGISWLQE  QG.VTTCLEI   GPDGTLSALA   QDSLSA....   ....P.....
atrif02a   FSDAVTALGA  QG.ASTFLEL   GPGGALAAMA   LGTLGG....   ....P.EQSC
atmon03a   FHDGLRALSE  QGVVR.YLEL   GPDPVLATMV   QDGLPA....   ....P.AEGE
atave12a   FGDAISRLHT  DG.VRTFMEL   GPDGTLSALA   EECLEATADS   HPADD.DTGT
atrif09a   FAEGVAAATE  SGG.SLFVEL   GPGAALTALV   EET.......   ..........
atmon00a   FLSGVRGLCE  RG.VTTFVEL   GPDAPLSAMA   RDCFPAPADR   SRPRP.....
attyl03a   FLDAMRTLRA  DG.IDTFVEL   GPDGVLSAMA   RDCADDRPDG   DTTGAGDGET
```

Fig 2r

```
                451                                                        500
ataveOOx    TADTVIMGTL  RRGQGTLDHF  LTSLAQLRGH  GE..TSATTV  LSARLTALSP
atdebs00p   SSAAVV.PTL  QRGQGGMRRF  LLAAAQAFTG  GV..AVDWTA  AYDDVGA.EP
atepo06p    QGGAAV.GSL  RRGQDERATL  LEALGTLWAS  G..YPVSWAR  LFPAGG....
atepo07p    QGGAAV.GSL  RRGQDERATL  LEALGTLWAS  G..YPVSWAR  LFPAGG....
atepo01p    RAGAAV.GSL  RRGQDERPAM  LEALGTLWAQ  G..YPVPWGR  LFPAGG....
atepo05p    REGVAV.GSL  RRGQDERLSM  LEALGALWVH  G..QAVGWER  LFSAGGAGL.
atsora1x    RRGVVL.PSL  RRNEDERGVM  LDTLGVLYVR  G..APVRWDN  VYPA...AF.
atfkb01p    .E.RTV.ASL  RTDDGGWDRF  LAALAQAWTQ  GA..DVDWTT  LIEPA.....
atfkb09p    .E.RTV.ASL  RTDDGGWDRF  LTALAQAWTQ  GA..DVDWTT  LIAPA.....
atrap03p    .DVVTV.ATL  RRDDGDATRM  LTALAQAYVH  GV..TVDWPA  ILG.T.....
atrap06p    .DVVTV.ATL  RRDDGDATRM  LTALAQAYVH  GV..TVDWPA  ILG.T.....
atrap04p    .DVVTV.ATL  RRDDGDATRM  LTALAQAYVH  GV..TVDWPA  ILG.T.....
atrap13p    .DVVTV.ATL  RRDDGDATRM  LTALAQAYVH  GV..TVDWPA  ILG.T.....
atrap01p    .DVVTV.ATL  RRDDGDATRM  LTALAQAYVE  GV..TVDWPA  VLG.T.....
atrap07p    .DVVTV.ATL  RRDDGDATRM  LTALAQAFVE  GV..TVDWPA  ILG.T.....
atrap10p    .DVVTV.ATL  RRDDGDATRM  LTALAQAYVH  GV..TVDWRA  VLGDV.....
atfkb04x    ...TTV.GTL  RR.GGGADRV  LDSLAKAHTV  GV..AVDWST  VVAATGAADD
atty104p    RSVHAT.GTL  RRQDDSPHRL  LTSTAEAWAH  G..ATLTW..  ..........
atty106p    RSVHAT.GTL  RRQDDSPHRL  LTSTAEAWAH  G..ATLTW..  ..........
atty101p    RSVHAT.GTL  RRQDDSPHRL  LTSTAEAWAH  G..ATLTW..  ..........
atty102p    RSVHAT.GTL  RRQDDSPHRL  LTSTAEAWAH  G..ATLTW..  ..........
atty100p    RSVHAT.GTL  RRQDDSPHRL  LTSTAEAWAH  G..ATLTW..  ..........
atnid05b    TDAAVL.GTL  RRRHGGPRAL  ALAVCRAFAH  GVE..VDPEA  VF........
atty105b    GHGTVM.HTL  RRQKGSAKDF  GMALCLAYVN  GLE..IDGEA  LF........
atnid06x    VAATAL.HTL  QRGAGGLDRV  RNAVGAAFAH  GVR..VDWNA  LF........
atdebs01p   ADLSAI.HSL  RRGDGSLADF  GEALSRAFAA  GVA..VDWES  VH........
atmon02p    MPATVV.PTL  RRDHGDTTQL  TRAAAHAFTA  G..ADVDWRR  WF........
atmon10p    IPATVV.PTL  RRDHGDTTQL  TRAAAHAFTA  G..APVDWRR  WF........
atmon04p    IPATVV.PTL  RRDHGDTTQL  TRAAAHAFTA  G..ADVDWRR  WF........
atmon07p    IPATVV.PTL  RRDHGDTTQL  TRAAAHAFTA  G..ATVDWRR  WF........
atmon11p    GTAVTI.PTL  RRDHGDTTQL  TRAAAHAFTA  G..APVDWRR  WF........
atmon12p    MPATVV.PTL  RRDHGDAAQL  TRAAAQAFGA  G..AEVDWTG  WF........
atmon05b    VPATVV.PTL  RRDHGDTTQL  ARAAAHAFAA  G..ADVDWRR  WF........
atmon01p    VDAVTV.PTL  RREDGGRARL  ARSLAQAFGA  G..CAVRWEN  WF........
atdebs02p   SDAAVL.GTL  ERDAGDADRF  LTALADAHTR  GVA..VDWEA  VL........
atdebs06p   ADAVAI.GSL  HRDTAE.EHL  IAELARAHVH  GVA..VDWRN  VF........
atave01p    ..VTAI.GSL  RRGDNDTRRF  LTALAHTHTT  GIGTPTTWHH  HY........
atave07p    ..VTAI.GSL  RRGDNDTRRF  LTALAHTHTT  GIGTPTTWHH  HY........
atave06p    ..ITAT.GSL  RRGDNDTHRF  LTALAHTHTT  GIGTPTTWHH  HY........
atave09p    ..ITAT.GSL  RRGDNDTHRF  LTALAHTHTT  GIRTPTTWHH  HY........
atnys01p    VTAVAT.GTL  RRDQGGAGRF  LLSAAEVFVR  GV..DVDWAG  AF........
atnys11p    VPAVAA.GTL  RRDQGGTDRF  LLSAAEVFVR  GV..DVDWAG  LF........
atrif05p    ..AVVT.GTL  RRDDGGVRRL  LTSMAELFVR  GV..PVDWAT  MA........
atrif07p    ..AVVT.GTL  RRDDGGLRRL  LTSMAELFVR  GV..RVDWAT  LV........
atrif08p    TDAVVT.GSL  RREEGGLRRL  LTSMAELFVR  GV..DVDWAT  MV........
atrif10p    TAAVVT.GSL  RRDDGGLRRL  LTSMAELFVR  GV..EVDWTS  LV........
atrif03p    ..AVVT.GSL  RRDDGGLRRL  LASAAELYVR  GV..AVDWTA  AV........
atrif06p    ..AVVT.GSL  RREDGGLRRL  LTSMAELYVQ  GV..PLDWTA  VL........
atrif04p    TEAVVT.GTL  RREDGGLRRL  LASAAELFVR  GV..TVDWSG  VL........
atrif01p    ....AI.GTL  RREDGGLRRL  LASMGELFVR  GI..DVDWTA  MV........
atnys02p    GSAVVL.GSL  RRDEGGPRRF  LTSLAEAHTH  GA..PVDWTT  TF........
atfkb02p    PNTAVT.GTL  RRGDGGARRF  TRSLAELWVR  GV..PVSW..  ..........
atave11p    LDSLVV.GSL  RRGEGGLRRF  LMSVAELFVG  GV..AVEWSG  VF........
atdebs03p   .DAVVV.GSL  HRDGGDLSAF  LRSMATAHVS  GV..DIRWDV  AL........
atnid04p    .GAVAV.GSL  RRDDGGLRRF  LTSAAEAQVA  GV..PVDWAA  LC........
atdebs05p   AGACVV.GTL  RRDRGGLADF  HTALGEAYAQ  GV..EVDWSP  AF........
atdebs04p   AEVTCV.PTL  RREQSGPHEF  LRNLLRAHVH  GVGADL....  ..........
```

Fig 2s

```
atave02a    PQTH......  ..........  .....LLTNL  AK......TT  T..TWHPHHY
atave05a    PQTH......  ..........  .....LLTNL  AK......TT  T..TWHPHHY
atave04a    PQTH......  ..........  .....LLTNL  AK......TT  T..TWHPHHY
atave08a    PQTH......  ..........  .....LLTNL  AK......TT  T..TWHPHHY
atave03a    PQTH......  ..........  .....LLTNL  AK......TT  T..TWHPHHY
atrap02a    ......IAML  HGD.HE....  ..AQAAVGAL  AHLYVNG.VS  V..EW.SAVL
atrap11a    ......VAML  HGD.HE....  ..AQAAVGAL  AHLYVNG.VS  V..EW.SAVL
atrap08a    ......VAML  HGD.HE....  ..AQAAVSAL  AHLYVNG.VT  V..DW.PALL
atrap12a    ......VAML  HGD.HE....  ..IQAAIGAL  AHLYVNG.VT  V..DW.PALL
atrap05a    ......VAML  HTD.HE....  ..AQAAISAL  AHLYVNG.VT  V..DW.TALL
atrap09a    ......VAML  HGD.HE....  ..TQAAIGAL  AHLYVNG.VT  V..DW.TALL
atfkb03a    ......IPVL  HGE.DE....  ..ARSAMTAL  ARLHTGG.VA  V..DW.PEVI
atfkb07x    ......IPTQ  TGTPEE....  ..VQALHTAL  ARLHTRG.GV  V..DW.PTVL
atfkb08x    ......IALQ  NGTADE....  ..VHALHTAL  ARLFTRG.AT  L..DW.SRIL
atnid01a    ....TTIPTL  HREHPEPETL  TTAL....AT  ..LHTTGHTT  T.........
atnid03a    ....TTIPTL  HREHPEPETL  TTAL....AT  ..LHTTGHTT  T.........
atnid02a    ....TTIPTL  HREHPEPETL  TTAL....AT  ..LHTTGHTT  T.........
atnid00a    ....TTIPTL  HRERPEPETL  TQAI....AA  VGVRTDGIDW  A.........
atfkb10a    .......AVL  RARTGEES..  ....AALTAV  AELHAHG.AP  V..DL.AAVL
atrap14a    .......AVL  RPRSPEDV..  ....CLMTAI  AELHAGG.TA  I..DW.AKVL
atmon06a    ....VLVASL  AGERPEES..  ....AFVEAM  ARLHTAG.VA  V..DW.SVLF
atmon08a    ....VLVSSL  AGERPEES..  ....AFVEAM  ARLHTAG.VA  V..DW.SVLF
atmon09a    ....VVTASL  HPDRPDDV..  ....AFAHAM  ADLHVAG.IS  V..DW.SAYF
atepo02a    ....TLLASL  RAGREEA...  ...AGVLEAL  GRLWAAGGS.  V..SW.PGVF
atepo03x    ....TLLASL  RAGREEA...  ...AGVLEAL  GRLWAAGGS.  V..SW.PGVF
atepo08a    ....VLLPAS  RAGRDEA...  ...ASALEAL  GGFWVVGGS.  V..TW.SGVF
atepo00a    ....ALLASS  RAGRDEP...  ...ATVLEAL  GGLWAVGGL.  V..SW.AGLF
atepo04a    ....VLVPSL  RADRSEC...  ...EVVLAAL  GAWYAWGGA.  L..DW.KGVF
atnid07a    AFAAALRRGR  ....PEC...  ...ATVLPAA  ATAFVQG.AH  V..DW.AAPY
attyl07a    LLPAIHKPGT  APHGPAA...  ...PGALRAA  AAAYGRG.AR  V..DW.AGMH
atsor02a    PCAFL..PTL  RKGRDDA...  ...EAFTAAL  GALHAAG.LT  P..DW.SAFF
atsorb1a    PCAFL..PTL  RKGRDDA...  ...EAFTAAL  GALHAAG.LT  P..DW.NAFF
atnys09a    .AVTL..PAL  RAGRPEE...  ...HTLTTAL  AGLHVHG.AT  L..DW.TGCF
atnys12a    .AL.L..PTL  RGDRPEE...  ...PALVTAV  AAAHAHG.AR  V..DW.SGYF
atnys16a    .L.VT..PTL  RKDRDEE...  ...SALLAGL  ARLHVAG.VT  V..DW.SAAL
atnys17a    .E.VV..PAL  RKGRPEE...  ...HTALTAA  AQLHVAG.VD  I..DW.TAVL
atnys03a    .A.AV..PLL  RKDRPEE...  ...LSAVTGL  ARAHVRG.VT  V..RW.AGLF
atnys15a    .V.SV..PVL  RKDRDEE...  ...PAAVAAL  ARLHTAG.VP  V..DW.TAFY
atnys07a    .L.AV..PLL  RKDRPEE...  ...PAALAAL  AQLHIAG.AR  V..DW.PVLF
atnys08a    .V.TV..PVL  RKDRGEE...  ...STALTAR  AHLHTRG.LI  E..DW.QDFF
atnys05a    .A.TV..PAL  RKDRDEE...  ...TSALTAL  AHLHTAG.LR  V..DW.AAFF
atnys06a    .V.TV..PVL  RRNMPEE...  ...RTLLTAL  GRLHTTG.TP  I..DW.AALL
atnys04a    .G.TI..PLL  RRDRPEE...  ...QAVLAAL  CHLQVLG.VE  A..DW.SATF
atnys14a    .V.VV..PAL  RRNRDED...  ...ETLVGAV  ARLHVHG.AG  P..RW.DAYF
atnys00a    .TDVV..PAL  SKGRPEE...  ...TAFAGAL  GRLHTLG.VP  V..DW.PAFY
atnys10a    .AELV..PML  RAGRAEE...  ...LAAATAL  ARLQVRG.VD  V..DW.AAYL
atnys18a    .LVAV..PVL  RKERPEE...  ...TTVLAAL  GTLWAHG.AD  V..DW.DAVF
atnys13a    PAVVV..PLQ  RRDRAGD...  ...LALLEGL  ATLHTHG.TG  P..SW.PAYF
atave10a    .ARAI..PAL  RPDQPEA...  ...RSVMTAL  AELFVAG.TA  V..EW.AGVF
atrif02a    ....V..ATL  RKNGAEV...  ...PDVLTAL  AELHVRG.VG  V..DW.TTVL
atmon03a    EPEPVVAAAL  RSKHDEG...  ...RTLLGAV  AALHTDG.QP  A..DL.TALF
atave12a    PQENLLIPLL  RPDSPEP...  ...GTLLTGL  ARLHTHGAAA  V..NW.PAAL
atrif09a    .AEVTCVAAL  RDDRPEV...  ...TALITAV  AELFVRG.VA  V..DW.PALL
atmon00a    ....AAIATC  RRGRDEV...  ...ATFLRSL  AQAYVRG.AD  V..DF.TRAY
attyl03a    PDPLLTLPLL  RRSVPETGDA  EHPGGFERAL  ATAYAHGV..  ......PLRL
```

Fig 2t

```
              501                                        550
atave00x      TQQQSLLLDL VRAHTMAVLN DDGN~~~~~~ ~~~~~~~~~~ ~~~~~~~~~~
atdebs00p     GSLPE.FAPA EEEDEPAESG VDWNAPPHVL RER~~~~~~~ ~~~~~~~~~~
atepo06p      .......... RRVPLPTYPW QHERCWIEVE PDARR~~~~~ ~~~~~~~~~~
atepo07p      .......... RRVPLPTYPW QHERYWIEDS VHGSKPSLRL RQLRNGATDH
atepo01p      .......... RRVPLPTYPW QRERYWIEAP AKSAAGDRRG VRAGGHPLLG
atepo05p      .......... RRVPLPTYPW QRERYWVDAP TGGAAGGSRF AHAGSHPLL~
atsora1x      .......... ESMPLPSTAG ~~~~~~~~~~ ~~~~~~~~~~ ~~~~~~~~~~
atfkb01p      ........P.H RVLDLPTYPF DHKRYWLQPA PVT~~~~~~~ ~~~~~~~~~~
atfkb09p      ........P.D RLLDLPTYPF DHKRYWIEAT GAADLTALGL TDTAHP~~~~
atrap03p      .......TTT RVLDLPTYAF QHQRYWVE.. .GVDRSAAG. ...GHPLLGV
atrap06p      .......ATT RVLDLPTYAF QHQRYWLR.. .SVDRAAAD. ...GHPLLGT
atrap04p      .......TTA RVLDLPTYAF QHQRYWVK.. .SVDRAAAD. ...GHPLLGA
atrap13p      .......TTT RVLDLPTYAF QHQRYWLK.. .SVDRAAAD. ...GHPLLGT
atrap01p      .......TAA RVLDLPTYAF QHQRYWLK.. .GVDRAAAD. ...GHPLLGT
atrap07p      .......ATT RVPDLPTYAF QHQRFWAE.. .GADRSVAG. ...GHPLLGV
atrap10p      .......PAT RVLDLPTYAF QHQRYWAEAG RSADVSAAGL DAVGHPLLGA
atfkb04x      AASVTAHDTG TAHDLPTYAF HHERYWIEPA TGTDASGLGL D~~~~~~~~~
attyl04p      ...DPALPPG HLTTLPTYPF NHHHYWLDTT PTTPA.TTTQ SPTDAQNPAD
attyl06p      ...DPALPPG HLTTLPTYPF NHHHYWLDTT PTTPA.TTTQ SPTDAWR...
attyl01p      ...DPALPPG HLTTLPTYPF NHHHYWLDTT PTTPA.TTTQ SPTDAWR...
attyl02p      ...DPALPPG HLTTLPTYPF NHHHYWAVTS PAGVG.DAA. ....AGR...
attyl00p      ...DPALPPG HLTTLPTYPF NHHHYWLDTI DGGGGDDATQ EKESGPLTRE
atnid05b      .G.....PGA RPVELPTYPF QRERYWCHP. GVRGGDPASL GMDGADHPLL
attyl05b      .G.....PDS RRVNPPTYPF QRERYWYHPT SGRRGDITAA GVAEAEHPLL
atnid06x      EG.....TGA RRVPLPSYAF HRDRFWLPTA AARRPATSSS ~~~~~~~~~~
atdebs01p     LG.....TGA RRVPLPTYPF QRERVWLEPK PVARRSTEVD EV~~~~~~~~
atmon02p      ....PADPAP RTIDLPTYAF QRRRYWLADT VKRDSWDPA  GS~~~~~~~~
atmon10p      ....PADPTP RTVDLPTYAF QHQHYWLERS ASASGAVSGE QSA~~~~~~~
atmon04p      ....PADPTP RTVDLPTYAF QHQHYWLEEP SGLTGDAADL GMVA~~~~~~
atmon07p      ....PADPTP RTIDLPTYAF QRRSYWL..P VDGVGDVRSA GLRRVE~~~~
atmon11p      ....PADPTP RTVDLPTYAF QHKHYWVEPP AAVAAVGGGH DPVEA~~~~~
atmon12p      ....PAVPLP RVVDLPTYAF QRERFWLEGR RGLAGDPAGL GL~~~~~~~~
atmon05b      ....PADPAP RTVDLPTYAF QRQDFWPAPA GGRSGDPAGL GLAASGHP~~
atmon01p      ....PATGT. STVELPTYAF QRRRYWLEAP TG.TQDAAGL GL~~~~~~~~
atdebs02p     .......GRA GLVDLPGYPF QGKRFWLLPD RTTPRDEL.D GWF~~~~~~~
atdebs06p     .......PAA PPVALPNYPF EPQRYWLAPE VS...DQLAD SRYRVD~~~~
atave01p      THHHTHPHPH THLDLPTYPF QHQHYWLESS QPGAGSGSG~ ~~~~~~~~~~
atave07p      THHHTHPHNH .HLDLPTYPF QRQHYWLD.A PTGAGDV~~~ ~~~~~~~~~~
atave06p      TQTHPHPNPH THLDLPTYPF QHQHYWLQPP TTTTDLTTTG LTPTHHPL~~
atave09p      TQTHPHPHNH .HLDLPTYPF QHQHYWLQ~~ ~~~~~~~~~~ ~~~~~~~~~~
atnys01p      E.....GTGA ARVDLPTYAF QRERYW.NTR TAADRTPADA PMDAEFWA~~
atnys11p      E.....GTGA SRIDLPTYAF QHEHLW.AVP PAPEAVAAAD PDDAAFWTAV
atrif05p      .......PPA .RVELPTYAF DHQHFW..LS PPAVA.DAPA LGLAGADHPL
atrif07p      .......PPA .RVDLPTYAF DHQHFW..LR PAAQA.DAVS LGQAAAEHPL
atrif08p      .......PPA .RVDLPTYAF DHQHYW..LR YVETATDAA~ ~~~~~~~~~~
atrif10p      .......PPA .RADLPTYAF DHEHYW..LR AADTASDAVS LGLAGADHPL
atrif03p      .......PAA GWVDLPTYAF DRRHFW..LH EAETAEAAEG M~~~~~~~~~
atrif06p      .......PRT GRVDLPKYAF DHRHYW..LR PAESATDAAS LGQGAADHPL
atrif04p      .......PPS RRVELPTYAF DHQHYW..LQ MGGSATDAV~ ~~~~~~~~~~
atrif01p      .......PAA GWVDLPTYAF EHRHYW..LE PAEPASAGDP LLGT~~~~~~
atnys02p      A.....RSAY QPVDLPTYPF QRQDFWPEAR PATPAAGADA SD~~~~~~~~
atfkb02p      P.....FGEL RGVPLPTYPF RRDRYWVDAE PAGTSGHP~~ ~~~~~~~~~~
atave11p      GSVGRGVAGG CGVELPTYAF ERERFWLDVE GAPRGSGVSG QW~~~~~~~~
atdebs03p     .......PGA APFALPTYPF QRKRYWLQPA APAAASDELA YRV~~~~~~~
atnid04p      .......PRA GWVDLPTYAF QRERYWVAPA EPGPAAGAGS AAATGPAAA~
atdebs05p     .......ADA RPVELPVYPF QRQRYWLPIP TGGRARDEDD DWR~~~~~~~
atdebs04p     ...RPAVAGG RPAELPTYPF EHQRFWPRPH RPADVSALGV R~~~~~~~~~
```

Fig 2u

```
atave02a    THHDNQPHTH  THLDLPTYPF  QHHHYWLE..  STQPGAGNV~  ~~~~~~~~~~
atave05a    THHHNQPHTH  THLDLPTYPF  QHHHYWLELP  SAQTSPGQRR  SRRSAPD~~~
atave04a    THHHNQPHTH  THLDLPTYPF  QHQHYWLE..  STQPGAGSGS  GSGSGRAG~~
atave08a    THHHNQPHTH  THLDLPTYPF  QHHHYWLE..  STQPGAGNVS  AA~~~~~~~~
atave03a    THHHNQPHTH  THLDLPTYPF  QHHHYWLQ..  ..PPGKPSDP  SP~~~~~~~~
atrap02a    GDVPVTRV..  ..LDLPTYAF  QHQRYWLE..  .GTDRATAG.  ...GHPLLGS
atrap11a    GDVPVTRV..  ..LDLPTYAF  QHQRYWLE..  .GTDRATAG.  ...GHPLLGS
atrap08a    GDAPATRV..  ..LDLPTYAF  QHQRYWLE..  .GTDRMAAG.  ...GHPLLGE
atrap12a    GDAPATRV..  ..LDLPTYAF  QHQRYWLE..  .GTDRATAG.  ...GHPLLGS
atrap05a    GDAPATRV..  ..LDLPTYAF  QHQRYWLE..  .GADRAAAG.  ...GHPLLGP
atrap09a    GDVPVTRV..  ..LDLPTYAF  QQQRYWAEVG  RSADVSGAGL  DAVGHPLLGA
atfkb03a    GAAP.TDL..  ..PHLPTYPF  ERTRYWLGSR  AAGDA~~~~~  ~~~~~~~~~~
atfkb07x    .GSDRAPV..  ...ALPTYPF  QHKDYWLRAT  AQVDVTGAGQ  EKVAHPLL~~
atfkb08x    GGASRHDP..  ...DVPSYAF  QRRPYWIE.S  APPATADSG.  ....HPVLGT
atnid01a    ..LHTTSPQT  HHLDLPTYPF  QRDRYWM.EP  VRVAQVSGQP  GADRLRYRVV
atnid03a    ..LHTTSPQS  HHLDLPTYPF  QRDRYWM.AV  PPRAAVGDLA  ~~~~~~~~~~
atnid02a    ..PHPSHIPA  QRVSLPAYPF  QRRAYWM..P  NSAAHIGRSD  AEAATRLGLA
atnid00a    ..VLCGASRP  RRVELPTYAF  QRRTHWAPGL  TPNHAPADRP  AAEPQRAMAV
atfkb10a    A........GG  RPVDLPVYPF  QHRSYWLAPA  VGGGSPTAVP  D~~~~~~~~~
atrap14a    S........GG  RAVDLPVYPF  QHQSYWLAPA  ..APDATAVA  PVVEEEGGEY
atmon06a    AGDRVPGL..  ..VELPTYAF  QRERFWLSG.  RSGGGDAATL  GLVAAG~~~~
atmon08a    AGDRVPGL..  ..VELPTYAF  QRERFWLSG.  RSGGGDAATL  GLVAAGHPL~
atmon09a    PDDPAPRT..  ..VDLPTYAF  QGRRFWLADI  AAPEAVSSTD  GEEA~~~~~~
atepo02a    ......PTAG  RRVPLPTYPW  QRQRYWIEAP  AE~~~~~~~~  ~~~~~~~~~~
atepo03x    ......PTAG  RRVPLPTYPW  QRQRYWPDIE  PDSRR.HAAA  DPTQGWFY~~
atepo08a    ......PSGG  RRVPLPTYPW  QRERYWIEAP  VDREA.DGTG  ~~~~~~~~~~
atepo00a    ......PSGG  RRVPLPTYPW  QRERYWIDTK  ADDAA.RGDR  RAPGAGHDEV
atepo04a    ......PDGA  RRVALPMYPW  QRERHWMDLT  PRSAA.PAGI  AGRWPLAGVG
atnid07a    ...EG..AGA  RRVDLPTYPF  QHTRYWL~~~  ~~~~~~~~~~  ~~~~~~~~~~
attyl07a    A..DGPEGPA  RRVELPVHAF  RHRRYWLAPG  RAA~~~~~~~  ~~~~~~~~~~
atsor02a    A.....PFAP  R~~~~~~~~~  ~~~~~~~~~~  ~~~~~~~~~~  ~~~~~~~~~~
atsorb1a    A.....PFAP  CKVPLPTYTF  ~~~~~~~~~~  ~~~~~~~~~~  ~~~~~~~~~~
atnys09a    AGT.....GA  RRTDLPTYAF  QRRYWPKAL   QSGTA.DLRS  VGLGAA~~~~
atnys12a    ADH.....GA  RRTTLPTYAF  QRERYWPDTT  AATSA.HTPG  SALDAEFW~~
atnys16a    TGT.....GA  RGTDLPTYAF  QRERYWPE..  LAAEP.AG..  GGADAADA~~
atnys17a    AGT.....GG  RRIALPTYAF  QRERYWPS..  LAAQA.PGDA  GG~~~~~~~~
atnys03a    DGT.....GA  RRADLPTYPF  QHQRFWPT..  AAR.A.AQDV  TAAGLGAADH
atnys15a    AGT.....GA  HRTDLPTYAF  QYERYWPK..  ATY.R.PADA  TGL~~~~~~~
atnys07a    AGV.....GA  GRVELPTYAF  QRGWFWPV..  GRVGV.GGDV  ~~~~~~~~~~
atnys08a    AGV.....GA  GRVELPTYAF  QRGWFWPV..  GRVGV.GGDV  GAVGLGSAGH
atnys05a    AGS.....GA  TRVDLPTYAF  QHATYWPT..  GTLPT..AHA  AAVGL~~~~~
atnys06a    APT.....GA  RPVDLPTYAF  QHRPFWPS..  GPRDT..ADA  AAVGIAGASH
atnys04a    RGL.....DP  VRVDLPTYAF  QHRWFWPA..  ARPAR.PDDV  RAAGLGAA~~
atnys14a    AGR.....GA  QWLDLPTYPF  QRGRFWPE..  SLPGA.ASAA  PAAGQPA~~~
atnys00a    AGT.....GA  RRVELPTYAF  QHVRHWPT..  PPRPN.GAGP  GALGHPLLG~
atnys10a    AGT.....GA  RRTDLPTYAF  QHAYYWPQ..  LPTPA.AALA  AADPADQQLW
atnys18a    AGT..RTPQA  DPVELPTYAF  QRARYWPTLG  ARHGD.PADL  G~~~~~~~~~
atnys13a    EAT.....GG  HRTDLPTYAF  QRERYWPELG  APVAT.APQD  PAAW~~~~~~
atave10a    EGTAREVGDG  CGVELPTYAF  ERERFWLDVE  EGSAG.GSGV  SGMWGGPLWE
atrif02a    ....DEPATA  VGTVLPTYAF  QHQRFWVDVD  ET~~~~~~~~  ~~~~~~~~~~
atmon03a    ......PADA  GQVPLPTYRF  QRRRYWRVAP  DAAAP.ARAA  GLQ~~~~~~~
atave12a    PERDR....A  RHLDLPTYAF  DHHRYWVDTS  AGHPG.DLSA  AGLGT~~~~~
atrif09a    PPVTGF....  ..VDLPKYAF  DQQHYWLQPA  AQATD.AASL  GQV~~~~~~~
atmon00a    GAT.....AT  RRFPLPTYPF  QRERHWPAAA  GVGQQ.PETP  ELP~~~~~~~
attyl03a    APAPDAASLA  VAAELPTYAF  QRTHYWLDAP  AAPAALPAGL  DDAGHPLLSA
                            ****                                      LPTY motif
```

Fig2v

| | | |
|---|---|---|
| 15500 | GGTGGTGCCGACGCCATGGCCCGTGAGCGCTCACAGCGCTTCCGCGCTGCGCGCAGGC | 15559 |
| 15560 | CGGTCGCCTGCGGACACTCGCGCGCCGCCACGCGCCCCACCCCGACGCCGCGGGTCGG | 15619 |
| 15620 | CCACGCGCTCGCCACCACCCGCGTCTGGGCCTCGCCGCGGTTCCTCGCTCGGCGGCGA | 15679 |
| 15680 | CACCGCCGAACTGCTGGGCTCCCTGGACGCGTGGAGGCGGCGAGACCGCGTCCAT | 15739 |
| 15740 | CGTGCGGCGCATGGGGCGTACACCGAGGCGGAGTTGTATGCCGTCTTCCGCGACGCTCT | 15799 |
| 15800 | GCAACGCCCTCGGCATGGGGCCCCTGGACGTACATCTGACCGCCACTGCGCGAGATCGTCTT | 15859 |
| 15860 | CGACGAGGCGGTTTCGCCCGCGGTGGGAACGTCTCGGTGAGAATGTCATCGGCGAGGGTGCCGA | 15919 |
| 15920 | GGGCGAGACCGACTCGGGTGGGAACGTCTCGGTGAGAATGTCATCGGCGAGGGTGCCGA | 15979 |
| 15980 | CCATCAGGCACTCCTCGACCAGACCGCCTACACCCAGCCCGCTCTTCGCGATCGAGAC | 16039 |
| 16040 | GAGCCTGTACCGGCTGGCAGCCCTCCTTCGGAAGCCGGACTACGTCCTCGGCCCACTC | 16099 |
| 16100 | GGTCGGCGAGATCGCCGCGGACCGCCACGTCGCCGTGCTCCTCGTTCGCGACGCGAGCGC | 16159 |
| 16160 | TCTGGTGGCCACGCGGGGACGGCTCATGCAGGCCGAACAGCTCGCCGGGCGCGATGGCCGC | 16219 |
| 16220 | GTGGCAGGCCACGCGGCGAGCGGCCCGACTCCGTGGTCGTCTCGCCGGCACGAGCGCACGTCAC | 16279 |
| 16280 | CGTGGCCGCGCGTCAACGGCCCGCCTGGCGGGACGCGCCCCATCCGTGGTCGTCTCGCCACCGTCGA | 16339 |
| 16340 | CGAACTGACCGCCACTCCCCGCACATGGACCCCATCCTCGACGAGCTGCGCCGTCGCCGCGG | 16399 |
| 16400 | CGCCTTCCACTCCCCGCACATGGACCGGTCATTCCGTCTCTCCAACGTCACCGGTGAACTGGTGAC | 16459 |
| 16460 | CCTGACCTTCCACGAGCCGGTCATTCCGTCTCTCCAACGTCACCGGTGAACTGGTGAC | 16519 |
| 16520 | CGCGACCGCGACGGGAGCGCCAGGCCAGGCCGAGTACTGGGCGCGGGGTGACCAC | 16579 |
| 16580 | GCGCGAGCTCGGCCGTTCCTGCCGGACCACCGTGTCCGGATGCGCCGACTGCTTCCCCGC | 16639 |
| 16640 | GTTGGTCAGCGGGACCGGAGCCCGTCCGCGCCCGGCCATGCGCCACATGCGCCTGTCCCCGGCGGA | 16699 |
| 16700 | CCCCGCGGGACCGGAGCCCGTCCGCGCCCGGCCATGCGCCGCTTCCGGCGCCGATGTCGA | 16759 |
| 16760 | CGAGGTGGCCACGTTCCTGAGGTCGCCACCAGGCCGCCACGCGCCGCTTCCCCGCGCCGATGTCGA | 16819 |
| 16820 | CTTCACCCGGCCTACGGCCTGCCTTGGGCCTGCCGCACGCGCCAGCCGGAGACCCCGGA | 16879 |
| 16880 | CCAGCGCGAGCGCCATTGGCCTGCCTTGCCGGAGCAGGCAGCGGGAGCGGAGGAGGGCGCG | 16939 |
| 16940 | ACTTCCGGAATCCTCGGAGTCCTCGGAGCCTTGAAGGGCCTTGCCGGCCTTGAACGACCAGGAGCGGGT | 16999 |
| 17000 | CGCGTGGGGCGGGCCTGGTCACCAAGCACCTTCAAGGACACAGTTGGGCTTCGGGGACGCCCTCGGCACGGT | 17059 |
| 17060 | CCTCCTCGGCCCTGGTCACCAAGCACCTTCAAGGACACAGTTGGGCTTCGACTGCTTCGACTGCGAG | 17119 |
| 17120 | ACAAGCCGCCCCCTCGGCACGGAGACGGGCCTGCCGTTGCCGCGCCACCTTCGACTACCC | 17179 |
| 17180 | CGAACGGCTCGGACGCTCGCCGTCCGCCGCCACCTGCGGCGAGCTCACCCGGTACCGCCCCCGGC | 17239 |
| 17240 | GACCCTCTGGCCGCCCACGGGCCTCGGACGTCGAGGTGACCTCGGCGCGCCACGGACGAGGACCC | 17299 |
| 17300 | CGGCTCCGCGCCCACGGGCCTCGGACCTCGGCGGGTGACCTCGGCGCGCCACGGACGAGGACCC | 17359 |
| 17360 | GGTCGCCATCG 17370 | |

Fig 5

POLYKETIDES AND THEIR SYNTHESIS

This application is a 371 of PCT/GB01/03642, filed Aug. 14, 2001, which claims the benefit of foreign priority of United Kingdom 00119986.9, filed Aug. 14, 2000.

TECHNICAL FIELD

The present invention relates to processes and materials (including enzyme systems, nucleic acids, vectors and cultures) which can be used to influence the selection of acylthioester units for the synthesis of polyketides, and to the resulting polyketides, which may be novel. It is particularly concerned with macrolides, polyethers or polyenes and their preparation making use of recombinant synthesis.

In preferred types of embodiment, polyketide biosynthetic genes or portions of them, which may be derived from different polyketide biosynthetic gene clusters, are manipulated to allow the production of specific polyketides, such as 12-, 14- and 16-membered macrolides, of predicted structure. The invention is particularly concerned with the modification of an Acyl CoA:ACP transferase (AT) function, generally by modifying genetic material encoding it in order to prepare polyketides with a predetermined ketide unit, e.g. incorporating (a) a malonate extender unit; or (b) a methylmalonate extender unit; or (c) an ethylmalonate extender unit; or (d) a further type of extender unit; or (e) an acetate and/or malonate starter unit; or (f) a propionate and/or methylmalonate starter unit; or (g) a butyrate and/or ethylmalonate starter unit; or (h) a further type of starter unit. Of course the invention can be used to influence more than one ketide unit of a polyketide. The method enables one to minimise alteration to the protein structure of the polyketide synthase.

Polyketides are a large and structurally diverse class of natural products that includes many compounds possessing antibiotic or other pharmacological properties, such as erythromycin, tetracyclines, rapamycin, avermectin, monensin, epothilone and FK506. In particular, polyketides are abundantly produced by Streptomyces and related actinomycete bacteria. They are synthesised by the repeated stepwise condensation of acylthioesters in a manner analogous to that of fatty acid biosynthesis. The structural diversity found among natural polyketides arises in part from the selection of (usually) acetate (malonyl-CoA) or propionate (methylmalonyl-CoA) as "starter" or "extender" units (although one of a variety of other types of unit may occasionally be selected); as well as from the differing degree of processing of the β-keto group formed after each condensation. Examples of processing steps include reduction to β-hydroxyacyl-, reduction followed by dehydration to 2-enoyl-, and complete reduction to the saturated acylthioester. The stereochemical outcome of these processing steps is also specified for each cycle of chain extension. Methylation at the α-carbon or β-hydroxy is also sometimes observed.

The biosynthesis of polyketides is performed by a group of chain-forming enzymes known as polyketide synthases. Two broad classes of polyketide synthase (PKS) have been described in actinomycetes. One class, named Type I PKSs, represented by the PKSs for the macrolides erythromycin, oleandomycin, avermectin, and rapamycin and by the PKS for the polyether monensin, consists of a different set or "module" of enzymes for each cycle of polyketide chain extension. For an example see FIG. 1 (Cortés, J. et al. Nature (1990) 348:176-178; Donadio, S. et al. Science (1991) 2523: 675-679; Swan, D. G. et al. Mol. Gen. Genet. (1994) 242: 358-362; MacNeil, D. J. et al. Gene (1992) 115:119-125; Schwecke, T. et al. Proc. Natl. Acad. Sci. USA (1995) 92:7839-7843; also Patent application WO98/01546). The genes encoding numerous Type I PKSs have been sequenced and these sequences disclosed in publicly available DNA and protein sequence databases including Genbank, Swissprot and EMBL. For example, the sequences are available for the PKSs governing the synthesis of erythromycin (Cortes, J. et al. Nature (1990) 348:176-178); accession number X62569, Donadio, S. et al. Science (1991) 252:675-679; accession number M63677); rapamycin (Schwecke, T. et al. Proc. Natl. Acad. Sci. (1995) 92:7839-7843; accession number X86780); rifamycin (August, P. et al. Chem. Biol. (1998) 5:69-79; accession number AF040570) and tylosin (Eli Lilly, accession number U78289), among many others.

The term "polyketide synthase" (PKS) as used herein refers to a complex of enzyme activities responsible for the biosynthesis of polyketides. These enzyme activities include β-ketoacyl ACP synthase (KS), acyltransferase (AT), acyl carrier protein (ACP), β-ketoreductase (KR), dehydratase (DH), enoylreductase (ER) and thioesterase (TE) but are not limited to these activities. Each of these activities lies on a separate protein or polypeptide fragment responsible for this activity. Such a fragment is termed a "domain". The terms "motif" or "signature sequence" used herein refer to a small stretch of amino acids (usually less than 10 amino acids) within a domain responsible (at least in part) for one aspect of the catalytic function, for example, choice of substrate. The term "extension module" as used herein refers to the set of contiguous domains, from a β-ketoacyl-ACP synthase ("KS") domain to the next acyl carrier protein ("ACP") domain, which accomplishes one cycle of polyketide chain extension; this may or may not include domains responsible for the reductive processing of the polyketide chain. The term "loading module" is used to refer to any group of contiguous domains that accomplishes the loading of the starter unit onto the PKS and thus renders it available to the KS domain of a specific extension module.

BACKGROUND ART

Several approaches to altering the nature of the polyketide product of a PKS by genetic engineering have been proposed: see particularly WO 93/13663 and WO 98/01571. The length of polyketide formed has been altered, in the case of erythromycin biosynthesis, by specific relocation using genetic engineering of the enzymatic domain of the erythromycin-producing PKS that contains the chain-releasing thioesterase/cyclase activity (Cortés, J. et al. Science (1995) 268:1487-1489; Kao, C. M. et al. J. Am. Chem. Soc. (1995) 117:9105-9106).

In-frame deletion of the DNA encoding part of the ketoreductase domain in module 5 of the erythromycin-producing PKS (also known as 6-deoxyerythronolide B synthase, DEBS) has been shown to lead to the formation of erythromycin analogues 5,6-dideoxy-3-α-mycarosyl-5-oxoerythronolide B, 5,6-dideoxy-5-oxoerythronolide B and 5,6-dideoxy, 6 β-epoxy-5-oxoerythronolide B (Donadio, S. et al. Science (1991) 252:675-679). Likewise, alteration of active site residues in the enoylreductase domain of module 4 in DEBS, by genetic engineering of the corresponding PKS-encoding DNA and its introduction into *Saccharopolyspora erythraea*, led to the production of 6,7-anhydroerythromycin C (Donadio, S. et al. Proc Natl. Acad. Sci. USA (1993) 90:7119-7123).

Patent application WO 00/01827 describes further methods of manipulating a PKS to change the oxidation state of the β-carbon. Substituting the reductive domain of module 2 of the erythromycin-producing PKS with domains derived from rapamycin PKS modules 10 and 13 led to the formation of C10-C11 olefin-erythromycin A and C10-C11 dihydroerythromycin A respectively.

The second class of PKS, named Type II PKSs, is represented by the synthases for aromatic compounds. Type II PKSs contain only a single set of enzymatic activities for chain extension and these are re-used as appropriate in successive cycles (Bibb, M. J. et al. EMBO J. (1989) 8:2727-2736; Sherman, D. H. et al. EMBO J. (1989) 8:2717-2725; Fernandez-Moreno, M. A. et al. J. Biol. Chem. (1992) 267: 19278-19290). The "extender" units for the Type II PKSs are usually acetate (malonyl-CoA) units, and the presence of specific cyclases dictates the preferred pathway for cyclisation of the completed chain into an aromatic product (Hutchinson, C. R. and Fujii, I. Annu. Rev. Microbiol. (1995) 49:201-238). Hybrid polyketides have been obtained by the introduction of cloned Type II PKS gene-containing DNA into another strain containing a different Type II PKS gene cluster, for example by introduction of DNA derived from the gene cluster for actinorhodin, a blue-pigmented polyketide from *Streptomyces coelicolor*, into an anthraquinone polyketide-producing strain of *Streptomyces galileus* (Bartel, P. L. et al. J. Bacteriol. (1990) 172:4816-4826). Occasionally, unusual starter units are incorporated by Type II PKS, particularly in the biosynthesis of oxytetracycline, frenolicin and daunorubicin and in these cases a separate AT is used to transfer the starter unit to the PKS.

Fungal PKSs such as the 6-methylsalicylic acid or lovastatin PKS typically consist of a single multi-domain polypeptide which include most of the activities required for the synthesis of the polyketide portion of these molecules (Hutchinson C. R. and Fujii I. Annu. Rev. Microbiol. (1995) 49:201-238). Type II Fungal PKSs are also known.

A number of mixed systems comprising polyketide synthase and nonribosomal peptide synthase modules have been identified including the epothilone and bleomycin biosynthetic clusters.

Although large numbers of therapeutically important polyketides have been identified, there remains a need to obtain novel polyketides that have enhanced properties or possess completely novel bioactivity. The complex polyketides produced by Type I PKSs are particularly valuable, in that they include compounds with known utility as anthelminthics, insecticides, anticancer, immunosuppressants, antifungal or antibacterial agents. Because of their structural complexity, such novel polyketides are not readily obtainable by total chemical synthesis, or by chemical modifications of known polyketides. Particular changes that are desired are changes to the carbon skeleton by altering the nature of the starter and/or extender unit(s) incorporated, changes to the oxidation level of the β-keto carbon and therefore the pattern of oxygen substituents by altering the series of reductive steps that occur after chain extension and changes to the post PKS "tailoring" steps which generally comprise hydroxylation, methylation or glycosylation of the polyketide molecule.

There is also a need to develop reliable and specific ways of deploying individual modules in practice so that all, or a large fraction, of hybrid PKS genes that are constructed, are viable and produce the desired polyketide product. Various strategies have been described to produce these hybrid PKSs particularly utilising recombinant DNA technology and denovo biosynthesis. There is a particular need to develop methods of manipulating these PKS in a manner that minimises the alteration to the PKS protein structure. Existing methods of achieving these manipulations sometimes produce hybrid PKS multienzymes which give the desired product at only 1% or less of the rate that the unmodified PKS produces product.

WO 93/13663 and WO 98/01571 describe novel methods of engineering PKSs. A well-established method of altering the nature of the extender unit used at any position in the polyketide molecule, particularly malonyl-, methylmalonyl- or ethylmalonyl-CoA is by domain substitution. For example, WO98/01546 and U.S. Pat. No. 6,063,561 disclose methods of accomplishing this modification to form modified erythromycins. Novel polyketide molecules, in this case particularly novel erythromycins, are produced by the replacement of an entire AT domain-encoding DNA fragment on the *Saccharopolyspora erythraea* chromosome with an equivalent heterologous AT domain-encoding fragment from another PKS cluster. It is well known to those skilled in the art that selection of the exact DNA/protein splice sites into which to insert the heterologous domain requires detailed analysis of the corresponding DNA and protein sequences. Different researchers choose to use splice sites at conserved, semi-conserved or non-conserved regions of the protein, or at sites either within or at the boundaries of the AT domains. A further drawback of this technique is that it is hard to predict whether a particular heterologous domain will work in any given context. A domain that works successfully in one module may not work at all in an adjoining module or may produce polyketides at a vastly reduced yield. Oliynyk, M. et al. (Chem. Biol. (1996) 3:833-839) and Ruan et al. (J. Bact. (1997) 179:6416-6425) have published studies that exchange a methylmalonyl-CoA specific AT domain for malonyl-CoA specific AT domains in modules of the erythromycin PKS. Products were observed only for changes in modules 1 and 2, with module 2 at a vastly lowered yield. Stassi et al. (Proc. Natl. Acad. Sci. (1998) 95:7305-9) exchange the methylmalonyl-CoA specific AT of module 4 of the erythromycin PKS for an ethylmalonyl-CoA specific AT and again product yield was low even after the addition of the crotonyl-CoA reductase gene thought to increase the supply of the required ethylmalonyl-CoA precursor. A possible reason for the limiting yields is the structural or mechanistic non-compatibility of a heterologous AT domain with the adjoining KS and ACP domains with which it must interact properly for efficient polyketide chain synthesis. Consequently, it is often necessary to try multiple domain swaps to achieve a novel polyketide-producing strain that displays adequate efficiency—a process made particularly arduous when these changes must be made by gene replacement on the chromosome through a two step double integration process. The introduction of splice sites at the DNA level is time consuming and technically challenging, requiring careful analysis to ensure the PKS protein coding reading frame is not disrupted. The introduction of restriction enzyme sites often requires changes at the amino acid level which lead to further PKS protein structure disruption and consequent loss of catalytic efficiency.

A method that could utilise the numerous techniques available for site directed mutagenesis to influence the AT substrate specificity with minimal disruption to the protein tertiary structure would be a valuable addition to the current techniques.

Changes to an active site have been shown to alter substrate specificity in other systems. For example, in an early study, Scrutton et al. (Nature (1990) 343:38-43) used site directed mutagenesis to switch the coenzyme substrate specificity of a glutathione reductase. Identifying and changing a 'fingerprint' structural motif in the NADP+ binding domain they could convert the enzyme into one displaying a marked preference for NAD+. The techniques of directed evolution have been used to improve/change enzyme catalytic function. Of many examples in the literature, Zhang et al. (PNAS (1997) 94:4504-4509) illustrate the conversion of a galactosidase to a fucosidase by these techniques. The resulting protein bears 6 mutations, of which 3 lie in, or in close proximity to the active site.

Minor but directed changes to a PKS domain can make significant changes to its catalytic function. Patent application WO 00/00500 teaches that an extender ketosynthase domain is converted to a decarboxylating (and hence loading) ketosynthase domain by site directed mutagenesis at the active site. U.S. Pat. Nos. 6,004,787 and 6,066,721 and Jacobsen et al. Science (1997)277:367-369 describe the deletion of residues in the KS1 active site to inactivate this activity to allow the production of novel polyketides by feeding of synthetic precursors to the modified PKS.

Several studies have attempted to correlate the primary amino acid sequence of the AT to determine amino acids directly involved with the recognition of the appropriate substrate, and particularly the nature of the substrate side chain (i.e. the malonyl portion of the acyl-CoA thioester). Studies by Haydock et al. (FEBS Lett. (1995) 374:246-248) correlated the substrate specificity of malonyl- or methylmalonyl-CoA specific AT with a motif 11 amino acids upstream of the known active site. Comparisons between this motif and the protein structure of a known acyltransferase from *E. coli* fatty acid synthase allowed the authors to assess the proximity of the motif residues to the active site (and hence its ability to select the substrate). The authors acknowledged that "this divergent region thus identified lies near the acyltransferase active site though not close enough to make direct contact with the substrate". Other studies (Katz, L. Chem Rev. (1997) 97:2557-2575, Tang, L. et al., Gene (1998) 216:255-265) have correlated additional residues with a specific extender unit using these residues as a tool to predict the AT substrate specificity from a protein sequence derived from polyketide gene cluster sequencing projects. It has remained unclear which residues have mechanistic importance. In only one case have regions within the PKS AT domain been exchanged in an attempt to swap AT specificity; patent application WO 00/01838 and Lau et al. Biochemistry (1999) 38:1643-51) implicated a 'hypervariable region' at the C-terminus of the AT domain in the selection of extender unit. These workers interchanged this 25-30 amino acid stretch and showed that this change was sufficient to alter the substrate specificity of the AT, concluding "a short (23-35 amino acid) C-terminal segment present in all AT domains is the principal determinant of their substrate specificity. Interestingly its length and amino acid sequence vary considerably among the known AT domains. We therefore suggest that the choice of extender units by the PKS modules is influenced by a "hypervariable region", which could be manipulated via combinatorial mutagenesis to generate novel AT domains possessing relaxed or altered substrate specificity". Surprisingly, our structure molecular modelling studies indicate this region lies at a surface accessible region away from the active site and hence is unlikely to directly interact with (and hence directly select) the malonyl portion or the substrate used. The effect on substrate specificity is therefore likely to be imprecise and due to more indirect effects via, for example, disruption of tertiary structure.

DISCLOSURE OF INVENTION

According to a first aspect of the present invention there is provided a method of synthesising a compound whereof at least a portion is the product of a polyketide synthase (PKS) enzyme complex or is derived from such a product, said PKS enzyme complex including at least one acyltransferase (AT) domain. The method includes a step of providing said PKS enzyme complex in which said AT domain has been altered to change selectively a minor proportion of amino acid residues. The altered residue(s) may comprise one or more motifs which are present in the active site pocket of the AT domain and which influence the substrate specificity of the AT domain, the alteration affecting the substrate specificity; and/or one or more residues of a motif which influences the substrate specificity of the AT domain and which comprises a four-residue sequence corresponding to the YASH motif of the AT domain of the first module of DEBS, the alteration affecting the substrate specificity. Synthesis is then effected by means of said PKS enzyme complex to produce a compound or mixture of compounds different from what could have been produced by means of a PKS enzyme in which said AT domain had not been altered.

The PKS enzyme complex may be at least part of a modular type I PKS enzyme complex, or it may be derived from a type II PKS system, a fungal PKS system or a hybrid system comprising PKS and nonribosomal peptide synthase modules.

The present invention teaches that by altering a few amino acid residues in the AT domain and particularly residues close to the AT active site comprising one or more residues of a short signature "motif" within the AT domain it is possible to influence the acylthioester selected by that AT domain. Novel polyketides can be made by a modified PKS on which the signature motif on one or more modules is altered, e.g. being replaced with one associated with a different specificity for malonyl substrate. Furthermore, the invention provides a method of reducing the proportion of mixed polyketide products that are occasionally found in natural systems due to non-specific incorporation of the incorrect extender units. Conversely, the invention provides a method of giving a mixed population of polyketide products thus increasing the diversity of polyketides produced by a PKS.

The invention allows the preparation of a modified PKS by substitution of an existing amino acid residue motif in the AT that specifies incorporation of one of the common extender acylthioesters with another motif found in another AT specifying an alternative acylthioester. This alters the substrate specificity of the polyketide synthase when it is expressed in a polyketide-producing organism.

The DNA sequences have been disclosed for numerous Type I PKS gene clusters. Comprehensive sequence analysis of AT domains derived from Type I PKS modules responsible for the formation of macrolides, particularly erythromycin, rapamycin, avermectin, rifamycin, FK506, epothilone, tylosin, and niddamycin, ionophore polyethers, particularly monensin, and polyenes, particularly nystatin, allowed us to identify amino acids that are characteristic of AT domains.

FIG. 2 shows the sequence comparison of these AT domains. This sequence comparison has been generated in a generally conventional way, employing a computer using a procedure that creates a multiple sequence alignment from a group of related sequences. We used a program called PileUp (Wisconsin Package, Genetics Computer Group (GCG), Madison, Wis., USA), which creates a multiple sequence alignment using simplification of the progressive alignment method of Feng and Doolittle (journal of Molecular Evolution 25; 351-360 (1987)). The method used is similar to the method described by Higgins and Sharp (CABIOS 5; 151-153 (1989)). The program executes a series of progressive, pairwise alignments that allows a large number of sequences to be compared together to form a final alignment throughout all the sequences. Gaps can be inserted throughout individual sequences to allow alignment of regions of strong similarity. This is often required as strongly conserved regions are often separated by more variable regions, both in terms of numbers of amino acids and type of amino acids. Different programs use different mathematical algorithms to make these comparisons, resulting in alignments that differ in minor ways. However, it can be expected that regions of strong homology would still align whatever alignment program is utilised. The particular motifs that are discussed are marked.

These motifs include the conserved GQG motif that is close to the start of the domain, the GHS motif that contains the active site serine that covalently binds the acyl chain prior to transfer to the ACP, and a LPTY (SEQ ID NO:115) motif that is close to the end of the domain. Other residues common to all ATs including an arginine, believed to stabilise the carboxylate group of the acylthioester. Further detailed sequence analysis allowed us to identify amino acid residues that differed between ATs responsible for the incorporation of malonyl-, methylmalonyl- and ethylmalonyl-CoA. Some of these amino acids or motifs had been previously identified during the sequence analysis of the clusters as previously discussed. While these motifs could predict whether a malonyl-/methylmalonyl-CoA might be used they generally fail to show a difference between methylmalonyl- vs ethylmalonyl-CoA or the other larger extender unit commonly used. We viewed this as an important requirement for identification of the most important and key residues involved in substrate recognition and consequently residues most suitable for alteration. Closer analysis identified a string of four residues (location identified clearly in FIG. 2) of which two residues are virtually invariant throughout all ATs, and two residues differ consistently depending on the extender unit. Particularly, in the vast majority of ATs responsible for recognition of malonyl-CoA the sequence of residues HAFH (SEQ ID NO:117) was identified. In the majority of ATs responsible for recognition of methylmalonyl-CoA the equivalent segment was substituted by residues YASH (SEQ ID NO:114). In ATs responsible for ethylmalonyl-CoA or other similar sized CoA unit incorporation the overall motif was different, less conserved but generally displayed the sequence XAGH (where X is most frequently but not limited to F, T, V or H; SEQ ID NO:116) We typically use the terms HAFH (SEQ ID NO:117), YASH (SEQ ID NO:114) and TAGH (SEQ ID NO:118) to describe these motifs with respect to malonyl-CoA, methylmalonyl-CoA and ethylmalonyl/further CoA specificity but use these terms herein to allow substitutions in the motif, particularly at residue 1 as described. Potential substitutions and the exact location of the motif will be clear to those skilled in the art by inspection of FIG. 2 or similar sequence analysis.

There are three possible methods to locate the position of the motif within an AT sequence that does not appear in FIG. 2. It is likely a combination of the methods will be used.

I) By simple visual inspection and comparison of the sequence to identify the motifs HAFH, YASH or TAGH. Since substitutions of residue one are often encountered a useful procedure is to look for an alanine (A) separated by one amino acid (usually F, S or G) from a histidine (H).

II) By counting amino acids from the active site serine. The start of the motif is typically (but should not be limited to) between 90 and 100 amino acids downstream of the GHS active site motif.

III) By computer generated multiple alignment that allows the new sequence to be directly compared to the sequences and motifs we have annotated in FIG. 2 or to other ATs.

It is preferable to use the third method as this allows the motif to be identified unequivocally when there are substitutions within the motif. This is particularly necessary in some of the more unusual types of AT in which one of the residues can be substituted by proline (P). The third method will also identify the motif when the number of residues between the motif and the AT active site serine differs significantly from the norm. The third method will also better identify the motif when the same or similar string of amino acids occurs elsewhere in the domain.

A particular feature of these motif residues is the relationship of the size of the third residue compared to the substrate selected. Hence, when malonyl-CoA is required the third residue is large (phenylalanine), when methylmalonyl-CoA is required this residue is intermediate (serine), and when ethylmalonyl-CoA is required this residue is small (glycine). The inverse relationship between substrate side chain size and this third residue is particularly noteworthy. Interestingly, this relationship applies also when considering the incorporation of the more unusual extender units such as methoxymalonyl-CoA, required for some cycles of chain extension during production of for example FK506 (HAGH; SEQ ID NO:119). Currently, only a single example of an AT responsible for the incorporation of a five carbon-CoA unit has been disclosed. In this case the AT displays a different motif at this point, CPTH (SEQ ID NO:120), in which only the histidine is conserved. The incorporation of a proline residue in the motif may be indicative of an AT specifying a larger substrate. Proline is also found in the motif in ATs that incorporate the larger unusual starter acids as seen in the case of avermectin and soraphen. Residues in and around this area, but lying in the active site of the AT domain define the specificity of the domain towards the substrate chosen.

Motifs that represent hybrids of motifs for malonyl- and methylmalonyl-CoA or methylmalonyl- and ethylmalonyl-CoA were identified. Particularly, epothilone module 3-expected HAFH (SEQ ID NO:117) or YASH (SEQ ID NO:114) (malonyl-CoA or methylmalonyl-CoA specific), found HASH (SEQ ID NO:121) or monensin module 5-expected TAGH (SEQ ID NO:118) (ethylmalonyl-CoA specific), found VAGH (SEQ ID NO:122). Significantly, in both these cases the products of the PKS are a mixture due to the incorporation of 2 different extender units by the module containing the hybrid motif, causing formation of monensins A and B and epothilones A and B. However, it is known that substrate supply is a significant determinant of the proportion of monensins A and B formed (Liu, H. and Reynolds, K. A (1999) J. Bact. 181:6806-6813).

Many of the previously-proposed "predictive" motifs are unlikely to be the principal determinant of substrate specificity because they are not located in the active site pocket. A particular requirement of any motif that can serve to distinguish between substrates is that it lies close to the active site and preferably within the substrate binding pocket. In this analysis we consider the substrate binding pocket to be the part of the pocket that binds/recognises the malonyl portion of the acylthioester rather than necessarily the coenzyme A portion. In all probability some of the similarities previously identified by sequence analysis are due to evolutionary conservation rather than a mechanistic requirement. In contrast the residues we have identified lie in or close to the substrate binding pocket. To assess the exact location of the motif in space we compared the protein sequence of ATs derived from Type I PKS with that of *E. coli* fatty acid malonyl-CoA:ACP acyltransferase, for which there is a high resolution X-ray crystal structure (Serre, L. et al., J. Biol. Chem. (1995) 270: 12961-12964). While overall level of sequence similarity between these proteins is low, key residues (and particularly those with mechanistic importance) are conserved and the overall spatial arrangement of amino acids is expected to be conserved. Many groups have used this structure as a model AT and it is well known in the art that conservation of structure can be greater than the level of sequence conservation. Structural analysis showed that the identified motif would lie within the active site pocket opposite the active site serine and the arginine thought to be involved in binding the substrate carboxylate and close enough to the acyltransferase site to interact with the bound substrate side chain. The invariant histidine found in the motif is thought be part of a catalytic triad with the active site serine as is typically found in serine hydrolases (Serre et al, Supra). FIG. 3 shows the position of the motif loop and important active site residues in the model AT structure.

Broadly the invention concerns modifying an AT domain by changing the four-residue sequence or motif responsible for selecting a substrate so that its specificity is altered. We may also change a small number of other residues close to the active site. Generally the total number of residues changed is less than 5% of the residues of the AT.

The motif is the four-residue sequence corresponding to the YASH (SEQ ID NO:114) motif found at about residues 334-337 of the AT domain of the first module of DEBS, numbering as shown in FIG. 2. It lies in the active site pocket. It typically starts 80-110, more particularly 90-100, amino acids downstream of the GHS active site motif.

In a preferred embodiment of this invention polyketides of desired structure are produced by the replacement of an existing AT motif on a PKS with an alternative one responsible for selection of an alternative extender or starter unit, or responsible for an altered degree of selectivity (in most cases, increased selectivity). This may be carried out in one or more of the modules encoding a PKS cluster. One type of embodiment is a PKS including two adjoining domains, which are "naturally" adjoining or otherwise coupled domains, wherein the first of them is an AT domain where the four-residue motif has been altered to change its specificity, the AT domain acting to transfer a substrate to the second domain.

In one class of embodiments, this invention provides a PKS multienzyme or part thereof, or nucleic acid (generally DNA) encoding it, said multienzyme or part comprising a loading module and a plurality of extension modules for the generation of a polyketide, preferably selected from, macrolides, polyethers, or polyenes, wherein the loading or extension modules or at least one thereof contain a modified AT domain adapted to load and transfer an optionally substituted malonyl-CoA residue to (preferably) the ACP. The AT domain is preferably modified to alter its substrate specificity. This AT domain may differ from one naturally found in this position in the module only by the modification of a few amino acids lying in the active site. This modification comprises the exchange of all or part of a motif particularly but not limited to HAFH with YASH or TAGH or vice versa. Optionally, alterations to amino acids outside this sequence, but preferably lying close to the AT active site, are made.

A second class of embodiments provides a method of synthesising polyketides having a desired extension unit at any point around the polyketide molecule by providing a PKS multienzyme incorporating one or more modified AT domains and particularly but not limited to an AT domain possessing the motif HAFH (SEQ ID NO:117) or YASH (SEQ ID NO:114) or TAGH (SEQ ID NO:118) where these motifs replace the existing natural motif. Optionally, alterations to amino acids outside this sequence, but preferably lying close to the AT active site, are made.

A third class of embodiments provides a method of synthesising polyketides having a desired starter unit by providing a PKS multienzyme incorporating a modified AT domain in the loading module and particularly (but not limited to) an AT domain possessing the motif HAFH (SEQ ID NO:117) or YASH (SEQ ID NO:114) or TAGH (SEQ ID NO:118) or a motif incorporating a proline residue where these motifs replace the existing natural motif. Optionally, alterations to amino acids outside this sequence, but preferably lying close to the AT active site, are made. Preferentially, this AT will follow a KSQ domain but other loading systems are known in the art (e.g. AT-ACP). Patent application WO 00/00500 describes some of the known loading systems. The modification of the loading module can be combined with similar modifications in other extension units.

A further class of embodiments provides a method of synthesising polyketides free of natural co-produced analogues and having a desired extender or loading unit by replacing an existing hybrid or alternative protein motif with the sequences HAFH (SEQ ID NO:117), YASH (SEQ ID NO:114) or TAGH (SEQ ID NO:118). It is particularly useful to make this alteration in the epothilone or monensin PKS gene cluster.

In still further aspects this invention provides a method of synthesising a mixed population of polyketides by providing a PKS multienzyme incorporating an AT with a altered or hybrid motif, particularly, but not limited to HASH or VAGH. One particular utility of this method, though not limited to this utility, is the production of combinatorial libraries of compounds.

In a further aspect the PKS containing a modified AT domain may be spliced to a hybrid PKS produced for example as in WO 98/01546 and WO 98/01571 or WO 00/01827 or WO 00/00500. It is particularly useful to link such a modified PKS to gene assemblies that produce novel derivatives of natural polyketides, for example 14-membered macrolides.

Each of these aspects and classes of embodiment may involve providing nucleic acid encoding the polyketide synthase multienzyme and introducing it into a organism where it can be expressed. Suitable plasmids and host cells are described below. The polyketide synthase so produced or portions thereof may be isolated from the host cells by routine methods, though it is usually preferable not to do so. The host cells may also be capable of producing the required acylthioester, eg. by producing ethylmalonyl CoA for example. It may be advantageous to remove the PKS from a strain with a particularly strong supply of an undesired acylthioester or express the altered PKS in a strain specifically chosen to have a strong supply of a particular acylthioester, or alternatively to develop media or growth conditions to enhance expression of the desired product. Conversely, such techniques could be used to promote formation of mixtures of products if so desired. It may also be beneficial to supply chemical precursors to the desired acylthioesters in the media e.g. supply diethylethylmalonate or cyclobutane carboxylic acid etc. The host cells may also be capable of modifying the initial PKS products, e.g. by carrying out all or some of the biosynthetic modifications normal in the production of erythromycin (as shown in FIG. 4) and for other polyketides. Use may be made of mutant organisms such that some or all of the normal pathways are blocked, e.g. to produce products without one or more "natural" hydroxy groups or methyl groups or sugar groups.

The invention should not be limited to the exact motifs described. We have described some of the known variations within the motif, particularly at residue 1 as can be determined by inspection of FIG. 2 or by inspection of similar sequence data. However other modifications can be envisaged; substitution of, for example, the phenylalanine in the malonyl-CoA motif by the similar sized tyrosine may still display the same selectivity. Similarly substitution of the small residue glycine found in the motif responsible for ethylmalonyl-CoA/other extender incorporation by for example but not limited to alanine. It is well known to those skilled in the art that these and other similar conservative substitutions frequently maintain the same selectivity. Similarly the serine residue found in the motif for incorporation of methylmalonyl-CoA could be substituted by a residue intermediate in size and/or displaying a similar charge distribution.

The invention should not be limited to changes only in this motif. Alterations to other residues around the AT domain may also be required to increase the level of specificity or catalytic efficiency, i.e. to increase the proportion or amounts of the desired products. These residues are preferentially close to the substrate binding pocket. The requirement for these additional alterations will depend on the particular context or change desired. Particular residues to alter can be readily identified by inspection of FIG. 2 or other similar sequence analysis data or alternatively by analysis of the structural model.

Residues that may be altered in addition to the motif can be divided into two classes. Some of these residues may have been previously identified in the motifs used to predict the specificity of a motif (ie. Haydock et al. (FEBS Lett. (1995) 374:246-248). These residues are preferentially close to the substrate-binding pocket. These residues should not be limited to the particular examples described.

I) The first class of potential residues to change includes residues close to the motif on the polypeptide chain. A particular example is the residue immediately after the 4 residue motif described in the present invention. In malonyl-CoA specific ATs this residue is generally serine (S), i.e. the protein sequence at this point is generally HAFHS (SEQ ID NO:123), whereas in methylmalonyl-CoA specific ATs this residue can be S but can also be T, G, or C for example. Thus to change a methylmalonyl-CoA specific AT to a malonyl-CoA specific AT by changing the signature motif it may be beneficial also to ensure that the residue immediately after the motif is an S. Since this residue is close to the motif on the polypeptide chain it lies close to the substrate binding pocket.

II) The second class includes residues that are close to the motif or active site in space. These residues are best identified by reference to the model AT structure described previously or another AT structure that may be subsequently derived. It is known to those skilled in the art that it is possible to thread related protein sequences into an existing structure by using structure molecular modelling or related techniques. Alternatively, an acylthioester may be modelled into the active site. These are the preferred methods, but often-simple inspection of the existing structure using the highly conserved motifs as a reference point gives a reasonable approximation.

A particular example of a residue close in space to the motif that might be changed is the residue immediately after the GHS active site motif. In methylmalonyl-CoA specific ATs this residue is generally glutamine (Q), i.e. the protein sequence at this point is GHSQ (SEQ ID NO:124), whereas in malonyl-CoA specific ATs this residue is often V, I or L for example. Thus to change a malonyl-CoA specific AT to a methylmalonyl-CoA specific AT by changing the signature motif it may be beneficial also to ensure that the residue immediately after the GHS motif is a Q. Since this residue is close to the active site serine it lies within the substrate-binding pocket.

A further example of a residue close in space that might be altered is the residue lying three residues downstream of the GQG motif. In methylmalonyl-CoA specific ATs this residue is generally tryptophan (W), i.e. the protein sequence at this point is GQGXXW (SEQ ID NO:125), whereas in malonyl-CoA specific ATs this residue is often R, H or T for example. Thus to change a malonyl-CoA specific AT to a methylmalonyl-CoA specific AT by changing the signature motif it may be beneficial also to ensure that this particular residue after the GQG motif is a W. Analysis of the model AT structure shows that the GQG motif lies close to the active site pocket and consequently so does this tryptophan.

A further example of a residue close in space that might be altered is the residue 4 residues downstream from the conserved arginine referred to above, which is believed to stabilise the carboxylate group of the acylthioester substrate. In malonyl-CoA specific ATs this residue downstream of the R is generally methionine (M), i.e. the protein sequence at this point is RXXXMQ. In methylmalonyl-CoA specific ATs this residue is generally I or L, and in ethylmalonyl-CoA specific ATs it is often W. Thus, for example, to change a methylmalonyl-CoA specific AT to a malonyl-CoA specific AT by changing the signature motif it may be beneficial also to ensure that this particular residue is a methionine. Analysis of the model AT structure shows that this residue lies close to the active site pocket.

In further aspects the present invention provides vectors, such as plasmids or phages (preferably plasmids), including nucleic acids as defined in the above aspects and host cells particularly *Saccharopolyspora* or *Streptomyces* species transformed with such nucleic acids or constructs. It will be readily apparent to those skilled in the art that there are multiple molecular biological methods for achieving the desired alterations to the AT domain, particularly at the nucleic acid level, e.g. techniques of site directed mutagenesis or directed evolution. Suitable plasmid vectors and genetically engineered cells suitable for expression of PKS genes with modules incorporating an altered AT domain can readily be designed or selected by those skilled in the art. They include those described in WO 98/01546 as being suitable for expression of hybrid PKS genes of Type I. Examples of effective hosts are *Saccharopolyspora erythraea, Streptomyces coelicolor, Streptomyces avermitilis, Streptomyces griseofuscus, Streptomyces cinnamonensis, Streptomyces fradiae, Streptomyces longisporoflavus, Streptomyces hygroscopicus, Micromonospora griseorubida, Streptomyces lasaliensis, Streptomyces venezuelae, Streptomyces antibioticus, Streptomyces lividans, Streptomyces rimosus, Streptomyces albus, Amycolatopsis mediterranei,* and *Streptomyces tsukubaensis.* These include hosts in which SCP2*-derived plasmids are known to replicate autonomously, such as for example *S. coelicolor, S. avermitilis* and *S. griseofuscus*; and other hosts such as *Saccharopolyspora erythraea* in which SCP2*-derived plasmids become integrated into the chromosome through homologous recombination between sequences on the plasmid insert and on the chromosome; and all such vectors which are integratively transformed by suicide plasmid vectors. A plasmid with an int sequence will integrate into a specific attachment site on the host's chromosome.

It is apparent to those skilled in the art that the overall sequence similarity between nucleic acids encoding comparable AT domains from Type I PKSs is sufficiently high and the domain organisation of different Type I PKSs so consistent between different polyketide-producing organisms, that the processes for obtaining novel hybrid polyketides described will be generally applicable to all natural modular Type I PKSs or their derivatives.

The present invention will now be illustrated, but is not intended to be limited, by means of some examples.

Amino acids have been defined throughout by their standard one letter codes as follows. A—alanine, R—arginine, N—asparagine, D—aspartic acid, C—cysteine, Q—glutamine, E—glutamic acid, G—glycine, H—histidine, I—isoleucine, L—leucine, K—lysine, M—methionine, F—phenylalanine, P—proline, S—serine, T—threonine, W—tryptophan, Y—tyrosine and V—valine.

BRIEF DESCRIPTION OF DRAWINGS

FIG. 1 is a diagram showing the functioning of 6-deoxyerythronolide B synthase (DEBS), a modular PKS producing 6-deoxyerythronolide B, a precursor of erythromycin A.

FIG. 2a-v gives the amino acid sequence comparison of the AT domains of representative Type I PKS gene clusters (SEQ ID NOs: 1-112). The motifs GQG, GHS and LPTY (SEQ ID NO: 115) are marked at the base of the figure along with the arginine (at position 252 in the sequence alignment, which corresponds to residue 144 of SEQ ID NO:26) and the motif defined in the invention as defining specificity. The abbreviations used at the side to define the PKS used are: aye: avermectin, debs: 6-deoxyerythronolide B synthase or erythromycin, epo:epothilone, sor: soraphen, fkb: FK506, rap: rapamycin, tyl: tylosin, mon: monensin, nid:niddamycin, nys: nystatin, rif: rifamycin. The numbers represent the module number. The letter at the end of the designation indicates malonyl-CoA specific AT, the letter p indicates methylmalonyl-CoA specific AT, and the letter b indicates ethylmalonyl-CoA specific AT. Further types of AT with unusual or ill-defined AT specificity are indicated with letter x. Due to the numbers of sequences considered, in the pileup each section of 50 amino acids spreads over two pages. The sequences of the monensin ATs are unpublished. They are set out in PCT/GB00/02072.

FIG. 5 shows the DNA sequence from the monensin PKS encoding the loading AT used in Example 8 (SEQ ID NO:113.

MODES FOR CARRYING OUT THE INVENTION

Example 1

Construction of Plasmid pHP41

Figure 3:
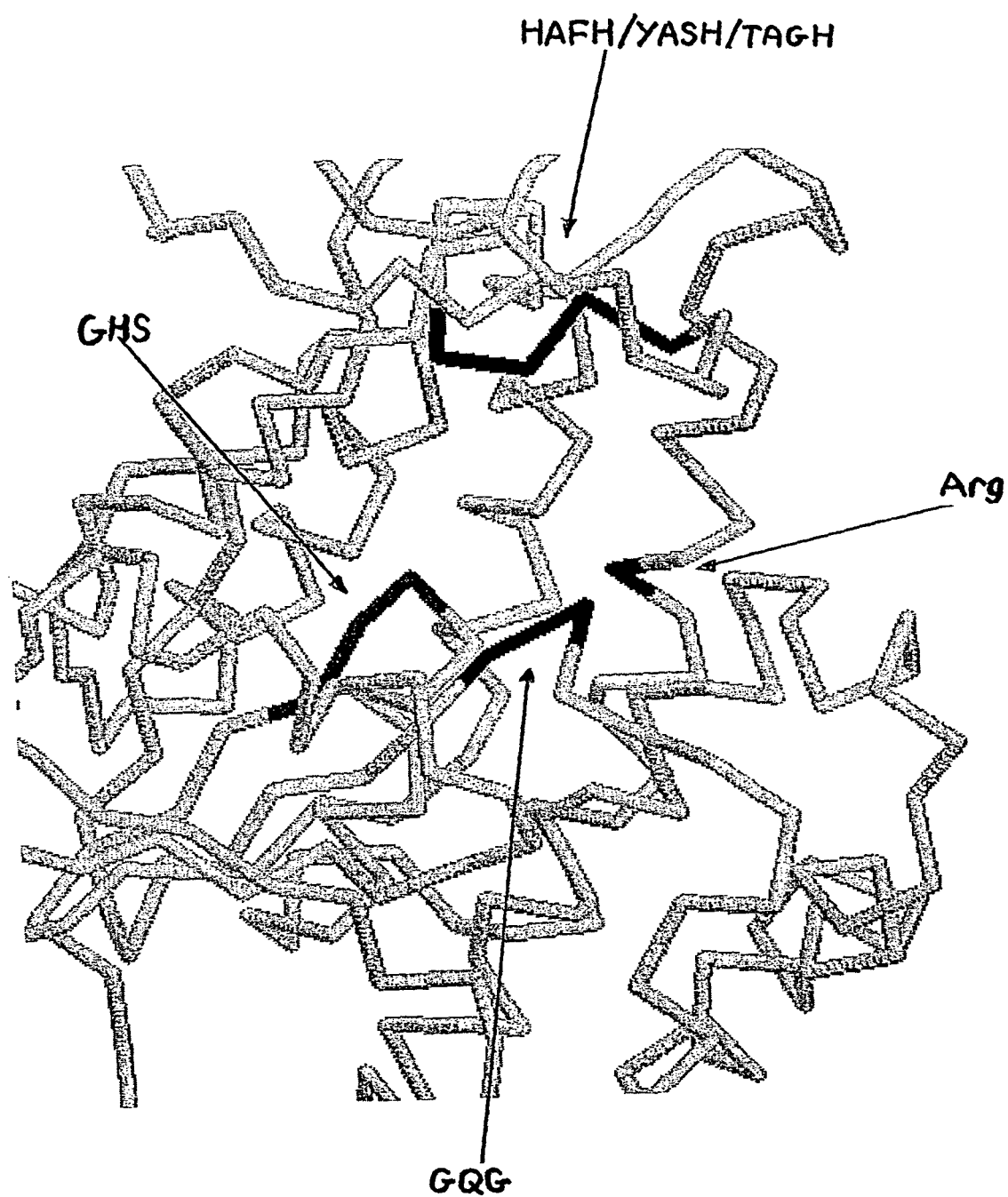
FIG. 3 shows a three-dimensional representation of the active site of the *E. coli* acyltransferase. The spatial arrangement of the motifs described in the text are shown by arrows and the atoms shown in bold.
Figure 4:
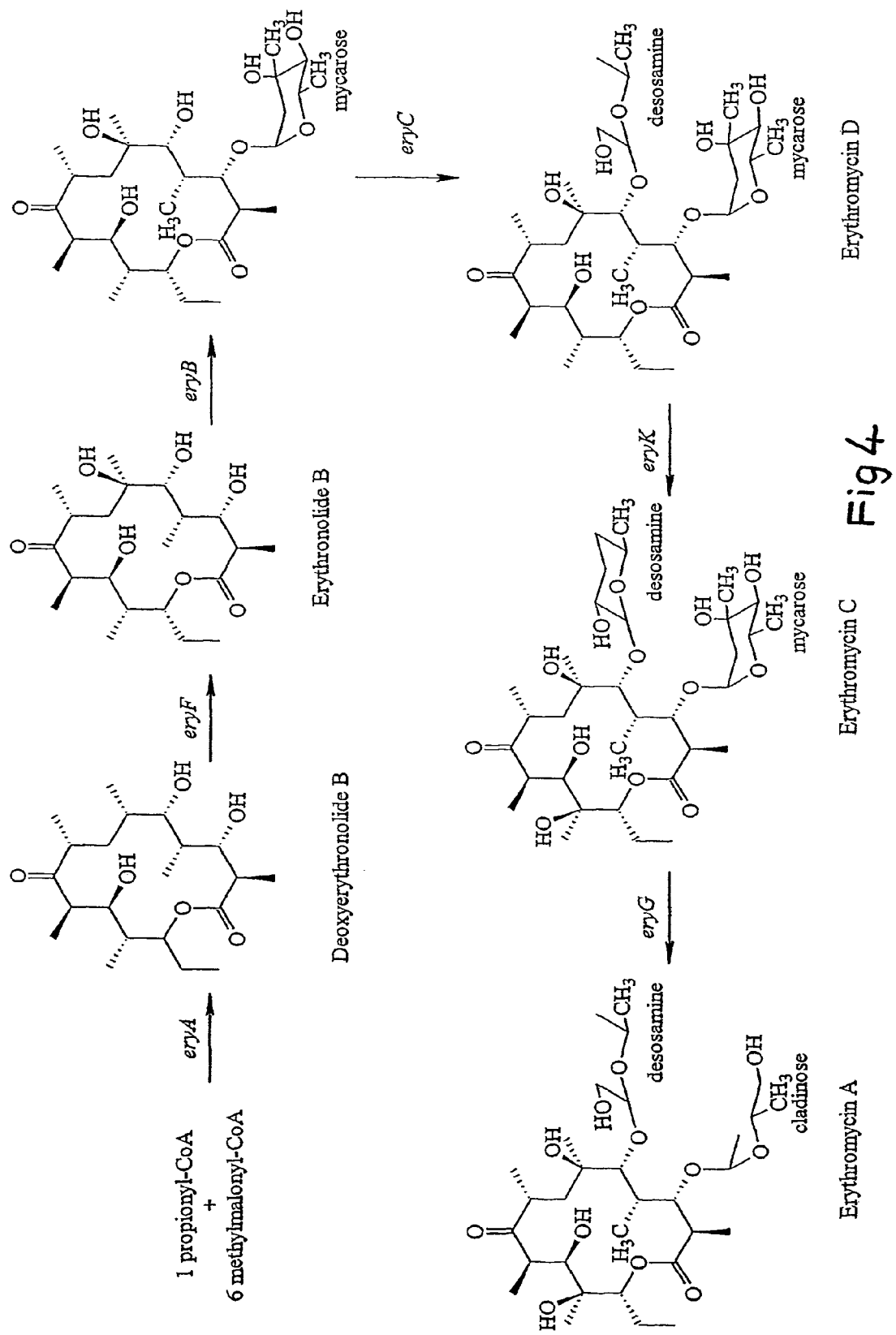
FIG. 4 shows the enzymatic steps that convert 6-deoxyerythronolide B into erythromycin A in *Saccharopolyspora erythraea*.

Plasmid pHP41 is a pCJR24-based plasmid containing the DEBS1 PKS gene comprising a loading module, the first and second extension modules of DEBS and the chain terminating thioesterase. The motif YASH (SEQ ID NO:114) of the AT domain of first module has been altered to HAFH (SEQ ID NO:117). Plasmid pHP41 was constructed by several intermediate plasmids as follows. Plasmid pD1AT2 (Oliynyk, M. et al. Chem. Biol. (1996) 3:833-839) was digested with NdeI and XbaI. A ~11 kbp fragment was isolated by gel electrophoresis and the DNA purified from the gel. This fragment was ligated into pCJR24 (Rowe, C. J. et al. Gene (1998) 216:215-223) that had been linearised by digestion with NdeI and XbaI and treated with alkaline phosphatase. The ligation mixture was used to transform electrocompetent *E. coli* DH10B cells and individual clones checked for the desired plasmid pCJR26. Plasmid pCJR26 was identified by restriction pattern. pCJR26 was transformed into *E. coli* strain ET12567 (McNeil, D. J. et al. Gene (1992) 111:61-68) and an individual colony grown overnight to isolate demethylated DNA. This DNA was linearised using MscI and AvrII and the ~13 kb fragment (Fragment A) isolated by gel electrophoresis and purification from the gel.

A DNA segment of the eryAI gene (start nucleotide 45368, end nucleotide 34734) from *S. erythraea* extending from nucleotide 42104 to nucleotide 41542 was amplified by PCR using the following oligonucleotide primers; 5'-TTTTTTTG-GCCAGGGTTGGCAGTGGGCGGGCA-3' (SEQ ID NO:127) and 5'-TTTTTACGGCCAGCCGCTTGGCGCG-GAT-3' (SEQ ID NO:128). The DNA from a plasmid designated pCJR65 derived from pCJR24 and DEBS1TE was used as a template. The design of the primers introduced a MscI site at nucleotide 42105 and the second primed across a BstXI site at position 41546. The 574 bp PCR product was treated with T4 polynucleotide kinase and ligated to plasmid pUC18 that had been linearised by digestion with SmaI and then treated with alkaline phosphatase. The ligation mixture was used to transform electrocompetent *E. coli* DH10B and individual clones checked for the presence of the desired plasmid pHP39. Plasmid pHP39 was identified by restriction pattern and sequence analysis. Demethylated DNA was produced by transforming *E. coli* strain ET12567 with plasmid DNA. The resulting DNA was linearised by digestion with MscI and BstXI and the resulting 552 bp fragment (Fragment B) isolated by gel electrophoresis and purified from the gel. A DNA segment of the eryAI gene from *S. erythraea* extending from nucleotide 41557 to nucleotide 41120 was amplified by PCR using the following oligonucleotide primers; 5'-CGGTGC-CTAGGTGCACCGACTCCCAGTCC-3'(SEQ ID NO:129) 5'-TTTTTCCAAGCGGCTGGCCGTGGAC-CACGCGTTCCACTCCTCGCACGTCGAGACGAT-3' (SEQ ID NO:130) DNA from plasmid pCJR65 was used as a template. The design of the primers introduced an AvrII site at nucleotide 41125 and the second primed across a BstXI site at nucleotide 41557 and mutated the amino acid sequence YASH (SEQ ID NO:114) to HAFH (SEQ ID NO:117) (encoded by nucleotides 41537-41526). The 442 bp PCR product was treated with T4 polynucleotide kinase and ligated to plasmid pUC18 that had been linearised by digestion with SmaI and then treated with alkaline phosphatase. The ligation mixture was used to transform electrocompetent *E. coli* DH10B and individual clones checked for the presence of the desired plasmid pHP40. Plasmid pHP40 was identified by restriction pattern and sequence analysis. Plasmid pHP40 was linearised by digestion with restriction enzymes AvrII and BstXI, and a 427 bp fragment (Fragment C) isolated by gel electrophoresis and purified from the gel. Fragments A, B, and C were ligated together and the resulting ligation mixture used to transform electrocompetent *E. coli* DH10B. Individual clones were checked for the presence of an insert derived from DEBS1. The resulting plasmid was designated pHP41. Sequence analysis was used to confirm the clone contained the correct motif HAFH (SEQ ID NO:117).

Example 2

Construction of *S. erythraea* NRRL2338 JC2/pHP41 and Production of Triketides

*S. erythraea* NRRL2338 JC2 contains a deletion of the eryAI, eryAII and eryAIII apart from the TE (Rowe, C. J. et al. Gene 216, 215-223). Plasmid pHP41 was used to transform *S. erythraea* NRRL2338 JC2 protoplasts using the TE as a homology region. Thiostrepton resistant colonies were selected on R2T20 agar containing 40 µg/ml thiostrepton. *S. erythraea* NRRL2338 JC2 (pHP41) was plated onto SM3 agar (see patent application WO 00/01827) containing 40 µg/ml thiostrepton and allowed to grow for 11 days at 30° C. Approximately 1 cm² of the agar was homogenised and extracted with a mixture of 1.2 ml ethyl acetate and 20 µl formic acid. The solvent was decanted and removed by evaporation and the residue dissolved in methanol and analysed by GC/MS. The major products were identified by comparison with authentic standards (Oliynyk, M. et al. Chem. Biol. (1996) 3:833-839) as triketide lactones (2S,3R,5R)-2-methyl-3,5-dihydroxy-n-hexanoic δ-lactone (AAP, i.e. Acetate, Acetate, Propionate incorporation), (2S,3R,5R)-2-methyl-3,5-dihydroxy-n-heptanoic δ-lactone (PAP), (2R,3S, 4S,5R) 2, 4-dimethyl-3,5-dihydroxy-n-heptanoic δ-lactone (PPP) and (2R,3S,4S,5R) 2, 4-dimethyl-3,5-dihydroxy-n-hexanoic δ-lactone (APP). These products were identified as their ammonium adducts corresponding to exact mass 144, 158, 172 and 158. Four products were produced because in this strain, and under the conditions of the experiment the loading module loads both acetate and propionate and the modified AT loads malonyl-CoA and methylmalonyl-CoA. Only three triketide lactone peaks could be observed in the GC/MS spectra under standard conditions, this was due to the co-elution of the equivalent mass APP and PAP compounds. An isocratic gradient was used to verify this peak was comprised of two components. In further sets of experiments *S. erythraea* JC2 (pHP41) was used to inoculate 5 ml TSB containing 5 µg/ml thiostrepton. After three days growth 1.5 ml of this culture was used to inoculate 25 ml SM3 media containing 5 µg/ml thiostrepton in a 250 ml flask. The flask was incubated at 30° C., 250 rpm for 6 days. At this time the supernatant was adjusted to pH 3.0 with formic acid and extracted twice with an equal volume of ethyl acetate. The solvent was removed by evaporation and the residue analysed by GC/MS. In each experiment we could identify the 4 products AAP, PAP, PPP and APP but the absolute ratios and quantities were variable, presumably depending on exact media and growth conditions within each flask (FIG. 6).

Example 3

Construction of *S. erythraea* NRRL2338 (pHP41) and Its Use to Produce 12-desmethyl Erythromycin B Plasmid pHP41 was used to transform *S. erythraea* NRRL2338 protoplasts. Thiostrepton resistant colonies were selected on R2T20 agar containing 40 µg/ml thiostrepton. Several clones were tested for the presence of pHP41 integrated into the chromosome by Southern blot hybridisation of their genomic DNA with DIG labelled vector DNA. A clone with a correctly integrated copy of pHP41 was identified in this way. *S. erythraea* NRRL2338 (pHP41) was used to inoculate 5 ml TSB containing 5 µg/ml thiostrepton. After three days growth 1.5 ml of this culture was used to inoculate 25 ml EryP media (see patent application WO 00/00500) containing 5 µg/ml thiostrepton in a 250 ml flask. The flask was incubated at 30° C., 250 rpm for 6 days. At this time the supernatant was adjusted to pH 9.0 with ammonia and extracted twice with an equal volume of ethyl acetate. The solvent was removed by evaporation and the residue analysed by HPLC/MS. A peak of molecular mass m/z (M+H)=704 was observed required for C-12 desmethyl erythromycin B in addition to a peak corresponding to erythromycin A (M+H)= 734. Other peaks corresponding to partially processed erythromycin intermediates could be identified.

Example 4

Construction of Plasmid pHP048

Plasmid pHP048 is a pCJR24-based plasmid containing the DEBS1 PKS gene comprising a loading module, the first and second extension modules of DEBS1 and the chain terminating thioesterase. The motif YASH of the AT domain of first module has been altered to HASH. Plasmid pHP048 was constructed by several intermediate plasmids as follows.

A DNA segment of the eryAI gene from *S. erythraea* extending from nucleotide 41557 to nucleotide 41120 was amplified by PCR using the following oligonucleotide primers; 5'-CGGTGCCTAGGTGCACCGACTCCCAGTCC-3' (SEQ ID NO:129) and 5'-TTTTTCCAAGCGGCTGGC-CGTGGACCACGCGTCGCACTCCTCG-CACGTCGAGACGAT-3' (SEQ ID NO:131). The DNA from plasmid pCJR65 was used a as template. The design of the primers introduced a AvrII site at nucleotide 41125 and the second extended to a BstXI site at nucleotide 41557, also mutated the amino acid sequence YASH (SEQ ID NO:114) (encoded by nucleotides 41537-41526) to HASH (SEQ ID NO:121). The 442 bp PCR product was treated with T4 polynucleotide kinase and ligated to plasmid pUC18 that had been linearised by digestion with SmaI and then treated with alkaline phosphatase. The ligation mixture was used to transform electrocompetent *E. coli* DH10B and individual clones checked for the presence of the desired plasmid pHP022. Plasmid pHP022 was identified by restriction pattern and sequence analysis. Plasmid pHP022 was linearised by digestion with restriction enzymes AvrII and BstXI, and the fragment (Fragment D) isolated by gel electrophoresis and purified from the gel. Fragment D was ligated with Fragments A and B described previously and the resulting ligation mixture used to transform electrocompetent *E. coli* DH10B. Individual clones were checked for the presence of an insert derived from DEBS1. The resulting plasmid was designated pHP048. Sequence analysis was used to confirm the clone contained the correct motif HASH (SEQ ID NO:121).

Example 5

Construction of *S. erythraea* NRRL2338 JC2 (pHP048) and Its Use to Produce Triketides

*S. erythraea* NRRL2338 JC2 contains a deletion of the eryAI, eryAII and eryAIII apart from the TE (Rowe, C. J. et al. Gene 216, 215-223). Plasmid pHP048 was used to transform *S. erythraea* NRRL2338 JC2 protoplasts using the TE as a homology region. Thiostrepton resistant colonies were selected on R2T20 agar containing 40 g/ml thiostrepton. *S. erythraea* JC2 (pHP048) was used to inoculate 5 ml TSB containing 5:g/ml thiostrepton. After three days growth 1.5 ml of this culture was used to inoculate 25 ml SM3 media containing 5 :g/ml thiostrepton in a 250 ml flask. The flask was incubated at 30° C., 250 rpm for 6 days. At this time the supernatant was adjusted to pH 3.0 with formic acid and extracted twice with an equal volume of ethyl acetate. The solvent was removed by evaporation and the residue analysed by GC/MS. A mixture of products were identified as their ammonium adducts corresponding to the AAP, PAP, APP and PPP triketide lactones as described in example 2. In this example, under the media/growth conditions described the PKS with the HASH (SEQ ID NO:121) change is more catalytically active than the HAFH (SEQ ID NO:117) change (example 2) as judged by total amounts of triketide lactone produced, however in this case the modified PKS appears to display lower selectivity towards acetate as judged by the ratio of AAP to PPP triketide lactone.

Example 6

Construction of Plasmid pHP47

Plasmid pHP47 is a pCJR24-based plasmid containing the DEBS1 PKS gene comprising a loading module, the first and second extension modules of DEBS1 and the chain terminating thioesterase. The motif YASH of the AT domain of first module has been altered to VAGH. Plasmid pHP47 was constructed by several intermediate plasmids as follows.

A DNA segment of the eryAI gene from *S. erythraea* extending from nucleotide 41557 to nucleotide 41120 was amplified by PCR using the following oligonucleotide primers; 5'-CGGTGCCTAGGTGCACCGACTCCCAGTCC-3' (SEQ ID NO:129) and 5'-TTTTTCCAAGCGGCTGGC-CGTGGACGTCGCGGGGCACTCCTCG-CACGTCGAGACGAT-3' (SEQ ID NO:130). The DNA from plasmid pCJR65 was used as a template. The design of the primers introduced a AvrII site at nucleotide 41125 and the second extended to a BstXI site at nucleotide 41557, also mutated the amino acid sequence YASH (SEQ ID NO:114) (encoded by nucleotides 41537-41526) to VAGH. The 442 bp PCR product was treated with T4 polynucleotide kinase and ligated to plasmid pUC18 that had been linearised by digestion with SmaI and then treated with alkaline phosphatase. The ligation mixture was used to transform electrocompetent *E. coli* DH10B and individual clones checked for the presence of the desired plasmid pHP46. Plasmid pHP46 was identified by restriction pattern and sequence analysis. Plasmid pHP46 was linearised by digestion with restriction enzymes AvrII and BstXI, and the fragment (Fragment E) isolated by gel electrophoresis and purified from the gel. Fragment E was ligated with Fragments A and B described previously and the resulting ligation mixture used to transform electrocompetent *E. coli* DH10B. Individual clones were checked for the presence of an insert derived from DEBS1. The resulting plasmid was designated pHP47. Sequence analysis was used to confirm the clone contained the correct motif VAGH (SEQ ID NO:122).

Example 7

Construction of Plasmid pLS007

Plasmid pLS007 contains the crotonyl-CoA reductase (CCR) gene from *S. cinnamonensis* that is believed to influence the level of ethylmalonyl-CoA within the cell. Plasmid pSG142 (Gaisser et al. Mol. Microbiol. (2000) 36 391-401) places genes under the control of the actI promoter and can be used to integrate either in the right hand side of the erythromycin gene cluster or in the act promoter region of a previously transformed actinomycete. Two oligonucleotide primers; 5'-GGCAAACATATGAAGGAAATCCTGGACGCG-3' (SEQ ID NO:133) and 5'-TCCGCGGATCCTCAGTGCGT-TCAGATCAGTGC-3' (SEQ ID NO:134) were used to amplify the *S. cinnamonensis* CCR gene using genomic DNA as template. The design of the primers incorporated NdeI and BamHI restriction sites to facilitate cloning. The 1.4 kb PCR product was isolated by gel electrophoresis and purified from the gel and ligated with pSG142 that had been digested with NdeI and BglII. The resulting ligation mixture was used to transform electrocompetent *E. coli* DH10B cells. Plasmid pLS003 was identified by restriction analysis and sequencing to ensure errors were not introduced during amplification. A discrepancy with the published sequence was identified. However, further analysis by comparison with other published CCR protein sequences indicated pLS003 was correct. Plasmid pLS003 was digested with NdeI and XbaI and the resulting 4.5 kb fragment (fragment F) isolated by gel electrophoresis and purified from the gel. This fragment was ligated to pLSB2 a derivative of pKC1132 containing the actI/actII promoter region behind an NdeI site. Plasmid pLSB2 was digested with NdeI and XbaI and the resulting ~4 kb fragment (Fragment G) purified by gel electrophoresis and purified from the gel. Fragments F and G were ligated together and the resulting ligation mixture was used to transform electrocompetent *E. coli* DH10B cells. Plasmid pLS007 was identified by restriction analysis.

Example 8

Construction of *S. erythraea* NRRL2338 JC2 (pHP47/pLS007) and Its Use to Produce Triketides

*S. erythraea* NRRL2338 JC2 contains a deletion of the eryAI, eryAII and eryAIII apart from the TE (Rowe, C. J. et al. Gene 216, 215-223). Plasmid pHP47 was used to transform *S. erythraea* NRRL2338 JC2 protoplasts using the TE as a homology region. Thiostrepton resistant colonies were selected on R2T20 agar containing 40 µg/ml thiostrepton. pLS007 was used to transform protoplasts of *S. erythraea* NRRL2338 JC2 (pHP47), thiostrepton and apramycin resistant clones were selected on R2T20 agar containing 40 µg/ml thiostrepton and 50 µg/ml apramycin plus 10 mM magnesium chloride and the resistance markers verified by plating on tapwater media containing the same antibiotics. *S. erythraea* NRRL2338 JC2 (pHP47/pLS007) was used to inoculate 5 ml TSB containing 5 µg/ml thiostrepton and 50 µg/ml apramycin. After three days growth 1.5 ml of this culture was used to inoculate 25 ml SM3 media containing 5 µg/ml thiostrepton and 50 µg/ml apramycin in a 250 ml flask. The flask was incubated at 30° C., 250 rpm for 6 days. At this time the supernatant was adjusted to pH 3.0 with formic acid and extracted twice with an equal volume of ethyl acetate. The solvent was removed by evaporation and the residue analysed by GC/MS. In this experiment amounts of triketide product were lower but a mixture of products could be identified as their ammonium adducts corresponding to exact masses 158 172 and 186.

Example 9

Construction of *S. erythraea* NRRL2338 (pHP47) and Its Use to Produce Erythromycins Plasmid pHP47 was used to transform *S. erythraea* NRRL2338 protoplasts. Thiostrepton resistant colonies were selected on R2T20 agar containing 40 µg/ml thiostrepton. *S. erythraea* NRRL2338 (pHP47) was used to inoculate 5 ml TSB containing 5 µg/ml thiostrepton. After three days growth 1.5 ml of this culture was used to inoculate 25 ml EryP media containing 5 µg/ml thiostrepton in a 250 ml flask. The flask was incubated at 30° C., 250 rpm for 6 days. At this time the supernatant was adjusted to pH 9.0 with ammonia and extracted twice with an equal volume of ethyl acetate. The solvent was removed by evaporation and the residue analysed by HPLC/MS. Peaks of mass m/z (M+H)=734 corresponding to erythromycin A were observed.

Example 10

Construction of Plasmid pSGK051 pSGK051 is a pPFL43 based plasmid (WO 00/00500). The motif HAFH (SEQ ID NO:117) of the AT domain of the loading domain has been altered to YASH (SEQ ID NO:114). Plasmid pSGK051 was constructed by several intermediate plasmids as follows.

Plasmid pPFL43 was linearised by digestion with restriction enzymes NcoI and NotI and a 858 bp fragment (Fragment Q) isolated by gel electrophoresis and purified from the gel.

A DNA segment of the monensin loading domain from nucleotide 16360-17366 (see FIG. 5 and PCT/GB00/02072) was amplified by PCR using the following oligonucleotide primers;

```
                                              (SEQ ID NO: 135)
5'-GGGGACGCGGCCGCAAGGCCCACCACCTGAAGGTCAGCTACGC

CTCCCACTCCCCGCACATGGACCCCAT-3'  and (SEQ ID NO: 136)
5'-GGCTAGCGGGTCCTCGTCCGTGCCGAGGTCA-3'.
```

The design of the primers amplified across a NotI site at nucleotide 16367 and changed the amino acid sequence HAFH (SEQ ID NO:117) to YASH (SEQ ID NO:114) at nucleotides 16398-16409, the second introduced a NheI site equivalent to that in pPFL43. The DNA from plasmid pPFL43 was used as a template. The 1006 bp PCR product was treated with T4 polynucleotide kinase and ligated to plasmid pUC18 that had been linearised by digestion with SmaI and treated with alkaline phosphatase. The ligation mixture was used to transform electrocompetent *E. coli* DH10B and individual clones checked for the presence of the desired plasmid pCSAT9. Plasmid pCSAT9 was identified by restriction pattern and sequence analysis. Plasmid pCSAT9 was linearised by digestion with restriction enzymes NotI and NheI and a 995 bp fragment (Fragment R) isolated by gel electrophoresis and purified from the gel. Plasmid pPFL43 was digested with NcoI and NheI to remove a 1.8 kb fragment and the larger fragment (Fragment S) isolated by gel electrophoresis and purified from the gel. Fragments Q, R and S were ligated together and the resulting ligation mixture used to transform electrocompetent *E. coli* DH10B. Individual clones were checked for the desired plasmid pSGK051. The resulting plasmid was analysed by restriction digest and sequenced to confirm the presence of the correct motif YASH (SEQ ID NO:114).

Example 11

Construction of *S. erythraea* NRRL2338 JC2/pSGK051 and Production of Triketides Plasmid pSGK051 was used to transform *S. erythraea* NRRL2338 JC2 protoplasts using the TE as a homology region. Thiostrepton resistant colonies were selected on R2T20 agar containing 40 µg/ml thiostrepton. *S. erythraea* NRRL2338 JC2 (pSGK051) was plated onto R2T20 agar containing 40 µg/ml thiostrepton and allowed to grow for 11 days at 30° C. Approximately 1 cm² of the agar was homogenised and extracted with a mixture of 1.2 ml ethyl acetate and 20 µl formic acid. The solvent was decanted and removed by evaporation and the residue dissolved in methanol and analysed by GC/MS. The major products were identified by comparison with authentic standards as triketide lactones (2S,3R, 4S,5R)-2,4-dimethyl-3,5-dihydroxy-n-heptanoic δ-lactone and (2S,3R,4S,5R)-2,4-dimethyl-3,5-dihydroxy-n-hexanoic δ-lactone.

Example 12

Construction of *S. erythraea* NRRL2338 (pSGK051) and Its Use to Produce Erythromycins Plasmid pSGK051 was used to transform *S. erythraea* NRRL2338 protoplasts. Thiostrepton resistant colonies were selected on R2T20 agar containing 40 µg/ml thiostrepton. *S. erythraea* NRRL2338 (pSGK051) was plated onto R2T20 agar containing 40 µg/ml thiostrepton and allowed to grow for 10 days at 30° C. Approximately 2 cm² of the agar was homogenised and extracted with a mixture of 1.2 ml ethyl acetate and 20 µl dilute ammonia. The solvent decanted and was removed by evaporation and the residue analysed by HPLC/MS. Peaks of mass m/z (M+H)=734 and 720 could be observed alongside likely products of incomplete processing. Comparison to authentic standards proved the compounds produced were erythromycin A and 13-methyl erythromycin A.

---

The invention claimed is:

1. An isolated nucleic acid encoding a polyketide synthase (PKS) enzyme complex including an altered acyltransferase (AT) domain, wherein said AT domain has been altered to substitute selectively fewer than 9 amino acid residues of the AT domain with a different amino acid residue, the substituted residue(s) consisting of one or more residues of one or more motifs which are present in the active site pocket of the AT domain and which influence the substrate specificity of the AT domain, at least one substitution affecting the substrate specificity, wherein said substituted residue(s) consists of:
   (a) all or part of the four-residue sequence corresponding to the YASH motif (SEQ ID NO: 114) of the AT domain of the first module of DEBS (6-deoxyerythronolide B synthase); and, optionally, one or more selected from:
   (b) the residue that is immediately downstream of said four-residue sequence corresponding to the YASH motif of the AT domain of the first module of DEBS;
   (c) the residue that is immediately downstream of the GHS motif;
   (d) the residue that is three residues downstream of the GQG motif; and
   (e) the residue that is four residues downstream of the conserved arginine residue as found at position 144 of SEQ ID NO:26, wherein the SEQ ID NO:26 is the AT domain of the first module of DEBS.

2. A vector comprising the nucleic acid according to claim 1.

3. An isolated host cell comprising the nucleic acid according to claim 1 and able to express the PKS enzyme complex.

4. The host cell according to claim 3 which is adapted to synthesize a polyketide resulting from the action of the PKS enzyme complex.

5. A method of synthesizing a polyketide synthase (PKS) enzyme complex, said method comprising culturing the host cell of claim 3 under suitable conditions and expressing the PKS enzyme complex.

6. The nucleic acid of claim 1, wherein the PKS enzyme complex comprises DEBS.

7. The nucleic acid according to claim 1, wherein said AT domain has been altered so as to alter a motif selected from XAFH (SEQ ID NO:137), XASH (SEQ ID NO: 138), and XAGH (SEQ ID NO:116) and/or to create such a motif, wherein X is any amino acid.

8. The nucleic acid according to claim 7, wherein the motif is XAGH (SEQ ID NO: 116), and X is selected from Phe, Thr, Val and His.

9. The nucleic acid according to claim 7, wherein the motif is XAFH (SEQ ID NO:137), and X is His.

10. The nucleic acid according to claim 7, wherein the motif is XASH (SEQ ID NO: 138), and X is selected from Tyr, His, Trp and Val.

11. The nucleic acid according to claim 1, wherein said four-residue sequence corresponding to the YASH motif of the AT domain of the first module of DEBS has been substituted with a different amino acid to produce or alter a motif containing proline.

12. The nucleic acid according to claim 1, wherein said four-residue sequence corresponding to the YASH motif of the AT domain of the first module of DEBS has been substituted with a different amino acid followed by S which was produced by amino acid substitution if not already present.

13. The nucleic acid according to claim 1, wherein said four-residue sequence corresponding to the YASH motif of the AT domain of the first module of DEBS has been substituted with a different amino acid to produce a motif specific for methylmalonyl-CoA, and the motif is followed by Ser, Gly, Cys or Thr which was produced by amino acid substitution if not already present.

14. The nucleic acid according to claim 1, wherein said AT domain has been substituted with a different amino acid to produce a motif specific for methylmalonyl-CoA, and the residue following the GHS motif in the active site is Gln which was produced by amino acid substitution if not already present.

15. The nucleic acid according to claim 1, wherein said AT domain has been substituted with a different amino acid to produce a motif specific for malonyl-CoA, and the residue following the GHS motif in the active site is Val, Ile or Leu which was produced by amino acid substitution if not already present.

16. The nucleic acid according to claim 1, wherein said AT domain has been substituted with a different amino acid to produce a motif specific for methylmalonyl-CoA, and the residue that is 3 residues downstream of the GQG motif is Trp which was produced by amino acid substitution if not already present.

17. The nucleic acid according to claim 1, wherein said AT domain has been substituted with a different amino acid to produce a motif specific for malonyl-CoA, and the residue that is 3 residues downstream of the GQG motif is Arg, His or Thr which was produced by amino acid substitution if not already present.

18. The nucleic acid according to claim 1, wherein said AT domain has been substituted with a different amino acid to produce a motif specific for malonyl-CoA and the residue that is 4 residues downstream of the conserved Arg as found at position 144 of SEQ ID NO:26 is Met which was produced by amino acid substitution if not already present.

19. The nucleic acid according to claim 1, wherein said AT domain has been substituted with a different amino acid to produce a motif specific for methylmalonyl-CoA and the residue that is 4 residues downstream of the conserved Arg as found at position 144 of SEQ ID NO:26 is Ile or Leu which was produced by amino acid substitution if not already present.

20. The nucleic acid according to claim 1, wherein said AT domain has been substituted with a different amino acid to produce a motif specific for ethylmalonyl-CoA and the residue that is 4 residues downstream of the conserved Arg as found at position 144 of SEQ ID NO:26 is Trp which was produced by amino acid substitution if not already present.

21. The nucleic acid according to claim 1, which encodes a PKS which includes, in addition to said AT domain, a natural cognate ACP domain which, prior to the amino acid substitution, is adapted to receive a substrate transferred by the AT; and the substitution causes the AT to transfer a different substrate to said cognate ACP domain.

22. The nucleic acid of claim 1 wherein said substituted residue(s) comprise the residue that is immediately downstream of said four-residue sequence corresponding to the YASH motif of the AT domain of the first module of DEBS.

23. The nucleic acid of claim 1 wherein said substituted residue(s) comprise the residue that is immediately downstream of the GHS motif.

24. The nucleic acid of claim 1 wherein said substituted residue(s) comprise the residue that is three residues downstream of the GQG motif.

25. The nucleic acid of claim 1 wherein said substituted residue(s) comprise the residue that is four residues downstream of the conserved arginine residue as found at position 144 of SEQ ID NO:26.

* * * * *

UNITED STATES PATENT AND TRADEMARK OFFICE
CERTIFICATE OF CORRECTION

PATENT NO.        : 7,595,175 B2
APPLICATION NO.   : 10/344738
DATED             : September 29, 2009
INVENTOR(S)       : Petkovic et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1045 days.

Signed and Sealed this

Twenty-eighth Day of September, 2010

David J. Kappos
*Director of the United States Patent and Trademark Office*

SEQUENCE LISTING

```
<160> NUMBER OF SEQ ID NOS: 138

<210> SEQ ID NO 1
<211> LENGTH: 395
<212> TYPE: PRT
<213> ORGANISM: Streptomyces avermitilis

<400> SEQUENCE: 1

Val Gln Arg Met Asp Gly Gly Glu Glu Pro Arg Pro Ala Ala Gly Glu
 1               5                  10                  15

Val Leu Gly Val Ala Asp Glu Ala Asp Gly Gly Val Val Phe Val Phe
            20                  25                  30

Pro Gly Gln Gly Pro Gln Trp Pro Gly Met Gly Arg Glu Leu Leu Asp
        35                  40                  45

Ala Ser Asp Val Phe Arg Glu Ser Val Arg Ala Cys Glu Ala Ala Phe
    50                  55                  60

Ala Pro Tyr Val Asp Trp Ser Val Glu Gln Val Leu Arg Asp Ser Pro
65                  70                  75                  80
```

Asp Ala Pro Gly Leu Asp Arg Val Asp Val Val Gln Pro Thr Leu Phe
                85                  90                  95

Ala Val Met Ile Ser Leu Ala Ala Leu Trp Arg Ser Gln Gly Val Glu
            100                 105                 110

Pro Cys Ala Val Leu Gly His Ser Leu Gly Glu Ile Ala Ala Ala His
        115                 120                 125

Val Ser Gly Gly Leu Ser Leu Ala Asp Ala Ala Arg Val Val Thr Leu
130                 135                 140

Trp Ser Gln Ala Gln Thr Thr Leu Ala Gly Thr Gly Ala Leu Val Ser
145                 150                 155                 160

Val Ala Ala Thr Pro Asp Glu Leu Leu Pro Arg Ile Ala Pro Trp Thr
                165                 170                 175

Glu Asp Asn Pro Ala Arg Leu Ala Val Ala Ala Val Asn Gly Pro Arg
            180                 185                 190

Ser Thr Val Val Ser Gly Ala Arg Glu Ala Val Ala Asp Leu Val Ala
        195                 200                 205

Asp Leu Thr Ala Ala Gln Val Arg Thr Arg Met Ile Pro Val Asp Val
210                 215                 220

Pro Ala His Ser Pro Leu Met Tyr Ala Ile Glu Glu Arg Val Val Ser
225                 230                 235                 240

Gly Leu Leu Pro Ile Thr Pro Arg Pro Ser Arg Ile Pro Phe His Ser
                245                 250                 255

Ser Val Thr Gly Gly Arg Leu Asp Thr Arg Glu Leu Asp Ala Ala Tyr
            260                 265                 270

Trp Tyr Arg Asn Met Ser Ser Thr Val Arg Phe Glu Pro Ala Ala Arg
        275                 280                 285

Leu Leu Leu Gln Gln Gly Pro Lys Thr Phe Val Glu Met Ser Pro His
290                 295                 300

Pro Val Leu Thr Met Gly Leu Gln Glu Leu Ala Pro Asp Leu Gly Asp
305                 310                 315                 320

Thr Thr Gly Thr Ala Asp Thr Val Ile Met Gly Thr Leu Arg Arg Gly
                325                 330                 335

Gln Gly Thr Leu Asp His Phe Leu Thr Ser Leu Ala Gln Leu Arg Gly
            340                 345                 350

His Gly Glu Thr Ser Ala Thr Thr Val Leu Ser Ala Arg Leu Thr Ala
        355                 360                 365

Leu Ser Pro Thr Gln Gln Ser Leu Leu Leu Asp Leu Val Arg Ala
370                 375                 380

His Thr Met Ala Val Leu Asn Asp Asp Gly Asn
385                 390                 395

<210> SEQ ID NO 2
<211> LENGTH: 383
<212> TYPE: PRT
<213> ORGANISM: Saccharopolyspora erythraea

<400> SEQUENCE: 2

Val Ala Asp Gly Arg Pro His Ala Ser Val Val Arg Gly Val Ala Arg
1               5                   10                  15

Pro Ser Ala Pro Val Val Phe Val Phe Pro Gly Gln Gly Ala Gln Trp
            20                  25                  30

Ala Gly Met Ala Gly Glu Leu Leu Gly Glu Ser Arg Val Phe Ala Ala
        35                  40                  45

Ala Met Asp Ala Cys Ala Arg Ala Phe Glu Pro Val Thr Asp Trp Thr
    50                  55                  60

```
Leu Ala Gln Val Leu Asp Ser Pro Glu Gln Ser Arg Arg Val Glu Val
 65                  70                  75                  80

Val Gln Pro Ala Leu Phe Ala Val Gln Thr Ser Leu Ala Ala Leu Trp
                 85                  90                  95

Arg Ser Phe Gly Val Thr Pro Asp Ala Val Val Gly His Ser Ile Gly
            100                 105                 110

Glu Leu Ala Ala His Val Cys Gly Ala Gly Ala Ala Asp Ala
        115                 120                 125

Ala Arg Ala Ala Ala Leu Trp Ser Arg Glu Met Ile Pro Leu Val Gly
        130                 135                 140

Asn Gly Asp Met Ala Ala Val Ala Leu Ser Ala Asp Glu Ile Glu Pro
145                 150                 155                 160

Arg Ile Ala Arg Trp Asp Asp Val Val Leu Ala Gly Val Asn Gly
                165                 170                 175

Pro Arg Ser Val Leu Leu Thr Gly Ser Pro Glu Pro Val Ala Arg Arg
            180                 185                 190

Val Gln Glu Leu Ser Ala Glu Gly Val Arg Ala Gln Val Ile Asn Val
            195                 200                 205

Ser Met Ala Ala His Ser Ala Gln Val Asp Asp Ile Ala Glu Gly Met
210                 215                 220

Arg Ser Ala Leu Ala Trp Phe Ala Pro Gly Gly Ser Glu Val Pro Phe
225                 230                 235                 240

Tyr Ala Ser Leu Thr Gly Gly Ala Val Asp Thr Arg Glu Leu Val Ala
                245                 250                 255

Asp Tyr Trp Arg Arg Ser Phe Arg Leu Pro Val Arg Phe Asp Glu Ala
                260                 265                 270

Ile Arg Ser Ala Leu Glu Val Gly Pro Gly Thr Phe Val Glu Ala Ser
                275                 280                 285

Pro His Pro Val Leu Ala Ala Leu Gln Gln Thr Leu Asp Ala Glu
    290                 295                 300

Gly Ser Ser Ala Ala Val Val Pro Thr Leu Gln Arg Gly Gln Gly Gly
305                 310                 315                 320

Met Arg Arg Phe Leu Leu Ala Ala Ala Gln Ala Phe Thr Gly Gly Val
                325                 330                 335

Ala Val Asp Trp Thr Ala Ala Tyr Asp Asp Val Gly Ala Glu Pro Gly
                340                 345                 350

Ser Leu Pro Glu Phe Ala Pro Ala Glu Glu Asp Glu Pro Ala Glu
        355                 360                 365

Ser Gly Val Asp Trp Asn Ala Pro Pro His Val Leu Arg Glu Arg
        370                 375                 380

<210> SEQ ID NO 3
<211> LENGTH: 379
<212> TYPE: PRT
<213> ORGANISM: Sorangium cellulosum

<400> SEQUENCE: 3

Ala Ala Ala Gln Gly His Thr Pro Pro Gly Ala Val Arg Gly Arg Ala
  1               5                  10                  15

Ser Gly Gly Ser Ala Pro Lys Val Val Phe Val Phe Pro Gly Gln Gly
                 20                  25                  30

Ser Gln Trp Val Gly Met Gly Arg Lys Leu Met Ala Glu Glu Pro Val
             35                  40                  45

Phe Arg Ala Ala Leu Glu Gly Cys Asp Arg Ala Ile Glu Ala Glu Ala
         50                  55                  60
```

```
Gly Trp Ser Leu Leu Gly Glu Leu Ser Ala Asp Glu Ala Ala Ser Gln
 65                  70                  75                  80

Leu Gly Arg Ile Asp Val Val Gln Pro Val Leu Phe Ala Met Glu Val
                 85                  90                  95

Ala Leu Ser Ala Leu Trp Arg Ser Trp Gly Val Glu Pro Glu Ala Val
            100                 105                 110

Val Gly His Ser Met Gly Glu Val Ala Ala His Val Ala Gly Ala
        115                 120                 125

Leu Ser Leu Glu Asp Ala Val Ala Ile Ile Cys Arg Arg Ser Arg Leu
    130                 135                 140

Leu Arg Arg Ile Ser Gly Gln Gly Glu Met Ala Leu Val Glu Leu Ser
145                 150                 155                 160

Leu Glu Glu Ala Glu Ala Ala Leu Arg Gly His Glu Gly Arg Leu Ser
                165                 170                 175

Val Ala Val Ser Asn Ser Pro Arg Ser Thr Val Leu Ala Gly Glu Pro
                180                 185                 190

Ala Ala Leu Ser Glu Val Leu Ala Ala Leu Thr Ala Lys Gly Val Phe
            195                 200                 205

Trp Arg Gln Val Lys Val Asp Val Ala Ser His Ser Pro Gln Val Asp
    210                 215                 220

Pro Leu Arg Glu Glu Leu Ile Ala Ala Leu Gly Ala Ile Arg Pro Arg
225                 230                 235                 240

Ala Ala Ala Val Pro Met Arg Ser Thr Val Thr Gly Gly Val Ile Ala
                245                 250                 255

Gly Pro Glu Leu Gly Ala Ser Tyr Trp Ala Asp Asn Leu Arg Gln Pro
            260                 265                 270

Val Arg Phe Ala Ala Ala Gln Ala Leu Leu Glu Gly Gly Pro Ala
    275                 280                 285

Leu Phe Ile Glu Met Ser Pro His Pro Ile Leu Val Pro Pro Leu Asp
    290                 295                 300

Glu Ile Gln Thr Ala Ala Glu Gln Gly Gly Ala Ala Val Gly Ser Leu
305                 310                 315                 320

Arg Arg Gly Gln Asp Glu Arg Ala Thr Leu Leu Glu Ala Leu Gly Thr
                325                 330                 335

Leu Trp Ala Ser Gly Tyr Pro Val Ser Trp Ala Arg Leu Phe Pro Ala
            340                 345                 350

Gly Gly Arg Arg Val Pro Leu Pro Thr Tyr Pro Trp Gln His Glu Arg
            355                 360                 365

Cys Trp Ile Glu Val Glu Pro Asp Ala Arg Arg
    370                 375

<210> SEQ ID NO 4
<211> LENGTH: 405
<212> TYPE: PRT
<213> ORGANISM: Sorangium cellulosum

<400> SEQUENCE: 4

Ser Ser Arg Glu Ala Leu Arg Gly Ala Leu Ser Ala Ala Ala Gln Gly
  1               5                  10                  15

His Thr Pro Pro Gly Ala Val Arg Gly Arg Ala Ser Gly Gly Ser Ala
                 20                  25                  30

Pro Lys Val Val Phe Val Phe Pro Gly Gln Gly Ser Gln Trp Val Gly
             35                  40                  45

Met Gly Arg Lys Leu Met Ala Glu Glu Pro Val Phe Arg Ala Ala Leu
     50                  55                  60
```

```
Glu Gly Cys Asp Arg Ala Ile Glu Ala Glu Ala Gly Trp Ser Leu Leu
 65                  70                  75                  80

Gly Glu Leu Ser Ala Asp Glu Ala Ala Ser Gln Leu Gly Arg Ile Asp
                 85                  90                  95

Val Val Gln Pro Val Leu Phe Ala Met Glu Val Ala Leu Ser Ala Leu
            100                 105                 110

Trp Arg Ser Trp Gly Val Glu Pro Glu Ala Val Val Gly His Ser Met
        115                 120                 125

Gly Glu Val Ala Ala Ala His Val Ala Gly Ala Leu Ser Leu Glu Asp
    130                 135                 140

Ala Val Ala Ile Ile Cys Arg Arg Ser Arg Leu Leu Arg Arg Ile Ser
145                 150                 155                 160

Gly Gln Gly Glu Met Ala Leu Val Glu Leu Ser Leu Glu Glu Ala Glu
                165                 170                 175

Ala Ala Leu Arg Gly His Glu Gly Arg Leu Ser Val Ala Val Ser Asn
            180                 185                 190

Ser Pro Arg Ser Thr Val Leu Ala Gly Glu Pro Ala Ala Leu Ser Glu
        195                 200                 205

Val Leu Ala Ala Leu Thr Ala Lys Gly Val Phe Trp Arg Gln Val Lys
    210                 215                 220

Val Asp Val Ala Ser His Ser Pro Gln Val Asp Pro Leu Arg Glu Glu
225                 230                 235                 240

Leu Ile Ala Ala Leu Gly Ala Ile Arg Pro Arg Ala Ala Ala Val Pro
                245                 250                 255

Met Arg Ser Thr Val Thr Gly Gly Val Ile Ala Gly Pro Glu Leu Gly
            260                 265                 270

Ala Ser Tyr Trp Ala Asp Asn Leu Arg Gln Pro Val Arg Phe Ala Ala
        275                 280                 285

Ala Ala Gln Ala Leu Leu Glu Gly Gly Pro Ala Leu Phe Ile Glu Met
    290                 295                 300

Ser Pro His Pro Ile Leu Val Pro Pro Leu Asp Glu Ile Gln Thr Ala
305                 310                 315                 320

Ala Glu Gln Gly Gly Ala Ala Val Gly Ser Leu Arg Arg Gly Gln Asp
                325                 330                 335

Glu Arg Ala Thr Leu Leu Glu Ala Leu Gly Thr Leu Trp Ala Ser Gly
            340                 345                 350

Tyr Pro Val Ser Trp Ala Arg Leu Phe Pro Ala Gly Gly Arg Arg Val
        355                 360                 365

Pro Leu Pro Thr Tyr Pro Trp Gln His Glu Arg Tyr Trp Ile Glu Asp
    370                 375                 380

Ser Val His Gly Ser Lys Pro Ser Leu Arg Leu Arg Gln Leu Arg Asn
385                 390                 395                 400

Gly Ala Thr Asp His
                405

<210> SEQ ID NO 5
<211> LENGTH: 399
<212> TYPE: PRT
<213> ORGANISM: Sorangium cellulosum

<400> SEQUENCE: 5

Arg Glu Gly Leu Asp Ala Ala Arg Gly Gln Thr Pro Pro Gly Ala
 1               5                  10                  15

Val Arg Gly Arg Cys Ser Pro Gly Asn Val Pro Lys Val Val Phe Val
            20                  25                  30
```

Phe Pro Gly Gln Gly Ser Gln Trp Val Gly Met Gly Arg Gln Leu Leu
                35                  40                  45

Ala Glu Glu Pro Val Phe His Ala Ala Leu Ser Ala Cys Asp Arg Ala
 50                  55                  60

Ile Gln Ala Glu Ala Gly Trp Ser Leu Leu Ala Glu Leu Ala Ala Asp
 65                  70                  75                  80

Glu Gly Ser Ser Gln Leu Glu Arg Ile Asp Val Val Gln Pro Val Leu
                 85                  90                  95

Phe Ala Leu Ala Val Ala Phe Ala Ala Leu Trp Arg Ser Trp Gly Val
                100                 105                 110

Ala Pro Asp Val Val Ile Gly His Ser Met Gly Glu Val Ala Ala Ala
                115                 120                 125

His Val Ala Gly Ala Leu Ser Leu Glu Asp Ala Val Ala Ile Ile Cys
                130                 135                 140

Arg Arg Ser Arg Leu Leu Arg Arg Ile Ser Gly Gln Gly Glu Met Ala
145                 150                 155                 160

Val Thr Glu Leu Ser Leu Ala Glu Ala Glu Ala Ala Leu Arg Gly Tyr
                165                 170                 175

Glu Asp Arg Val Ser Val Ala Val Ser Asn Ser Pro Arg Ser Thr Val
                180                 185                 190

Leu Ser Gly Glu Pro Ala Ala Ile Gly Glu Val Leu Ser Ser Leu Asn
                195                 200                 205

Ala Lys Gly Val Phe Cys Arg Arg Val Lys Val Asp Val Ala Ser His
                210                 215                 220

Ser Pro Gln Val Asp Pro Leu Arg Glu Asp Leu Leu Ala Ala Leu Gly
225                 230                 235                 240

Gly Leu Arg Pro Gly Ala Ala Val Pro Met Arg Ser Thr Val Thr
                245                 250                 255

Gly Ala Met Val Ala Gly Pro Glu Leu Gly Ala Asn Tyr Trp Met Asn
                260                 265                 270

Asn Leu Arg Gln Pro Val Arg Phe Ala Glu Val Val Gln Ala Gln Leu
                275                 280                 285

Gln Gly Gly His Gly Leu Phe Val Glu Met Ser Pro His Pro Ile Leu
                290                 295                 300

Thr Thr Ser Val Glu Glu Met Arg Arg Ala Ala Gln Arg Ala Gly Ala
305                 310                 315                 320

Ala Val Gly Ser Leu Arg Arg Gly Gln Asp Glu Arg Pro Ala Met Leu
                325                 330                 335

Glu Ala Leu Gly Thr Leu Trp Ala Gln Gly Tyr Pro Val Pro Trp Gly
                340                 345                 350

Arg Leu Phe Pro Ala Gly Gly Arg Arg Val Pro Leu Pro Thr Tyr Pro
                355                 360                 365

Trp Gln Arg Glu Arg Tyr Trp Ile Glu Ala Pro Ala Lys Ser Ala Ala
                370                 375                 380

Gly Asp Arg Arg Gly Val Arg Ala Gly His Pro Leu Leu Gly
385                 390                 395

<210> SEQ ID NO 6
<211> LENGTH: 389
<212> TYPE: PRT
<213> ORGANISM: Sorangium cellulosum

<400> SEQUENCE: 6

```
Pro Pro Ala Ala Ala Arg Gly His Ala Ser Thr Gly Ser Ala Pro Lys
 1               5                  10                  15

Val Val Phe Val Phe Pro Gly Gln Gly Ser Gln Trp Leu Gly Met Gly
            20                  25                  30

Gln Lys Leu Leu Ser Glu Glu Pro Val Phe Arg Asp Ala Leu Ser Ala
        35                  40                  45

Cys Asp Arg Ala Ile Gln Ala Glu Ala Gly Trp Ser Leu Leu Ala Glu
    50                  55                  60

Leu Ala Ala Asp Glu Thr Thr Ser Gln Leu Gly Arg Ile Asp Val Val
 65                  70                  75                  80

Gln Pro Ala Leu Phe Ala Ile Glu Val Ala Leu Ser Ala Leu Trp Arg
                85                  90                  95

Ser Trp Gly Val Glu Pro Asp Ala Val Val Gly His Ser Met Gly Glu
            100                 105                 110

Val Ala Ala His Val Ala Gly Ala Leu Ser Leu Glu Asp Ala Val
            115                 120                 125

Ala Ile Ile Cys Arg Arg Ser Leu Leu Leu Arg Arg Ile Ser Gly Gln
    130                 135                 140

Gly Glu Met Ala Val Val Glu Leu Ser Leu Ala Glu Ala Glu Ala Ala
145                 150                 155                 160

Leu Leu Gly Tyr Glu Asp Arg Leu Ser Val Ala Val Ser Asn Ser Pro
                165                 170                 175

Arg Ser Thr Val Leu Ala Gly Glu Pro Ala Ala Leu Ala Glu Val Leu
            180                 185                 190

Ala Ile Leu Ala Ala Lys Gly Val Phe Cys Arg Arg Val Lys Val Asp
    195                 200                 205

Val Ala Ser His Ser Pro Gln Ile Asp Pro Leu Arg Asp Glu Leu Leu
    210                 215                 220

Ala Ala Leu Gly Glu Leu Glu Pro Arg Gln Ala Thr Val Ser Met Arg
225                 230                 235                 240

Ser Thr Val Thr Ser Thr Ile Met Ala Gly Pro Glu Leu Val Ala Ser
                245                 250                 255

Tyr Trp Ala Asp Asn Val Arg Gln Pro Val Arg Phe Ala Glu Ala Val
            260                 265                 270

Gln Ser Leu Met Glu Asp Gly His Gly Leu Phe Val Glu Met Ser Pro
        275                 280                 285

His Pro Ile Leu Thr Thr Ser Val Glu Glu Ile Arg Arg Ala Thr Lys
    290                 295                 300

Arg Glu Gly Val Ala Val Gly Ser Leu Arg Arg Gly Gln Asp Glu Arg
305                 310                 315                 320

Leu Ser Met Leu Glu Ala Leu Gly Ala Leu Trp Val His Gly Gln Ala
                325                 330                 335

Val Gly Trp Glu Arg Leu Phe Ser Ala Gly Ala Gly Leu Arg Arg
            340                 345                 350

Val Pro Leu Pro Thr Tyr Pro Trp Gln Arg Glu Arg Tyr Trp Val Asp
        355                 360                 365

Ala Pro Thr Gly Gly Ala Gly Gly Ser Arg Phe Ala His Ala Gly
    370                 375                 380

Ser His Pro Leu Leu
385
```

<210> SEQ ID NO 7
<211> LENGTH: 340
<212> TYPE: PRT
<213> ORGANISM: Sorangium cellulosum

<400> SEQUENCE: 7

Val Phe Val Phe Ala Gly Gln Gly Ala Gln Trp Phe Gly Met Gly Arg
 1               5                  10                  15

Ala Leu Leu Gln Arg Glu Pro Val Phe Arg Thr Thr Ile Glu Gln Cys
            20                  25                  30

Ser Ser Phe Ile Gln Gln Asn Leu Gly Trp Ser Leu Leu Asp Glu Leu
        35                  40                  45

Met Thr Asp Arg Glu Ser Ser Arg Leu Asp Glu Ile Asp Val Ser Leu
    50                  55                  60

Pro Ala Ile Ile Ser Ile Glu Ile Ala Leu Ala Ala Gln Trp Arg Ala
 65                 70                  75                  80

Trp Gly Val Glu Pro Ala Phe Val Val Gly His Ser Thr Gly Glu Ile
                85                  90                  95

Ala Ala Ala His Val Ala Gly Val Leu Ser Ile Glu Asp Ala Met Arg
            100                 105                 110

Thr Ile Cys Ala Tyr Gly Arg Ile Ile Arg Lys Leu Arg Gly Lys Gly
        115                 120                 125

Gly Met Gly Leu Val Ala Leu Ser Trp Glu Asp Ala Gly Lys Glu Leu
    130                 135                 140

Thr Gly Tyr Glu Gly Arg Leu Phe Arg Ala Ile Glu His Ser Ala Asp
145                 150                 155                 160

Ser Thr Val Leu Ala Gly Glu Pro Asp Ala Leu Asp Ala Leu Leu Gln
                165                 170                 175

Ala Leu Glu Arg Lys Asn Val Phe Cys Arg Arg Val Ala Met Asp Val
            180                 185                 190

Ala Pro His Cys Pro Gln Val Asp Cys Leu Arg Asp Glu Leu Phe Asp
        195                 200                 205

Ala Leu Arg Glu Val Arg Pro Asn Lys Ala Gln Ile Pro Ile Val Ser
    210                 215                 220

Glu Val Thr Gly Thr Ala Leu Asp Gly Glu Arg Phe Asp Ala Ser His
225                 230                 235                 240

Trp Val Arg Asn Phe Gly Asp Pro Ala Leu Phe Ser Thr Ala Ile Asp
                245                 250                 255

His Leu Leu Gln Glu Gly Phe Asp Ile Phe Leu Glu Leu Thr Pro His
            260                 265                 270

Pro Leu Ala Leu Pro Ala Ile Glu Ser Asn Leu Arg Arg Ser Gly Arg
        275                 280                 285

Arg Gly Val Val Leu Pro Ser Leu Arg Arg Asn Glu Asp Glu Arg Gly
    290                 295                 300

Val Met Leu Asp Thr Leu Gly Val Leu Tyr Val Arg Gly Ala Pro Val
305                 310                 315                 320

Arg Trp Asp Asn Val Tyr Pro Ala Ala Phe Glu Ser Met Pro Leu Pro
                325                 330                 335

Ser Thr Ala Gly
            340

<210> SEQ ID NO 8
<211> LENGTH: 348
<212> TYPE: PRT
<213> ORGANISM: Streptomyces sp.

<400> SEQUENCE: 8

| | | | | | | | | | | | | | | |
|---|---|---|---|---|---|---|---|---|---|---|---|---|---|---|
|Ser|Ala|Val|Ala|Gly|Val|Ala|Val|Glu|Gly|Ala|Arg|Thr|Val|Phe|Val|
|1| | | |5| | | | |10| | | | |15| |

Phe Pro Gly Gln Gly Ser Gln Trp Val Gly Met Gly Arg Glu Leu Met
                   20               25               30

Gly Ala Ser Glu Val Phe Ala Ala Arg Met Arg Glu Cys Ala Ala Val
        35              40              45

Leu Glu Pro His Thr Gly Trp Asp Leu Leu Asp Val Leu Gly Glu Ala
    50              55                 60

Val Val Val Asp Arg Val Glu Val Leu Gln Pro Ala Ser Trp Ala Val
65                70              75             80

Ala Val Ser Leu Ala Ala Leu Trp Gln Ala His Gly Val Val Pro Asp
            85              90              95

Ala Val Val Gly His Ser Gln Gly Glu Ile Ala Ala Ala Cys Val Ala
        100             105             110

Gly Ala Leu Ser Leu Glu Asp Ala Ala Arg Val Val Ala Leu Arg Ser
        115             120             125

Gln Ala Ile Ala Ala Arg Leu Ala Gly Arg Gly Ala Met Ala Ser Ile
   130               135              140

Ala Val Pro Ala Ser Ala Val Glu Thr Val Glu Gly Val Trp Ile Ala
145              150              155            160

Ala Arg Asn Gly Pro Glu Ser Thr Val Val Ala Gly Asp Pro Ala Ala
            165             170             175

Val Glu Arg Val Leu Ala Arg Tyr Glu Ala Glu Gly Val Arg Val Arg
        180             185             190

Arg Ile Ala Val Asp Tyr Ala Ser His Thr Pro His Val Glu Ala Ile
       195            200             205

Glu Ala Gln Leu Ala Asp Ala Leu Glu Gly Ile Thr Ser Ser Thr Pro
   210               215              220

Ser Val Pro Trp Trp Ser Thr Val Asp Ser Gly Trp Val Thr Glu Pro
225              230              235            240

Phe Gly Asp Ala Tyr Trp Tyr Arg Asn Leu Arg Gln Pro Val Ala Met
            245             250             255

Asp Thr Ala Val Ser Glu Leu Asp Gly Ser Leu Phe Ile Glu Cys Ser
        260             265             270

Ala His Pro Val Leu Leu Pro Ala Leu Asp Gln Glu Arg Thr Val Ala
       275            280             285

Ser Leu Arg Thr Asp Asp Gly Gly Trp Asp Arg Phe Leu Ala Ala Leu
   290               295              300

Ala Gln Ala Trp Thr Gln Gly Ala Asp Val Asp Trp Thr Thr Leu Ile
305              310              315            320

Glu Pro Ala Pro His Arg Val Leu Asp Leu Pro Thr Tyr Pro Phe Asp
            325             330             335

His Lys Arg Tyr Trp Leu Gln Pro Ala Pro Val Thr
            340             345

<210> SEQ ID NO 9
<211> LENGTH: 348
<212> TYPE: PRT
<213> ORGANISM: Streptomyces sp.

<400> SEQUENCE: 9

```
Val Phe Val Phe Pro Gly Gln Gly Ser Gln Trp Val Gly Met Gly Arg
 1               5                  10                  15

Glu Leu Met Gly Cys Ser Glu Val Phe Ala Ala Arg Met Arg Glu Cys
            20                  25                  30

Ala Ala Val Leu Glu Pro Tyr Thr Gly Trp Asp Leu Leu Asp Val Leu
        35                  40                  45

Gly Glu Ala Val Val Ala Glu Arg Val Glu Val Leu Gln Pro Ala Ser
    50                  55                  60

Trp Ala Val Ala Val Ser Leu Ala Ala Leu Trp Gln Ala His Gly Val
 65                  70                  75                  80

Ser Pro Asp Ala Val Ile Gly His Ser Gln Gly Glu Ile Ala Ala Ala
                85                  90                  95

Cys Val Ala Gly Ala Leu Ser Leu Glu Asp Ala Ala Arg Ile Val Ala
            100                 105                 110

Leu Arg Ser Gln Thr Ile Ala Ala His Leu Ala Gly Arg Gly Ala Met
        115                 120                 125

Ala Ser Ile Ala Leu Pro Ala Thr Ala Val Glu Thr Val Glu Gly Val
    130                 135                 140

Trp Val Ala Ala Arg Asn Gly Pro Glu Ser Thr Val Val Ala Gly Asp
145                 150                 155                 160

Pro Ser Ala Val Glu Arg Val Leu Ala Arg Tyr Glu Ala Glu Gly Val
                165                 170                 175

Arg Val Arg Arg Ile Ala Val Asp Tyr Ala Ser His Thr Pro His Val
            180                 185                 190

Glu Ala Ile Gln Glu Gln Leu Ala Asp Val Leu Gly Asp Ile Thr Ser
        195                 200                 205

Ser Ala Pro Ser Val Pro Trp Trp Ser Thr Val Asp Gly Gly Trp Val
    210                 215                 220

Thr Glu Pro Ala Gly Asp Asp Tyr Trp Tyr Arg Asn Leu Arg Gln Pro
225                 230                 235                 240

Val Ala Met Asp Thr Ala Ile Gly Glu Leu Asp Gly Ser Leu Phe Ile
                245                 250                 255

Glu Cys Ser Ala His Pro Val Leu Leu Pro Ala Leu Asp Gln Glu Arg
            260                 265                 270

Thr Val Ala Ser Leu Arg Thr Asp Asp Gly Gly Trp Asp Arg Phe Leu
        275                 280                 285

Thr Ala Leu Ala Gln Ala Trp Thr Gln Gly Ala Asp Val Asp Trp Thr
    290                 295                 300

Thr Leu Ile Ala Pro Ala Pro Asp Arg Leu Leu Asp Leu Pro Thr Tyr
305                 310                 315                 320

Pro Phe Asp His Lys Arg Tyr Trp Ile Glu Ala Thr Gly Ala Ala Asp
                325                 330                 335

Leu Thr Ala Leu Gly Leu Thr Asp Thr Ala His Pro
            340                 345
```

<210> SEQ ID NO 10
<211> LENGTH: 411
<212> TYPE: PRT
<213> ORGANISM: Streptomyces hygroscopicus

<400> SEQUENCE: 10

```
Ser Ala Lys Thr Gln Pro Ala Leu Thr Glu His Glu Asp Arg Leu Arg
  1               5                  10                  15

Ala Tyr Leu Ala Ala Ser Pro Gly Ala Asp Thr Arg Ala Val Ala Ser
             20                  25                  30

Thr Leu Ala Val Thr Arg Ser Val Phe Glu His Arg Ala Val Leu Leu
         35                  40                  45

Gly Asp Asp Thr Val Thr Gly Thr Ala Val Ser Asp Pro Arg Val Val
     50                  55                  60

Phe Val Phe Pro Gly Gln Gly Trp Gln Trp Leu Gly Met Gly Ser Ala
 65                  70                  75                  80

Leu Arg Asp Ser Ser Val Val Phe Ala Glu Arg Met Ala Glu Cys Ala
                 85                  90                  95

Ala Ala Leu Ser Glu Phe Val Asp Trp Asp Leu Thr Val Leu Asp Asp
            100                 105                 110

Pro Ala Val Val Asp Arg Val Asp Val Val Gln Pro Ala Ser Trp Ala
        115                 120                 125

Val Met Val Ser Leu Ala Ala Val Trp Gln Ala Gly Val Arg Pro
    130                 135                 140

Asp Ala Val Ile Gly His Ser Gln Gly Glu Ile Ala Ala Ala Cys Val
145                 150                 155                 160

Ala Gly Ala Val Ser Leu Arg Asp Ala Ala Arg Ile Val Thr Leu Arg
                165                 170                 175

Ser Gln Ala Ile Ala Arg Gly Leu Ala Gly Arg Gly Ala Met Ala Ser
            180                 185                 190

Val Ala Leu Pro Ala Gln Asp Val Glu Leu Val Asp Gly Ala Trp Ile
        195                 200                 205

Ala Ala His Asn Gly Pro Ala Ser Thr Val Ile Ala Gly Thr Pro Glu
    210                 215                 220

Ala Val Asp His Val Leu Thr Ala His Glu Ala Arg Gly Val Arg Val
225                 230                 235                 240

Arg Arg Ile Thr Val Asp Tyr Ala Ser His Thr Pro His Val Glu Leu
                245                 250                 255

Ile Arg Asp Glu Leu Leu Asp Ile Thr Ser Asp Ser Ser Gln Ala
            260                 265                 270

Pro Leu Val Pro Trp Leu Ser Thr Val Asp Gly Ser Trp Val Asp Ser
        275                 280                 285

Pro Leu Asp Gly Glu Tyr Trp Tyr Arg Asn Leu Arg Glu Pro Val Gly
    290                 295                 300

Phe His Pro Ala Val Gly Gln Leu Gln Ala Gln Gly Asp Thr Val Phe
305                 310                 315                 320

Val Glu Val Ser Ala Ser Pro Val Leu Leu Gln Ala Met Asp Asp
                325                 330                 335

Val Val Thr Val Ala Thr Leu Arg Arg Asp Gly Asp Ala Thr Arg
            340                 345                 350

Met Leu Thr Ala Leu Ala Gln Ala Tyr Val His Gly Val Thr Val Asp
        355                 360                 365

Trp Pro Ala Ile Leu Gly Thr Thr Thr Arg Val Leu Asp Leu Pro
    370                 375                 380

Thr Tyr Ala Phe Gln His Gln Arg Tyr Trp Val Glu Gly Val Asp Arg
385                 390                 395                 400

Ser Ala Ala Gly Gly His Pro Leu Leu Gly Val
                405                 410
```

<210> SEQ ID NO 11
<211> LENGTH: 409
<212> TYPE: PRT
<213> ORGANISM: Streptomyces hygroscopicus

<400> SEQUENCE: 11

```
Thr Gln Pro Ala Leu Thr Glu His Glu Asp Arg Leu Arg Ala Tyr Leu
 1               5                  10                  15

Ala Ala Ser Pro Gly Val Asp Thr Arg Ala Val Ala Ser Thr Leu Ala
            20                  25                  30

Val Thr Arg Ser Val Phe Glu His Arg Ala Val Leu Leu Gly Asp Asp
        35                  40                  45

Thr Val Thr Gly Thr Ala Val Ser Asp Pro Arg Val Val Phe Val Phe
    50                  55                  60

Pro Gly Gln Gly Trp Gln Trp Leu Gly Met Gly Ser Ala Leu Arg Asp
65                  70                  75                  80

Ser Ser Ile Val Phe Ala Glu Arg Met Ala Glu Cys Ala Pro Ala Leu
                85                  90                  95

Arg Glu Phe Val Asp Trp Asp Leu Phe Thr Val Leu Asp Asp Pro Ala
            100                 105                 110

Val Val Asp Arg Val Asp Val Gln Pro Ala Ser Trp Arg Met Met
        115                 120                 125

Val Ser Leu Ala Ala Val Trp Gln Ala Ala Gly Val Arg Pro Asp Ala
    130                 135                 140

Val Ile Gly His Ser Gln Gly Glu Ile Ala Ala Cys Val Ala Gly
145                 150                 155                 160

Ala Val Ser Met Arg Asp Ala Ala Arg Ile Val Thr Leu Arg Ser Glu
                165                 170                 175

Ala Ile Ala Arg Gly Leu Ala Gly Arg Gly Ala Met Ala Ser Val Ala
            180                 185                 190

Leu Pro Ala Gln Asp Val Glu Leu Val Asp Gly Ala Trp Ile Ala Ala
        195                 200                 205

His Asn Gly Pro Ala Ser Thr Val Ile Ala Gly Thr Pro Glu Ala Val
    210                 215                 220

Asp His Val Leu Thr Ala His Glu Ala Arg Gly Val Arg Val Arg Arg
225                 230                 235                 240

Ile Thr Val Asp Tyr Ala Ser His Thr Pro His Val Glu Leu Ile Arg
                245                 250                 255

Asp Glu Leu Leu Asp Ile Thr Ser Asp Ser Ser Gln Ala Pro Val
            260                 265                 270

Val Pro Trp Leu Ser Thr Val Asp Gly Ser Trp Val Asp Ser Pro Leu
        275                 280                 285

Asp Val Glu Tyr Trp Tyr Arg Asn Leu Arg Glu Pro Val Gly Phe His
    290                 295                 300

Pro Ala Val Gly Gln Leu Gln Ala Glu Gly Asp Thr Val Phe Val Glu
305                 310                 315                 320

Val Ser Ala Ser Pro Val Leu Leu Gln Ala Met Asp Asp Val Val
                325                 330                 335

Thr Val Ala Thr Leu Arg Arg Asp Asp Gly Asp Ala Thr Arg Met Leu
            340                 345                 350

Thr Ala Leu Ala Gln Ala Tyr Val His Gly Val Thr Val Asp Trp Pro
        355                 360                 365

Ala Ile Leu Gly Thr Ala Thr Thr Arg Val Leu Asp Leu Pro Thr Tyr
    370                 375                 380
```

```
Ala Phe Gln His Gln Arg Tyr Trp Leu Arg Ser Val Asp Arg Ala Ala
385                 390                 395                 400

Ala Asp Gly His Pro Leu Leu Gly Thr
                405

<210> SEQ ID NO 12
<211> LENGTH: 416
<212> TYPE: PRT
<213> ORGANISM: Streptomyces hygroscopicus

<400> SEQUENCE: 12

Pro Leu Val Ile Ser Ala Lys Thr Gln Pro Ala Leu Thr Glu His Glu
  1               5                  10                  15

Asp Arg Leu Arg Ala Tyr Leu Ala Ala Ser Pro Gly Ala Asp Thr Arg
                 20                  25                  30

Ala Val Ala Ser Thr Leu Ala Val Thr Arg Ser Val Phe Glu His Arg
             35                  40                  45

Ala Val Leu Leu Gly Asp Ala Val Thr Gly Thr Ala Val Thr Asp
         50                  55                  60

Pro Arg Val Val Phe Val Phe Pro Gly Gln Gly Trp Gln Trp Leu Gly
 65                  70                  75                  80

Met Gly Ser Ala Leu Arg Asp Ser Ser Val Val Phe Ala Glu Arg Met
                 85                  90                  95

Ala Glu Cys Ala Ala Ala Leu Ser Glu Phe Val Asp Trp Asp Leu Phe
            100                 105                 110

Ala Val Leu Asp Asp Pro Ala Val Val Asp Arg Val Asp Val Val Gln
        115                 120                 125

Pro Ala Ser Trp Ala Val Met Val Ser Leu Ala Ala Val Trp Gln Ala
130                 135                 140

Ala Gly Val Arg Pro Asp Ala Val Ile Gly His Ser Gln Gly Glu Ile
145                 150                 155                 160

Ala Ala Ala Cys Val Ala Gly Ala Val Ser Leu Arg Asp Ala Ala Arg
                165                 170                 175

Ile Val Thr Leu Arg Ser Gln Ala Ile Ala Arg Gly Leu Ala Gly Arg
            180                 185                 190

Ala Ala Met Ala Ser Val Ala Leu Pro Ala His Glu Ile Glu Leu Val
        195                 200                 205

Asp Gly Ala Trp Ile Ala Ala His Asn Gly Pro Ala Ser Thr Val Ile
210                 215                 220

Ala Gly Thr Pro Glu Ala Val Asp His Val Leu Thr Ala His Glu Ala
225                 230                 235                 240

Arg Gly Val Arg Val Arg Arg Ile Thr Val Asp Tyr Ala Ser His Thr
                245                 250                 255

Pro His Val Glu Leu Ile Arg Asp Glu Leu Leu Gly Ile Thr Ala Gly
            260                 265                 270

Ile Gly Ser Gln Pro Pro Val Pro Trp Leu Ser Thr Val Asp Gly
        275                 280                 285

Ser Trp Val Asp Ser Pro Leu Asp Gly Glu Tyr Trp Tyr Arg Asn Leu
290                 295                 300

Arg Glu Pro Val Gly Phe His Pro Ala Val Ser Gln Leu Gln Ala Gln
305                 310                 315                 320

Gly Asp Ala Val Phe Val Glu Val Ser Ala Ser Pro Val Leu Leu Gln
                325                 330                 335

Ala Met Asp Asp Asp Val Val Thr Val Ala Thr Leu Arg Arg Asp Asp
            340                 345                 350
```

```
Gly Asp Ala Thr Arg Met Leu Thr Ala Leu Ala Gln Ala Tyr Val His
        355                 360                 365

Gly Val Thr Val Asp Trp Pro Ala Ile Leu Gly Thr Thr Thr Ala Arg
370                 375                 380

Val Leu Asp Leu Pro Thr Tyr Ala Phe Gln His Gln Arg Tyr Trp Val
385                 390                 395                 400

Lys Ser Val Asp Arg Ala Ala Ala Asp Gly His Pro Leu Leu Gly Ala
            405                 410                 415

<210> SEQ ID NO 13
<211> LENGTH: 433
<212> TYPE: PRT
<213> ORGANISM: Streptomyces hygroscopicus

<400> SEQUENCE: 13

Ala Glu Glu Ala Gln Pro Val Glu Thr Pro Val Val Ala Ser Asp Val
  1               5                  10                  15

Leu Pro Leu Val Ile Ser Ala Lys Thr Gln Pro Ala Leu Thr Glu His
                 20                  25                  30

Glu Asp Arg Leu Arg Ala Tyr Leu Ala Ala Ser Pro Gly Ala Asp Ile
            35                  40                  45

Arg Ala Val Ala Ser Thr Leu Ala Val Thr Arg Ser Val Phe Glu His
 50                  55                  60

Arg Ala Val Leu Leu Gly Asp Asp Thr Val Thr Gly Thr Ala Val Thr
 65                  70                  75                  80

Asp Pro Arg Ile Val Phe Val Phe Pro Gly Gln Gly Trp Gln Trp Leu
                 85                  90                  95

Gly Met Gly Ser Ala Leu Arg Asp Ser Ser Val Val Phe Ala Glu Arg
                100                 105                 110

Met Ala Glu Cys Ala Ala Ala Leu Arg Glu Phe Val Asp Trp Asp Leu
            115                 120                 125

Phe Thr Val Leu Asp Asp Pro Ala Val Val Asp Arg Val Asp Val Val
130                 135                 140

Gln Pro Ala Ser Trp Ala Met Met Val Ser Leu Ala Ala Val Trp Gln
145                 150                 155                 160

Ala Ala Gly Val Arg Pro Asp Ala Val Ile Gly His Ser Gln Gly Glu
                165                 170                 175

Ile Ala Ala Ala Cys Val Ala Gly Ala Val Ser Leu Arg Asp Ala Ala
            180                 185                 190

Arg Ile Val Thr Leu Arg Ser Gln Ala Ile Ala Arg Gly Leu Ala Gly
            195                 200                 205

Arg Gly Ala Met Ala Ser Val Ala Leu Pro Ala Gln Asp Val Glu Leu
        210                 215                 220

Val Asp Gly Ala Trp Ile Ala Ala His Asn Gly Pro Ala Ser Thr Val
225                 230                 235                 240

Ile Ala Gly Thr Pro Glu Ala Val Asp His Val Leu Thr Ala His Glu
                245                 250                 255

Ala Gln Gly Val Arg Val Arg Arg Ile Thr Val Asp Tyr Ala Ser His
            260                 265                 270

Thr Pro His Val Glu Leu Ile Arg Asp Glu Leu Leu Asp Ile Thr Ser
        275                 280                 285

Asp Ser Ser Ser Gln Thr Pro Leu Val Pro Trp Leu Ser Thr Val Asp
    290                 295                 300

Gly Thr Trp Val Asp Ser Pro Leu Asp Gly Glu Tyr Tyr Arg Asn
305                 310                 315                 320
```

```
Leu Arg Glu Pro Val Gly Phe His Pro Ala Val Ser Gln Leu Gln Ala
            325                 330                 335

Gln Gly Asp Thr Val Phe Val Glu Val Ser Ala Ser Pro Val Leu Leu
        340                 345                 350

Gln Ala Met Asp Asp Val Val Thr Val Ala Thr Leu Arg Arg Asp
            355                 360                 365

Asp Gly Asp Ala Thr Arg Met Leu Thr Ala Leu Ala Gln Ala Tyr Val
        370                 375                 380

His Gly Val Thr Val Asp Trp Pro Ala Ile Leu Gly Thr Thr Thr Thr
385                 390                 395                 400

Arg Val Leu Asp Leu Pro Thr Tyr Ala Phe Gln His Gln Arg Tyr Trp
                405                 410                 415

Leu Lys Ser Val Asp Arg Ala Ala Ala Asp Gly His Pro Leu Leu Gly
            420                 425                 430

Thr

<210> SEQ ID NO 14
<211> LENGTH: 381
<212> TYPE: PRT
<213> ORGANISM: Streptomyces hygroscopicus

<400> SEQUENCE: 14

Leu Ala Val Thr Arg Ser Leu Phe Glu His Arg Ala Val Leu Leu Gly
1               5                   10                  15

Asp Asp Ser Val Thr Gly Thr Gly Thr Ala Val Ser Asp Pro Arg Val
            20                  25                  30

Val Phe Val Phe Pro Gly Gln Gly Trp Gln Trp Leu Gly Met Gly Ser
        35                  40                  45

Ala Leu Arg Thr Ser Ser Met Val Phe Ala Glu Arg Met Ala Glu Cys
    50                  55                  60

Ala Ala Ala Leu Ser Glu Phe Val Asp Trp Asp Leu Phe Ala Val Leu
65                  70                  75                  80

Asp Asp Pro Ala Val Val Ala Arg Val Asp Val Val Gln Pro Ala Ser
                85                  90                  95

Trp Ala Val Met Val Ser Leu Ala Ala Val Trp Gln Ala Ala Gly Val
            100                 105                 110

Arg Pro Asp Ala Val Val Gly His Ser Gln Gly Glu Ile Ala Ala Ala
        115                 120                 125

Cys Val Ala Gly Ala Val Ser Leu Arg Asp Ala Ala Arg Val Val Thr
    130                 135                 140

Leu Arg Ser Gln Val Ile Ala Arg Gly Leu Ala Gly Arg Gly Ala Met
145                 150                 155                 160

Ala Ser Val Ala Leu Pro Ala Gln Asp Val Glu Leu Val Asp Gly Ala
                165                 170                 175

Trp Val Ala Ala Arg Asn Gly Pro Ala Ser Thr Val Val Ala Gly Ala
            180                 185                 190

Pro Glu Ala Val Asp Arg Val Leu Ala Val His Glu Ala Arg Gly Val
        195                 200                 205

Arg Val Arg Arg Ile Ala Val Asp Tyr Ala Ser His Thr Pro His Val
    210                 215                 220

Glu Leu Ile Arg Asp Glu Leu Leu Gly Val Ile Ala Gly Val Asp Ser
225                 230                 235                 240

Arg Ala Pro Val Val Pro Trp Leu Ser Thr Val Asp Gly Thr Trp Val
                245                 250                 255
```

```
                                              -continued

Glu Gly Pro Leu Asp Ala Glu Tyr Trp Tyr Arg Asn Leu Arg Glu Pro
            260                 265                 270

Val Gly Phe Glu Pro Ala Ala Gly Gln Leu Gln Ala Gln Gly Asp Thr
        275                 280                 285

Val Phe Val Glu Val Ser Ala Ser Pro Val Leu Leu Gln Ala Met Asp
    290                 295                 300

Asp Asp Val Val Thr Val Ala Thr Leu Arg Arg Asp Asp Gly Asp Ala
305                 310                 315                 320

Thr Arg Met Leu Thr Ala Leu Ala Gln Ala Tyr Val Glu Gly Val Thr
                325                 330                 335

Val Asp Trp Pro Ala Val Leu Gly Thr Thr Ala Ala Arg Val Leu Asp
            340                 345                 350

Leu Pro Thr Tyr Ala Phe Gln His Gln Arg Tyr Trp Leu Lys Gly Val
        355                 360                 365

Asp Arg Ala Ala Ala Asp Gly His Pro Leu Leu Gly Thr
    370                 375                 380

<210> SEQ ID NO 15
<211> LENGTH: 428
<212> TYPE: PRT
<213> ORGANISM: Streptomyces hygroscopicus

<400> SEQUENCE: 15

Pro Val Val Ala Ser Glu Leu Val Pro Leu Val Ile Ser Ala Lys Thr
  1               5                  10                  15

Leu Pro Ala Leu Thr Glu His Glu Asp Arg Leu Arg Ala Tyr Leu Ala
             20                  25                  30

Ala Ser Pro Gly Ala Asp Met Arg Ala Val Gly Ser Thr Leu Ala Leu
         35                  40                  45

Thr Arg Ser Val Phe Glu His Arg Ala Val Leu Leu Gly His Asp Thr
     50                  55                  60

Val Thr Val Thr Gly Thr Gly Thr Ala Val Ser Asn Pro Arg Val Val
 65                  70                  75                  80

Phe Val Phe Pro Gly Gln Gly Trp Gln Trp Leu Gly Met Gly Ser Ala
                 85                  90                  95

Leu Arg Gly Ser Ser Val Val Phe Ala Glu Arg Met Ala Glu Cys Ala
            100                 105                 110

Ala Ala Leu Ser Glu Phe Val Asp Trp Asp Leu Phe Ala Val Leu Asp
        115                 120                 125

Asp Pro Ala Val Val Asp Arg Val Asp Val Val Gln Pro Ala Ser Trp
    130                 135                 140

Ala Val Met Val Ser Leu Ala Ala Val Trp Gln Ala Asp Gly Val Arg
145                 150                 155                 160

Pro Asp Ala Val Ile Gly His Ser Gln Gly Glu Ile Ala Ala Ala Cys
                165                 170                 175

Val Ala Gly Ala Val Ser Leu Arg Asp Ala Ala Arg Ser Val Thr Leu
            180                 185                 190

Arg Ser Gln Ala Ile Ala Arg Gly Leu Ala Gly Arg Gly Ala Met Ala
        195                 200                 205

Ser Val Ala Leu Pro Ala His Glu Ile Glu Leu Val Asp Gly Ala Trp
    210                 215                 220

Ile Ala Ala His Asn Gly Pro Ala Ser Thr Val Val Ala Gly Ala Pro
225                 230                 235                 240

Glu Ala Val Asp Arg Val Leu Ala Val His Glu Ala Arg Gly Val Arg
                245                 250                 255
```

```
Val Arg Arg Ile Ala Val Asp Tyr Ala Ser His Thr Pro His Val Glu
            260                 265                 270

Leu Ile Arg Asp Glu Leu Leu Asp Ile Thr Ala Gly Ile Gly Ser Gln
        275                 280                 285

Ala Pro Val Val Pro Trp Leu Ser Thr Val Asp Gly Thr Trp Val Glu
    290                 295                 300

Gly Pro Leu Asp Val Glu Tyr Trp Tyr Arg Asn Leu Arg Glu Pro Val
305                 310                 315                 320

Gly Phe Asp Ser Ala Val Gly Gln Leu Arg Ala Glu Gly Asp Thr Val
                325                 330                 335

Phe Val Glu Val Ser Ala Ser Pro Val Leu Leu Gln Ala Met Asp Asp
            340                 345                 350

Asp Val Val Thr Val Ala Thr Leu Arg Arg Asp Gly Asp Ala Thr
            355                 360                 365

Arg Met Leu Thr Ala Leu Ala Gln Ala Phe Val Glu Gly Val Thr Val
    370                 375                 380

Asp Trp Pro Ala Ile Leu Gly Thr Ala Thr Thr Arg Val Pro Asp Leu
385                 390                 395                 400

Pro Thr Tyr Ala Phe Gln His Gln Arg Phe Trp Ala Glu Gly Ala Asp
                405                 410                 415

Arg Ser Val Ala Gly Gly His Pro Leu Leu Gly Val
            420                 425

<210> SEQ ID NO 16
<211> LENGTH: 391
<212> TYPE: PRT
<213> ORGANISM: Streptomyces hygroscopicus

<400> SEQUENCE: 16

Ala Val Ala Ser Thr Leu Ala Val Thr Arg Ser Val Phe Glu His Arg
1               5                   10                  15

Ala Val Leu Leu Gly Asp Glu Thr Val Thr Gly Thr Ala Val Ser Asp
            20                  25                  30

Pro Arg Ile Val Phe Val Phe Pro Gly Gln Gly Trp Gln Trp Leu Gly
        35                  40                  45

Met Gly Ser Ala Leu Arg Asp Ser Ser Val Val Phe Ala Glu Arg Met
    50                  55                  60

Ala Glu Cys Ala Ala Ala Leu Ser Glu Phe Val Asp Trp Asp Leu Phe
65                  70                  75                  80

Ala Val Leu Asp Asp Pro Ala Val Val Asp Arg Val Asp Val Val Gln
                85                  90                  95

Pro Ala Ser Trp Ala Val Met Val Ser Leu Ala Ala Val Trp Gln Ala
            100                 105                 110

Ala Gly Val Arg Pro Asp Ala Val Ile Gly His Ser Gln Gly Glu Ile
        115                 120                 125

Ala Ala Ala Cys Val Ala Gly Ala Val Ser Met Arg Asp Ala Ala Arg
130                 135                 140

Ile Val Thr Leu Arg Ser Gln Ala Ile Ala Arg Gly Leu Ala Gly Arg
145                 150                 155                 160

Gly Ala Met Ala Ser Val Ala Leu Pro Ala Gln Asp Val Glu Leu Val
                165                 170                 175

Asp Gly Ala Trp Ile Ala Ala His Asn Gly Pro Ala Ser Thr Val Ile
            180                 185                 190

Ala Gly Thr Pro Glu Ala Val Asp His Val Leu Thr Ala Leu Arg Gln
        195                 200                 205
```

```
Arg Gly Ala Gly Ala Ala Asp His Val Asp Tyr Ala Ser His Thr Pro
        210                 215                 220

His Val Glu Leu Ile Arg Asp Glu Leu Leu Asp Ile Thr Ser Asp Ser
225                 230                 235                 240

Ser Ser Gln Asp Pro Leu Val Pro Trp Leu Ser Thr Val Asp Gly Thr
                245                 250                 255

Trp Val Asp Ser Pro Leu Asp Gly Glu Tyr Trp Tyr Arg Asn Leu Arg
                260                 265                 270

Glu Pro Val Gly Phe His Pro Ala Val Ser Gln Leu Gln Ala Gln Gly
                275                 280                 285

Asp Thr Val Phe Val Glu Val Ser Ala Ser Pro Val Leu Met Gln Ala
        290                 295                 300

Met Asp Asp Val Val Thr Val Ala Thr Leu Arg Arg Asp Asp Gly
305                 310                 315                 320

Asp Ala Thr Arg Met Leu Thr Ala Leu Ala Gln Ala Tyr Val His Gly
                325                 330                 335

Val Thr Val Asp Trp Arg Ala Val Leu Gly Asp Val Pro Ala Thr Arg
                340                 345                 350

Val Leu Asp Leu Pro Thr Tyr Ala Phe Gln His Gln Arg Tyr Trp Ala
                355                 360                 365

Glu Ala Gly Arg Ser Ala Asp Val Ser Ala Ala Gly Leu Asp Ala Val
        370                 375                 380

Gly His Pro Leu Leu Gly Ala
385                 390

<210> SEQ ID NO 17
<211> LENGTH: 367
<212> TYPE: PRT
<213> ORGANISM: Streptomyces sp.

<400> SEQUENCE: 17

Val Val Thr Gly Thr Ala Leu Thr Ala Pro Arg Thr Val Phe Val Phe
1               5                   10                  15

Pro Gly Gln Gly Ser Gln Trp Leu Gly Met Gly Arg Glu Leu Met Ala
                20                  25                  30

Glu Ser Pro Val Phe Ala Ala Arg Met Arg Gln Cys Ala Asp Ala Leu
            35                  40                  45

Ala Glu His Thr Gly Arg Asp Leu Ile Ala Met Leu Asp Asp Pro Ala
        50                  55                  60

Val Lys Ser Arg Val Asp Val His Pro Val Cys Trp Ala Val Met
65                  70                  75                  80

Val Ser Leu Ala Ala Val Trp Glu Ala Ala Gly Val Arg Pro Asp Ala
                85                  90                  95

Val Val Gly His Ser Gln Gly Glu Ile Ala Ala Ala Cys Val Ala Gly
                100                 105                 110

Ala Ile Ser Leu Glu Asp Gly Ala Arg Leu Val Ala Leu Arg Ser Ala
        115                 120                 125

Leu Leu Val Arg Glu Leu Ala Gly Arg Gly Ala Met Gly Ser Ile Ala
    130                 135                 140

Phe Ala Ala Ala Ala Arg Ile Asp Gly Val Trp Val Ala Gly Arg Asn
145                 150                 155                 160

Gly Thr Ala Thr Thr Ile Val Ser Gly Arg Pro Asp Ala Val Glu Thr
                165                 170                 175

Leu Ile Ala Asp Tyr Glu Ala Arg Gly Val Trp Val Thr Arg Leu Val
                180                 185                 190
```

-continued

```
Val Asp Cys Pro Thr His Thr Pro Phe Val Asp Pro Leu Tyr Asp Glu
        195                 200                 205

Leu Gln Arg Ile Val Ala Ala Thr Ser Arg Ala Pro Glu Ile Pro
    210                 215                 220

Trp Phe Ser Thr Ala Asp Glu Arg Trp Ile Asp Ala Pro Leu Asp Asp
225                 230                 235                 240

Glu Tyr Trp Phe Arg Asn Met Arg Asn Pro Val Gly Phe Ala Ala Ala
                245                 250                 255

Val Ala Ala Ala Arg Glu Pro Gly Asp Thr Val Phe Ile Glu Val Ser
            260                 265                 270

Ala His Pro Val Leu Leu Pro Ala Ile Asn Gly Thr Thr Val Gly Thr
        275                 280                 285

Leu Arg Arg Gly Gly Gly Ala Asp Arg Val Leu Asp Ser Leu Ala Lys
    290                 295                 300

Ala His Thr Val Gly Val Ala Val Asp Trp Ser Thr Val Val Ala Ala
305                 310                 315                 320

Thr Gly Ala Ala Asp Asp Ala Ala Ser Val Thr Ala His Asp Thr Gly
                325                 330                 335

Thr Ala His Asp Leu Pro Thr Tyr Ala Phe His His Glu Arg Tyr Trp
            340                 345                 350

Ile Glu Pro Ala Thr Gly Thr Asp Ala Ser Gly Leu Gly Leu Asp
        355                 360                 365

<210> SEQ ID NO 18
<211> LENGTH: 445
<212> TYPE: PRT
<213> ORGANISM: Streptomyces fradiae

<400> SEQUENCE: 18

Val Val Arg Glu Ala Ala Gly Arg Leu Ala Glu Val Val Glu Ala Gly
1               5                   10                  15

Gly Val Gly Leu Ala Asp Val Ala Val Thr Met Ala Gly Arg Ser Arg
            20                  25                  30

Phe Gly Tyr Arg Ala Val Val Leu Ala Arg Gly Glu Ala Glu Leu Ala
        35                  40                  45

Gly Arg Leu Arg Ala Leu Ala Gly Gly Asp Pro Asp Ala Gly Val Val
    50                  55                  60

Thr Gly Ala Val Val Asp Pro Glu Thr Gly Ser Gly Gly Gly Gly Val
65                  70                  75                  80

Val Leu Val Phe Pro Gly Gln Gly Thr Gln Trp Val Gly Met Gly Ala
                85                  90                  95

Gly Leu Leu Gly Ser Ser Glu Val Phe Ala Ala Ser Met Arg Glu Cys
            100                 105                 110

Ala Arg Ala Leu Ser Val His Val Gly Trp Asp Leu Leu Glu Val Val
        115                 120                 125

Ser Gly Gly Ala Gly Leu Glu Arg Val Asp Val Val Gln Pro Val Thr
    130                 135                 140

Trp Ala Val Met Val Ser Leu Ala Arg Tyr Trp Gln Ala Met Gly Val
145                 150                 155                 160

Asp Val Ala Ala Val Gly His Ser Gln Gly Glu Ile Ala Ala Ala
                165                 170                 175

Thr Val Ala Gly Ala Leu Ser Leu Glu Asp Ala Ala Ala Val Val Ala
            180                 185                 190

Leu Arg Ala Gly Leu Ile Gly Arg Tyr Leu Ala Gly Arg Gly Ala Met
        195                 200                 205
```

```
Ala Ala Val Pro Leu Pro Ala Gly Glu Val Glu Ala Gly Leu Ala Lys
            210                 215                 220

Trp Pro Gly Val Glu Val Ala Ala Val Asn Gly Pro Ala Ser Thr Val
225                 230                 235                 240

Val Ser Gly Asp Arg Arg Ala Val Ala Gly Tyr Val Ala Val Cys Gln
                245                 250                 255

Ala Glu Gly Val Gln Ala Arg Leu Ile Pro Val Asp Tyr Ala Ser His
            260                 265                 270

Ser Arg His Val Glu Asp Leu Lys Gly Glu Leu Glu Arg Val Leu Ser
        275                 280                 285

Gly Ile Arg Pro Arg Ser Pro Arg Val Pro Val Cys Ser Thr Val Ala
290                 295                 300

Gly Glu Gln Pro Gly Glu Pro Val Phe Asp Ala Gly Tyr Trp Phe Arg
305                 310                 315                 320

Asn Leu Arg Asn Arg Val Glu Phe Ser Ala Val Val Gly Gly Leu Leu
                325                 330                 335

Glu Glu Gly His Arg Arg Phe Ile Glu Val Ser Ala His Pro Val Leu
            340                 345                 350

Val His Ala Ile Glu Gln Thr Ala Glu Ala Ala Asp Arg Ser Val His
        355                 360                 365

Ala Thr Gly Thr Leu Arg Arg Gln Asp Asp Ser Pro His Arg Leu Leu
370                 375                 380

Thr Ser Thr Ala Glu Ala Trp Ala His Gly Ala Thr Leu Thr Trp Asp
385                 390                 395                 400

Pro Ala Leu Pro Pro Gly His Leu Thr Thr Leu Pro Thr Tyr Pro Phe
                405                 410                 415

Asn His His His Tyr Trp Leu Asp Thr Thr Pro Thr Thr Pro Ala Thr
            420                 425                 430

Thr Thr Gln Ser Pro Thr Asp Ala Gln Asn Pro Ala Asp
        435                 440                 445

<210> SEQ ID NO 19
<211> LENGTH: 436
<212> TYPE: PRT
<213> ORGANISM: Streptomyces fradiae

<400> SEQUENCE: 19

Gly Arg Leu Ala Glu Val Val Glu Ala Gly Gly Val Gly Leu Ala Asp
1               5                   10                  15

Val Ala Val Thr Met Ala Gly Arg Ser Arg Phe Gly Tyr Arg Ala Val
            20                  25                  30

Val Leu Ala Arg Gly Glu Ala Glu Leu Ala Gly Arg Leu Arg Ala Leu
        35                  40                  45

Ala Gly Gly Asp Pro Asp Ala Gly Val Val Thr Gly Ala Val Val Asp
    50                  55                  60

Pro Glu Thr Gly Ser Gly Gly Gly Val Val Leu Val Phe Pro Gly
65                  70                  75                  80

Gln Gly Thr Gln Trp Val Gly Met Gly Ala Gly Leu Leu Gly Ser Ser
                85                  90                  95

Glu Val Phe Ala Ala Ser Met Arg Glu Cys Ala Arg Ala Leu Ser Val
            100                 105                 110

His Val Gly Trp Asp Leu Leu Glu Val Val Ser Gly Gly Ala Gly Leu
        115                 120                 125

Glu Arg Val Asp Val Val Gln Pro Val Thr Trp Ala Val Met Val Ser
    130                 135                 140
```

```
Leu Ala Arg Tyr Trp Gln Ala Met Gly Val Asp Val Ala Val Val
145                 150                 155                 160

Gly His Ser Gln Gly Glu Ile Ala Ala Thr Val Ala Gly Ala Leu
                165                 170                 175

Ser Leu Glu Asp Ala Ala Val Val Ala Leu Arg Ala Gly Leu Ile
            180                 185                 190

Gly Arg Tyr Leu Ala Gly Arg Gly Ala Met Ala Ala Val Pro Leu Pro
        195                 200                 205

Ala Gly Glu Val Glu Ala Gly Leu Ala Lys Trp Pro Gly Val Glu Val
210                 215                 220

Ala Ala Val Asn Gly Pro Ala Ser Thr Val Val Ser Gly Asp Arg Arg
225                 230                 235                 240

Ala Val Ala Gly Tyr Val Ala Val Cys Gln Ala Glu Gly Val Gln Ala
            245                 250                 255

Arg Leu Ile Pro Val Asp Tyr Ala Ser His Ser Arg His Val Glu Asp
            260                 265                 270

Leu Lys Gly Glu Leu Glu Arg Val Leu Ser Gly Ile Arg Pro Arg Ser
        275                 280                 285

Pro Arg Val Pro Val Cys Ser Thr Val Ala Gly Glu Gln Pro Gly Glu
        290                 295                 300

Pro Val Phe Asp Ala Gly Tyr Trp Phe Arg Asn Leu Arg Asn Arg Val
305                 310                 315                 320

Glu Phe Ser Ala Val Val Gly Leu Leu Glu Glu Gly His Arg Arg
            325                 330                 335

Phe Ile Glu Val Ser Ala His Pro Val Leu Val His Ala Ile Glu Gln
            340                 345                 350

Thr Ala Glu Ala Ala Asp Arg Ser Val His Ala Thr Gly Thr Leu Arg
            355                 360                 365

Arg Gln Asp Asp Ser Pro His Arg Leu Leu Thr Ser Thr Ala Glu Ala
    370                 375                 380

Trp Ala His Gly Ala Thr Leu Thr Trp Asp Pro Ala Leu Pro Pro Gly
385                 390                 395                 400

His Leu Thr Thr Leu Pro Thr Tyr Pro Phe Asn His His His Tyr Trp
                405                 410                 415

Leu Asp Thr Thr Pro Thr Thr Pro Ala Thr Thr Thr Gln Ser Pro Thr
            420                 425                 430

Asp Ala Trp Arg
        435

<210> SEQ ID NO 20
<211> LENGTH: 416
<212> TYPE: PRT
<213> ORGANISM: Streptomyces fradiae

<400> SEQUENCE: 20

Met Ala Gly Arg Ser Arg Phe Gly Tyr Arg Ala Val Val Leu Ala Arg
1               5                   10                  15

Gly Glu Ala Glu Leu Ala Gly Arg Leu Arg Ala Leu Ala Gly Gly Asp
            20                  25                  30

Pro Asp Ala Gly Val Val Thr Gly Ala Val Val Asp Pro Glu Thr Gly
        35                  40                  45

Ser Gly Gly Gly Gly Val Val Leu Val Phe Pro Gly Gln Gly Thr Gln
    50                  55                  60

Trp Val Gly Met Gly Ala Gly Leu Leu Gly Ser Ser Glu Val Phe Ala
65                  70                  75                  80
```

-continued

```
Ala Ser Met Arg Glu Cys Ala Arg Ala Leu Ser Val His Val Glu Trp
                85                  90                  95

Asp Leu Leu Glu Val Val Ser Gly Gly Ala Gly Leu Glu Arg Val Asp
            100                 105                 110

Val Val Gln Pro Val Thr Trp Ala Val Met Val Ser Leu Ala Arg Tyr
        115                 120                 125

Trp Gln Ala Met Gly Val Asp Val Ala Ala Val Gly His Ser Gln
    130                 135                 140

Gly Glu Ile Ala Ala Ala Thr Val Ala Gly Ala Leu Ser Leu Glu Asp
145                 150                 155                 160

Ala Ala Ala Val Val Ala Leu Arg Ala Gly Leu Ile Gly Arg Tyr Leu
                165                 170                 175

Ala Gly Arg Gly Ala Met Ala Ala Val Pro Leu Pro Ala Gly Glu Val
            180                 185                 190

Glu Ala Gly Leu Ala Lys Trp Pro Gly Val Glu Val Ala Ala Val Asn
        195                 200                 205

Gly Pro Ala Ser Thr Val Val Ser Gly Asp Arg Arg Ala Val Ala Gly
    210                 215                 220

Tyr Val Ala Val Cys Gln Ala Glu Gly Val Gln Ala Arg Leu Ile Pro
225                 230                 235                 240

Val Asp Tyr Ala Ser His Ser Arg His Val Glu Asp Leu Lys Gly Glu
                245                 250                 255

Leu Glu Arg Val Leu Ser Gly Ile Arg Pro Arg Ser Pro Arg Val Pro
            260                 265                 270

Val Cys Ser Thr Val Ala Gly Glu Gln Pro Gly Glu Pro Val Phe Asp
        275                 280                 285

Ala Gly Tyr Trp Phe Arg Asn Leu Arg Asn Arg Val Glu Phe Ser Ala
    290                 295                 300

Val Val Gly Gly Leu Leu Glu Glu Gly His Arg Arg Phe Ile Glu Val
305                 310                 315                 320

Ser Ala His Pro Val Leu Val His Ala Ile Glu Gln Thr Ala Glu Ala
                325                 330                 335

Ala Asp Arg Ser Val His Ala Thr Gly Thr Leu Arg Arg Gln Asp Asp
            340                 345                 350

Ser Pro His Arg Leu Leu Thr Ser Thr Ala Glu Ala Trp Ala His Gly
        355                 360                 365

Ala Thr Leu Thr Trp Asp Pro Ala Leu Pro Pro Gly His Leu Thr Thr
    370                 375                 380

Leu Pro Thr Tyr Pro Phe Asn His His His Tyr Trp Leu Asp Thr Thr
385                 390                 395                 400

Pro Thr Thr Pro Ala Thr Thr Gln Ser Pro Thr Asp Ala Trp Arg
                405                 410                 415

<210> SEQ ID NO 21
<211> LENGTH: 388
<212> TYPE: PRT
<213> ORGANISM: Streptomyces fradiae

<400> SEQUENCE: 21

Arg Leu Arg Ala Leu Ala Gly Gly Asp Pro Asp Ala Gly Val Val Thr
  1               5                  10                  15

Gly Ala Val Val Asp Pro Glu Thr Gly Ser Gly Gly Gly Gly Val Val
             20                  25                  30

Leu Val Phe Pro Gly Gln Gly Thr Gln Trp Val Gly Met Gly Ala Gly
         35                  40                  45
```

```
Leu Leu Gly Ser Ser Glu Val Phe Ala Ala Ser Met Arg Glu Cys Ala
     50                  55                  60

Arg Ala Leu Ser Val His Val Glu Trp Asp Leu Leu Glu Val Val Ser
 65                  70                  75                  80

Gly Gly Ala Gly Leu Glu Arg Val Asp Val Gln Pro Val Thr Trp
                 85                  90                  95

Ala Val Met Val Ser Leu Ala Arg Tyr Trp Gln Ala Met Gly Val Asp
                100                 105                 110

Val Ala Ala Val Val Gly His Ser Gln Gly Glu Ile Ala Ala Ala Thr
                115                 120                 125

Val Ala Gly Ala Leu Ser Leu Glu Asp Ala Ala Ala Val Val Ala Leu
            130                 135                 140

Arg Ala Gly Leu Ile Gly Arg Tyr Leu Ala Gly Arg Gly Ala Met Ala
145                 150                 155                 160

Ala Val Pro Leu Pro Ala Gly Glu Val Glu Ala Gly Leu Ala Lys Trp
                165                 170                 175

Pro Gly Val Gln Val Ala Ala Val Asn Gly Pro Ala Ser Thr Val Val
                180                 185                 190

Ser Gly Asp Arg Arg Ala Val Ala Gly Tyr Val Ala Val Cys Gln Ala
            195                 200                 205

Glu Gly Val Gln Ala Arg Leu Ile Pro Val Asp Tyr Ala Ser His Ser
    210                 215                 220

Arg His Val Glu Asp Leu Lys Gly Glu Leu Glu Arg Val Leu Ser Gly
225                 230                 235                 240

Ile Arg Pro Arg Ser Pro Arg Val Pro Val Cys Ser Thr Val Ala Gly
                245                 250                 255

Glu Gln Pro Gly Glu Pro Val Phe Asp Ala Gly Tyr Trp Phe Arg Asn
            260                 265                 270

Leu Arg Asn Arg Val Glu Phe Ser Ala Val Val Gly Leu Leu Glu
        275                 280                 285

Gln Gly His Arg Arg Phe Ile Glu Val Ser Ala His Pro Val Leu Val
    290                 295                 300

His Ala Ile Glu Gln Thr Ala Glu Ala Ala Asp Arg Ser Val His Ala
305                 310                 315                 320

Thr Gly Thr Leu Arg Arg Gln Asp Asp Ser Pro His Arg Leu Leu Thr
                325                 330                 335

Ser Thr Ala Glu Ala Trp Ala His Gly Ala Thr Leu Thr Trp Asp Pro
            340                 345                 350

Ala Leu Pro Pro Gly His Leu Thr Thr Leu Pro Thr Tyr Pro Phe Asn
        355                 360                 365

His His His Tyr Trp Ala Val Thr Ser Pro Ala Gly Val Gly Asp Ala
    370                 375                 380

Ala Ala Gly Arg
385

<210> SEQ ID NO 22
<211> LENGTH: 444
<212> TYPE: PRT
<213> ORGANISM: Streptomyces fradiae

<400> SEQUENCE: 22

Asp Val Ala Val Thr Met Ala Asp Arg Ser Arg Phe Gly Tyr Arg Ala
  1               5                  10                  15

Val Val Leu Ala Arg Gly Glu Ala Glu Leu Ala Gly Arg Leu Arg Ala
                 20                  25                  30
```

-continued

```
Leu Ala Gly Gly Asp Pro Asp Ala Gly Val Val Thr Gly Ala Val Leu
         35                  40                  45

Asp Gly Gly Val Val Gly Ala Ala Pro Gly Gly Ala Gly Ala Ala
 50                  55                  60

Gly Gly Ala Gly Ala Ala Gly Gly Ala Gly Gly Gly Val Val Leu
 65                  70                  75                  80

Val Phe Pro Gly Gln Gly Thr Gln Trp Val Gly Met Gly Ala Gly Leu
                 85                  90                  95

Leu Gly Ser Ser Glu Val Phe Ala Ala Ser Met Arg Glu Cys Ala Arg
                100                 105                 110

Ala Leu Ser Val His Val Gly Trp Asp Leu Leu Glu Val Val Ser Gly
             115                 120                 125

Gly Ala Gly Leu Glu Arg Val Asp Val Val Gln Pro Val Thr Trp Ala
 130                 135                 140

Val Met Val Ser Leu Ala Arg Tyr Trp Gln Ala Met Gly Val Asp Val
145                 150                 155                 160

Ala Ala Val Val Gly His Ser Gln Gly Glu Ile Ala Ala Ala Thr Val
                 165                 170                 175

Ala Gly Ala Leu Ser Leu Glu Asp Ala Ala Val Val Ala Leu Arg
             180                 185                 190

Ala Gly Leu Ile Gly Arg Tyr Leu Ala Gly Arg Gly Ala Met Ala Ala
         195                 200                 205

Val Pro Leu Pro Ala Gly Glu Val Glu Ala Gly Leu Ala Lys Trp Pro
     210                 215                 220

Gly Val Glu Val Ala Ala Val Asn Gly Pro Ala Ser Thr Val Val Ser
225                 230                 235                 240

Gly Asp Arg Arg Ala Val Ala Gly Tyr Val Ala Val Cys Gln Ala Glu
                 245                 250                 255

Gly Val Gln Ala Arg Leu Ile Pro Val Asp Tyr Ala Ser His Ser Arg
             260                 265                 270

His Val Glu Asp Leu Lys Gly Glu Leu Glu Arg Val Leu Ser Gly Ile
         275                 280                 285

Arg Pro Arg Ser Pro Arg Val Pro Val Cys Ser Thr Val Ala Gly Glu
     290                 295                 300

Gln Pro Gly Glu Pro Val Phe Asp Ala Gly Tyr Trp Phe Arg Asn Leu
305                 310                 315                 320

Arg Asn Arg Val Glu Phe Ser Ala Val Val Gly Gly Leu Leu Glu Glu
                 325                 330                 335

Gly His Arg Arg Phe Ile Glu Val Ser Ala His Pro Val Leu Val His
             340                 345                 350

Ala Ile Glu Gln Thr Ala Glu Ala Ala Asp Arg Ser Val His Ala Thr
         355                 360                 365

Gly Thr Leu Arg Arg Gln Asp Asp Ser Pro His Arg Leu Leu Thr Ser
     370                 375                 380

Thr Ala Glu Ala Trp Ala His Gly Ala Thr Leu Thr Trp Asp Pro Ala
385                 390                 395                 400

Leu Pro Pro Gly His Leu Thr Thr Leu Pro Thr Tyr Pro Phe Asn His
                 405                 410                 415

His His Tyr Trp Leu Asp Thr Ile Asp Gly Gly Gly Asp Asp Ala
             420                 425                 430

Thr Gln Glu Lys Glu Ser Gly Pro Leu Thr Arg Glu
         435                 440
```

<210> SEQ ID NO 23
<211> LENGTH: 419
<212> TYPE: PRT
<213> ORGANISM: Streptomyces caelestis

<400> SEQUENCE: 23

```
Leu Leu Ser Thr Arg Ala Arg Phe Pro Arg Arg Ala Val Val Gly
 1               5                  10                  15

Glu Ser Met Thr Glu Leu Ala Glu Ala Leu Asp Ala Val Ala Glu Gly
             20                  25                  30

Gly Pro His Pro Leu Ala Ala Thr Gly Thr Ala Gly Thr Ala Asp Arg
             35                  40                  45

Val Val Phe Val Phe Pro Gly Gln Gly Ser Gln Trp Ala Gly Met Ala
 50                  55                  60

Glu Gly Leu Leu Glu Arg Ser Gly Ala Phe Arg Ser Ala Ala Asp Ser
 65                  70                  75                  80

Cys Asp Ala Ala Leu Arg Pro Tyr Leu Gly Trp Ser Val Leu Ser Val
                 85                  90                  95

Leu Arg Gly Glu Pro Asp Ala Pro Ser Leu Asp Arg Val Asp Val Val
                100                 105                 110

Gln Pro Val Leu Phe Thr Met Met Val Ser Leu Ala Ala Val Trp Arg
            115                 120                 125

Ala Leu Gly Val Glu Pro Ala Ala Val Val Gly His Ser Gln Gly Glu
        130                 135                 140

Ile Ala Ala Ala His Val Ala Gly Ala Leu Ser Leu Asp Asp Ser Ala
145                 150                 155                 160

Arg Ile Val Ala Leu Arg Ser Arg Ala Trp Leu Gly Leu Ala Gly Lys
                165                 170                 175

Gly Gly Met Val Ala Val Pro Met Pro Ala Glu Glu Leu Arg Pro Arg
            180                 185                 190

Leu Val Thr Trp Gly Asp Arg Leu Ala Val Ala Ala Val Asn Ser Pro
        195                 200                 205

Gly Ser Cys Ala Val Ala Gly Asp Pro Glu Ala Leu Ala Glu Leu Val
    210                 215                 220

Ala Leu Leu Thr Gly Glu Gly Val His Ala Arg Pro Ile Pro Gly Val
225                 230                 235                 240

Asp Thr Ala Gly His Ser Pro Gln Val Asp Ala Leu Arg Ala His Leu
                245                 250                 255

Leu Glu Val Leu Ala Pro Val Ala Pro Arg Pro Ala Asp Ile Pro Phe
            260                 265                 270

Tyr Ser Thr Val Thr Gly Gly Leu Leu Asp Gly Thr Glu Leu Asp Ala
        275                 280                 285

Thr Tyr Trp Tyr Arg Asn Met Arg Glu Pro Val Glu Phe Glu Arg Ala
    290                 295                 300

Thr Arg Ala Leu Ile Ala Asp Gly His Asp Val Phe Leu Glu Thr Ser
305                 310                 315                 320

Pro His Pro Met Leu Ala Val Ala Leu Glu Gln Thr Val Thr Asp Ala
                325                 330                 335

Gly Thr Asp Ala Ala Val Leu Gly Thr Leu Arg Arg Arg His Gly Gly
            340                 345                 350

Pro Arg Ala Leu Ala Leu Ala Val Cys Arg Ala Phe Ala His Gly Val
        355                 360                 365

Glu Val Asp Pro Glu Ala Val Phe Gly Pro Gly Ala Arg Pro Val Glu
    370                 375                 380
```

```
Leu Pro Thr Tyr Pro Phe Gln Arg Glu Arg Tyr Trp Cys His Pro Gly
385                 390                 395                 400

Val Arg Gly Gly Asp Pro Ala Ser Leu Gly Met Asp Gly Ala Asp His
                405                 410                 415

Pro Leu Leu

<210> SEQ ID NO 24
<211> LENGTH: 450
<212> TYPE: PRT
<213> ORGANISM: Streptomyces fradiae

<400> SEQUENCE: 24

Ala Ala Leu Arg Glu Gln Ser Thr Arg Leu Leu Asn Asp Leu Leu Glu
1               5                   10                  15

His Pro Asp Glu His Pro Ala Asp Val Gly Tyr Thr Leu Ile Thr Gly
                20                  25                  30

Arg Ala His Phe Gly His Arg Ala Ala Val Ile Gly Glu Ser Arg Glu
            35                  40                  45

Glu Leu Leu Asp Ala Leu Lys Ala Leu Ala Glu Gly Arg Glu His His
    50                  55                  60

Thr Val Val Arg Gly Asp Gly Thr Ala His Pro Asp Arg Arg Val Val
65                  70                  75                  80

Phe Val Phe Pro Gly Gln Gly Ser Gln Trp Pro Ser Met Ala Arg Asp
                85                  90                  95

Leu Leu Asp Arg Ala Pro Ala Phe Arg Glu Thr Ala Lys Ala Cys Asp
            100                 105                 110

Ala Ala Leu Ser Val His Leu Asp Trp Ser Val Leu Asp Val Leu Gln
        115                 120                 125

Glu Lys Pro Asp Ala Pro Pro Leu Ser Arg Val Asp Val Val Gln Pro
    130                 135                 140

Val Leu Phe Thr Met Met Leu Ser Leu Ala Ala Cys Trp Arg Asp Leu
145                 150                 155                 160

Gly Val His Pro Ala Ala Val Val Gly His Ser Gln Gly Glu Ile Ala
                165                 170                 175

Ala Ala Cys Val Ala Gly Ala Leu Ser Leu Glu Asp Ala Ala Arg Ile
            180                 185                 190

Val Ala Leu Arg Ser Arg Ala Trp Leu Thr Leu Ala Gly Lys Gly Gly
        195                 200                 205

Met Ala Ala Val Ser Leu Pro Glu Ala Arg Leu Arg Glu Arg Ile Glu
    210                 215                 220

Arg Phe Gly Gln Arg Leu Ser Val Ala Ala Val Asn Ser Pro Gly Thr
225                 230                 235                 240

Ala Ala Val Ala Gly Asp Val Asp Ala Leu Arg Glu Leu Leu Ala Glu
                245                 250                 255

Leu Thr Ala Glu Gly Ile Arg Ala Lys Pro Ile Pro Gly Val Asp Thr
            260                 265                 270

Ala Gly His Ser Ala Gln Val Asp Gly Leu Lys Glu His Leu Phe Glu
        275                 280                 285

Val Leu Ala Pro Val Ser Pro Arg Ser Ser Asp Ile Pro Phe Tyr Ser
    290                 295                 300

Thr Val Thr Gly Ala Pro Leu Asp Thr Glu Arg Leu Asp Ala Gly Tyr
305                 310                 315                 320

Trp Tyr Arg Asn Met Arg Glu Pro Val Glu Phe Glu Lys Ala Val Arg
                325                 330                 335
```

```
Ala Leu Ile Ala Asp Gly Tyr Asp Leu Phe Leu Glu Cys Asn Pro His
            340                 345                 350

Pro Met Leu Ala Met Ser Leu Asp Glu Thr Leu Thr Asp Ser Gly Gly
            355                 360                 365

His Gly Thr Val Met His Thr Leu Arg Arg Gln Lys Gly Ser Ala Lys
            370                 375                 380

Asp Phe Gly Met Ala Leu Cys Leu Ala Tyr Val Asn Gly Leu Glu Ile
385                 390                 395                 400

Asp Gly Glu Ala Leu Phe Gly Pro Asp Ser Arg Arg Val Asn Pro Pro
                405                 410                 415

Thr Tyr Pro Phe Gln Arg Glu Arg Tyr Trp Tyr His Pro Thr Ser Gly
            420                 425                 430

Arg Arg Gly Asp Ile Thr Ala Ala Gly Val Ala Glu Ala Glu His Pro
            435                 440                 445

Leu Leu
    450

<210> SEQ ID NO 25
<211> LENGTH: 385
<212> TYPE: PRT
<213> ORGANISM: Streptomyces caelestis

<400> SEQUENCE: 25

Arg Ser Val Ala Glu Glu Arg Pro Glu Pro Asp Val Val Leu Gly Glu
  1               5                   10                  15

Ala Gly Ser Asp Arg Ala Pro Ala Phe Val Phe Pro Gly Gln Gly Ala
             20                  25                  30

Gln Trp Ala Gly Leu Gly Ala Arg Leu Leu Ala Asp Ser Pro Val Phe
         35                  40                  45

Arg Ala Arg Ala Glu Ala Cys Ala Arg Ala Leu Glu Pro His Leu Asp
     50                  55                  60

Trp Ser Val Leu Asp Val Leu Ala Gly Ala Pro Gly Thr Pro Pro Ile
 65                  70                  75                  80

Asp Arg Ala Asp Val Val Gln Pro Val Leu Phe Thr Thr Met Val Ser
                 85                  90                  95

Leu Ala Ala Leu Trp Glu Ala His Gly Val Arg Pro Ala Ala Val Val
            100                 105                 110

Gly His Ser Gln Gly Glu Val Ala Ala Ala Cys Val Ala Gly Ala Leu
        115                 120                 125

Ser Leu Asp Asp Ala Ala Leu Val Ile Ala Gly Arg Ser Arg Leu Trp
    130                 135                 140

Gly Arg Leu Ala Gly Asn Gly Gly Met Leu Ala Val Met Ala Pro Ala
145                 150                 155                 160

Glu Arg Ile Arg Glu Leu Leu Glu Pro Trp Arg Gln Arg Ile Ser Val
                165                 170                 175

Ala Ala Val Asn Gly Pro Ala Ser Val Thr Val Ser Gly Asp Ala Leu
            180                 185                 190

Ala Leu Glu Glu Phe Gly Ala Arg Leu Ser Ala Glu Gly Val Leu Arg
        195                 200                 205

Trp Pro Leu Pro Gly Val Asp Phe Ala Gly His Ser Pro Gln Val Glu
    210                 215                 220

Glu Phe Arg Ala Glu Leu Leu Asp Leu Leu Ser Gly Val Arg Pro Ala
225                 230                 235                 240

Pro Ser Arg Ile Pro Phe Phe Ser Thr Val Thr Ala Gly Pro Cys Gly
                245                 250                 255
```

```
Gly Asp Gln Leu Asp Gly Ala Tyr Trp Tyr Arg Asn Thr Arg Glu Pro
        260                 265                 270

Val Glu Phe Asp Ala Thr Val Arg Ala Leu Leu Arg Ala Gly His His
    275                 280                 285

Thr Phe Ile Glu Val Gly Pro His Pro Leu Leu Asn Ala Ala Ile Asp
290                 295                 300

Glu Ile Ala Ala Asp Glu Gly Val Ala Ala Thr Ala Leu His Thr Leu
305                 310                 315                 320

Gln Arg Gly Ala Gly Gly Leu Asp Arg Val Arg Asn Ala Val Gly Ala
                325                 330                 335

Ala Phe Ala His Gly Val Arg Val Asp Trp Asn Ala Leu Phe Glu Gly
            340                 345                 350

Thr Gly Ala Arg Arg Val Pro Leu Pro Ser Tyr Ala Phe His Arg Asp
        355                 360                 365

Arg Phe Trp Leu Pro Thr Ala Ala Arg Arg Pro Ala Thr Ser Ser
    370                 375                 380

Ser
385

<210> SEQ ID NO 26
<211> LENGTH: 388
<212> TYPE: PRT
<213> ORGANISM: Saccharopolyspora erythraea

<400> SEQUENCE: 26

Gly Leu Ala Thr Gly Asn Ala Asp Gly Ala Ala Val Gly Thr Ser Arg
1               5                   10                  15

Ala Gln Gln Arg Ala Val Phe Val Phe Pro Gly Gln Gly Trp Gln Trp
            20                  25                  30

Ala Gly Met Ala Val Asp Leu Leu Asp Thr Ser Pro Val Phe Ala Ala
        35                  40                  45

Ala Leu Arg Glu Cys Ala Asp Ala Leu Glu Pro His Leu Asp Phe Glu
    50                  55                  60

Val Ile Pro Phe Leu Arg Ala Glu Ala Arg Arg Glu Gln Asp Ala
65                  70                  75                  80

Ala Leu Ser Thr Glu Arg Val Asp Val Val Gln Pro Val Met Phe Ala
                85                  90                  95

Val Met Val Ser Leu Ala Ser Met Trp Arg Ala His Gly Val Glu Pro
            100                 105                 110

Ala Ala Val Ile Gly His Ser Gln Gly Glu Ile Ala Ala Ala Cys Val
        115                 120                 125

Ala Gly Ala Leu Ser Leu Asp Asp Ala Ala Arg Val Val Ala Leu Arg
    130                 135                 140

Ser Arg Val Ile Ala Thr Met Pro Gly Asn Lys Gly Met Ala Ser Ile
145                 150                 155                 160

Ala Ala Pro Ala Gly Glu Val Arg Ala Ile Gly Asp Arg Val Glu
                165                 170                 175

Ile Ala Ala Val Asn Gly Pro Arg Ser Val Val Ala Gly Asp Ser
            180                 185                 190

Asp Glu Leu Asp Arg Leu Val Ala Ser Cys Thr Thr Glu Cys Ile Arg
        195                 200                 205

Ala Lys Arg Leu Ala Val Asp Tyr Ala Ser His Ser Ser His Val Glu
    210                 215                 220

Thr Ile Arg Asp Ala Leu His Ala Glu Leu Gly Glu Asp Phe His Pro
225                 230                 235                 240
```

```
Leu Pro Gly Phe Val Pro Phe Phe Ser Thr Val Thr Gly Arg Trp Thr
                245                 250                 255

Gln Pro Asp Glu Leu Asp Ala Gly Tyr Trp Tyr Arg Asn Leu Arg Arg
            260                 265                 270

Thr Val Arg Phe Ala Asp Ala Val Arg Ala Leu Ala Glu Gln Gly Tyr
        275                 280                 285

Arg Thr Phe Leu Glu Val Ser Ala His Pro Ile Leu Thr Ala Ala Ile
    290                 295                 300

Glu Glu Ile Gly Asp Gly Ser Gly Ala Asp Leu Ser Ala Ile His Ser
305                 310                 315                 320

Leu Arg Arg Gly Asp Gly Ser Leu Ala Asp Phe Gly Glu Ala Leu Ser
                325                 330                 335

Arg Ala Phe Ala Ala Gly Val Ala Val Asp Trp Glu Ser Val His Leu
            340                 345                 350

Gly Thr Gly Ala Arg Arg Val Pro Leu Pro Thr Tyr Pro Phe Gln Arg
        355                 360                 365

Glu Arg Val Trp Leu Glu Pro Lys Pro Val Ala Arg Ser Thr Glu
    370                 375                 380

Val Asp Glu Val
385

<210> SEQ ID NO 27
<211> LENGTH: 386
<212> TYPE: PRT
<213> ORGANISM: Streptomyces cinnamonensis

<400> SEQUENCE: 27

Gly Ala Leu Ala Ala Gly Glu Ala Ser Ala Gly Val Val Ala Gly Val
  1               5                  10                  15

Ala Gly Asp Val Gly Pro Gly Pro Val Leu Val Phe Pro Gly Gln Gly
                 20                  25                  30

Ala Gln Trp Val Gly Met Gly Ala Gln Leu Leu Asp Glu Ser Ala Val
             35                  40                  45

Phe Ala Ala Arg Ile Ala Glu Cys Glu Arg Ala Leu Ser Ala His Val
         50                  55                  60

Asp Trp Ser Leu Ser Ala Val Leu Arg Gly Asp Gly Ser Glu Leu Ser
 65                  70                  75                  80

Arg Val Glu Val Val Gln Pro Val Leu Trp Ala Val Met Val Ser Leu
                 85                  90                  95

Ala Ala Val Trp Ala Asp Tyr Gly Val Thr Pro Ala Ala Val Ile Gly
            100                 105                 110

His Ser Gln Gly Glu Met Ala Ala Ala Cys Val Ala Gly Ala Leu Ser
        115                 120                 125

Leu Glu Asp Ala Ala Arg Ile Val Ala Val Arg Ser Asp Ala Leu Arg
    130                 135                 140

Gln Leu Gln Gly His Gly Asp Met Ala Ser Leu Ser Thr Gly Ala Glu
145                 150                 155                 160

Gln Ala Ala Glu Leu Ile Gly Asp Arg Pro Gly Val Val Val Ala Ala
                165                 170                 175

Val Asn Gly Pro Ser Ser Thr Val Ile Ser Gly Pro Pro Glu His Val
            180                 185                 190

Ala Ala Val Val Ala Asp Ala Glu Ala Arg Gly Leu Arg Ala Arg Val
        195                 200                 205

Ile Asp Val Gly Tyr Ala Ser His Gly Pro Gln Ile Asp Gln Leu His
    210                 215                 220
```

-continued

```
Asp Leu Leu Thr Glu Arg Leu Ala Asp Ile Arg Pro Thr Asn Thr Asp
225                 230                 235                 240

Val Ala Phe Tyr Ser Thr Val Thr Ala Glu Arg Leu Thr Asp Thr Thr
                245                 250                 255

Ala Leu Asp Thr Asp Tyr Trp Val Thr Asn Leu Arg Gln Pro Val Arg
            260                 265                 270

Phe Ala Asp Thr Ile Glu Ala Leu Leu Ala Asp Gly Tyr Arg Leu Phe
        275                 280                 285

Ile Glu Ala Ser Ala His Pro Val Leu Gly Leu Gly Met Glu Glu Thr
    290                 295                 300

Ile Glu Gln Ala Asp Met Pro Ala Thr Val Val Pro Thr Leu Arg Arg
305                 310                 315                 320

Asp His Gly Asp Thr Thr Gln Leu Thr Arg Ala Ala His Ala Phe
                325                 330                 335

Thr Ala Gly Ala Asp Val Asp Trp Arg Arg Trp Phe Pro Ala Asp Pro
            340                 345                 350

Ala Pro Arg Thr Ile Asp Leu Pro Thr Tyr Ala Phe Gln Arg Arg Arg
        355                 360                 365

Tyr Trp Leu Ala Asp Thr Val Lys Arg Asp Ser Gly Trp Asp Pro Ala
    370                 375                 380

Gly Ser
385

<210> SEQ ID NO 28
<211> LENGTH: 388
<212> TYPE: PRT
<213> ORGANISM: Streptomyces cinnamonensis

<400> SEQUENCE: 28

Leu Gly Ala Leu Ala Ala Gly Glu Ala Ser Ala Gly Val Val Ala Gly
1               5                   10                  15

Val Ala Gly Asp Val Gly Pro Gly Pro Val Leu Val Phe Pro Gly Gln
                20                  25                  30

Gly Ser Gln Trp Val Gly Met Gly Ala Gln Leu Leu Asp Glu Ser Pro
            35                  40                  45

Val Phe Ala Ala Arg Ile Ala Glu Cys Glu Arg Ala Leu Ser Ala Tyr
        50                  55                  60

Val Asp Trp Ser Leu Ser Ala Val Leu Arg Gly Asp Gly Ser Glu Leu
65                  70                  75                  80

Ser Arg Val Glu Val Val Gln Pro Val Leu Trp Ala Val Met Val Ser
                85                  90                  95

Leu Ala Ala Val Trp Ala Asp Tyr Gly Val Thr Pro Ala Ala Val Ile
            100                 105                 110

Gly His Ser Gln Gly Glu Met Ala Ala Ala Cys Val Ala Gly Ala Leu
        115                 120                 125

Ser Leu Glu Asp Ala Ala Arg Ile Val Ala Val Arg Ser Asp Ala Leu
    130                 135                 140

Arg Arg Leu Gln Gly His Gly Asp Met Ala Ser Leu Ser Thr Gly Ala
145                 150                 155                 160

Glu Gln Ala Ala Glu Leu Ile Gly Asp Arg Pro Gly Val Val Val Ala
                165                 170                 175

Ala Val Asn Gly Pro Ser Ser Thr Val Ile Ser Gly Pro Pro Glu His
            180                 185                 190

Val Ala Ala Val Val Ala Asp Ala Glu Ala Arg Gly Leu Arg Ala Arg
        195                 200                 205
```

```
Val Ile Asp Val Gly Tyr Ala Ser His Gly Pro Gln Ile Asp Gln Leu
    210                 215                 220

His Asp Leu Leu Thr Glu Arg Leu Ala Asp Ile Arg Pro Ala Asn Thr
225                 230                 235                 240

Asp Val Ala Phe Tyr Ser Thr Val Thr Ala Glu Arg Leu Thr Asp Thr
                245                 250                 255

Thr Ala Leu Asp Thr Asp Tyr Trp Val Thr Asn Leu Arg Gln Pro Val
                260                 265                 270

Arg Phe Ala Asp Thr Ile Glu Ala Leu Leu Ala Asp Gly Tyr Arg Leu
                275                 280                 285

Phe Ile Glu Ala Ser Ala His Pro Val Leu Gly Leu Gly Met Glu Glu
    290                 295                 300

Thr Ile Glu Gln Ala Asp Ile Pro Ala Thr Val Val Pro Thr Leu Arg
305                 310                 315                 320

Arg Asp His Gly Asp Thr Thr Gln Leu Thr Arg Ala Ala His Ala
                325                 330                 335

Phe Thr Ala Gly Ala Pro Val Asp Trp Arg Arg Trp Phe Pro Ala Asp
                340                 345                 350

Pro Thr Pro Arg Thr Val Asp Leu Pro Thr Tyr Ala Phe Gln His Gln
                355                 360                 365

His Tyr Trp Leu Glu Arg Ser Ala Ser Ala Ser Gly Ala Val Ser Gly
    370                 375                 380

Glu Gln Ser Ala
385

<210> SEQ ID NO 29
<211> LENGTH: 386
<212> TYPE: PRT
<213> ORGANISM: Streptomyces cinnamonensis

<400> SEQUENCE: 29

Leu Ala Ala Gly Glu Thr Pro Thr Asp Val Val Ser Gly Ala Ala Ala
  1               5                  10                  15

Ser Ser Gly Ala Gly Pro Val Leu Val Phe Pro Gly Gln Gly Ser Gln
                 20                  25                  30

Trp Val Gly Met Gly Ala Gln Leu Leu Asp Glu Ser Pro Val Phe Ala
             35                  40                  45

Ala Arg Ile Ala Glu Cys Glu Gln Ala Leu Ser Ala Tyr Val Asp Trp
         50                  55                  60

Ser Leu Ser Asp Val Leu Arg Gly Asp Gly Ser Glu Leu Ser Arg Val
 65                  70                  75                  80

Glu Val Val Gln Pro Val Leu Trp Ala Val Met Val Ser Leu Ala Ala
                 85                  90                  95

Val Trp Ala Asp Tyr Gly Val Thr Pro Ala Ala Val Val Gly His Ser
                100                 105                 110

Gln Gly Glu Met Ala Ala Ala Cys Val Ala Gly Ala Leu Ser Leu Glu
            115                 120                 125

Asp Ala Ala Arg Ile Val Ala Val Arg Ser Asp Ala Leu Arg Gln Leu
130                 135                 140

Gln Gly His Gly Asp Met Ala Ser Leu Gly Thr Gly Ala Glu Gln Ala
145                 150                 155                 160

Ala Glu Leu Ile Gly Asp Arg Pro Gly Val Val Ala Ala Val Asn
                165                 170                 175

Gly Pro Ser Ser Thr Val Ile Ser Gly Pro Pro Glu His Val Ala Ala
                180                 185                 190
```

```
Val Val Ala Glu Ala Glu Ala Arg Gly Leu Arg Ala Arg Val Ile Asp
        195                 200                 205
Val Gly Tyr Ala Ser His Gly Pro Gln Ile Asp Gln Leu His Asp Leu
    210                 215                 220
Leu Thr Glu Gly Leu Ala Asp Ile Arg Pro Ala Asn Thr Asp Val Ala
225                 230                 235                 240
Phe Tyr Ser Thr Val Thr Ala Glu Arg Leu Thr Asp Thr Thr Ala Leu
                245                 250                 255
Asp Thr Asp Tyr Trp Val Thr Asn Leu Arg Gln Pro Val Arg Phe Ala
            260                 265                 270
Asp Thr Ile Glu Ala Leu Leu Ala Asp Gly Tyr Arg Leu Phe Ile Glu
        275                 280                 285
Ala Ser Ala His Pro Val Leu Gly Leu Gly Met Glu Glu Thr Ile Glu
    290                 295                 300
Gln Ala Asp Ile Pro Ala Thr Val Pro Thr Leu Arg Arg Asp His
305                 310                 315                 320
Gly Asp Thr Thr Gln Leu Thr Arg Ala Ala His Ala Phe Thr Ala
                325                 330                 335
Gly Ala Asp Val Asp Trp Arg Arg Trp Phe Pro Ala Asp Pro Thr Pro
            340                 345                 350
Arg Thr Val Asp Leu Pro Thr Tyr Ala Phe Gln His Gln His Tyr Trp
        355                 360                 365
Leu Glu Glu Pro Ser Gly Leu Thr Gly Asp Ala Ala Asp Leu Gly Met
    370                 375                 380
Val Ala
385

<210> SEQ ID NO 30
<211> LENGTH: 387
<212> TYPE: PRT
<213> ORGANISM: Streptomyces cinnamonensis

<400> SEQUENCE: 30

Ala Leu Ala Ala Gly Glu Glu Ser Ala Asp Val Val Ala Gly Val Ala
  1               5                  10                  15
Gly Asp Val Gly Pro Gly Pro Val Leu Val Phe Pro Gly Gln Gly Ser
               20                  25                  30
Gln Trp Val Gly Met Gly Ala Gln Leu Leu Asp Glu Ser Pro Val Phe
           35                  40                  45
Ala Ala Arg Ile Ala Glu Cys Glu Gln Ala Leu Ser Ala Tyr Val Asp
        50                  55                  60
Trp Ser Leu Ser Ala Val Leu Arg Gly Asp Gly Ser Glu Leu Ser Arg
 65                  70                  75                  80
Val Glu Val Val Gln Pro Val Leu Trp Ala Val Met Val Ser Leu Ala
                 85                  90                  95
Ala Val Trp Ala Asp Tyr Gly Val Thr Pro Ala Ala Val Ile Gly His
            100                 105                 110
Ser Gln Gly Glu Met Ala Ala Cys Val Ala Gly Ala Leu Ser Leu
        115                 120                 125
Glu Asp Ala Ala Arg Val Val Ala Val Arg Ser Asp Ala Leu Arg Gln
    130                 135                 140
Leu Met Gly Gln Gly Asp Met Ala Ser Leu Gly Ala Ser Ser Glu Gln
145                 150                 155                 160
Ala Ala Glu Leu Ile Gly Asp Arg Pro Gly Val Cys Ile Ala Ala Val
                165                 170                 175
```

-continued

Asn Gly Pro Ser Ser Thr Val Ile Ser Gly Pro Glu His Val Ala
            180                 185                 190

Ala Val Val Ala Asp Ala Glu Glu Arg Gly Leu Arg Ala Arg Val Ile
        195                 200                 205

Asp Val Gly Tyr Ala Ser His Gly Pro Gln Ile Asp Gln Leu His Asp
    210                 215                 220

Leu Leu Thr Asp Arg Leu Ala Asp Ile Arg Pro Ala Thr Thr Asp Val
225                 230                 235                 240

Ala Phe Tyr Ser Thr Val Thr Ala Glu Arg Leu Thr Asp Thr Thr Ala
                245                 250                 255

Leu Asp Thr Asp Tyr Trp Val Thr Asn Leu Arg Gln Pro Val Arg Phe
            260                 265                 270

Ala Asp Thr Ile Asp Ala Leu Leu Ala Asp Gly Tyr Arg Leu Phe Ile
        275                 280                 285

Glu Ala Ser Ala His Pro Val Leu Gly Leu Gly Met Glu Glu Thr Ile
    290                 295                 300

Glu Gln Ala Asp Ile Pro Ala Thr Val Val Pro Thr Leu Arg Arg Asp
305                 310                 315                 320

His Gly Asp Thr Thr Gln Leu Thr Arg Ala Ala His Ala Phe Thr
                325                 330                 335

Ala Gly Ala Thr Val Asp Trp Arg Arg Trp Phe Pro Ala Asp Pro Thr
            340                 345                 350

Pro Arg Thr Ile Asp Leu Pro Thr Tyr Ala Phe Gln Arg Arg Ser Tyr
        355                 360                 365

Trp Leu Pro Val Asp Gly Val Gly Asp Val Arg Ser Ala Gly Leu Arg
    370                 375                 380

Arg Val Glu
385

<210> SEQ ID NO 31
<211> LENGTH: 391
<212> TYPE: PRT
<213> ORGANISM: Streptomyces cinnamonensis

<400> SEQUENCE: 31

Ala Leu Ala Ala Gly Glu Ala Ser Ala Asp Val Val Ala Gly Val Ala
1               5                   10                  15

Gly Asp Val Gly Pro Gly Pro Val Leu Val Phe Pro Gly Gln Gly Ser
            20                  25                  30

Gln Trp Val Gly Met Gly Ala Gln Leu Leu Asp Glu Ser Pro Val Phe
        35                  40                  45

Ala Ala Arg Ile Ala Glu Cys Glu Gln Ala Leu Ser Ala His Val Asp
    50                  55                  60

Trp Ser Leu Ser Asp Val Leu Arg Gly Asp Gly Ser Glu Leu Ser Arg
65                  70                  75                  80

Val Glu Val Val Gln Pro Val Leu Trp Ala Val Met Val Ser Leu Ala
                85                  90                  95

Ala Val Trp Ala Asp Tyr Gly Ile Thr Pro Ala Ala Val Ile Gly His
            100                 105                 110

Ser Gln Gly Glu Met Ala Ala Ala Cys Val Ala Gly Ala Leu Ser Leu
        115                 120                 125

Glu Asp Ala Ala Arg Ile Val Ala Val Arg Ser Asp Ala Leu Arg Gln
    130                 135                 140

Leu Gln Gly His Gly Asp Met Ala Ser Leu Ser Thr Gly Ala Glu Gln
145                 150                 155                 160

```
Ala Ala Glu Leu Ile Gly Asp Arg Pro Gly Val Val Ala Ala Val
            165                 170                 175

Asn Gly Pro Ser Ser Thr Val Ile Ser Gly Pro Pro Glu His Val Ala
        180                 185                 190

Ala Val Val Ala Asp Ala Glu Ala Gln Gly Leu Arg Ala Arg Val Ile
        195                 200                 205

Asp Val Arg Tyr Ala Ser His Gly Pro Gln Ile Asp Gln Leu His Asp
    210                 215                 220

Leu Leu Thr Asp Arg Leu Ala Asp Ile Gln Pro Thr Thr Thr Asp Val
225                 230                 235                 240

Ala Phe Tyr Ser Thr Val Thr Ala Glu Arg Leu Asp Asp Thr Thr Ala
                245                 250                 255

Leu Asp Thr Ala Tyr Trp Val Thr Asn Leu Arg Gln Pro Val Arg Phe
            260                 265                 270

Ala Asp Thr Ile Glu Ala Leu Leu Ala Asp Gly Tyr Arg Leu Phe Ile
        275                 280                 285

Glu Ala Ser Pro His Pro Val Leu Asn Leu Gly Ile Gln Glu Thr Ile
        290                 295                 300

Glu Gln Gln Ala Gly Ala Ala Gly Thr Ala Val Thr Ile Pro Thr Leu
305                 310                 315                 320

Arg Arg Asp His Gly Asp Thr Thr Gln Leu Thr Arg Ala Ala Ala His
                325                 330                 335

Ala Phe Thr Ala Gly Ala Pro Val Asp Trp Arg Arg Trp Phe Pro Ala
            340                 345                 350

Asp Pro Thr Pro Arg Thr Val Asp Leu Pro Thr Tyr Ala Phe Gln His
        355                 360                 365

Lys His Tyr Trp Val Glu Pro Pro Ala Ala Val Ala Ala Val Gly Gly
    370                 375                 380

Gly His Asp Pro Val Glu Ala
385                 390

<210> SEQ ID NO 32
<211> LENGTH: 385
<212> TYPE: PRT
<213> ORGANISM: Streptomyces cinnamonensis

<400> SEQUENCE: 32

Leu Ala Ala Gly Glu Pro Ser Pro Asp Val Val Glu Gly Ala Val Gln
  1               5                  10                  15

Gly Ala Ser Gly Ala Gly Pro Val Leu Val Phe Pro Gly Gln Gly Ser
            20                  25                  30

Gln Trp Val Gly Met Gly Ala Gln Leu Leu Asp Glu Ser Pro Val Phe
        35                  40                  45

Ala Ala Arg Ile Ala Glu Cys Glu Arg Ala Leu Ser Ala His Val Asp
    50                  55                  60

Trp Ser Leu Ser Ala Val Leu Arg Gly Asp Gly Ser Glu Leu Ser Arg
 65                 70                  75                  80

Val Glu Val Val Gln Pro Val Leu Trp Ala Val Met Val Ser Leu Ala
                85                  90                  95

Ser Val Trp Ala Asp Tyr Gly Ile Thr Pro Ala Ala Val Ile Gly His
            100                 105                 110

Ser Gln Gly Glu Met Ala Ala Ala Cys Val Ala Gly Ala Leu Ser Leu
        115                 120                 125

Glu Asp Ala Ala Arg Ile Val Ala Val Arg Ser Asp Ala Leu Arg Gln
    130                 135                 140
```

```
Leu Met Gly Gln Gly Asp Met Ala Ser Leu Gly Ala Gly Ser Glu Gln
145                 150                 155                 160

Val Ala Glu Leu Ile Gly Asp Arg Pro Gly Val Cys Val Ala Ala Val
                165                 170                 175

Asn Gly Pro Ser Ser Thr Val Ile Ser Gly Pro Pro Glu His Val Ala
            180                 185                 190

Ala Val Val Ala Asp Ala Glu Ala Arg Gly Leu Arg Ala Arg Val Ile
        195                 200                 205

Asp Val Gly Tyr Ala Ser His Gly Pro Gln Ile Asp Gln Leu His Asp
    210                 215                 220

Leu Leu Thr Glu Arg Leu Ala Asp Ile Arg Pro Thr Thr Thr Asp Val
225                 230                 235                 240

Ala Phe Tyr Ser Thr Val Thr Ala Glu Arg Leu Asp Asp Thr Thr Thr
                245                 250                 255

Leu Asp Thr Asp Tyr Trp Val Thr Asn Leu Arg Gln Pro Val Arg Phe
            260                 265                 270

Ala Asp Thr Ile Glu Ala Leu Leu Ala Asp Gly Tyr Arg Leu Phe Ile
        275                 280                 285

Glu Ala Ser Pro His Pro Val Leu Asn Leu Gly Met Glu Glu Thr Ile
    290                 295                 300

Glu Arg Ala Asp Met Pro Ala Thr Val Val Pro Thr Leu Arg Arg Asp
305                 310                 315                 320

His Gly Asp Ala Ala Gln Leu Thr Arg Ala Ala Gln Ala Phe Gly
                325                 330                 335

Ala Gly Ala Glu Val Asp Trp Thr Gly Trp Phe Pro Ala Val Pro Leu
            340                 345                 350

Pro Arg Val Val Asp Leu Pro Thr Tyr Ala Phe Gln Arg Glu Arg Phe
        355                 360                 365

Trp Leu Glu Gly Arg Arg Gly Leu Ala Gly Asp Pro Ala Gly Leu Gly
    370                 375                 380

Leu
385

<210> SEQ ID NO 33
<211> LENGTH: 391
<212> TYPE: PRT
<213> ORGANISM: Streptomyces cinnamonensis

<400> SEQUENCE: 33

Ser Leu Ala Ala Gly Glu Ala Ser Pro Asp Val Val Ser Gly Ala Val
1               5                   10                  15

Gly Pro Thr Gly Pro Gly Pro Val Met Val Phe Pro Gly Gln Gly Gly
                20                  25                  30

Gln Trp Val Gly Met Gly Ala Arg Leu Leu Asp Glu Ser Pro Val Phe
            35                  40                  45

Ala Ala Arg Ile Ala Glu Cys Glu Gln Ala Leu Ser Ala Tyr Val Asp
        50                  55                  60

Trp Ser Leu Thr Asp Val Leu Arg Gly Asp Gly Ser Glu Leu Ala Arg
65                  70                  75                  80

Ile Asp Val Val Gln Pro Val Leu Trp Ala Val Met Val Ala Leu Ala
                85                  90                  95

Ala Val Trp Ala Asp Gln Gly Ile Glu Pro Ala Ala Val Val Gly His
            100                 105                 110

Ser Gln Gly Glu Ile Ala Ala Ala Cys Val Val Gly Ala Ile Ser Leu
        115                 120                 125
```

```
Asp Glu Ala Ala Arg Ile Val Ala Val Arg Ser Val Leu Leu Arg Gln
            130                 135                 140

Leu Ser Gly Arg Gly Gly Met Ala Ser Leu Gly Met Gly Gln Glu Gln
145                 150                 155                 160

Ala Ala Asp Leu Ile Asp Gly His Pro Gly Val Val Ala Ala Val
                165                 170                 175

Asn Gly Pro Ser Ser Thr Val Ile Ser Gly Pro Glu Gly Ile Ala
                180                 185                 190

Ala Val Val Ala Asp Ala Gln Glu Arg Gly Leu Arg Ala Arg Ala Val
                195                 200                 205

Ala Ser Asp Val Ala Gly His Gly Pro Gln Leu Asp Ala Ile Leu Asp
            210                 215                 220

Gln Leu Thr Glu Gly Leu Ala Gly Ile Arg Pro Ala Ala Thr Asp Val
225                 230                 235                 240

Ala Phe Tyr Ser Thr Val Thr Ala Gly His Leu Thr Asp Thr Thr Glu
                245                 250                 255

Leu Asp Thr Ala Tyr Trp Val Arg Asn Val Arg Arg Thr Val Arg Phe
                260                 265                 270

Ala Asp Thr Ile Asp Ala Leu Leu Ala Asp Gly Tyr Arg Leu Phe Ile
                275                 280                 285

Glu Val Ser Pro His Pro Val Leu Asn Leu Ala Leu Glu Gly Leu Ile
                290                 295                 300

Glu Arg Ala Ala Val Pro Ala Thr Val Pro Thr Leu Arg Arg Asp
305                 310                 315                 320

His Gly Asp Thr Thr Gln Leu Ala Arg Ala Ala His Ala Phe Ala
                325                 330                 335

Ala Gly Ala Asp Val Asp Trp Arg Arg Trp Phe Pro Ala Asp Pro Ala
                340                 345                 350

Pro Arg Thr Val Asp Leu Pro Thr Tyr Ala Phe Gln Arg Gln Asp Phe
                355                 360                 365

Trp Pro Ala Pro Ala Gly Gly Arg Ser Gly Asp Pro Ala Gly Leu Gly
                370                 375                 380

Leu Ala Ala Ser Gly His Pro
385                 390

<210> SEQ ID NO 34
<211> LENGTH: 383
<212> TYPE: PRT
<213> ORGANISM: Streptomyces cinnamonensis

<400> SEQUENCE: 34

Glu Ala Leu Ala Ala Gly Asp Ala Ser Pro Asp Val Val Cys Gly Val
1               5                   10                  15

Ala Gly Asp Val Gly Pro Gly Pro Val Leu Val Phe Pro Gly Gln Gly
                20                  25                  30

Ser Gln Trp Val Gly Met Gly Ala Gln Leu Leu Gly Glu Ser Ala Val
            35                  40                  45

Phe Ala Ala Arg Ile Asp Ala Cys Glu Gln Ala Leu Ser Pro Tyr Val
        50                  55                  60

Asp Trp Ser Leu Thr Glu Val Leu Arg Gly Asp Gly Arg Glu Leu Ser
65              70                  75                  80

Arg Val Asp Val Val Gln Pro Val Leu Trp Ala Val Met Val Ser Leu
                85                  90                  95

Ala Ala Val Trp Ala Asp His Gly Val Thr Pro Ala Ala Val Val Gly
                100                 105                 110
```

```
His Ser Gln Gly Glu Ile Ala Ala Val Val Ala Gly Ala Leu Thr
        115                 120                 125

Leu Glu Asp Gly Ala Lys Ile Val Ala Leu Arg Ser Arg Ala Leu Arg
130                 135                 140

Gln Leu Ser Gly Gly Ala Met Ala Ser Leu Gly Val Gly Gln Glu
145                 150                 155                 160

Gln Ala Ala Glu Leu Val Glu Gly His Pro Gly Val Gly Ile Ala Ala
                    165                 170                 175

Val Asn Gly Pro Ser Ser Thr Val Ile Ser Gly Pro Glu Gln Val
                180                 185                 190

Ala Ala Val Val Ala Asp Ala Glu Ala Arg Glu Leu Arg Gly Arg Val
            195                 200                 205

Ile Asp Val Asp Tyr Ala Ser His Ser Pro Gln Val Asp Ala Ile Thr
210                 215                 220

Asp Glu Leu Thr His Thr Leu Ser Gly Val Arg Pro Thr Thr Ala Pro
225                 230                 235                 240

Val Ala Phe Tyr Ser Ala Val Thr Gly Thr Arg Ile Asp Thr Ala Gly
                245                 250                 255

Leu Asp Thr Asp Tyr Trp Val Thr Asn Leu Arg Arg Pro Val Arg Phe
                260                 265                 270

Ala Asp Ala Val Thr Ala Leu Leu Ala Asp Gly His Arg Val Phe Ile
                275                 280                 285

Glu Ala Ser Ser His Pro Val Leu Thr Leu Gly Leu Gln Glu Thr Phe
                290                 295                 300

Glu Glu Ala Gly Val Asp Ala Val Thr Val Pro Thr Leu Arg Arg Glu
305                 310                 315                 320

Asp Gly Gly Arg Ala Arg Leu Ala Arg Ser Leu Ala Gln Ala Phe Gly
                325                 330                 335

Ala Gly Cys Ala Val Arg Trp Glu Asn Trp Phe Pro Ala Thr Gly Thr
                340                 345                 350

Ser Thr Val Glu Leu Pro Thr Tyr Ala Phe Gln Arg Arg Arg Tyr Trp
                355                 360                 365

Leu Glu Ala Pro Thr Gly Thr Gln Asp Ala Ala Gly Leu Gly Leu
                370                 375                 380

<210> SEQ ID NO 35
<211> LENGTH: 381
<212> TYPE: PRT
<213> ORGANISM: Saccharopolyspora erythraea

<400> SEQUENCE: 35

Ala Asp Gly Ala Val Val Pro Gly Val Val Thr Gly Ser Ala Ser Asp
1               5                   10                  15

Gly Gly Ser Val Phe Val Phe Pro Gly Gln Gly Ala Gln Trp Glu Gly
                20                  25                  30

Met Ala Arg Glu Leu Leu Pro Val Pro Val Phe Ala Glu Ser Ile Ala
            35                  40                  45

Glu Cys Asp Ala Val Leu Ser Glu Val Ala Gly Phe Ser Val Ser Glu
        50                  55                  60

Val Leu Glu Pro Arg Pro Asp Ala Pro Ser Leu Glu Arg Val Asp Val
65                  70                  75                  80

Val Gln Pro Val Leu Phe Ala Val Met Val Ser Leu Ala Arg Leu Trp
                85                  90                  95

Arg Ala Cys Gly Ala Val Pro Ser Ala Val Ile Gly His Ser Gln Gly
            100                 105                 110
```

```
Glu Ile Ala Ala Ala Val Val Ala Gly Ala Leu Ser Leu Glu Asp Gly
            115                 120                 125

Met Arg Val Val Ala Arg Arg Ser Arg Ala Val Arg Ala Val Ala Gly
            130                 135                 140

Arg Gly Ser Met Leu Ser Val Arg Gly Gly Arg Ser Asp Val Glu Lys
145                 150                 155                 160

Leu Leu Ala Asp Asp Ser Trp Thr Gly Arg Leu Glu Val Ala Ala Val
                165                 170                 175

Asn Gly Pro Asp Ala Val Val Ala Gly Asp Ala Gln Ala Ala Arg
                180                 185                 190

Glu Phe Leu Glu Tyr Cys Glu Gly Val Gly Ile Arg Ala Arg Ala Ile
            195                 200                 205

Pro Val Asp Tyr Ala Ser His Thr Ala His Val Glu Pro Val Arg Asp
            210                 215                 220

Glu Leu Val Gln Ala Leu Ala Gly Ile Thr Pro Arg Arg Ala Glu Val
225                 230                 235                 240

Pro Phe Phe Ser Thr Leu Thr Gly Asp Phe Leu Asp Gly Thr Glu Leu
                245                 250                 255

Asp Ala Gly Tyr Trp Tyr Arg Asn Leu Arg His Pro Val Glu Phe His
                260                 265                 270

Ser Ala Val Gln Ala Leu Thr Asp Gln Gly Tyr Ala Thr Phe Ile Glu
            275                 280                 285

Val Ser Pro His Pro Val Leu Ala Ser Ser Val Gln Glu Thr Leu Asp
            290                 295                 300

Asp Ala Glu Ser Asp Ala Ala Val Leu Gly Thr Leu Glu Arg Asp Ala
305                 310                 315                 320

Gly Asp Ala Asp Arg Phe Leu Thr Ala Leu Ala Asp Ala His Thr Arg
                325                 330                 335

Gly Val Ala Val Asp Trp Glu Ala Val Leu Gly Arg Ala Gly Leu Val
                340                 345                 350

Asp Leu Pro Gly Tyr Pro Phe Gln Gly Lys Arg Phe Trp Leu Leu Pro
            355                 360                 365

Asp Arg Thr Thr Pro Arg Asp Glu Leu Asp Gly Trp Phe
            370                 375             380

<210> SEQ ID NO 36
<211> LENGTH: 375
<212> TYPE: PRT
<213> ORGANISM: Saccharopolyspora erythraea

<400> SEQUENCE: 36

Arg Ala Val Ala Glu Gly Val Ala Ala Pro Gly Ala Thr Thr Gly Thr
1               5                   10                  15

Ala Ser Ala Gly Gly Val Val Phe Val Phe Pro Gly Gln Gly Ala Gln
                20                  25                  30

Trp Glu Gly Met Ala Arg Gly Leu Leu Ser Val Pro Val Phe Ala Glu
            35                  40                  45

Ser Ile Ala Glu Cys Asp Ala Val Leu Ser Glu Val Ala Gly Phe Ser
        50                  55                  60

Ala Ser Glu Val Leu Glu Gln Arg Pro Asp Ala Pro Ser Leu Glu Arg
65                  70                  75                  80

Val Asp Val Val Gln Pro Val Leu Phe Ser Val Met Val Ser Leu Ala
                85                  90                  95

Arg Leu Trp Gly Ala Cys Gly Val Ser Pro Ser Ala Val Ile Gly His
            100                 105                 110
```

```
Ser Gln Gly Glu Ile Ala Ala Val Val Ala Gly Val Leu Ser Leu
        115                 120                 125

Glu Asp Gly Val Arg Val Ala Leu Arg Ala Lys Ala Leu Arg Ala
130                 135                 140

Leu Ala Gly Lys Gly Gly Met Val Ser Leu Ala Ala Pro Gly Glu Arg
145                 150                 155                 160

Ala Arg Ala Leu Ile Ala Pro Trp Glu Asp Arg Ile Ser Val Ala Ala
                165                 170                 175

Val Asn Ser Pro Ser Val Val Ser Gly Asp Pro Glu Ala Leu
                180                 185                 190

Ala Glu Leu Val Ala Arg Cys Glu Asp Gly Val Arg Ala Lys Thr
                195                 200                 205

Leu Pro Val Asp Tyr Ala Ser His Ser Arg His Val Glu Ile Arg
                210                 215                 220

Glu Thr Ile Leu Ala Asp Leu Asp Gly Ile Ser Ala Arg Arg Ala Ala
225                 230                 235                 240

Ile Pro Leu Tyr Ser Thr Leu His Gly Glu Arg Arg Asp Met Gly Pro
                245                 250                 255

Arg Tyr Trp Tyr Asp Asn Leu Arg Ser Gln Val Arg Phe Asp Glu Ala
                260                 265                 270

Val Ser Ala Gln Ser Pro Asp Gly His Ala Thr Phe Val Glu Met Ser
                275                 280                 285

Pro His Pro Val Leu Thr Ala Ala Val Gln Glu Ile Ala Ala Asp Ala
                290                 295                 300

Val Ala Ile Gly Ser Leu His Arg Asp Thr Ala Glu Glu His Leu Ile
305                 310                 315                 320

Ala Glu Leu Ala Arg Ala His Val His Gly Val Ala Val Asp Trp Arg
                325                 330                 335

Asn Val Phe Pro Ala Ala Pro Pro Val Ala Leu Pro Asn Tyr Pro Phe
                340                 345                 350

Glu Pro Gln Arg Tyr Trp Leu Ala Pro Glu Val Ser Asp Gln Leu Ala
                355                 360                 365

Asp Ser Arg Tyr Arg Val Asp
                370                 375

<210> SEQ ID NO 37
<211> LENGTH: 395
<212> TYPE: PRT
<213> ORGANISM: Streptomyces avermitilis

<400> SEQUENCE: 37

Gly Leu Gly Ala Leu Ala Ala Gly Glu Pro Asp Arg Arg Val Thr Thr
1               5                   10                  15

Gly His Ala Pro Gly Gly Asp Arg Gly Val Val Phe Val Phe Pro
                20                  25                  30

Gly Gln Gly Gly Gln Trp Ala Gly Met Gly Val Arg Leu Leu Ala Ser
            35                  40                  45

Ser Pro Val Phe Ala Arg Arg Met Gln Ala Cys Glu Glu Ala Leu Ala
        50                  55                  60

Pro Trp Val Asp Trp Ser Val Asp Ile Leu Arg Arg Asp Ala Gly
65                  70                  75                  80

Asp Ala Val Trp Glu Arg Ala Asp Val Val Gln Pro Val Leu Phe Ser
                85                  90                  95

Val Met Val Ser Leu Ala Ala Leu Trp Arg Ser Tyr Gly Ile Glu Pro
                100                 105                 110
```

Asp Ala Val Leu Gly His Ser Gln Gly Glu Ile Ala Ala Ala His Val
            115                 120                 125

Cys Gly Ala Leu Ser Leu Lys Asp Ala Ala Lys Thr Val Ala Leu Arg
        130                 135                 140

Ser Arg Ala Leu Ala Ala Val Arg Gly Arg Gly Met Ala Ser Val
145                 150                 155                 160

Pro Leu Pro Ala Gln Glu Val Glu Gln Leu Ile Gly Glu Arg Trp Ala
                165                 170                 175

Gly Arg Leu Trp Val Ala Ala Val Asn Gly Pro Arg Ser Thr Ala Val
            180                 185                 190

Ser Gly Asp Ala Glu Ala Val Asp Glu Val Leu Ala Tyr Cys Ala Gly
        195                 200                 205

Thr Gly Val Arg Ala Arg Arg Ile Pro Val Asp Tyr Ala Ser His Cys
    210                 215                 220

Pro His Val Gln Pro Leu Arg Glu Glu Leu Leu Glu Leu Leu Gly Asp
225                 230                 235                 240

Ile Ser Pro Gln Pro Ser Gly Val Pro Phe Phe Ser Thr Val Glu Gly
                245                 250                 255

Thr Trp Leu Asp Thr Thr Thr Leu Asp Ala Ala Tyr Trp Tyr Arg Asn
            260                 265                 270

Leu His Gln Pro Val Arg Phe Ser Asp Ala Val Gln Ala Leu Ala Asp
        275                 280                 285

Asp Gly His Arg Val Phe Val Glu Val Ser Pro His Pro Thr Leu Val
    290                 295                 300

Pro Ala Ile Glu Asp Thr Thr Glu Asp Thr Ala Glu Asp Val Thr Ala
305                 310                 315                 320

Ile Gly Ser Leu Arg Arg Gly Asp Asn Asp Thr Arg Arg Phe Leu Thr
                325                 330                 335

Ala Leu Ala His Thr His Thr Thr Gly Ile Gly Thr Pro Thr Thr Trp
            340                 345                 350

His His His Tyr Thr His His His Thr His Pro His Pro His Thr His
        355                 360                 365

Leu Asp Leu Pro Thr Tyr Pro Phe Gln His Gln His Tyr Trp Leu Glu
    370                 375                 380

Ser Ser Gln Pro Gly Ala Gly Ser Gly Ser Gly
385                 390                 395

<210> SEQ ID NO 38
<211> LENGTH: 391
<212> TYPE: PRT
<213> ORGANISM: Streptomyces avermitilis

<400> SEQUENCE: 38

Gly Leu Gly Ala Leu Ala Ala Gly Glu Pro Asp Arg Arg Val Thr Thr
1               5                   10                  15

Gly His Ala Pro Gly Gly Asp Arg Gly Val Val Phe Val Phe Pro
            20                  25                  30

Gly Gln Gly Gly Gln Trp Ala Gly Met Gly Val Arg Leu Leu Ala Ser
        35                  40                  45

Ser Pro Val Phe Ala Arg Arg Met Gln Ala Cys Glu Glu Ala Leu Ala
    50                  55                  60

Pro Trp Val Asp Trp Ser Val Val Asp Ile Leu Arg Arg Asp Ala Gly
65                  70                  75                  80

Asp Ala Val Trp Glu Arg Ala Asp Val Val Gln Pro Val Leu Phe Ser
                85                  90                  95

```
Val Met Val Ser Leu Ala Ala Leu Trp Arg Ser Tyr Gly Ile Glu Pro
            100                 105                 110

Asp Ala Val Leu Gly His Ser Gln Gly Glu Ile Ala Ala Ala His Val
        115                 120                 125

Cys Gly Ala Leu Ser Leu Lys Asp Ala Ala Lys Thr Val Ala Leu Arg
130                 135                 140

Ser Arg Ala Leu Ala Ala Val Arg Gly Arg Gly Gly Met Ala Ser Val
145                 150                 155                 160

Pro Leu Pro Ala Gln Glu Val Glu Gln Leu Ile Gly Glu Arg Trp Ala
                165                 170                 175

Gly Arg Leu Trp Val Ala Ala Val Asn Gly Pro Arg Ser Thr Ala Val
            180                 185                 190

Ser Gly Asp Ala Glu Ala Val Asp Glu Val Leu Ala Tyr Cys Ala Gly
        195                 200                 205

Thr Gly Val Arg Ala Arg Arg Ile Pro Val Asp Tyr Ala Ser His Cys
    210                 215                 220

Pro His Val Gln Pro Leu Arg Glu Glu Leu Leu Glu Leu Leu Gly Asp
225                 230                 235                 240

Ile Ser Pro Gln Pro Ser Gly Val Pro Phe Phe Ser Thr Val Glu Gly
                245                 250                 255

Thr Trp Leu Asp Thr Thr Thr Leu Asp Ala Ala Tyr Trp Tyr Arg Asn
            260                 265                 270

Leu His Gln Pro Val Arg Phe Ser Asp Ala Val Gln Ala Leu Ala Asp
        275                 280                 285

Asp Gly His Arg Val Phe Val Glu Val Ser Pro His Pro Thr Leu Val
    290                 295                 300

Pro Ala Ile Glu Asp Thr Thr Glu Asp Thr Ala Glu Asp Val Thr Ala
305                 310                 315                 320

Ile Gly Ser Leu Arg Arg Gly Asp Asn Asp Thr Arg Arg Phe Leu Thr
                325                 330                 335

Ala Leu Ala His Thr His Thr Thr Gly Ile Gly Thr Pro Thr Thr Trp
            340                 345                 350

His His His Tyr Thr His His Thr His Pro His Asn His His Leu
        355                 360                 365

Asp Leu Pro Thr Tyr Pro Phe Gln Arg Gln His Tyr Trp Leu Asp Ala
    370                 375                 380

Pro Thr Gly Ala Gly Asp Val
385                 390

<210> SEQ ID NO 39
<211> LENGTH: 405
<212> TYPE: PRT
<213> ORGANISM: Streptomyces avermitilis

<400> SEQUENCE: 39

Gln Ala Leu Thr Ala Leu Ala Ala Gly Glu Pro His Pro His Ile Thr
 1               5                  10                  15

Thr Gly His Thr Arg Gly Gly Asp Arg Gly Gly Val Val Phe Val Phe
            20                  25                  30

Pro Gly Gln Gly Gly Gln Trp Ala Gly Met Gly Leu Thr Leu Leu Thr
        35                  40                  45

Ser Ser Pro Val Phe Ala Glu His Ile Asp Ala Cys Glu Lys Ala Leu
    50                  55                  60

Thr Pro Trp Val Pro Trp Ser Leu Thr Asp Ile Leu His Arg Asp Pro
65                  70                  75                  80
```

-continued

```
Asp Asp Pro Ala Trp Gln Gln Ala Asp Val Val Gln Pro Val Leu Phe
                85                  90                  95
Ser Ile Met Val Ser Leu Ala Ala Leu Trp Arg Ser Tyr Gly Ile Glu
            100                 105                 110
Pro Asp Ala Val Leu Gly His Ser Gln Gly Glu Ile Ala Ala Ala His
        115                 120                 125
Ile Cys Gly Ala Leu Ser Leu Lys Asp Ala Ala Lys Thr Val Ala Leu
    130                 135                 140
Arg Ser Arg Ala Leu Ala Ala Val Arg Gly Arg Gly Ala Met Ala Ser
145                 150                 155                 160
Leu Pro Leu Pro Ala Gln Asp Val Gln Gln Leu Ile Ser Glu Arg Trp
                165                 170                 175
Glu Gly Gln Leu Trp Val Ala Ala Leu Asn Gly Pro His Ser Thr Thr
            180                 185                 190
Val Ser Gly Asp Thr Lys Ala Val Asp Glu Val Leu Ala His Cys Thr
        195                 200                 205
Asp Thr Gly Leu Arg Ala Lys Arg Ile Pro Val Asp Tyr Ala Ser His
    210                 215                 220
Cys Pro His Val Gln Pro Leu His Asp Glu Leu Leu His Leu Leu Gly
225                 230                 235                 240
Asp Ile Thr Pro Gln Pro Ser Thr Val Pro Phe Phe Ser Thr Val Glu
                245                 250                 255
Gly Thr Trp Leu Asp Thr Thr Thr Leu Asp Ala Ala Tyr Trp Tyr Arg
            260                 265                 270
Asn Leu His Gln Pro Val Arg Phe Ser His Ala Ile Gln Thr Leu Thr
        275                 280                 285
Asp Asp Gly His Arg Ala Phe Ile Glu Ile Ser Pro His Pro Thr Leu
    290                 295                 300
Val Pro Ala Ile Glu Asp Thr Thr Glu Asn Thr Thr Glu Asn Ile Thr
305                 310                 315                 320
Ala Thr Gly Ser Leu Arg Arg Gly Asp Asn Asp Thr His Arg Phe Leu
                325                 330                 335
Thr Ala Leu Ala His Thr His Thr Thr Gly Ile Gly Thr Pro Thr Thr
            340                 345                 350
Trp His His His Tyr Thr Gln Thr His Pro His Pro Asn Pro His Thr
        355                 360                 365
His Leu Asp Leu Pro Thr Tyr Pro Phe Gln His Gln His Tyr Trp Leu
    370                 375                 380
Gln Pro Pro Thr Thr Thr Asp Leu Thr Thr Thr Gly Leu Thr Pro
385                 390                 395                 400
Thr His His Pro Leu
            405

<210> SEQ ID NO 40
<211> LENGTH: 383
<212> TYPE: PRT
<213> ORGANISM: Streptomyces avermitilis

<400> SEQUENCE: 40

Leu Thr Ala Leu Ala Ala Gly Glu Pro His Pro His Ile Thr Thr Gly
 1               5                  10                  15
His Thr Arg Gly Ser Asp Arg Gly Val Val Phe Val Phe Pro Gly
            20                  25                  30
Gln Gly Gly Gln Trp Ala Gly Met Gly Leu Thr Leu Leu Thr Ser Ser
        35                  40                  45
```

Pro Val Phe Ala Glu His Ile Asp Ala Cys Glu Lys Ala Leu Thr Pro
    50                  55                  60

Trp Val Pro Trp Ser Leu Thr Asp Ile Leu His Arg Asp Pro Asp Asp
 65                  70                  75                  80

Pro Ala Trp Gln Gln Ala Asp Val Val Gln Pro Val Leu Phe Ser Ile
                85                  90                  95

Met Val Ser Leu Ala Ala Leu Trp Arg Ser Tyr Gly Ile Glu Pro Asp
            100                 105                 110

Ala Val Leu Gly His Ser Gln Gly Glu Ile Ala Ala His Ile Cys
            115                 120                 125

Gly Ala Leu Ser Leu Lys Asp Ala Lys Thr Val Ala Leu Arg Ser
130                 135                 140

Gln Ala Leu Ala Ala Val Arg Gly Arg Gly Ala Met Val Ser Leu Pro
145                 150                 155                 160

Leu Pro Ala Gln Asp Val Gln Gln Leu Ile Ser Glu Arg Trp Glu Gly
                165                 170                 175

Gln Leu Trp Val Ala Ala Leu Asn Gly Pro His Ser Thr Thr Val Ser
            180                 185                 190

Gly Asp Thr Thr Ala Val Glu Glu Leu Leu Thr His Cys Ala Asp Thr
            195                 200                 205

Gly Leu Arg Ala Lys Arg Ile Pro Val Asp Tyr Ala Ser His Cys Pro
210                 215                 220

His Val Gln Pro Leu His Asp Glu Leu Leu His Leu Leu Gly Asp Ile
225                 230                 235                 240

Thr Pro Gln Pro Ser Thr Met Pro Phe Phe Ser Thr Val Val Gly His
                245                 250                 255

Leu Val Trp Tyr Thr Thr Thr Leu Asp Ala Ala Tyr Trp Tyr Arg Asn
            260                 265                 270

Leu His Gln Pro Val Arg Phe Ser His Ala Ile Gln Thr Leu Thr Asp
            275                 280                 285

Asp Gly His Arg Pro Phe Ile Glu Ile Ser Pro His Pro Thr Leu Val
290                 295                 300

Pro Ala Ile Glu Asp Thr Thr Glu Asn Thr Thr Glu Asn Ile Thr Ala
305                 310                 315                 320

Thr Gly Ser Leu Arg Arg Gly Asp Asn Asp Thr His Arg Phe Leu Thr
                325                 330                 335

Ala Leu Ala His Thr His Thr Thr Gly Ile Arg Thr Pro Thr Thr Trp
            340                 345                 350

His His His Tyr Thr Gln Thr His Pro His Pro His Asn His His Leu
            355                 360                 365

Asp Leu Pro Thr Tyr Pro Phe Gln His Gln His Tyr Trp Leu Gln
370                 375                 380

<210> SEQ ID NO 41
<211> LENGTH: 377
<212> TYPE: PRT
<213> ORGANISM: Streptomyces noursei

<400> SEQUENCE: 41

Leu Ala Asp Val Glu Gly Arg Thr Val Phe Val Phe Pro Gly Gln Gly
 1               5                  10                  15

Ser Gln Trp Val Gly Met Gly Ala Gln Leu Leu Asp Glu Ser Ala Val
                20                  25                  30

Phe Ala Glu Arg Ile Ala Glu Cys Ala Ala Ala Leu Ala Glu Phe Thr
            35                  40                  45

-continued

```
Asp Trp Ser Leu Val Asp Val Leu Arg Gly Val Val Gly Ala Pro Ser
 50                  55                  60
Leu Glu Arg Val Asp Val Val Gln Pro Ala Ser Phe Ala Val Met Val
 65                  70                  75                  80
Ser Leu Ala Ala Leu Trp Gly Ser Arg Gly Val Leu Pro Asp Ala Val
                 85                  90                  95
Val Gly His Ser Gln Gly Glu Ile Ala Ala Val Val Ser Gly Ala
            100                 105                 110
Leu Ser Leu Arg Asp Gly Ala Arg Val Val Ala Leu Arg Ser Gln Ala
            115                 120                 125
Ile Gly Arg Ala Leu Ala Gly Arg Gly Met Met Ser Val Ala Leu
 130                 135                 140
Ser Val Asp Val Leu Glu Pro Arg Leu Val Glu Phe Glu Gly Arg Val
145                 150                 155                 160
Ser Val Ala Ala Val Asn Gly Pro Arg Ser Val Val Ala Gly Glu
                165                 170                 175
Pro Glu Ala Leu Asp Ala Leu His Ala Arg Leu Thr Ala Asp Asp Ile
            180                 185                 190
Arg Ala Arg Arg Ile Ala Val Asp Tyr Ala Ser His Ser His Gln Val
            195                 200                 205
Glu Asp Leu His Glu Glu Leu Leu Glu Val Leu Ala Glu Leu Ala Pro
 210                 215                 220
Arg Thr Ser Glu Val Pro Phe Phe Ser Thr Val Thr Gly Asp Trp Leu
225                 230                 235                 240
Asp Thr Ala Arg Met Asp Ala Gly Tyr Trp Phe Arg Asn Leu Arg Gly
                245                 250                 255
Arg Val Arg Phe Ala Asp Ala Val Ala Asp Leu Leu Ala Ala Glu Tyr
            260                 265                 270
Arg Ala Phe Val Glu Val Ser Ser His Pro Val Leu Thr Met Ala Val
            275                 280                 285
Leu Asp Leu Ile Glu Glu Ala Gly Val Thr Ala Val Ala Thr Gly Thr
 290                 295                 300
Leu Arg Arg Asp Gln Gly Gly Ala Gly Arg Phe Leu Leu Ser Ala Ala
305                 310                 315                 320
Glu Val Phe Val Arg Gly Val Asp Val Asp Trp Ala Gly Ala Phe Glu
                325                 330                 335
Gly Thr Gly Ala Ala Arg Val Asp Leu Pro Thr Tyr Ala Phe Gln Arg
            340                 345                 350
Glu Arg Tyr Trp Asn Thr Arg Thr Ala Ala Asp Arg Thr Pro Ala Asp
            355                 360                 365
Ala Pro Met Asp Ala Glu Phe Trp Ala
 370                 375
```

<210> SEQ ID NO 42
<211> LENGTH: 393
<212> TYPE: PRT
<213> ORGANISM: Streptomyces noursei

<400> SEQUENCE: 42

```
Ala Val Ala Thr Asp Gly Pro Ser Pro Val Val Ala Arg Gly Val Ala
 1               5                  10                  15
Asp Val Glu Gly Arg Thr Val Phe Val Phe Pro Gly Gln Gly Ser Gln
             20                  25                  30
Trp Val Gly Met Gly Ser Gln Leu Leu Asp Glu Ser Ala Val Phe Ala
         35                  40                  45
```

```
Glu Arg Ile Ala Glu Cys Ala Ala Ala Leu Ala Glu Phe Thr Asp Trp
 50                  55                  60

Ser Leu Val Asp Val Leu Arg Gly Val Val Gly Ala Pro Ser Leu Glu
 65                  70                  75                  80

Arg Val Asp Val Val Gln Pro Ala Ser Phe Ala Val Met Val Ser Leu
                     85                  90                  95

Ala Ala Leu Trp Arg Ser Arg Gly Val Leu Pro Asp Ala Val Val Gly
                100                 105                 110

His Ser Gln Gly Glu Ile Ala Ala Val Val Ser Gly Ala Leu Ser
                115                 120                 125

Leu Arg Asp Gly Ala Arg Val Ala Leu Arg Ser Gln Ala Ile Gly
130                 135                 140

Arg Ala Leu Ala Gly Arg Gly Met Met Ser Val Ala Leu Ser Val
145                 150                 155                 160

Asp Val Leu Glu Pro Arg Leu Val Glu Phe Glu Gly Arg Val Ser Val
                165                 170                 175

Ala Ala Val Asn Gly Pro Arg Ser Val Val Ala Gly Glu Pro Glu
                180                 185                 190

Ala Leu Asp Ala Leu His Ala Arg Leu Thr Ala Asp Ile Arg Ala
                195                 200                 205

Arg Arg Ile Ala Val Asp Tyr Ala Ser His Ser His Gln Val Glu Asp
210                 215                 220

Leu His Glu Glu Leu Leu Glu Val Leu Ala Glu Leu Ala Pro Arg Thr
225                 230                 235                 240

Ser Glu Val Pro Phe Phe Ser Thr Val Thr Gly Asp Trp Leu Asp Thr
                245                 250                 255

Ala Arg Met Asp Ala Gly Tyr Trp Phe Arg Asn Leu Arg Gly Arg Val
                260                 265                 270

Arg Phe Ala Asp Ala Val Ala Asp Leu Leu Ala Ala Glu Tyr Arg Ala
                275                 280                 285

Phe Val Glu Val Ser Ser His Pro Val Leu Ser Met Ala Val Gln Glu
                290                 295                 300

Ala Ile Asp Glu Ala Gly Val Pro Ala Val Ala Gly Thr Leu Arg
305                 310                 315                 320

Arg Asp Gln Gly Gly Thr Asp Arg Phe Leu Leu Ser Ala Ala Glu Val
                325                 330                 335

Phe Val Arg Gly Val Asp Val Asp Trp Ala Gly Leu Phe Glu Gly Thr
                340                 345                 350

Gly Ala Ser Arg Ile Asp Leu Pro Thr Tyr Ala Phe Gln His Glu His
                355                 360                 365

Leu Trp Ala Val Pro Pro Ala Pro Glu Ala Val Ala Ala Asp Pro
370                 375                 380

Asp Asp Ala Ala Phe Trp Thr Ala Val
385                 390

<210> SEQ ID NO 43
<211> LENGTH: 377
<212> TYPE: PRT
<213> ORGANISM: Amycolatopsis mediterranei

<400> SEQUENCE: 43

Thr Ala Leu Ala Arg Gly Glu Ser Ala Ser Gly Leu Val Thr Gly Thr
 1               5                  10                  15

Ala Gly Met Pro Gly Lys Thr Val Trp Val Phe Pro Gly Gln Gly Thr
                 20                  25                  30
```

```
Gln Trp Ala Gly Met Gly Arg Glu Leu Leu Glu Ala Ser Pro Val Phe
         35                  40                  45

Ala Glu Arg Ile Glu Glu Cys Ala Ala Ala Leu Gln Pro Trp Ile Asp
     50                  55                  60

Trp Ser Leu Leu Asp Val Leu Arg Gly Glu Gly Glu Leu Asp Arg Val
 65                  70                  75                  80

Asp Val Leu Gln Pro Ala Cys Phe Ala Val Met Val Gly Leu Ala Ala
                 85                  90                  95

Val Trp Ala Ser Val Gly Val Val Pro Asp Ala Val Leu Gly His Ser
                100                 105                 110

Gln Gly Glu Ile Ala Ala Ala Cys Val Ser Gly Ala Leu Ser Leu Glu
            115                 120                 125

Asp Ala Ala Lys Val Val Ala Leu Arg Ser Gln Ala Ile Ala Ala Glu
        130                 135                 140

Leu Ser Gly Arg Gly Gly Met Ala Ser Ile Gln Leu Ser His Asp Glu
145                 150                 155                 160

Val Ala Ala Arg Leu Ala Pro Trp Ala Gly Arg Val Glu Ile Ala Ala
                165                 170                 175

Val Asn Gly Pro Ala Ser Val Val Ile Ala Gly Asp Ala Glu Ala Leu
            180                 185                 190

Thr Glu Ala Val Glu Val Leu Gly Gly Arg Arg Val Ala Val Asp Tyr
        195                 200                 205

Ala Ser His Thr Arg His Val Glu Asp Ile Gln Asp Thr Leu Ala Glu
    210                 215                 220

Thr Leu Ala Gly Ile Asp Ala Gln Ala Pro Val Pro Phe Tyr Ser
225                 230                 235                 240

Thr Val Ala Gly Glu Trp Ile Thr Asp Ala Gly Val Val Asp Gly Gly
                245                 250                 255

Tyr Trp Tyr Arg Asn Leu Arg Asn Gln Val Gly Phe Gly Pro Ala Val
            260                 265                 270

Ala Glu Leu Ile Glu Gln Gly His Gly Val Phe Val Glu Val Ser Ala
        275                 280                 285

His Pro Val Leu Val Gln Pro Ile Ser Glu Leu Thr Asp Ala Val Val
    290                 295                 300

Thr Gly Thr Leu Arg Arg Asp Asp Gly Gly Val Arg Arg Leu Leu Thr
305                 310                 315                 320

Ser Met Ala Glu Leu Phe Val Arg Gly Val Pro Val Asp Trp Ala Thr
                325                 330                 335

Met Ala Pro Pro Ala Arg Val Glu Leu Pro Thr Tyr Ala Phe Asp His
            340                 345                 350

Gln His Phe Trp Leu Ser Pro Pro Ala Val Ala Asp Ala Pro Ala Leu
        355                 360                 365

Gly Leu Ala Gly Ala Asp His Pro Leu
    370                 375

<210> SEQ ID NO 44
<211> LENGTH: 384
<212> TYPE: PRT
<213> ORGANISM: Amycolatopsis mediterranei

<400> SEQUENCE: 44

Gly Leu Gly Ala Leu Ala Arg Gly Glu Ala Ala Pro Gly Val Val Thr
 1               5                  10                  15

Gly Thr Ala Gly Lys Pro Gly Lys Val Val Trp Val Phe Pro Gly Gln
            20                  25                  30
```

```
Gly Thr Gln Trp Val Gly Met Gly Arg Glu Leu Leu Asp Ala Ser Pro
         35                  40                  45

Val Phe Ala Glu Arg Ile Lys Glu Cys Ala Ala Ala Leu Asp Gln Trp
         50                  55                  60

Thr Asp Trp Ser Leu Leu Asp Val Leu Arg Gly Asp Gly Asp Leu Asp
 65                  70                  75                  80

Ser Val Glu Val Leu Gln Pro Ala Cys Phe Ala Val Met Val Gly Leu
                 85                  90                  95

Ala Ala Val Trp Glu Ser Ala Gly Val Arg Pro Asp Ala Val Val Gly
                100                 105                 110

His Ser Gln Gly Glu Ile Ala Ala Ala Cys Val Ser Gly Ala Leu Thr
            115                 120                 125

Leu Asp Asp Ala Ala Lys Val Val Ala Leu Arg Ser Gln Ala Ile Ala
        130                 135                 140

Ala Arg Leu Ser Gly Arg Gly Gly Met Ala Ser Val Ala Leu Ser Glu
145                 150                 155                 160

Asp Glu Ala Asn Ala Arg Leu Gly Leu Trp Asp Gly Arg Ile Glu Val
                165                 170                 175

Ala Ala Val Asn Gly Pro Ala Ser Val Val Ile Ala Gly Asp Ala Gln
                180                 185                 190

Ala Leu Asp Glu Ala Leu Glu Val Leu Ala Gly Asp Gly Val Arg Val
        195                 200                 205

Arg Gln Val Ala Val Asp Tyr Ala Ser His Thr Arg His Val Glu Asp
    210                 215                 220

Ile Arg Asp Thr Leu Ala Glu Thr Leu Ala Gly Ile Thr Ala Gln Ala
225                 230                 235                 240

Pro Asp Val Pro Phe Arg Ser Thr Val Thr Gly Gly Trp Val Arg Asp
                245                 250                 255

Ala Asp Val Leu Asp Gly Gly Tyr Trp Tyr Arg Asn Leu Arg Asn Gln
                260                 265                 270

Val Arg Phe Gly Pro Ala Val Ala Glu Leu Leu Glu Gln Gly His Gly
            275                 280                 285

Val Phe Val Glu Val Ser Ala His Pro Val Leu Val Gln Pro Ile Ser
        290                 295                 300

Glu Leu Thr Asp Ala Val Val Thr Gly Thr Leu Arg Arg Asp Asp Gly
305                 310                 315                 320

Gly Leu Arg Arg Leu Leu Thr Ser Met Ala Glu Leu Phe Val Arg Gly
                325                 330                 335

Val Arg Val Asp Trp Ala Thr Leu Val Pro Pro Ala Arg Val Asp Leu
                340                 345                 350

Pro Thr Tyr Ala Phe Asp His Gln His Phe Trp Leu Arg Pro Ala Ala
            355                 360                 365

Gln Ala Asp Ala Val Ser Leu Gly Gln Ala Ala Glu His Pro Leu
        370                 375                 380

<210> SEQ ID NO 45
<211> LENGTH: 381
<212> TYPE: PRT
<213> ORGANISM: Amycolatopsis mediterranei

<400> SEQUENCE: 45

Ala Gly Leu Ala Ala Leu Ala Arg Gly Glu Ser Ala Ala Asp Val Val
 1               5                  10                  15

Thr Gly Thr Val Ala Ala Ser Gly Val Pro Gly Lys Leu Val Trp Val
                20                  25                  30
```

```
Phe Pro Gly Gln Gly Ser Gln Trp Val Gly Met Gly Arg Glu Leu Leu
             35                  40                  45

Glu Ala Ser Pro Val Phe Ala Arg Ile Ala Glu Cys Ala Ala Ala
     50                  55                  60

Leu Glu Pro Trp Ile Asp Trp Ser Leu Leu Asp Val Leu Arg Gly Glu
 65                  70                  75                  80

Gly Asp Leu Asp Arg Val Asp Val Val Gln Pro Ala Ser Phe Ala Val
                 85                  90                  95

Met Val Gly Leu Ala Ala Val Trp Ser Ser Val Gly Val Val Pro Asp
             100                 105                 110

Ala Val Leu Gly His Ser Gln Gly Glu Ile Ala Ala Cys Val Ser
             115                 120                 125

Gly Ala Leu Ser Leu Gln Asp Ala Ala Lys Val Ala Leu Arg Ser
     130                 135                 140

Gln Ala Ile Ala Ala Lys Leu Ala Gly Arg Gly Gly Met Ala Ser Val
145                 150                 155                 160

Ala Leu Ser Glu Glu Asp Ala Val Ala Arg Leu Arg His Trp Ala Asp
                 165                 170                 175

Arg Val Glu Val Ala Ala Val Asn Ser Pro Ser Ser Val Val Ile Ala
             180                 185                 190

Gly Asp Ala Glu Ala Leu Asp Gln Ala Leu Glu Ala Leu Thr Gly Gln
             195                 200                 205

Asp Ile Arg Val Arg Arg Val Ala Val Asp Tyr Ala Ser His Thr Arg
             210                 215                 220

His Val Glu Asp Ile Gln Glu Pro Leu Ala Glu Ala Leu Ala Gly Ile
225                 230                 235                 240

Glu Ala His Ala Pro Thr Leu Pro Phe Phe Ser Thr Leu Thr Gly Asp
                 245                 250                 255

Trp Ile Arg Glu Ala Gly Val Val Asp Gly Gly Tyr Trp Tyr Arg Asn
             260                 265                 270

Leu Arg Asn Gln Val Gly Phe Gly Pro Ala Val Ala Glu Leu Leu Gly
         275                 280                 285

Leu Gly His Arg Val Phe Glu Val Ser Ala His Pro Val Leu Val
     290                 295                 300

Gln Ala Ile Ser Ala Ile Ala Asp Asp Thr Asp Ala Val Val Thr Gly
305                 310                 315                 320

Ser Leu Arg Arg Glu Glu Gly Gly Leu Arg Arg Leu Leu Thr Ser Met
                 325                 330                 335

Ala Glu Leu Phe Val Arg Gly Val Asp Val Asp Trp Ala Thr Met Val
             340                 345                 350

Pro Pro Ala Arg Val Asp Leu Pro Thr Tyr Ala Phe Asp His Gln His
             355                 360                 365

Tyr Trp Leu Arg Tyr Val Glu Thr Ala Thr Asp Ala Ala
     370                 375                 380

<210> SEQ ID NO 46
<211> LENGTH: 397
<212> TYPE: PRT
<213> ORGANISM: Amycolatopsis mediterranei

<400> SEQUENCE: 46

Ala Asp Ser Ala Glu Glu Ala Arg Ala Gly Leu Gly Ala Leu Ala Arg
 1               5                  10                  15

Gly Glu Asp Ala Pro Gly Leu Val Arg Gly Arg Val Pro Ala Ser Gly
             20                  25                  30
```

```
Leu Pro Gly Lys Leu Val Trp Val Phe Pro Gly Gln Gly Thr Gln Trp
             35                  40                  45

Val Gly Met Gly Arg Glu Leu Leu Glu Glu Ser Pro Val Phe Ala Glu
 50                  55                  60

Arg Ile Ala Glu Cys Ala Ala Leu Glu Pro Trp Ile Gly Trp Ser
 65                  70                  75                  80

Leu Phe Asp Val Leu Arg Gly Asp Gly Asp Leu Asp Arg Val Asp Val
                 85                  90                  95

Leu Gln Pro Ala Cys Phe Ala Val Met Val Gly Leu Ala Ala Val Trp
             100                 105                 110

Ser Ser Ala Gly Val Val Pro Asp Ala Val Leu Gly His Ser Gln Gly
             115                 120                 125

Glu Ile Ala Ala Ala Cys Val Ser Gly Ala Leu Ser Leu Glu Asp Ala
             130                 135                 140

Ala Lys Val Val Ala Leu Arg Ser Gln Ala Ile Ala Ala Lys Leu Ser
145                 150                 155                 160

Gly Arg Gly Gly Met Ala Ser Val Ala Leu Gly Glu Ala Asp Val Val
                 165                 170                 175

Ser Arg Leu Ala Asp Gly Val Glu Val Ala Ala Val Asn Gly Pro Ala
                 180                 185                 190

Ser Val Val Ile Ala Gly Asp Ala Gln Ala Leu Asp Glu Thr Leu Glu
             195                 200                 205

Ala Leu Ser Gly Ala Gly Ile Arg Ala Arg Val Ala Val Asp Tyr
 210                 215                 220

Ala Ser His Thr Arg His Val Glu Asp Ile Glu Asp Thr Leu Ala Glu
225                 230                 235                 240

Ala Leu Ala Gly Ile Asp Ala Arg Ala Pro Leu Val Pro Phe Leu Ser
                 245                 250                 255

Thr Leu Thr Gly Glu Trp Ile Arg Asp Glu Gly Val Val Asp Gly Gly
             260                 265                 270

Tyr Trp Tyr Arg Asn Leu Arg Gly Arg Val Arg Phe Gly Pro Ala Val
             275                 280                 285

Glu Ala Leu Leu Ala Gln Gly His Gly Val Phe Val Glu Leu Ser Ala
 290                 295                 300

His Pro Val Leu Val Gln Pro Ile Thr Glu Leu Thr Asp Glu Thr Ala
305                 310                 315                 320

Ala Val Val Thr Gly Ser Leu Arg Arg Asp Asp Gly Gly Leu Arg Arg
                 325                 330                 335

Leu Leu Thr Ser Met Ala Glu Leu Phe Val Arg Gly Val Glu Val Asp
             340                 345                 350

Trp Thr Ser Leu Val Pro Pro Ala Arg Ala Asp Leu Pro Thr Tyr Ala
             355                 360                 365

Phe Asp His Glu His Tyr Trp Leu Arg Ala Ala Asp Thr Ala Ser Asp
 370                 375                 380

Ala Val Ser Leu Gly Leu Ala Gly Ala Asp His Pro Leu
385                 390                 395

<210> SEQ ID NO 47
<211> LENGTH: 380
<212> TYPE: PRT
<213> ORGANISM: Amycolatopsis mediterranei
```

<400> SEQUENCE: 47

```
Gln Asp Gly Leu Gln Ala Leu Ala Arg Gly Glu Asn Ala Pro Gly Val
  1               5                  10                  15

Val Thr Gly Thr Ala Gly Lys Pro Gly Lys Val Val Trp Val Phe Pro
             20                  25                  30

Gly Gln Gly Ser Gln Trp Met Gly Met Gly Arg Asp Leu Leu Asp Ser
         35                  40                  45

Ser Pro Val Phe Ala Ala Arg Ile Lys Glu Cys Ala Ala Ala Leu Glu
     50                  55                  60

Gln Trp Thr Asp Trp Ser Leu Leu Asp Val Leu Arg Gly Asp Ala Asp
 65                  70                  75                  80

Leu Leu Asp Arg Val Asp Val Val Gln Pro Ala Ser Phe Ala Met Met
                 85                  90                  95

Val Gly Leu Ala Ala Val Trp Thr Ser Leu Gly Val Thr Pro Asp Ala
            100                 105                 110

Val Leu Gly His Ser Gln Gly Glu Ile Ala Ala Cys Val Ser Gly
            115                 120                 125

Ala Leu Ser Leu Asp Asp Ala Ala Lys Val Val Ala Leu Arg Ser Gln
        130                 135                 140

Ala Ile Ala Gly Glu Leu Ala Gly Arg Gly Gly Met Ala Ser Val Ala
145                 150                 155                 160

Leu Ser Glu Glu Asp Ala Val Ala Arg Leu Thr Pro Trp Ala Asn Arg
                165                 170                 175

Val Glu Val Ala Ala Val Asn Ser Pro Ser Ser Val Val Ile Ala Gly
            180                 185                 190

Asp Ala Gln Ala Leu Asp Glu Ala Leu Glu Leu Ala Gly Asp Gly
        195                 200                 205

Val Arg Val Arg Arg Val Ala Val Asp Tyr Ala Ser His Thr Arg His
    210                 215                 220

Val Glu Ala Ile Ala Glu Thr Leu Ala Lys Thr Leu Ala Gly Ile Asp
225                 230                 235                 240

Ala Arg Val Pro Ala Ile Pro Phe Tyr Ser Thr Val Leu Gly Thr Trp
                245                 250                 255

Ile Glu Gln Ala Val Val Asp Ala Gly Tyr Trp Tyr Arg Asn Leu Arg
            260                 265                 270

Gln Gln Val Arg Phe Gly Pro Ser Val Ala Asp Leu Ala Gly Leu Gly
        275                 280                 285

His Thr Val Phe Val Glu Ile Ser Ala His Pro Val Leu Val Gln Pro
    290                 295                 300

Leu Ser Glu Ile Ser Asp Asp Ala Val Val Thr Gly Ser Leu Arg Arg
305                 310                 315                 320

Asp Asp Gly Gly Leu Arg Arg Leu Leu Ala Ser Ala Ala Glu Leu Tyr
                325                 330                 335

Val Arg Gly Val Ala Val Asp Trp Thr Ala Val Pro Ala Ala Gly
            340                 345                 350

Trp Val Asp Leu Pro Thr Tyr Ala Phe Asp Arg Arg His Phe Trp Leu
        355                 360                 365

His Glu Ala Glu Thr Ala Glu Ala Ala Glu Gly Met
    370                 375                 380

<210> SEQ ID NO 48
<211> LENGTH: 395
<212> TYPE: PRT
<213> ORGANISM: Amycolatopsis mediterranei
```

<400> SEQUENCE: 48

```
Ser Arg Glu Glu Ala Val Thr Asn Leu Glu Ala Leu Ala Arg Gly Glu
  1               5                  10                  15

Asp Pro Ala Ala Val Val Thr Gly Arg Ala Gly Ser Pro Gly Lys Leu
             20                  25                  30

Val Trp Val Phe Pro Gly Gln Gly Ser Gln Trp Ile Gly Met Gly Arg
         35                  40                  45

Glu Leu Leu Asp Ser Ser Pro Val Phe Ala Glu Arg Val Ala Glu Cys
     50                  55                  60

Ala Ala Ala Leu Glu Pro Trp Ile Asp Trp Ser Leu Leu Asp Val Leu
 65                  70                  75                  80

Arg Gly Glu Ser Asp Leu Leu Asp Arg Val Asp Val Val Gln Pro Ala
                 85                  90                  95

Ser Phe Ala Met Met Val Gly Leu Ala Ala Val Trp Gln Ser Val Gly
            100                 105                 110

Val Arg Pro Asp Ala Val Val Gly His Ser Gln Gly Glu Ile Ala Ala
            115                 120                 125

Ala Cys Val Ser Gly Ala Leu Ser Leu Gln Asp Ala Ala Lys Val Val
        130                 135                 140

Ala Leu Arg Ser Gln Ala Ile Ala Thr Arg Leu Ala Gly Arg Gly Gly
145                 150                 155                 160

Met Ala Ser Val Ala Leu Ser Glu Glu Asp Ala Thr Ala Trp Leu Ala
                165                 170                 175

Pro Trp Ala Asp Arg Val Gln Val Ala Ala Val Asn Ser Pro Ala Ser
            180                 185                 190

Val Val Ile Ala Gly Glu Ala Gln Ala Leu Asp Glu Val Val Asp Ala
        195                 200                 205

Leu Ser Gly Gln Glu Val Arg Val Arg Arg Val Ala Val Asp Tyr Gly
    210                 215                 220

Ser His Thr Asn Gln Val Glu Ala Ile Glu Asp Leu Leu Ala Glu Thr
225                 230                 235                 240

Leu Ala Gly Ile Glu Ala Gln Ala Pro Lys Val Pro Phe Tyr Ser Thr
                245                 250                 255

Leu Ile Gly Asp Trp Ile Arg Asp Ala Gly Ile Val Asp Gly Gly Tyr
            260                 265                 270

Trp Tyr Arg Asn Leu Arg Asn Gln Val Gly Phe Gly Pro Ala Val Ala
        275                 280                 285

Glu Leu Val Arg Gln Gly His Gly Val Phe Val Glu Val Ser Ala His
    290                 295                 300

Pro Val Leu Val Gln Pro Leu Ser Glu Leu Ser Asp Asp Ala Val Val
305                 310                 315                 320

Thr Gly Ser Leu Arg Arg Glu Asp Gly Gly Leu Arg Arg Leu Leu Thr
                325                 330                 335

Ser Met Ala Glu Leu Tyr Val Gln Gly Val Pro Leu Asp Trp Thr Ala
            340                 345                 350

Val Leu Pro Arg Thr Gly Arg Val Asp Leu Pro Lys Tyr Ala Phe Asp
        355                 360                 365

His Arg His Tyr Trp Leu Arg Pro Ala Glu Ser Ala Thr Asp Ala Ala
    370                 375                 380

Ser Leu Gly Gln Gly Ala Ala Asp His Pro Leu
385                 390                 395
```

<210> SEQ ID NO 49
<211> LENGTH: 378
<212> TYPE: PRT
<213> ORGANISM: Amycolatopsis mediterranei

<400> SEQUENCE: 49

```
Arg Ala Leu Ala Arg Gly Glu Ser Ala Pro Gly Leu Leu Ser Gly Arg
 1               5                  10                  15

Gly Ser Gly Val Pro Gly Lys Val Val Trp Val Phe Pro Gly Gln Gly
             20                  25                  30

Thr Gln Trp Ala Gly Met Gly Arg Glu Leu Leu Asp Ser Ser Glu Val
         35                  40                  45

Phe Ala Ala Arg Ile Ala Glu Cys Glu Thr Ala Leu Gly Arg Trp Val
     50                  55                  60

Asp Trp Ser Leu Thr Asp Val Leu Arg Gly Glu Ala Asp Leu Leu Asp
 65                  70                  75                  80

Arg Val Asp Val Val Gln Pro Ala Ser Phe Ala Val Met Val Gly Leu
                 85                  90                  95

Ala Ala Val Trp Ala Ser Leu Gly Val Glu Pro Glu Ala Val Val Gly
            100                 105                 110

His Ser Gln Gly Glu Ile Ala Ala Ala Cys Val Ser Gly Ala Leu Ser
        115                 120                 125

Leu Glu Asp Ala Ala Lys Val Val Ala Leu Arg Ser Gln Ala Ile Ala
130                 135                 140

Ala Ser Leu Ala Gly Arg Gly Gly Met Ala Ser Val Ala Leu Ser Glu
145                 150                 155                 160

Glu Asp Ala Thr Ala Arg Leu Glu Pro Trp Ala Gly Arg Val Glu Val
                165                 170                 175

Ala Ala Val Asn Gly Pro Thr Ser Val Val Ile Ala Gly Asp Ala Glu
            180                 185                 190

Ala Leu Asp Glu Ala Leu Asp Ala Leu Asp Asp Gln Gly Val Arg Ile
        195                 200                 205

Arg Arg Val Ala Val Asp Tyr Ala Ser His Thr Arg His Val Glu Ala
210                 215                 220

Ala Arg Asp Ala Leu Ala Glu Met Leu Gly Gly Ile Arg Ala Gln Ala
225                 230                 235                 240

Pro Glu Val Pro Phe Tyr Ser Thr Val Thr Gly Gly Trp Val Glu Asp
                245                 250                 255

Ala Gly Val Leu Asp Gly Gly Tyr Trp Tyr Arg Asn Leu Arg Arg Gln
            260                 265                 270

Val Arg Phe Gly Pro Ala Val Ala Glu Leu Ile Glu Gln Gly His Arg
        275                 280                 285

Val Phe Val Glu Val Ser Ala His Pro Val Leu Val Gln Pro Ile Asn
    290                 295                 300

Glu Leu Val Asp Asp Thr Glu Ala Val Val Thr Gly Thr Leu Arg Arg
305                 310                 315                 320

Glu Asp Gly Gly Leu Arg Arg Leu Leu Ala Ser Ala Ala Glu Leu Phe
                325                 330                 335

Val Arg Gly Val Thr Val Asp Trp Ser Gly Val Leu Pro Pro Ser Arg
            340                 345                 350

Arg Val Glu Leu Pro Thr Tyr Ala Phe Asp His Gln His Tyr Trp Leu
        355                 360                 365

Gln Met Gly Gly Ser Ala Thr Asp Ala Val
    370                 375
```

<210> SEQ ID NO 50
<211> LENGTH: 379
<212> TYPE: PRT
<213> ORGANISM: Amycolatopsis mediterranei

<400> SEQUENCE: 50

```
Val Val Val Ala Gly Ser Arg Glu Glu Ala Val Thr Gly Leu Arg Ala
  1               5                  10                  15

Leu Asn Thr Ala Gly Ser Gly Thr Pro Gly Lys Val Val Trp Val Phe
             20                  25                  30

Pro Gly Gln Gly Thr Gln Trp Ala Gly Met Gly Arg Glu Leu Leu Ala
         35                  40                  45

Glu Ser Pro Val Phe Ala Glu Arg Ile Ala Glu Cys Ala Ala Ala Leu
 50                  55                  60

Ala Pro Trp Ile Asp Trp Ser Leu Val Asp Val Leu Arg Gly Glu Gly
 65                  70                  75                  80

Asp Leu Gly Arg Val Asp Val Leu Gln Pro Ala Cys Phe Ala Val Met
                 85                  90                  95

Val Gly Leu Ala Ala Val Trp Glu Ser Val Gly Val Arg Pro Asp Ala
            100                 105                 110

Val Val Gly His Ser Gln Gly Glu Ile Ala Ala Ala Cys Val Ser Gly
            115                 120                 125

Ala Leu Ser Leu Glu Asp Ala Ala Lys Val Val Ala Leu Arg Ser Gln
130                 135                 140

Ala Ile Ala Ala Glu Leu Ser Gly Arg Gly Gly Met Ala Ser Val Ala
145                 150                 155                 160

Leu Gly Glu Asp Asp Val Val Ser Arg Leu Val Asp Gly Val Glu Val
                165                 170                 175

Ala Ala Val Asn Gly Pro Ser Ser Val Val Ile Ala Gly Asp Ala His
            180                 185                 190

Ala Leu Asp Ala Thr Leu Glu Ile Leu Ser Gly Glu Gly Ile Arg Val
        195                 200                 205

Arg Arg Val Ala Val Asp Tyr Ala Ser His Thr Arg His Val Glu Asp
    210                 215                 220

Ile Arg Asp Thr Leu Ala Glu Thr Leu Ala Gly Ile Ser Ala Gln Ala
225                 230                 235                 240

Pro Ala Val Pro Phe Tyr Ser Thr Val Thr Ser Glu Trp Val Arg Asp
                245                 250                 255

Ala Gly Val Leu Asp Gly Gly Tyr Trp Tyr Arg Asn Leu Arg Asn Gln
            260                 265                 270

Val Arg Phe Gly Ala Ala Ala Thr Ala Leu Leu Glu Gln Gly His Thr
        275                 280                 285

Val Phe Val Glu Val Ser Ala His Pro Val Thr Val Gln Pro Leu Ser
    290                 295                 300

Glu Leu Thr Gly Asp Ala Ile Gly Thr Leu Arg Arg Glu Asp Gly Gly
305                 310                 315                 320

Leu Arg Arg Leu Leu Ala Ser Met Gly Glu Leu Phe Val Arg Gly Ile
                325                 330                 335

Asp Val Asp Trp Thr Ala Met Val Pro Ala Ala Gly Trp Val Asp Leu
            340                 345                 350

Pro Thr Tyr Ala Phe Glu His Arg His Tyr Trp Leu Glu Pro Ala Glu
        355                 360                 365

Pro Ala Ser Ala Gly Asp Pro Leu Leu Gly Thr
    370                 375
```

<210> SEQ ID NO 51
<211> LENGTH: 406
<212> TYPE: PRT
<213> ORGANISM: Streptomyces noursei

<400> SEQUENCE: 51

```
Ala Val Val Val Gly Glu Arg Arg Glu Asp Phe Leu Arg Gly Leu Ala
 1               5                  10                  15

Ala Leu Ser Thr Gly Ala Ser Thr Ala Gly Leu Val Ser Gly Ile Ala
             20                  25                  30

Gly Pro Asp Pro Glu Gly Ala Val Phe Val Phe Pro Gly Gln Gly Ser
         35                  40                  45

Gln Trp Trp Gly Met Gly Arg Glu Leu Leu Ala Thr Ser Glu Val Phe
     50                  55                  60

Arg Thr Ala Ile Asp Asp Cys Ala Thr Ala Leu Ala Pro Tyr Val Asp
 65                  70                  75                  80

Trp Ser Leu His Asp Val Leu Ala Gly Glu Gly Asp Pro Ala Leu Leu
                 85                  90                  95

Glu Arg Val Asp Val Val Gln Pro Ala Leu Phe Ala Met Met Val Gly
            100                 105                 110

Leu Ser Ala Leu Trp Arg Ser His Gly Val Val Pro Ala Ala Val Val
        115                 120                 125

Gly His Ser Gln Gly Glu Ile Ala Ala Ala Cys Val Ala Gly Ala Leu
    130                 135                 140

Ser Leu Ala Asp Ala Ala Arg Val Val Ala Leu Arg Ser Gln Ala Leu
145                 150                 155                 160

Pro Gln Leu Ser Gly Arg Gly Met Met Ser Val Ser Ala Pro Val
                165                 170                 175

Glu Arg Val Thr Ala Leu Leu Ala Pro Trp Gln Glu Ala Leu Ser Val
            180                 185                 190

Ala Ala Val Asn Gly Pro Ser Val Val Val Ser Gly Asp Thr Asp
        195                 200                 205

Ala Leu Asp Ala Leu His Thr Ala Cys Gln Glu Gln Gly Val Arg Ala
    210                 215                 220

Arg Lys Val Ser Val Asp Tyr Ala Ser His Gly Arg His Val Glu Ala
225                 230                 235                 240

Val Arg Asp Glu Leu Ala Arg Val Leu Ala Pro Val Asp Pro Arg Ala
                245                 250                 255

Pro Glu Val Pro Phe Tyr Ser Thr Val Thr Gly Asp Arg Val Asp Asp
            260                 265                 270

Ala Ala Phe Asp Gly Ala Tyr Trp Tyr Thr Asn Leu Arg Gln Thr Val
        275                 280                 285

Arg Met Glu Glu Ala Thr Arg Ala Leu Leu Ala Ala Gly His Arg Val
    290                 295                 300

Phe Ile Glu Val Ser Pro His Pro Val Leu Ala Ala Pro Ile Gln Glu
305                 310                 315                 320

Thr Gln Glu Ala Val Ala Glu Ala Thr Gly Gly Ser Ala Val Val Leu
                325                 330                 335

Gly Ser Leu Arg Arg Asp Glu Gly Gly Pro Arg Arg Phe Leu Thr Ser
            340                 345                 350

Leu Ala Glu Ala His Thr His Gly Ala Pro Val Asp Trp Thr Thr Thr
        355                 360                 365

Phe Ala Arg Ser Ala Tyr Gln Pro Val Asp Leu Pro Thr Tyr Pro Phe
    370                 375                 380
```

```
Gln Arg Gln Asp Phe Trp Pro Glu Ala Arg Pro Ala Thr Pro Ala Ala
385                 390                 395                 400

Gly Ala Asp Ala Ser Asp
                405

<210> SEQ ID NO 52
<211> LENGTH: 365
<212> TYPE: PRT
<213> ORGANISM: Streptomyces sp.

<400> SEQUENCE: 52

Gly Glu Glu Val Pro Gly Val Val Arg Gly Thr Ala Asp Val Thr Asp
1               5                   10                  15

Thr Arg Ala Val Phe Val Phe Pro Gly Gln Gly Ser Gln Trp Asp Gly
            20                  25                  30

Met Gly Ala Glu Leu Leu Ala Thr Glu Pro Val Phe Ala Arg Arg Leu
        35                  40                  45

Gly Glu Cys Ala Glu Ala Leu Ala Pro Tyr Thr Gly Trp Asp Leu Leu
    50                  55                  60

Asp Val Ile Ala Arg Arg Pro Gly Ala Pro Glu Leu Asp Arg Val Asp
65                  70                  75                  80

Val Val Gln Pro Ala Ser Phe Ala Met Met Val Ala Leu Ala Glu Leu
                85                  90                  95

Trp Arg Ala His Gly Val Ala Pro Ala Ala Val Val Gly His Ser Gln
            100                 105                 110

Gly Glu Val Ala Ala Ala Cys Val Ala Gly Val Leu Thr Leu Asp Asp
        115                 120                 125

Ala Ala Lys Val Val Ala Leu Arg Ser Arg Leu Val Ala Thr Glu Arg
    130                 135                 140

Ala Gly His Gly Gly Met Val Ser Val Pro Pro Ala Asp Phe Asp Ala
145                 150                 155                 160

Ala Ala Trp Ala Gly Arg Leu Glu Val Ala Ala Val Asn Gly Pro Ala
                165                 170                 175

Ser Ile Val Val Ala Gly Ala Ala Asp Ala Val Glu Glu Leu Leu Ala
            180                 185                 190

Ala Thr Pro His Ala Arg Arg Ile Ala Val Asp Tyr Ala Ser His Thr
        195                 200                 205

Ala His Val Glu Ser Ile Arg Gly Ala Leu Leu Asp Ala Leu Ala Asp
    210                 215                 220

Leu Thr Pro Gly Ala Pro Glu Ile Pro Phe Phe Ser Thr Val Asp Glu
225                 230                 235                 240

Ala Trp Leu Asp Arg Pro Ala Asp Ala Ala Tyr Trp Tyr Asp Asn Val
                245                 250                 255

Arg Cys Pro Val Arg Phe Gly Ala Ala Ala Arg Leu Ala Glu Leu
            260                 265                 270

Gly His Arg Val Phe Val Glu Ala Ser Pro His Pro Val Leu Thr Thr
        275                 280                 285

Ala Leu Ala Asp Thr Leu Ala Gly His Pro Asn Thr Ala Val Thr Gly
    290                 295                 300

Thr Leu Arg Arg Gly Asp Gly Gly Ala Arg Arg Phe Thr Arg Ser Leu
305                 310                 315                 320

Ala Glu Leu Trp Val Arg Gly Val Pro Val Ser Trp Pro Phe Gly Glu
                325                 330                 335
```

```
Leu Arg Gly Val Pro Leu Pro Thr Tyr Pro Phe Arg Arg Asp Arg Tyr
                340                 345                 350

Trp Val Asp Ala Glu Pro Ala Gly Thr Ser Gly His Pro
            355                 360                 365

<210> SEQ ID NO 53
<211> LENGTH: 398
<212> TYPE: PRT
<213> ORGANISM: Streptomyces avermitilis

<400> SEQUENCE: 53

Leu His Ala Leu Asp Ala Leu Ala Glu Gly Ala Pro Thr Ala Gly Val
  1               5                  10                  15

Val Gln Gly Val Ala Gly Pro Ala Ala Asp Gly Lys Ile Ala Met Leu
                 20                  25                  30

Phe Gly Gly Gln Gly Thr His Trp Glu Gly Met Ala Gln Glu Leu Leu
             35                  40                  45

Gly Ser Ser Pro Val Phe Ala Gln Gln Met Ser Asp Cys Ala Gln Ala
         50                  55                  60

Leu Glu Pro Tyr Leu Asp Trp Ser Leu Leu Asp Val Leu Arg Gly Ala
 65                  70                  75                  80

Pro Asp Ala Pro Pro Leu Gln Arg Val Asp Val Gln Pro Val Leu
                 85                  90                  95

Phe Ala Val Met Val Ser Leu Ala Ala Leu Trp Arg Ser Tyr Gly Val
                100                 105                 110

His Pro Asp Ala Val Ala Gly His Ser Gln Gly Glu Ile Ala Ala Ala
            115                 120                 125

Tyr Val Ala Gly Ala Leu Ser Leu Asp Asp Ala Ala Arg Val Thr Ala
        130                 135                 140

Leu Arg Ser Gln Ala Leu Ala Ala Leu Ala Gly Gln Gly Ala Met Ala
145                 150                 155                 160

Ser Val Gly Leu Pro Val Glu Lys Leu Glu Pro Arg Leu Ala Thr Trp
                165                 170                 175

Gly Asp Arg Leu Val Ile Ala Ala Val Asn Gly Ala Arg Ser Ala Val
            180                 185                 190

Val Ser Gly Glu Pro Glu Ala Val Asp Ala Leu Val Glu Glu Leu Ser
        195                 200                 205

His Glu Asp Val Pro Ala Arg Arg Leu Met Val Asp Trp Ala Ser His
    210                 215                 220

Ser Pro Gln Val Glu Ala Ile Gln Gly Arg Leu Leu Glu Leu Leu Ala
225                 230                 235                 240

Pro Ile Arg Ala Arg Thr Gly Asp Val Pro Phe Tyr Ser Thr Val Thr
                245                 250                 255

Gly Glu Arg Ile Asp Gly Thr Glu Leu Asp Ala Asp Tyr Trp Tyr Arg
            260                 265                 270

Asn Leu Arg Gln Val Val Arg Phe Arg Asp Ala Thr Gln Ala Leu Val
        275                 280                 285

Arg Ala Gly His Thr Val Phe Ile Glu Ala Cys Pro His Pro Ala Val
    290                 295                 300

Ala Val Gly Val Gln Glu Thr Leu Asp Glu Met Gly Asp Leu Asp Ser
305                 310                 315                 320

Leu Val Val Gly Ser Leu Arg Arg Gly Glu Gly Leu Arg Arg Phe
                325                 330                 335

Leu Met Ser Val Ala Glu Leu Phe Val Gly Gly Val Ala Val Glu Trp
                340                 345                 350
```

```
Ser Gly Val Phe Gly Ser Val Gly Arg Gly Val Ala Gly Gly Cys Gly
        355                 360                 365

Val Glu Leu Pro Thr Tyr Ala Phe Glu Arg Glu Arg Phe Trp Leu Asp
        370                 375                 380

Val Glu Gly Ala Pro Arg Gly Ser Gly Val Ser Gly Gln Trp
385                 390                 395

<210> SEQ ID NO 54
<211> LENGTH: 383
<212> TYPE: PRT
<213> ORGANISM: Saccharopolyspora erythraea

<400> SEQUENCE: 54

Ala Ala Thr Ala Asp Ala Val Val Glu Gly Val Thr Glu Val Asp Gly
1               5                   10                  15

Arg Asn Val Val Phe Leu Phe Pro Gly Gln Gly Ser Gln Trp Ala Gly
            20                  25                  30

Met Gly Ala Glu Leu Leu Ser Ser Pro Val Phe Ala Gly Lys Ile
        35                  40                  45

Arg Ala Cys Asp Glu Ser Met Ala Pro Met Gln Asp Trp Lys Val Ser
    50                  55                  60

Asp Val Leu Arg Gln Ala Pro Gly Ala Pro Gly Leu Asp Arg Val Asp
65                  70                  75                  80

Val Val Gln Pro Val Leu Phe Ala Val Met Val Ser Leu Ala Glu Leu
                85                  90                  95

Trp Arg Ser Tyr Gly Val Glu Pro Ala Ala Val Val Gly His Ser Gln
            100                 105                 110

Gly Glu Ile Ala Ala Ala His Val Ala Gly Ala Leu Thr Leu Glu Asp
        115                 120                 125

Ala Ala Lys Leu Val Val Gly Arg Ser Arg Leu Met Arg Ser Leu Ser
130                 135                 140

Gly Glu Gly Gly Met Ala Ala Val Ala Leu Gly Glu Ala Ala Val Arg
145                 150                 155                 160

Glu Arg Leu Arg Pro Trp Gln Asp Arg Leu Ser Val Ala Ala Val Asn
                165                 170                 175

Gly Pro Arg Ser Val Val Val Ser Gly Glu Pro Gly Ala Leu Arg Ala
            180                 185                 190

Phe Ser Glu Asp Cys Ala Ala Glu Gly Ile Arg Val Arg Asp Ile Asp
        195                 200                 205

Val Asp Tyr Ala Ser His Ser Pro Gln Ile Glu Arg Val Arg Glu Glu
    210                 215                 220

Leu Leu Glu Thr Thr Gly Asp Ile Ala Pro Arg Pro Ala Arg Val Thr
225                 230                 235                 240

Phe His Ser Thr Val Glu Ser Arg Ser Met Asp Gly Thr Glu Leu Asp
                245                 250                 255

Ala Arg Tyr Trp Tyr Arg Asn Leu Arg Glu Thr Val Arg Phe Ala Asp
            260                 265                 270

Ala Val Thr Arg Leu Ala Glu Ser Gly Tyr Asp Ala Phe Ile Glu Val
        275                 280                 285

Ser Pro His Pro Val Val Gln Ala Val Glu Glu Ala Val Glu Glu
    290                 295                 300

Ala Asp Gly Ala Glu Asp Ala Val Val Gly Ser Leu His Arg Asp
305                 310                 315                 320

Gly Gly Asp Leu Ser Ala Phe Leu Arg Ser Met Ala Thr Ala His Val
                325                 330                 335
```

```
Ser Gly Val Asp Ile Arg Trp Asp Val Ala Leu Pro Gly Ala Ala Pro
            340                 345                 350

Phe Ala Leu Pro Thr Tyr Pro Phe Gln Arg Lys Arg Tyr Trp Leu Gln
        355                 360                 365

Pro Ala Ala Pro Ala Ala Ala Ser Asp Glu Leu Ala Tyr Arg Val
    370                 375                 380

<210> SEQ ID NO 55
<211> LENGTH: 433
<212> TYPE: PRT
<213> ORGANISM: Streptomyces caelestis

<400> SEQUENCE: 55

Ser Leu Ala Asp Ser Ala Gly Ile Gly His Gly Leu Ala Val Gly Arg
  1               5                  10                  15

Ala Ala Leu Pro His Arg Ala Val Leu Leu Gly Asp Gly Ala Ala Pro
                 20                  25                  30

Leu Asp Ala Leu Ala Ala Leu Ala Ser Gly Glu Val Ser Pro Asp Val
             35                  40                  45

Val Thr Gly Ser Ala Ala Asp Val Arg Arg Val Ala Phe Val Phe Pro
         50                  55                  60

Gly Gln Gly Ala Gln Trp Ala Gly Met Gly Ala Glu Leu Leu Asp Ser
 65                  70                  75                  80

Ser Pro Val Phe Ala Ala Glu Leu Ala Arg Cys Glu Ala Ala Leu Glu
                 85                  90                  95

Pro Phe Val Asp Trp Ser Leu Thr Asp Val Leu Arg Gly Ala Pro Gly
                100                 105                 110

Ala Pro Gly Leu Asp Arg Val Asp Val Val Gln Pro Val Thr Phe Ala
            115                 120                 125

Val Val Val Ala Leu Ala Ala Met Trp Arg Trp Leu Gly Val Glu Pro
        130                 135                 140

Ala Ala Val Val Gly His Ser Gln Gly Glu Ile Ala Ala Ala His Val
145                 150                 155                 160

Ala Gly Val Leu Ser Leu Glu Asp Ala Ala Arg Val Val Ala Leu Arg
                165                 170                 175

Ser Gln Leu Ile Ala Arg Glu Leu Ala Gly Arg Gly Ser Met Ala Ser
            180                 185                 190

Val Ala Leu Ala Ala Ala Asp Val Glu Ser Arg Leu Ala Gly Ala Glu
        195                 200                 205

Ala Gly Gly Gly Val Arg Asp Val Glu Ile Ala Ala Val Asn Gly Pro
    210                 215                 220

Glu Thr Thr Val Val Cys Gly Ala Pro Gly Ala Val Asp Ser Leu Leu
225                 230                 235                 240

Gly Val Leu Gln Gly Glu Gly Val Arg Val Arg Arg Ile Asp Val Asp
                245                 250                 255

Tyr Ala Ser His Ser Arg His Val Glu Gly Ile Arg Asp Glu Leu Ala
            260                 265                 270

Ala Val Leu Ala Gly Leu Arg Pro Arg Ala Gly Arg Val Pro Phe Tyr
        275                 280                 285

Ser Thr Val Glu Ala Glu Pro Leu Asp Gly Thr Ala Leu Asp Ala Gly
    290                 295                 300

Tyr Trp Tyr Arg Asn Leu Arg Gln Arg Val Arg Phe Glu Ser Ala Leu
305                 310                 315                 320

Arg Ala Met Leu Ala Asp Gly Val Asp Ala Phe Val Glu Cys Ser Pro
                325                 330                 335
```

```
His Pro Val Leu Thr Val Pro Val Arg Gln Thr Leu Glu Asp Ala Gly
                340                 345                 350

Ala Gly Ala Val Ala Val Gly Ser Leu Arg Arg Asp Gly Gly Leu
            355                 360                 365

Arg Arg Phe Leu Thr Ser Ala Ala Glu Ala Gln Val Ala Gly Val Pro
        370                 375                 380

Val Asp Trp Ala Ala Leu Cys Pro Arg Ala Gly Trp Val Asp Leu Pro
385                 390                 395                 400

Thr Tyr Ala Phe Gln Arg Glu Arg Tyr Trp Val Ala Pro Ala Glu Pro
                405                 410                 415

Gly Pro Ala Ala Gly Ala Gly Ser Ala Ala Thr Gly Pro Ala Ala
                420                 425                 430

Ala

<210> SEQ ID NO 56
<211> LENGTH: 383
<212> TYPE: PRT
<213> ORGANISM: Saccharopolyspora erythraea

<400> SEQUENCE: 56

Ala Asp Arg Arg Ile Ala Asp Arg Thr Ala Thr Gly Gln Gly Pro Asn
1               5                   10                  15

Ser Pro Arg Arg Val Ala Met Val Phe Pro Gly Gln Gly Ala Gln Trp
            20                  25                  30

Gln Gly Met Ala Arg Asp Leu Leu Arg Glu Ser Gln Val Phe Ala Asp
        35                  40                  45

Ser Ile Arg Asp Cys Glu Arg Ala Leu Ala Pro His Val Asp Trp Ser
    50                  55                  60

Leu Thr Asp Leu Leu Ser Gly Ala Arg Pro Leu Asp Arg Val Asp Val
65                  70                  75                  80

Val Gln Pro Ala Leu Phe Ala Val Met Val Ser Leu Ala Ala Leu Trp
                85                  90                  95

Arg Ser His Gly Val Glu Pro Ala Ala Val Val Gly His Ser Gln Gly
            100                 105                 110

Glu Ile Ala Ala Ala His Val Ala Gly Ala Leu Thr Leu Glu Asp Ala
        115                 120                 125

Ala Lys Leu Val Ala Val Arg Ser Arg Val Leu Arg Arg Leu Gly Gly
    130                 135                 140

Gln Gly Gly Met Ala Ser Phe Gly Leu Gly Thr Glu Gln Ala Ala Glu
145                 150                 155                 160

Arg Ile Gly Arg Phe Ala Gly Ala Leu Ser Ile Ala Ser Val Asn Gly
                165                 170                 175

Pro Arg Ser Val Val Ala Gly Glu Ser Gly Pro Leu Asp Glu Leu
            180                 185                 190

Ile Ala Glu Cys Glu Ala Glu Gly Ile Thr Ala Arg Arg Ile Pro Val
        195                 200                 205

Asp Tyr Ala Ser His Ser Pro Gln Val Glu Ser Leu Arg Glu Glu Leu
    210                 215                 220

Leu Thr Glu Leu Ala Gly Ile Ser Pro Val Ser Ala Asp Val Ala Leu
225                 230                 235                 240

Tyr Ser Thr Thr Thr Gly Gln Pro Ile Asp Thr Ala Thr Met Asp Thr
                245                 250                 255

Ala Tyr Trp Tyr Ala Asn Leu Arg Glu Gln Val Arg Phe Gln Asp Ala
                260                 265                 270
```

```
Thr Arg Gln Leu Ala Glu Ala Gly Phe Asp Ala Phe Val Glu Val Ser
        275                 280                 285

Pro His Pro Val Leu Thr Val Gly Ile Glu Ala Thr Leu Asp Ser Ala
        290                 295                 300

Leu Pro Ala Asp Ala Gly Ala Cys Val Val Gly Thr Leu Arg Arg Asp
305                 310                 315                 320

Arg Gly Gly Leu Ala Asp Phe His Thr Ala Leu Gly Glu Ala Tyr Ala
                325                 330                 335

Gln Gly Val Glu Val Asp Trp Ser Pro Ala Phe Ala Asp Ala Arg Pro
            340                 345                 350

Val Glu Leu Pro Val Tyr Pro Phe Gln Arg Gln Arg Tyr Trp Leu Pro
        355                 360                 365

Ile Pro Thr Gly Gly Arg Ala Arg Asp Glu Asp Asp Trp Arg
        370                 375                 380
```

<210> SEQ ID NO 57
<211> LENGTH: 382
<212> TYPE: PRT
<213> ORGANISM: Saccharopolyspora erythraea

<400> SEQUENCE: 57

```
Ala Leu Ala Glu Gly Arg Pro Ser Ala Asp Ala Val Ala Pro Val Thr
1               5                   10                  15

Ser Ala Pro Arg Lys Pro Val Leu Val Phe Pro Gly Gln Gly Ala Gln
            20                  25                  30

Trp Val Gly Met Ala Arg Asp Leu Leu Glu Ser Ser Glu Val Phe Ala
        35                  40                  45

Glu Ser Met Ser Arg Cys Ala Glu Ala Leu Ser Pro His Thr Asp Trp
    50                  55                  60

Lys Leu Leu Asp Val Val Arg Gly Asp Gly Gly Pro Asp Pro His Glu
65                  70                  75                  80

Arg Val Asp Val Leu Gln Pro Val Leu Phe Ser Ile Met Val Ser Leu
                85                  90                  95

Ala Glu Leu Trp Arg Ala His Gly Val Thr Pro Ala Ala Val Val Gly
            100                 105                 110

His Ser Gln Gly Glu Ile Ala Ala His Val Ala Gly Ala Leu Ser
        115                 120                 125

Leu Glu Ala Ala Ala Lys Val Val Ala Leu Arg Ser Gln Val Leu Arg
130                 135                 140

Glu Leu Asp Asp Gln Gly Gly Met Val Ser Val Gly Ala Ser Arg Asp
145                 150                 155                 160

Glu Leu Glu Thr Val Leu Ala Arg Trp Asp Gly Arg Val Ala Val Ala
                165                 170                 175

Ala Val Asn Gly Pro Gly Thr Ser Val Val Ala Gly Pro Thr Ala Glu
            180                 185                 190

Leu Asp Glu Phe Phe Ala Glu Ala Glu Ala Arg Glu Met Lys Pro Arg
        195                 200                 205

Arg Ile Ala Val Arg Tyr Ala Ser His Ser Pro Glu Val Ala Arg Ile
    210                 215                 220

Glu Asp Arg Leu Ala Ala Glu Leu Gly Thr Ile Thr Ala Val Arg Gly
225                 230                 235                 240

Ser Val Pro Leu His Ser Thr Val Thr Gly Glu Val Ile Asp Thr Ser
                245                 250                 255

Ala Met Asp Ala Ser Tyr Trp Tyr Arg Asn Leu Arg Arg Pro Val Leu
            260                 265                 270
```

```
Phe Glu Gln Ala Val Arg Gly Leu Val Glu Gln Gly Phe Asp Thr Phe
            275                 280                 285

Val Glu Val Ser Pro His Pro Val Leu Leu Met Ala Val Glu Glu Thr
        290                 295                 300

Ala Glu His Ala Gly Ala Glu Val Thr Cys Val Pro Thr Leu Arg Arg
305                 310                 315                 320

Glu Gln Ser Gly Pro His Glu Phe Leu Arg Asn Leu Leu Arg Ala His
                325                 330                 335

Val His Gly Val Gly Ala Asp Leu Arg Pro Ala Val Ala Gly Gly Arg
            340                 345                 350

Pro Ala Glu Leu Pro Thr Tyr Pro Phe Glu His Gln Arg Phe Trp Pro
        355                 360                 365

Arg Pro His Arg Pro Ala Asp Val Ser Ala Leu Gly Val Arg
    370                 375                 380

<210> SEQ ID NO 58
<211> LENGTH: 376
<212> TYPE: PRT
<213> ORGANISM: Streptomyces avermitilis

<400> SEQUENCE: 58

His Ser Ser Ala Pro Gly Gly Thr Gly Thr Gly Glu Ala Ala Gly Lys
  1               5                  10                  15

Thr Ala Phe Ile Cys Ser Gly Gln Gly Thr Gln Arg Pro Gly Met Ala
             20                  25                  30

His Gly Leu Tyr His Thr His Pro Val Phe Ala Ala Ala Leu Asn Asp
         35                  40                  45

Ile Cys Thr His Leu Asp Pro His Leu Asp His Pro Leu Leu Pro Leu
     50                  55                  60

Leu Thr Gln Asn Asp Asn Asp Asn Glu Asp Ala Ala Ala Leu Leu Gln
 65                  70                  75                  80

Gln Thr Arg Tyr Ala Gln Pro Ala Leu Phe Ala Phe Gln Val Ala Leu
                 85                  90                  95

His Arg Leu Leu Thr Asp Gly Tyr His Ile Thr Pro His Tyr Tyr Ala
            100                 105                 110

Gly His Ser Leu Gly Glu Ile Thr Ala Ala His Leu Ala Gly Ile Leu
        115                 120                 125

Thr Leu Thr Asp Ala Thr Thr Leu Ile Thr Gln Arg Ala Thr Leu Met
130                 135                 140

Gln Thr Met Pro Pro Gly Thr Met Thr Thr Leu His Thr Thr Pro His
145                 150                 155                 160

His Ile Thr His His Leu Thr Ala His Glu Asn Asp Leu Ala Ile Ala
                165                 170                 175

Ala Ile Asn Thr Pro Thr Ser Leu Val Ile Ser Gly Thr Pro His Thr
            180                 185                 190

Val Gln His Ile Thr Thr Leu Cys Gln Gln Gly Ile Lys Thr Lys
        195                 200                 205

Thr Leu Pro Thr Asn His Ala Phe His Ser Pro His Thr Asn Pro Ile
    210                 215                 220

Leu Asn Gln Leu His Gln His Thr Gln Thr Leu Thr Tyr His Pro Pro
225                 230                 235                 240

His Thr Pro Leu Ile Thr Ala Asn Thr Pro Asp Gln Leu Leu Thr
                245                 250                 255

Pro His Tyr Trp Thr Gln Gln Ala Arg Asn Thr Val Asp Tyr Ala Thr
            260                 265                 270
```

-continued

```
Thr Thr Gln Thr Leu His Gln His Gly Val Thr Thr Tyr Ile Glu Leu
            275                 280                 285

Gly Pro Asp Asn Thr Leu Thr Thr Leu Thr His His Asn Leu Pro Asn
            290                 295                 300

Pro Pro Thr Thr Thr Leu Thr Leu Thr His Pro His His Pro Gln
305                 310                 315                 320

Thr His Leu Leu Thr Asn Leu Ala Lys Thr Thr Thr Trp His Pro
                325                 330                 335

His His Tyr Thr His His Asp Asn Gln Pro His Thr His Thr His Leu
            340                 345                 350

Asp Leu Pro Thr Tyr Pro Phe Gln His His Tyr Trp Leu Glu Ser
            355                 360                 365

Thr Gln Pro Gly Ala Gly Asn Val
            370                 375

<210> SEQ ID NO 59
<211> LENGTH: 404
<212> TYPE: PRT
<213> ORGANISM: Streptomyces avermitilis

<400> SEQUENCE: 59

Gln Ala Leu Gln Ala Leu Ala Ala Gly Glu Pro His Pro Ala Val Ile
1               5                   10                  15

His Ser Ser Ala Pro Gly Gly Thr Gly Thr Gly Glu Ala Ala Gly Lys
                20                  25                  30

Thr Ala Phe Ile Cys Ser Gly Gln Gly Thr Gln Arg Pro Gly Met Ala
            35                  40                  45

His Gly Leu Tyr His Thr His Pro Val Phe Ala Ala Ala Leu Asn Asp
        50                  55                  60

Ile Cys Thr His Leu Asp Pro His Leu Asp His Pro Leu Leu Pro Leu
65                  70                  75                  80

Leu Thr Gln Asn Asp Asn Asp Asn Glu Asp Ala Ala Ala Leu
                85                  90                  95

Leu Gln Gln Thr Pro Tyr Ala Gln Pro Ala Leu Phe Ala Phe Gln Val
            100                 105                 110

Ala Leu His Arg Leu Leu Thr Asp Gly Tyr His Ile Thr Pro His Tyr
        115                 120                 125

Tyr Ala Gly His Ser Leu Gly Glu Ile Thr Ala Ala His Leu Ala Gly
    130                 135                 140

Ile Leu Thr Leu Thr Asp Ala Thr Thr Leu Ile Thr Gln Arg Ala Thr
145                 150                 155                 160

Leu Met Gln Thr Met Pro Pro Gly Thr Met Thr Thr Leu His Thr Thr
                165                 170                 175

Pro His His Ile Thr His His Leu Thr Ala His Glu Asn Asp Leu Ala
            180                 185                 190

Ile Ala Ala Ile Asn Thr Pro Thr Ser Leu Val Ile Ser Gly Thr Pro
        195                 200                 205

His Thr Val Gln His Ile Thr Thr Leu Cys Gln Gln Gln Gly Ile Lys
    210                 215                 220

Thr Lys Thr Leu Pro Thr Asn His Ala Phe His Ser Pro His Thr Asn
225                 230                 235                 240

Pro Ile Leu Asn Gln Leu His Gln His Thr Gln Thr Leu Thr Tyr His
                245                 250                 255

Pro Pro His Thr Pro Leu Ile Thr Ala Asn Thr Pro Pro Asp Gln Leu
            260                 265                 270
```

```
Leu Thr Pro His Tyr Trp Thr Gln Gln Ala Arg Asn Thr Val Asp Tyr
        275                 280                 285

Ala Thr Thr Thr Gln Thr Leu His Gln His Gly Val Thr Thr Tyr Ile
    290                 295                 300

Glu Leu Gly Pro Asp Asn Thr Leu Thr Thr Leu Thr His His Asn Leu
305                 310                 315                 320

Pro Asn Thr Pro Thr Thr Thr Leu Thr Leu Thr His Pro His His His
                325                 330                 335

Pro Gln Thr His Leu Leu Thr Asn Leu Ala Lys Thr Thr Thr Thr Trp
            340                 345                 350

His Pro His His Tyr Thr His His Asn Gln Pro His Thr His Thr
        355                 360                 365

His Leu Asp Leu Pro Thr Tyr Pro Phe Gln His His Tyr Trp Leu
    370                 375                 380

Glu Leu Pro Ser Ala Gln Thr Ser Pro Gly Gln Arg Arg Ser Arg Arg
385                 390                 395                 400

Ser Ala Pro Asp

<210> SEQ ID NO 60
<211> LENGTH: 406
<212> TYPE: PRT
<213> ORGANISM: Streptomyces avermitilis

<400> SEQUENCE: 60

Gln Ala Leu Gln Ala Leu Ala Ala Gly Glu Pro His Pro Ala Val Ile
1               5                   10                  15

His Ser Ser Ala Pro Gly Gly Thr Gly Thr Gly Glu Ala Ala Gly Lys
            20                  25                  30

Thr Ala Phe Ile Cys Ser Gly Gln Gly Thr Gln Arg Pro Gly Met Ala
        35                  40                  45

His Gly Leu Tyr His Thr His Pro Val Phe Ala Ala Ala Leu Asn Asp
    50                  55                  60

Ile Cys Thr His Leu Asp Pro His Leu Asp His Pro Leu Leu Pro Leu
65                  70                  75                  80

Leu Thr Gln Asp Pro Asn Thr Gln Asp Thr Thr Leu Glu Glu Ala
                85                  90                  95

Ala Ala Leu Leu Gln Gln Thr Pro Tyr Ala Gln Pro Ala Leu Phe Ala
            100                 105                 110

Phe Gln Val Ala Leu His Arg Leu Leu Thr Asp Gly Tyr His Ile Thr
        115                 120                 125

Pro His Tyr Tyr Ala Gly His Ser Leu Gly Glu Ile Thr Ala Ala His
    130                 135                 140

Leu Ala Gly Ile Leu Thr Leu Thr Asp Ala Thr Thr Leu Ile Thr Gln
145                 150                 155                 160

Arg Ala Thr Leu Met Gln Thr Met Pro Pro Gly Thr Met Thr Thr Leu
                165                 170                 175

His Thr Thr Pro His His Ile Thr His His Leu Thr Ala His Glu Asn
            180                 185                 190

Asp Leu Ala Ile Ala Ala Ile Asn Thr Pro Thr Ser Leu Val Ile Ser
        195                 200                 205

Gly Thr Pro His Thr Val Gln His Ile Thr Thr Leu Cys Gln Gln Gln
    210                 215                 220

Gly Ile Lys Thr Lys Thr Leu Pro Thr Lys Asn Ala Phe His Ser Pro
225                 230                 235                 240
```

```
His Thr Asn Pro Ile Leu Asn Gln Leu His Gln His Thr Gln Thr Leu
            245                 250                 255

Thr Tyr His Pro Pro His Thr Pro Leu Ile Thr Ala Asn Thr Pro Pro
        260                 265                 270

Asp Gln Leu Leu Thr Pro His Tyr Trp Thr Gln Ala Arg Asn Thr
            275                 280                 285

Val Asp Tyr Ala Thr Thr Thr Gln Thr Leu His Gln His Gly Val Thr
    290                 295                 300

Thr Tyr Ile Glu Leu Gly Pro Asp Asn Thr Leu Thr Thr Leu Thr His
305                 310                 315                 320

His Asn Leu Pro Asn Thr Pro Thr Thr Leu Thr Leu Thr His Pro
                325                 330                 335

His His His Pro Gln Thr His Leu Leu Thr Asn Leu Ala Lys Thr Thr
            340                 345                 350

Thr Thr Trp His Pro His His Tyr Thr His His Asn Gln Pro His
            355                 360                 365

Thr His Thr His Leu Asp Leu Pro Thr Tyr Pro Phe Gln His Gln His
    370                 375                 380

Tyr Trp Leu Glu Ser Thr Gln Pro Gly Ala Gly Ser Gly Ser Gly Ser
385                 390                 395                 400

Gly Ser Gly Arg Ala Gly
            405

<210> SEQ ID NO 61
<211> LENGTH: 400
<212> TYPE: PRT
<213> ORGANISM: Streptomyces avermitilis

<400> SEQUENCE: 61

Gln Ala Leu Gln Ala Leu Ala Ala Gly Glu Pro His Pro Ala Val Ile
  1               5                  10                  15

His Ser Ser Ala Pro Gly Gly Thr Gly Thr Gly Glu Ala Ala Gly Lys
             20                  25                  30

Thr Ala Phe Ile Cys Ser Gly Gln Gly Thr Gln Arg Pro Gly Met Ala
         35                  40                  45

His Gly Leu Tyr His Thr His Pro Val Phe Ala Ala Ala Leu Asn Asp
     50                  55                  60

Ile Cys Thr His Leu Asp Pro His Leu Asp His Pro Leu Leu Pro Leu
 65                  70                  75                  80

Leu Thr Gln Asp Pro Asn Thr Gln Asp Thr Thr Thr Leu Glu Glu Ala
             85                  90                  95

Ala Ala Leu Leu Gln Gln Thr Pro Tyr Ala Gln Pro Ala Leu Phe Ala
        100                 105                 110

Phe Gln Val Ala Leu His Arg Leu Leu Thr Asp Gly Tyr His Ile Thr
    115                 120                 125

Pro His Tyr Tyr Ala Gly His Ser Leu Gly Glu Ile Thr Ala Ala His
        130                 135                 140

Leu Ala Gly Ile Leu Thr Leu Thr Asp Ala Thr Thr Leu Ile Thr Gln
145                 150                 155                 160

Arg Ala Thr Leu Met Gln Thr Met Pro Pro Gly Thr Met Thr Thr Leu
                165                 170                 175

His Thr Thr Pro His His Ile Thr His Ile Thr Ala His Glu Asn
            180                 185                 190

Asp Leu Ala Ile Ala Ala Ile Asn Thr Pro Thr Ser Leu Val Ile Ser
    195                 200                 205
```

```
Gly Thr Pro His Thr Val Gln His Ile Thr Thr Leu Cys Gln Gln Gln
    210                 215                 220

Gly Ile Lys Thr Lys Thr Leu Pro Thr Asn His Ala Phe His Ser Pro
225                 230                 235                 240

His Thr Asn Pro Ile Leu Asn Gln Leu His Gln His Thr Gln Thr Leu
                245                 250                 255

Thr Tyr His Pro Pro His Thr Pro Leu Ile Thr Ala Asn Thr Pro Pro
            260                 265                 270

Asp Gln Leu Leu Thr Pro His Tyr Trp Thr Gln Gln Ala Arg Asn Thr
        275                 280                 285

Val Asp Ile Ala Thr Thr Gln Thr Leu His Gln His Gly Val Thr
    290                 295                 300

Thr Tyr Ile Glu Leu Gly Pro Asp Asn Thr Leu Thr Thr Leu Thr His
305                 310                 315                 320

His Asn Leu Pro Asn Thr Pro Thr Thr Leu Thr Leu Thr His Pro
                325                 330                 335

His His His Pro Gln Thr His Leu Leu Thr Asn Leu Ala Lys Thr Thr
            340                 345                 350

Thr Thr Trp His Pro His His Tyr Thr His His Asn Gln Pro His
            355                 360                 365

Thr His Thr His Leu Asp Leu Pro Thr Tyr Pro Phe Gln His His His
    370                 375                 380

Tyr Trp Leu Glu Ser Thr Gln Pro Gly Ala Gly Asn Val Ser Ala Ala
385                 390                 395                 400

<210> SEQ ID NO 62
<211> LENGTH: 398
<212> TYPE: PRT
<213> ORGANISM: Streptomyces avermitilis

<400> SEQUENCE: 62

Gln Ala Leu Gln Ala Leu Ala Ala Gly Glu Pro His Pro Ala Val Ile
  1               5                  10                  15

His Ser Ser Ala Pro Gly Gly Thr Gly Thr Gly Glu Ala Ala Gly Lys
                 20                  25                  30

Thr Ala Phe Ile Cys Ser Gly Gln Gly Thr Gln Arg Pro Gly Met Ala
             35                  40                  45

His Gly Leu Tyr His Thr His Pro Val Phe Ala Ala Ala Leu Asn Asp
         50                  55                  60

Ile Cys Thr His Leu Asp Pro His Leu Asp His Pro Leu Leu Pro Leu
 65                  70                  75                  80

Leu Thr Gln Asp Pro Asn Thr Gln Asp Thr Thr Thr Leu Glu Glu Ala
                 85                  90                  95

Ala Ala Leu Leu Gln Gln Thr Arg Tyr Ala Gln Pro Ala Leu Phe Ala
            100                 105                 110

Phe Gln Val Ala Leu His Arg Leu Leu Thr Asp Gly Tyr His Ile Thr
        115                 120                 125

Pro His Tyr Tyr Ala Gly His Ser Leu Gly Glu Ile Thr Ala Ala His
    130                 135                 140

Leu Ala Gly Ile Leu Thr Leu Thr Asp Ala Thr Thr Leu Ile Thr Gln
145                 150                 155                 160

Arg Ala Thr Leu Met Gln Thr Met Pro Pro Gly Thr Met Thr Thr Leu
                165                 170                 175

His Thr Thr Pro His His Ile Thr His His Leu Thr Ala His Glu Asn
            180                 185                 190
```

-continued

```
Asp Leu Ala Ile Ala Ala Ile Asn Thr Pro Thr Ser Leu Val Ile Ser
            195                 200                 205

Gly Thr Pro His Thr Val Gln His Ile Thr Thr Leu Cys Gln Gln Gln
        210                 215                 220

Gly Ile Lys Thr Lys Thr Leu Pro Thr Asn His Ala Phe His Ser Pro
225                 230                 235                 240

His Thr Asn Pro Ile Leu Asn Gln Leu His Gln His Thr Gln Thr Leu
                245                 250                 255

Thr Tyr His Pro Pro His Thr Pro Leu Ile Thr Ala Asn Thr Pro Pro
            260                 265                 270

Asp Gln Leu Leu Thr Pro His Tyr Trp Thr Gln Gln Ala Arg Asn Thr
        275                 280                 285

Val Asp Tyr Ala Thr Thr Thr Gln Thr Leu His Gln His Gly Val Thr
    290                 295                 300

Thr Tyr Ile Glu Leu Gly Pro Asp Asn Thr Leu Thr Thr Leu Thr His
305                 310                 315                 320

Asp Asn Leu Pro Asn Thr Pro Thr Thr Thr Leu Thr Leu Thr His Pro
                325                 330                 335

His His His Pro Gln Thr His Leu Leu Thr Asn Leu Ala Lys Thr Thr
            340                 345                 350

Thr Thr Trp His Pro His His Tyr Thr His His Asn Gln Pro His
        355                 360                 365

Thr His Thr His Leu Asp Leu Pro Thr Tyr Pro Phe Gln His His His
    370                 375                 380

Tyr Trp Leu Gln Pro Pro Gly Lys Pro Ser Asp Pro Ser Pro
385                 390                 395

<210> SEQ ID NO 63
<211> LENGTH: 360
<212> TYPE: PRT
<213> ORGANISM: Streptomyces hygroscopicus

<400> SEQUENCE: 63

Asp Thr Arg Ala Val Ala Ser Thr Leu Ala Met Thr Arg Ser Val Phe
  1               5                  10                  15

Glu Tyr Arg Ala Val Leu Ile Gly Asp Asp Thr Val Thr Gly Thr Ala
             20                  25                  30

Ala Thr Asp Pro Arg Val Val Phe Val Phe Pro Gly Gln Gly Ser Gln
         35                  40                  45

Arg Ala Gly Met Gly Glu Glu Leu Ala Ala Ala Phe Pro Val Phe Ala
     50                  55                  60

Arg Ile His Gln Gln Val Trp Asp Leu Leu Asp Val Pro Asp Leu Asp
 65                  70                  75                  80

Val Asn Glu Thr Gly Tyr Ala Gln Pro Ala Leu Phe Ala Leu Gln Val
                 85                  90                  95

Ala Leu Phe Gly Leu Leu Glu Ser Trp Gly Val Arg Pro Asp Ala Val
            100                 105                 110

Val Gly His Ser Val Gly Glu Leu Ala Ala Gly Tyr Val Ser Gly Leu
        115                 120                 125

Trp Ser Leu Glu Asp Ala Cys Thr Leu Val Ser Ala Arg Ala Arg Leu
    130                 135                 140

Met Gln Ala Leu Pro Ala Gly Gly Val Met Ala Ala Val Pro Val Ser
145                 150                 155                 160

Glu Asp Glu Ala Arg Ala Val Leu Gly Glu Gly Val Glu Ile Ala Ala
                165                 170                 175
```

```
Val Asn Gly Pro Ser Ser Val Val Leu Ser Gly Asp Glu Ala Ala Val
            180                 185                 190

Leu Gln Ala Ala Glu Gly Leu Gly Lys Trp Thr Arg Leu Pro Thr Ser
        195                 200                 205

His Ala Phe His Ser Ala Arg Met Glu Pro Met Leu Glu Glu Phe Arg
    210                 215                 220

Ala Val Ala Glu Gly Leu Thr Tyr Arg Thr Pro Gln Val Ala Met Ala
225                 230                 235                 240

Ala Gly Asp Gln Val Met Thr Ala Glu Tyr Trp Val Arg Gln Val Arg
                245                 250                 255

Asp Thr Val Arg Phe Gly Glu Gln Val Ala Ser Phe Glu Asp Ala Val
            260                 265                 270

Phe Val Glu Leu Gly Ala Asp Arg Ser Leu Ala Arg Leu Val Asp Gly
        275                 280                 285

Ile Ala Met Leu His Gly Asp His Glu Ala Gln Ala Ala Val Gly Ala
    290                 295                 300

Leu Ala His Leu Tyr Val Asn Gly Val Ser Val Glu Trp Ser Ala Val
305                 310                 315                 320

Leu Gly Asp Val Pro Val Thr Arg Val Leu Asp Leu Pro Thr Tyr Ala
                325                 330                 335

Phe Gln His Gln Arg Tyr Trp Leu Glu Gly Thr Asp Arg Ala Thr Ala
            340                 345                 350

Gly Gly His Pro Leu Leu Gly Ser
        355                 360

<210> SEQ ID NO 64
<211> LENGTH: 357
<212> TYPE: PRT
<213> ORGANISM: Streptomyces hygroscopicus

<400> SEQUENCE: 64

Ala Val Ala Ser Thr Leu Ala Met Thr Arg Ser Met Phe Glu His Arg
1               5                   10                  15

Gly Val Leu Leu Gly Asp Gly Thr Val Ser Gly Thr Ala Val Ser Asp
            20                  25                  30

Pro Arg Val Val Phe Val Phe Pro Gly Gln Gly Ser Gln Arg Ala Gly
        35                  40                  45

Met Gly Glu Glu Leu Ala Ala Ala Phe Pro Val Phe Ala Arg Ile His
    50                  55                  60

Gln Gln Val Trp Asp Leu Leu Asp Val Pro Asp Leu Asp Val Asn Glu
65                  70                  75                  80

Thr Gly Tyr Ala Gln Pro Ala Leu Phe Ala Leu Gln Val Ala Leu Phe
                85                  90                  95

Gly Leu Leu Glu Ser Trp Gly Val Arg Pro Asp Ala Val Ile Gly His
            100                 105                 110

Ser Val Gly Glu Leu Ala Ala Ala Tyr Val Ser Gly Val Trp Ser Leu
        115                 120                 125

Glu Asp Ala Cys Thr Leu Val Ser Ala Arg Ala Arg Leu Met Gln Ala
    130                 135                 140

Leu Pro Ala Gly Gly Val Met Val Ala Val Pro Val Ser Glu Asp Glu
145                 150                 155                 160

Ala Arg Ala Val Leu Gly Glu Gly Val Glu Ile Ala Ala Val Asn Gly
                165                 170                 175

Pro Ser Ser Val Val Leu Ser Gly Asp Glu Ala Ala Val Leu Gln Ala
            180                 185                 190
```

```
Ala Glu Gly Leu Gly Lys Trp Thr Arg Leu Ala Thr Ser His Ala Phe
            195                 200                 205

His Ser Ala Arg Met Glu Pro Met Leu Glu Glu Phe Arg Ala Val Ala
    210                 215                 220

Glu Gly Leu Thr Tyr Arg Thr Pro Gln Val Ser Met Ala Val Gly Asp
225                 230                 235                 240

Gln Val Thr Thr Ala Glu Tyr Trp Val Arg Gln Val Arg Asp Thr Val
                245                 250                 255

Arg Phe Gly Glu Gln Val Ala Ser Tyr Glu Asp Ala Val Phe Val Glu
            260                 265                 270

Leu Gly Ala Asp Arg Ser Leu Ala Arg Leu Val Asp Gly Val Ala Met
        275                 280                 285

Leu His Gly Asp His Glu Ala Gln Ala Ala Val Gly Ala Leu Ala His
    290                 295                 300

Leu Tyr Val Asn Gly Val Ser Val Glu Trp Ser Ala Val Leu Gly Asp
305                 310                 315                 320

Val Pro Val Thr Arg Val Leu Asp Leu Pro Thr Tyr Ala Phe Gln His
                325                 330                 335

Gln Arg Tyr Trp Leu Glu Gly Thr Asp Arg Ala Thr Ala Gly Gly His
            340                 345                 350

Pro Leu Leu Gly Ser
        355

<210> SEQ ID NO 65
<211> LENGTH: 407
<212> TYPE: PRT
<213> ORGANISM: Streptomyces hygroscopicus

<400> SEQUENCE: 65

Pro Pro Thr Gln Pro Ala Asp Asn Ala Val Ile Glu Arg Ala Pro Glu
  1               5                  10                  15

Trp Leu Pro Met Val Ile Ser Ala Arg Thr Gln Ser Ala Leu Thr Glu
                 20                  25                  30

His Glu Gly Arg Leu Arg Ala Tyr Leu Ala Ala Ser Pro Gly Val Asp
             35                  40                  45

Met Arg Ala Val Ala Ser Thr Leu Ala Ile Thr Arg Ser Val Phe Glu
 50                  55                  60

His Arg Ala Val Leu Leu Gly Asp Asp Thr Val Thr Gly Thr Ala Ala
 65                  70                  75                  80

Thr Asp Pro Arg Val Val Phe Val Phe Pro Gly Gln Gly Ser Gln Arg
                 85                  90                  95

Ala Gly Met Gly Glu Glu Leu Ala Ala Ala Phe Pro Val Phe Ala Arg
            100                 105                 110

Ile His Gln Gln Val Trp Asp Leu Leu Asp Val Pro Asp Leu Glu Val
        115                 120                 125

Asn Glu Thr Gly Tyr Ala Gln Pro Ala Leu Phe Ala Leu Gln Val Ala
    130                 135                 140

Leu Phe Gly Leu Leu Glu Ser Trp Gly Val Arg Pro Asp Ala Val Val
145                 150                 155                 160

Gly His Ser Val Gly Glu Leu Ala Ala Gly Tyr Val Ser Gly Leu Trp
                165                 170                 175

Ser Leu Glu Asp Ala Cys Thr Leu Val Ser Ala Arg Ala Arg Leu Met
            180                 185                 190

Gln Ala Leu Pro Ala Gly Gly Val Met Val Ala Val Pro Val Ser Glu
        195                 200                 205
```

```
Asp Glu Ala Arg Ala Val Leu Gly Glu Gly Val Glu Ile Ala Ala Val
    210                 215                 220

Asn Gly Pro Ser Ser Val Val Leu Ser Gly Asp Glu Ala Ala Val Leu
225                 230                 235                 240

Gln Ala Ala Glu Gly Leu Gly Lys Trp Thr Arg Leu Ala Thr Ser His
                245                 250                 255

Ala Phe His Ser Ala Arg Met Glu Pro Met Leu Glu Glu Phe Arg Ala
            260                 265                 270

Val Ala Glu Gly Leu Thr Tyr Arg Thr Pro Gln Val Ser Met Ala Ala
        275                 280                 285

Gly Asp Gln Leu Thr Thr Glu Tyr Trp Val Arg Gln Val Arg Asp
290                 295                 300

Thr Val Arg Phe Gly Glu Gln Val Ala Ser Tyr Glu Asp Ala Val Phe
305                 310                 315                 320

Val Glu Leu Gly Ala Asp Arg Ser Leu Ala Arg Leu Val Asp Gly Val
                325                 330                 335

Ala Met Leu His Gly Asp His Glu Ala Gln Ala Ala Val Ser Ala Leu
            340                 345                 350

Ala His Leu Tyr Val Asn Gly Val Thr Val Asp Trp Pro Ala Leu Leu
        355                 360                 365

Gly Asp Ala Pro Ala Thr Arg Val Leu Asp Leu Pro Thr Tyr Ala Phe
370                 375                 380

Gln His Gln Arg Tyr Trp Leu Glu Gly Thr Asp Arg Met Ala Ala Gly
385                 390                 395                 400

Gly His Pro Leu Leu Gly Glu
                405

<210> SEQ ID NO 66
<211> LENGTH: 378
<212> TYPE: PRT
<213> ORGANISM: Streptomyces hygroscopicus

<400> SEQUENCE: 66

Leu Thr Glu His Glu Gly Arg Leu Arg Ala Tyr Leu Ala Ala Ser Pro
  1               5                  10                  15

Gly Val Asp Met Arg Ala Val Ala Ser Thr Leu Ala Met Thr Arg Ser
                 20                  25                  30

Val Phe Glu His Arg Ala Val Leu Leu Gly Asp Asp Thr Val Thr Gly
             35                  40                  45

Thr Ala Val Ser Asp Pro Arg Ala Val Phe Val Phe Pro Gly Gln Gly
     50                  55                  60

Ser Gln Arg Ala Gly Met Gly Glu Glu Leu Ala Ala Ala Phe Pro Val
 65                  70                  75                  80

Phe Ala Arg Ile His Gln Gln Val Trp Asp Leu Leu Asp Val Pro Asp
                 85                  90                  95

Leu Glu Val Asn Glu Thr Gly Tyr Ala Gln Pro Ala Leu Phe Ala Met
            100                 105                 110

Gln Val Ala Leu Phe Gly Leu Leu Glu Ser Trp Gly Val Arg Pro Asp
        115                 120                 125

Ala Val Ile Gly His Ser Val Gly Glu Leu Ala Ala Ala Tyr Val Ser
    130                 135                 140

Gly Val Trp Ser Leu Glu Asp Ala Cys Thr Leu Val Ser Ala Arg Ala
145                 150                 155                 160

Arg Leu Met Gln Ala Leu Pro Ala Gly Gly Val Met Val Ala Val Pro
                165                 170                 175
```

-continued

```
Val Ser Glu Asp Glu Ala Arg Ala Val Leu Gly Gly Val Glu Ile
            180                 185                 190

Ala Ala Val Asn Gly Pro Ser Ser Val Val Leu Ser Gly Asp Glu Ala
        195                 200                 205

Ala Val Leu Gln Ala Ala Glu Gly Leu Gly Lys Trp Thr Arg Leu Ala
    210                 215                 220

Thr Ser His Ala Phe His Ser Ala Arg Met Glu Pro Met Leu Glu Glu
225                 230                 235                 240

Phe Arg Ala Val Ala Glu Gly Leu Thr Tyr Arg Thr Pro Gln Val Ser
                245                 250                 255

Met Ala Val Gly Asp Gln Val Thr Thr Ala Glu Tyr Trp Val Arg Gln
            260                 265                 270

Val Arg Asp Thr Val Arg Phe Gly Glu Gln Val Ala Ser Tyr Glu Asp
        275                 280                 285

Ala Val Phe Val Glu Leu Gly Ala Asp Arg Ser Leu Ala Arg Leu Val
    290                 295                 300

Asp Gly Val Ala Met Leu His Gly Asp His Glu Ile Gln Ala Ala Ile
305                 310                 315                 320

Gly Ala Leu Ala His Leu Tyr Val Asn Gly Val Thr Val Asp Trp Pro
                325                 330                 335

Ala Leu Leu Gly Asp Ala Pro Ala Thr Arg Val Leu Asp Leu Pro Thr
            340                 345                 350

Tyr Ala Phe Gln His Gln Arg Tyr Trp Leu Glu Gly Thr Asp Arg Ala
        355                 360                 365

Thr Ala Gly Gly His Pro Leu Leu Gly Ser
    370                 375

<210> SEQ ID NO 67
<211> LENGTH: 355
<212> TYPE: PRT
<213> ORGANISM: Streptomyces hygroscopicus

<400> SEQUENCE: 67

Ala Ser Thr Leu Ala Val Thr Arg Ser Val Phe Glu His Arg Ala Val
1               5                   10                  15

Leu Leu Gly Asp Asp Thr Val Thr Gly Thr Thr Val Ser Asp Pro Arg
            20                  25                  30

Val Val Phe Val Phe Pro Gly Gln Gly Ser Gln Arg Ala Gly Met Gly
        35                  40                  45

Glu Glu Leu Ala Ala Ala Phe Pro Val Phe Ala Arg Ile His Gln Gln
    50                  55                  60

Val Trp Gly Leu Leu Asp Val Pro Asp Leu Glu Val Asn Glu Thr Gly
65                  70                  75                  80

Tyr Ala Gln Pro Ala Leu Phe Ala Leu Gln Val Ala Leu Phe Gly Leu
                85                  90                  95

Leu Glu Ser Trp Gly Val Arg Pro Asp Ala Val Val Gly His Ser Val
            100                 105                 110

Gly Glu Leu Ala Ala Gly Tyr Val Ser Gly Leu Trp Ser Leu Glu Asp
        115                 120                 125

Ala Cys Thr Leu Val Ser Ala Arg Ala Arg Leu Met Gln Ala Leu Pro
    130                 135                 140

Pro Gly Gly Val Met Val Ala Val Pro Val Ser Glu Asp Glu Ala Arg
145                 150                 155                 160

Ala Val Leu Gly Glu Gly Val Glu Ile Ala Ala Val Asn Gly Pro Ser
                165                 170                 175
```

```
Ser Val Val Leu Ser Gly Asp Glu Thr Ala Val Leu Gln Ala Ala Ala
                180                 185                 190

Ala Leu Gly Lys Ser Thr Arg Leu Ala Thr Ser His Ala Phe His Ser
            195                 200                 205

Ala Arg Met Glu Pro Met Leu Glu Glu Phe Arg Thr Val Ala Glu Arg
    210                 215                 220

Leu Thr Tyr Gln Thr Pro Arg Leu Ala Met Ala Ala Gly Asp Arg Val
225                 230                 235                 240

Thr Thr Ala Glu Tyr Trp Val Arg Gln Val Arg Asp Thr Val Arg Phe
                245                 250                 255

Gly Glu Gln Val Ala Ser Tyr Glu Asp Ala Val Phe Ile Glu Leu Gly
            260                 265                 270

Ala Asp Arg Ser Leu Ala Arg Leu Val Asp Gly Val Ala Met Leu His
        275                 280                 285

Thr Asp His Glu Ala Gln Ala Ala Ile Ser Ala Leu Ala His Leu Tyr
    290                 295                 300

Val Asn Gly Val Thr Val Asp Trp Thr Ala Leu Leu Gly Asp Ala Pro
305                 310                 315                 320

Ala Thr Arg Val Leu Asp Leu Pro Thr Tyr Ala Phe Gln His Gln Arg
                325                 330                 335

Tyr Trp Leu Glu Gly Ala Asp Arg Ala Ala Ala Gly Gly His Pro Leu
            340                 345                 350

Leu Gly Pro
        355

<210> SEQ ID NO 68
<211> LENGTH: 416
<212> TYPE: PRT
<213> ORGANISM: Streptomyces hygroscopicus

<400> SEQUENCE: 68

Asp Asp Val Arg Pro Ala Asp Ala Pro Val Val Ala Ser Val Met Ala
  1               5                  10                  15

Ser Glu Leu Val Pro Leu Val Ile Ser Ala Lys Thr Gln Ser Ala Leu
                20                  25                  30

Ala Glu Tyr Glu Gly Arg Leu Arg Ala Tyr Leu Ala Ala Ser Pro Gly
            35                  40                  45

Val Asp Met Arg Ala Val Ala Ser Thr Leu Ala Met Thr Arg Ser Val
        50                  55                  60

Phe Glu His Arg Ala Val Ile Val Gly Asp Asp Thr Val Ser Gly Thr
 65                  70                  75                  80

Ala Ala Thr Asp Pro Arg Val Val Phe Val Phe Pro Gly Gln Gly Ser
                 85                  90                  95

Gln Arg Ala Gly Met Gly Ala Glu Leu Ala Ala Phe Pro Val Phe
            100                 105                 110

Ala Arg Ile His Gln Gln Val Trp Asp Leu Leu Asp Val Pro Asp Leu
        115                 120                 125

Glu Val Asn Glu Thr Gly Tyr Ala Gln Pro Ala Leu Phe Ala Leu Gln
    130                 135                 140

Val Ala Leu Phe Gly Leu Leu Glu Ser Trp Gly Val Arg Pro Asp Ala
145                 150                 155                 160

Val Ile Gly His Ser Val Gly Glu Leu Ala Ala Ala Tyr Val Ser Gly
                165                 170                 175

Leu Trp Ser Leu Glu Asp Ala Cys Thr Leu Val Ser Ala Arg Ala Arg
            180                 185                 190
```

```
Leu Met Gln Ala Leu Pro Ala Gly Gly Val Met Val Ala Val Pro Val
        195                 200                 205

Ser Glu Asp Glu Ala Arg Ala Val Leu Gly Glu Gly Val Glu Ile Ala
        210                 215                 220

Ala Val Asn Gly Pro Ser Ser Val Val Leu Ser Gly Asp Glu Ala Ala
225                 230                 235                 240

Val Leu Gln Ala Ala Glu Gly Leu Gly Lys Trp Thr Arg Leu Ala Thr
        245                 250                 255

Ser His Ala Phe His Ser Ala Arg Met Glu Pro Met Leu Glu Glu Phe
        260                 265                 270

Arg Ala Val Ala Gln Gly Leu Thr Tyr His Ala Pro Gly Val Val Met
        275                 280                 285

Ala Ala Gly Asp Arg Val Met Thr Ala Glu Tyr Trp Val Arg Gln Val
        290                 295                 300

Arg Asp Thr Val Arg Phe Gly Glu Gln Val Ala Ser Tyr Glu Asp Ala
305                 310                 315                 320

Val Phe Val Glu Leu Gly Ala Asp Arg Ser Leu Ala Arg Leu Val Asp
        325                 330                 335

Gly Val Ala Met Leu His Gly Asp His Glu Thr Gln Ala Ala Ile Gly
        340                 345                 350

Ala Leu Ala His Leu Tyr Val Asn Gly Val Thr Val Asp Trp Thr Ala
        355                 360                 365

Leu Leu Gly Asp Val Pro Val Thr Arg Val Leu Asp Leu Pro Thr Tyr
        370                 375                 380

Ala Phe Gln Gln Gln Arg Tyr Trp Ala Glu Val Gly Arg Ser Ala Asp
385                 390                 395                 400

Val Ser Gly Ala Gly Leu Asp Ala Val Gly His Pro Leu Leu Gly Ala
        405                 410                 415

<210> SEQ ID NO 69
<211> LENGTH: 335
<212> TYPE: PRT
<213> ORGANISM: Streptomyces sp.

<400> SEQUENCE: 69

His Arg Ala Ala Leu Ile Gly Thr Asp Leu Ile Thr Gly Thr Ala Glu
1               5                   10                  15

Pro Asp Arg Arg Leu Val Trp Leu Phe Ser Gly Gln Gly Ser Gln Arg
            20                  25                  30

Pro Gly Met Gly Asp Glu Leu Ala Ala Ala Tyr Asp Val Phe Ala Arg
        35                  40                  45

Thr Arg Arg Asp Val Leu Asp Ala Leu Gln Val Pro Ala Gly Leu Asp
    50                  55                  60

Val His Asp Thr Gly Tyr Ala Gln Pro Ala Val Phe Ala Leu Gln Val
65                  70                  75                  80

Ala Leu Ser Ala Gln Leu Asp Ala Trp Gly Val Arg Pro Asp Val Leu
            85                  90                  95

Val Gly His Ser Ile Gly Glu Leu Ala Ala Tyr Val Ala Gly Val
        100                 105                 110

Trp Ser Leu Asp Asp Ala Thr Glu Leu Val Ser Ala Arg Ala Arg Leu
        115                 120                 125

Met Gln Ala Leu Pro Pro Gly Ala Met Ala Ala Val Ser Ala Ser
    130                 135                 140

Glu Arg Asp Ala Leu Pro Leu Leu Cys Glu Gly Val Glu Ile Ala Ala
145                 150                 155                 160
```

```
Val Asn Gly Pro Ala Ser Ile Val Leu Ser Gly Asp Glu Asp Ala Val
            165                 170                 175

Leu Asp Val Ala Ala Arg Leu Gly Arg Phe Thr Arg Leu Arg Thr Ser
        180                 185                 190

His Ala Phe His Ser Ala Arg Met Glu Pro Met Leu Asp Glu Phe Arg
    195                 200                 205

Asp Val Ala Glu Arg Leu Thr Tyr His Glu Pro Lys Leu Pro Met Ala
210                 215                 220

Ala Gly Ala Asp Cys Ala Thr Pro Glu Tyr Trp Val Arg Gln Val Arg
225                 230                 235                 240

Asp Thr Val Arg Phe Ala Glu Gln Val Ala Ala Tyr Asp Gly Ala Ala
                245                 250                 255

Leu Leu Glu Ile Gly Pro Asp Arg Asn Leu Ala Arg Leu Val Asp Gly
            260                 265                 270

Ile Pro Val Leu His Gly Glu Asp Glu Ala Arg Ser Ala Met Thr Ala
        275                 280                 285

Leu Ala Arg Leu His Thr Gly Gly Val Ala Val Asp Trp Pro Glu Val
    290                 295                 300

Ile Gly Ala Ala Pro Thr Asp Leu Pro His Leu Pro Thr Tyr Pro Phe
305                 310                 315                 320

Glu Arg Thr Arg Tyr Trp Leu Gly Ser Arg Ala Ala Gly Asp Ala
                325                 330                 335

<210> SEQ ID NO 70
<211> LENGTH: 334
<212> TYPE: PRT
<213> ORGANISM: Streptomyces sp.

<400> SEQUENCE: 70

Leu Leu Gly Asp Thr Leu Ile Thr Ala Asp Pro Asn Ala Gly Ser Gly
1               5                   10                  15

Pro Val Val Phe Val Tyr Ser Gly Gln Ser Thr Leu His Pro His Thr
            20                  25                  30

Gly His Gln Leu Ala Ala Thr Tyr Ser Val Phe Ala Asp Ala Trp Gly
        35                  40                  45

Glu Val Leu Gly His Leu Asn Ala Asp Gln Gly Pro Ala Thr His Phe
    50                  55                  60

Ala His Gln Ile Ala Leu Thr Ala Leu Leu Arg Ser Trp Gly Ile Thr
65                  70                  75                  80

Pro His Ala Val Ile Gly His Ser Leu Gly Glu Ile Ser Ala Ala Cys
                85                  90                  95

Ala Ala Gly Val Leu Ser Ile Gly Asp Ala Ser Ala Leu Leu Ala Ala
            100                 105                 110

Arg Ser Arg Leu Met Asp Glu Leu Pro Thr Gly Gly Ala Met Val Thr
        115                 120                 125

Val Leu Thr Ser Glu Glu Asn Ala Leu Arg Ala Leu Arg Pro Gly Val
    130                 135                 140

Glu Ile Ala Ala Val Asn Gly Pro His Ser Val Val Leu Ser Gly Asp
145                 150                 155                 160

Glu Gly Pro Val Leu Asp Val Ala Gln Gln Leu Gly Ile His His Arg
                165                 170                 175

Leu Pro Thr Arg His Ala Gly His Ser Ala Arg Met Asp Pro Leu Val
            180                 185                 190

Ala Pro Leu Leu Glu Ala Ala Ser Gly Leu Thr Tyr His Gln Pro His
        195                 200                 205
```

```
Thr Ala Ile Pro Glu Asp Pro Thr Ala Ala Tyr Trp Ala Arg Gln
    210                 215                 220

Val Arg Asp Gln Val Arg Phe Gln Ala His Ala Glu Arg Tyr Pro Gly
225                 230                 235                 240

Ala Thr Phe Leu Glu Ile Gly Pro Asn Gln Asp Leu Ser Pro Val Val
                245                 250                 255

Asp Gly Ile Pro Thr Gln Thr Gly Thr Pro Glu Glu Val Gln Ala Leu
                260                 265                 270

His Thr Ala Leu Ala Arg Leu His Thr Arg Gly Gly Val Val Asp Trp
                275                 280                 285

Pro Thr Val Leu Gly Ser Asp Arg Ala Pro Val Ala Leu Pro Thr Tyr
    290                 295                 300

Pro Phe Gln His Lys Asp Tyr Trp Leu Arg Ala Thr Ala Gln Val Asp
305                 310                 315                 320

Val Thr Gly Ala Gly Gln Glu Lys Val Ala His Pro Leu Leu
                325                 330

<210> SEQ ID NO 71
<211> LENGTH: 331
<212> TYPE: PRT
<213> ORGANISM: Streptomyces sp.

<400> SEQUENCE: 71

Ile Gly Ala Pro Pro Ala Asp Gln Ala Asp Glu Leu Val Phe Val Tyr
 1               5                  10                  15

Ser Gly Gln Gly Thr Gln His Pro Ala Met Gly Glu Gln Leu Ala Ala
                20                  25                  30

Ala Phe Pro Val Phe Ala Asp Ala Trp His Asp Ala Leu Arg Arg Leu
            35                  40                  45

Asp Asp Pro Asp Pro His Asp Pro Thr Arg Ser Gln His Thr Leu Phe
    50                  55                  60

Ala His Gln Ala Ala Phe Thr Ala Leu Leu Arg Ser Trp Asp Ile Thr
65                  70                  75                  80

Pro His Ala Val Ile Gly His Ser Leu Gly Glu Ile Thr Ala Ala Tyr
                85                  90                  95

Ala Ala Gly Ile Leu Ser Leu Asp Asp Ala Cys Thr Leu Ile Thr Thr
            100                 105                 110

Arg Ala Arg Leu Met His Thr Leu Pro Pro Gly Ala Met Val Thr
    115                 120                 125

Val Leu Thr Ser Glu Glu Glu Ala Arg Gln Ala Leu Arg Pro Gly Val
130                 135                 140

Glu Ile Ala Ala Val Phe Gly Pro His Ser Val Val Leu Ser Gly Asp
145                 150                 155                 160

Glu Asp Ala Val Leu Asp Val Ala Gln Arg Leu Gly Ile His His Arg
                165                 170                 175

Leu Pro Ala Pro His Ala Gly His Ser Ala His Met Glu Pro Val Ala
            180                 185                 190

Ala Glu Leu Leu Ala Thr Thr Arg Glu Leu Arg Tyr Asp Arg Pro His
        195                 200                 205

Thr Ala Ile Pro Asn Asp Pro Thr Thr Ala Glu Tyr Trp Ala Glu Gln
    210                 215                 220

Val Arg Asn Pro Val Leu Phe His Ala His Thr Gln Arg Tyr Pro Asp
225                 230                 235                 240

Ala Val Phe Val Glu Ile Gly Pro Gly Gln Asp Leu Ser Pro Leu Val
                245                 250                 255
```

```
Asp Gly Ile Ala Leu Gln Asn Gly Thr Ala Asp Glu Val His Ala Leu
                260                 265                 270

His Thr Ala Leu Ala Arg Leu Phe Thr Arg Gly Ala Thr Leu Asp Trp
            275                 280                 285

Ser Arg Ile Leu Gly Gly Ala Ser Arg His Asp Pro Asp Val Pro Ser
        290                 295                 300

Tyr Ala Phe Gln Arg Arg Pro Tyr Trp Ile Glu Ser Ala Pro Pro Ala
305                 310                 315                 320

Thr Ala Asp Ser Gly His Pro Val Leu Gly Thr
                325                 330

<210> SEQ ID NO 72
<211> LENGTH: 397
<212> TYPE: PRT
<213> ORGANISM: Streptomyces caelestis

<400> SEQUENCE: 72

Lys His Arg Ala Val Ile Thr Gly Arg Thr Arg Thr Glu Leu His Thr
1               5                   10                  15

Lys Leu His Thr Leu Asp Ala Ile Gln Gly Thr Ala His Pro His Pro
            20                  25                  30

Arg Leu Thr Leu Leu Phe Thr Gly Gln Gly Ala Gln His Arg Gly Met
        35                  40                  45

Gly Gln Glu Leu Tyr Ala Thr Asp Pro His Phe Ala Ala Ala Leu Asp
    50                  55                  60

Glu Val Cys Glu Leu Gln Arg Cys Gly Thr Gln Asn Leu Arg Glu
65                  70                  75                  80

Val Met Phe Thr Pro Asp Gln Pro Asp Leu Leu Asp Arg Thr Glu Tyr
                85                  90                  95

Thr Gln Pro Ala Leu Phe Ala Leu Gln Thr Ala Leu Tyr Arg Thr Leu
            100                 105                 110

Thr Ala Arg Gly Thr Gln Ala His Leu Val Leu Gly His Ser Val Gly
        115                 120                 125

Glu Ile Thr Ala Ala His Ile Ala Gly Val Leu Asp Leu Pro Asp Ala
    130                 135                 140

Ala Arg Leu Ile Thr Ala Arg Ala His Leu Met Gly Gln Leu Pro His
145                 150                 155                 160

Gly Gly Ala Met Leu Ser Val Gln Ala Ala Glu His Asp Leu Asp Gln
                165                 170                 175

Leu Ala His Thr His Gly Val Glu Ile Ala Ala Val Asn Gly Pro Thr
            180                 185                 190

His Cys Val Leu Ser Gly Pro Arg Thr Ala Leu Glu Glu Thr Ala Gln
        195                 200                 205

Gln Leu His Gln Gly Ile Arg His Thr Trp Leu Lys Val Ser His
    210                 215                 220

Ala Phe His Ser Ala Leu Met Asp Pro Met Leu Gly Ala Phe Arg Asp
225                 230                 235                 240

Thr Leu Asn Thr Leu Asn Tyr Gln Pro Pro Thr Ile Pro Leu Ile Ser
                245                 250                 255

Asn Leu Thr Gly Gln Ile Ala Asp Pro Asn His Leu Cys Thr Pro Asp
            260                 265                 270

Tyr Trp Ile Asp His Ala Arg His Thr Val Arg Phe Ala Asp Ala Val
        275                 280                 285

Gln Thr Ala His Asp Gln Arg Thr Thr Tyr Leu Glu Ile Gly Ala
    290                 295                 300
```

```
His Pro Thr Leu Thr Thr Leu His His Thr Leu Asp Asn Pro Thr
305                 310                 315                 320

Thr Ile Pro Thr Leu His Arg Glu His Pro Glu Pro Glu Thr Leu Thr
            325                 330                 335

Thr Ala Leu Ala Thr Leu His Thr Thr Gly His Thr Thr Thr Leu His
        340                 345                 350

Thr Thr Ser Pro Gln Thr His His Leu Asp Leu Pro Thr Tyr Pro Phe
    355                 360                 365

Gln Arg Asp Arg Tyr Trp Met Glu Pro Val Arg Val Ala Gln Val Ser
370                 375                 380

Gly Gln Pro Gly Ala Asp Arg Leu Arg Tyr Arg Val Val
385                 390                 395

<210> SEQ ID NO 73
<211> LENGTH: 406
<212> TYPE: PRT
<213> ORGANISM: Streptomyces caelestis

<400> SEQUENCE: 73

Thr Gln Ala Asp Pro Gln Asp Ile Ala His Ala Leu Ala Thr Arg
  1               5                  10                  15

Thr His Phe Lys His Arg Ala Val Ile Thr Gly Arg Thr Arg Thr Glu
             20                  25                  30

Leu His Thr Lys Leu His Thr Leu Asp Ala Ile Gln Gly Thr Ala His
         35                  40                  45

Pro His Pro Arg Leu Thr Leu Leu Phe Thr Gly Gln Gly Ala Gln His
     50                  55                  60

Pro Gly Met Gly Gln Glu Leu Tyr Thr Thr Asp Pro His Phe Ala Ala
 65                  70                  75                  80

Ala Leu Asp Glu Val Cys Glu Glu Leu Gln Arg Cys Gly Thr Gln Asn
             85                  90                  95

Leu Arg Glu Val Met Phe Thr Pro Asp Gln Pro Asp Leu Leu Asp Arg
            100                 105                 110

Thr Glu Tyr Thr Gln Pro Ala Leu Phe Ala Leu Gln Thr Ala Leu Tyr
        115                 120                 125

Arg Thr Leu Thr Ala Arg Gly Thr Gln Ala His Leu Val Leu Gly His
    130                 135                 140

Ser Val Gly Glu Ile Thr Ala Ala His Ile Ala Gly Val Leu Asp Leu
145                 150                 155                 160

Pro Asp Ala Ala Arg Leu Ile Thr Ala Arg Ala His Leu Met Gly Gln
                165                 170                 175

Leu Pro His Gly Gly Ala Met Leu Ser Val Gln Ala Ala Glu His Asp
            180                 185                 190

Leu Asp Gln Leu Ala His Thr His Gly Val Glu Ile Ala Ala Val Asn
        195                 200                 205

Gly Pro Thr His Cys Val Leu Ser Gly Pro Arg Thr Ala Leu Glu Glu
    210                 215                 220

Thr Ala Gln His Leu Arg Glu Gln Asn Val Arg His Thr Trp Leu Lys
225                 230                 235                 240

Val Ser His Ala Phe His Ser Ala Leu Met Asp Pro Met Leu Gly Ala
                245                 250                 255

Phe Arg Asp Thr Leu Asn Thr Leu Asn Tyr Gln Pro Pro Thr Ile Pro
            260                 265                 270

Leu Ile Ser Asn Leu Thr Gly Gln Ile Ala Asp Pro Asn His Leu Cys
        275                 280                 285
```

-continued

```
Thr Pro Asp Tyr Trp Ile Asp His Ala Arg His Thr Val Arg Phe Ala
    290                 295                 300

Asp Ala Val Gln Thr Ala His His Gln Gly Thr Thr Thr Tyr Leu Glu
305                 310                 315                 320

Ile Gly Pro His Pro Thr Leu Thr Thr Leu Leu His His Thr Leu Asp
                325                 330                 335

Asn Pro Thr Thr Ile Pro Thr Leu His Arg Glu His Pro Glu Pro Glu
            340                 345                 350

Thr Leu Thr Thr Ala Leu Ala Thr Leu His Thr Thr Gly His Thr Thr
                355                 360                 365

Thr Leu His Thr Thr Ser Pro Gln Ser His His Leu Asp Leu Pro Thr
    370                 375                 380

Tyr Pro Phe Gln Arg Asp Arg Tyr Trp Met Ala Val Pro Pro Arg Ala
385                 390                 395                 400

Ala Val Gly Asp Leu Ala
                405

<210> SEQ ID NO 74
<211> LENGTH: 406
<212> TYPE: PRT
<213> ORGANISM: Streptomyces caelestis

<400> SEQUENCE: 74

His Ala Leu Ala Thr Thr Cys Thr His Phe Lys His Arg Ala Val Ile
  1               5                  10                  15

Thr Gly Arg Thr Arg Thr Glu Leu His Thr Lys Leu His Thr Leu Asp
             20                  25                  30

Ala Ile Gln Gly Thr Ala His Pro His Pro Arg Leu Thr Leu Leu Phe
         35                  40                  45

Thr Gly Gln Gly Ala Gln His Pro Gly Met Gly Gln Glu Leu Tyr Thr
     50                  55                  60

Thr Asp Pro His Phe Ala Ala Leu Asp Glu Ile Cys Glu Glu Leu
 65                  70                  75                  80

Gln Arg Cys Gly Thr Gln Asn Leu Arg Glu Val Met Phe Thr Pro Asp
                 85                  90                  95

Gln Pro Asp Leu Leu Asp Arg Thr Glu Tyr Thr Gln Pro Ala Leu Phe
            100                 105                 110

Ala Leu Gln Thr Ala Leu Tyr Arg Thr Leu Thr Ala His Gly Thr Gln
        115                 120                 125

Ala His Leu Val Leu Gly His Ser Val Gly Glu Ile Thr Ala Ala His
    130                 135                 140

Ile Ala Gly Val Leu Asp Leu Pro Asp Ala Ala Arg Leu Ile Thr Ala
145                 150                 155                 160

Arg Ala His Leu Met Gly Gln Leu Pro His Asp Gly Ala Met Leu Ser
                165                 170                 175

Val Gln Ala Ala Glu His Asp Leu Asp Gln Leu Ala His Thr His Gly
            180                 185                 190

Val Glu Ile Ala Ala Val Asn Gly Pro Thr His Cys Val Leu Ser Gly
        195                 200                 205

Pro Arg Thr Ala Leu Glu Glu Thr Ala Gln His Leu Arg Glu Gln Asn
    210                 215                 220

Val Arg His Thr Trp Leu Lys Val Ser His Ala Phe His Ser Ala Leu
225                 230                 235                 240

Met Asp Pro Met Leu Gly Ala Phe Arg Asp Thr Leu Asn Thr Leu Asn
                245                 250                 255
```

```
Tyr Gln Pro Pro Thr Ile Pro Leu Ile Ser Asn Leu Thr Gly Gln Ile
            260                 265                 270

Ala Asp Pro Asn His Leu Cys Thr Pro Asp Tyr Trp Ile Asp His Ala
            275                 280                 285

Arg His Thr Val Arg Phe Ala Asp Ala Val Gln Thr Ala His Asp Gln
            290                 295                 300

Arg Thr Thr Thr Tyr Leu Glu Ile Gly Pro His Pro Thr Leu Thr Thr
305                 310                 315                 320

Leu Leu His His Thr Leu Asp Asn Pro Thr Thr Ile Pro Thr Leu His
                325                 330                 335

Arg Glu His Pro Glu Pro Glu Thr Leu Thr Thr Ala Leu Ala Thr Leu
            340                 345                 350

His Thr Thr Gly His Thr Thr Thr Pro His Pro Ser His Ile Pro Ala
            355                 360                 365

Gln Arg Val Ser Leu Pro Ala Tyr Pro Phe Gln Arg Arg Ala Tyr Trp
            370                 375                 380

Met Pro Asn Ser Ala Ala His Ile Gly Arg Ser Asp Ala Glu Ala Ala
385                 390                 395                 400

Thr Arg Leu Gly Leu Ala
            405

<210> SEQ ID NO 75
<211> LENGTH: 393
<212> TYPE: PRT
<213> ORGANISM: Streptomyces caelestis

<400> SEQUENCE: 75

Ser Ser Ala Leu Ala Ala Leu Ala Ala Gly Gln Thr Pro Arg Gly Val
1               5                   10                  15

Arg Ile Gly Ser Thr Asp Ala Asp Gly Arg Leu Ala Leu Leu Phe Thr
            20                  25                  30

Gly Gln Gly Ala Gln His Pro Gly Met Gly Gln Glu Leu Tyr Thr Thr
        35                  40                  45

Asp Pro His Phe Ala Ala Ala Leu Asp Glu Val Cys Glu Glu Leu Gln
    50                  55                  60

Arg Cys Gly Thr Gln Asn Leu Arg Glu Val Met Phe Thr Pro Asp Gln
65                  70                  75                  80

Pro Asp Leu Leu Asp Arg Thr Glu Tyr Thr Gln Pro Ala Leu Phe Ala
                85                  90                  95

Leu Gln Thr Ala Leu Tyr Arg Thr Leu Thr Ala Arg Gly Thr Gln Ala
            100                 105                 110

His Leu Val Leu Gly His Ser Val Gly Glu Ile Thr Ala Ala His Ile
            115                 120                 125

Ala Gly Val Leu Asp Leu Pro Asp Ala Ala Arg Leu Ile Thr Ala Arg
            130                 135                 140

Ala His Val Met Gly Gln Leu Pro His Gly Gly Ala Met Leu Ser Val
145                 150                 155                 160

Gln Ala Ala Glu His Asp Leu Asp Gln Leu Ala His Thr His Gly Val
                165                 170                 175

Glu Ile Ala Ala Val Asn Gly Pro Thr His Cys Val Leu Ser Gly Pro
            180                 185                 190

Arg Thr Ala Leu Glu Glu Thr Ala Gln His Leu Arg Glu Gln Asn Val
            195                 200                 205

Arg His Thr Trp Leu Lys Val Ser His Ala Phe His Ser Ala Leu Met
            210                 215                 220
```

```
Asp Pro Met Leu Gly Ala Phe Arg Asp Thr Leu Asn Thr Leu Asn Tyr
225                 230                 235                 240

Gln Pro Pro Thr Ile Pro Leu Ile Ser Asn Leu Thr Gly Gln Ile Ala
            245                 250                 255

Asp Pro Asn His Leu Cys Thr Pro Asp Tyr Trp Ile Asp His Ala Arg
        260                 265                 270

His Thr Val Arg Phe Ala Asp Ala Val Gln Thr Ala His His Gln Gly
    275                 280                 285

Thr Thr Thr Tyr Leu Glu Ile Gly Pro His Pro Thr Leu Thr Thr Leu
290                 295                 300

Leu His His Thr Leu Asp Asn Pro Thr Thr Ile Pro Thr Leu His Arg
305                 310                 315                 320

Glu Arg Pro Glu Pro Glu Thr Leu Thr Gln Ala Ile Ala Ala Val Gly
                325                 330                 335

Val Arg Thr Asp Gly Ile Asp Trp Ala Val Leu Cys Gly Ala Ser Arg
            340                 345                 350

Pro Arg Arg Val Glu Leu Pro Thr Tyr Ala Phe Gln Arg Arg Thr His
        355                 360                 365

Trp Ala Pro Gly Leu Thr Pro Asn His Ala Pro Ala Asp Arg Pro Ala
    370                 375                 380

Ala Glu Pro Gln Arg Ala Met Ala Val
385                 390

<210> SEQ ID NO 76
<211> LENGTH: 365
<212> TYPE: PRT
<213> ORGANISM: Streptomyces sp.

<400> SEQUENCE: 76

Glu Ala Pro Glu Ser Ser Ala Glu Pro Pro Arg Ser Ala Arg Arg Phe
1               5                   10                  15

Leu Phe Asp Gly Gln Gly Ala Gln Arg Val Gly Met Gly Arg Glu Leu
            20                  25                  30

His Gly Arg Phe Pro Val Phe Ala Ala Ala Trp Asp Glu Val Ser Asp
        35                  40                  45

Ala Phe Gly Lys His Leu Glu His Ser Pro Thr Asp Val Phe His Gly
    50                  55                  60

Glu His Gly Asp Leu Ala His Asp Thr Leu Tyr Ala Gln Val Gly Leu
65                  70                  75                  80

Phe Thr Leu Glu Val Ala Leu Leu Arg Leu Leu Glu His Trp Gly Val
                85                  90                  95

Arg Pro Asp Val Val Val Gly His Ser Val Gly Glu Val Thr Ala Ala
            100                 105                 110

Tyr Ala Ala Gly Val Leu Thr Leu Ala Asp Ala Thr Thr Leu Ile Val
        115                 120                 125

Ala Arg Gly Arg Ala Leu Arg Ala Leu Pro Pro Gly Ala Met Thr Ala
    130                 135                 140

Val Glu Gly Ser Pro Ala Glu Val Gly Ala Phe Thr Asp Leu Asp Ile
145                 150                 155                 160

Ala Ala Val Asn Gly Pro Ser Ala Val Val Leu Thr Gly Ala Pro Asp
                165                 170                 175

Asp Val Ala Ala Phe Glu Arg Glu Trp Ala Ala Gly Arg Arg Ala
            180                 185                 190

Lys Arg Leu Asp Val Gly His Ala Phe His Ser Arg His Val Asp Gly
    195                 200                 205
```

```
Ala Leu Asp Asp Phe Arg Gly Val Leu Glu Ser Leu Ala Phe Gly Ala
    210                 215                 220

Ala Arg Leu Pro Val Val Ser Thr Thr Thr Gly Arg Asp Ala Ala Gly
225                 230                 235                 240

Asp Leu Ala Thr Pro Glu His Trp Leu Arg His Ala Arg Arg Pro Val
                245                 250                 255

Leu Tyr Ala Asp Ala Val Arg Glu Leu Ala Asp Leu Gly Val Asn Met
            260                 265                 270

Phe Val Ala Val Gly Pro Ser Gly Ala Leu Ser Ala Ala Ser Glu
        275                 280                 285

Asn Thr Gly Gly Ser Ala Gly Thr Tyr His Ala Val Leu Arg Ala Arg
    290                 295                 300

Thr Gly Glu Glu Ser Ala Ala Leu Thr Ala Val Ala Glu Leu His Ala
305                 310                 315                 320

His Gly Ala Pro Val Asp Leu Ala Ala Val Leu Ala Gly Gly Arg Pro
                325                 330                 335

Val Asp Leu Pro Val Tyr Pro Phe Gln His Arg Ser Tyr Trp Leu Ala
            340                 345                 350

Pro Ala Val Gly Gly Ser Pro Thr Ala Val Pro Asp
        355                 360                 365

<210> SEQ ID NO 77
<211> LENGTH: 397
<212> TYPE: PRT
<213> ORGANISM: Streptomyces hygroscopicus

<400> SEQUENCE: 77

Asp Phe Leu Arg Ala Leu Ser Lys Leu Ala Asp Gly Ala Pro Trp Pro
1               5                   10                  15

Gly Leu Thr Thr Ala Thr Ala Thr Ala Lys Ala Arg Arg Val Ala Phe
                20                  25                  30

Leu Phe Asp Gly Gln Gly Thr Gln Arg Leu Gly Met Gly Lys Glu Leu
            35                  40                  45

Tyr Asp Ser Tyr Pro Ala Phe Ala Arg Ala Trp Asp Thr Val Ser Ala
    50                  55                  60

Gly Phe Asp Lys His Leu Asp His Ser Leu Thr Asp Val Cys Phe Gly
65                  70                  75                  80

Glu Gly Gly Ser Thr Thr Ala Gly Leu Val Asp Asp Thr Leu Tyr Ala
                85                  90                  95

Gln Ala Gly Ile Phe Ala Met Glu Ala Ala Leu Phe Gly Leu Leu Glu
            100                 105                 110

Asp Trp Gly Val Arg Pro Asp Phe Val Ala Gly His Ser Ile Gly Glu
        115                 120                 125

Ala Thr Ala Ala Tyr Ala Ser Gly Met Leu Ser Leu Glu Asn Val Thr
    130                 135                 140

Thr Leu Ile Val Ala Arg Gly Arg Ala Leu Arg Thr Thr Pro Pro Gly
145                 150                 155                 160

Ala Met Val Ala Leu Arg Ala Gly Glu Glu Val Arg Glu Phe Leu
                165                 170                 175

Ser Arg Thr Gly Ala Ala Leu Asp Leu Ala Ala Val Asn Ser Pro Glu
            180                 185                 190

Ala Val Val Val Ser Gly Glu Pro Glu Pro Val Ala Asp Phe Glu Ala
        195                 200                 205

Ala Trp Thr Ala Ser Gly Arg Glu Ala Arg Lys Leu Lys Val Arg His
    210                 215                 220
```

```
Ala Phe His Ser Arg His Val Glu Ala Val Leu Asp Glu Phe Arg Thr
225                 230                 235                 240

Ala Leu Glu Ser Leu Lys Phe Arg Ala Pro Ala Leu Pro Val Val Ser
            245                 250                 255

Thr Val Thr Gly Arg Leu Ile Asp Gln Asp Glu Met Gly Thr Pro Glu
        260                 265                 270

Tyr Trp Leu Arg Gln Val Arg Arg Pro Val Arg Phe Gln Asp Ala Val
    275                 280                 285

Arg Glu Leu Ala Glu Gln Gly Val Gly Thr Phe Val Glu Val Gly Pro
290                 295                 300

Ser Gly Ala Leu Ala Ser Ala Gly Val Glu Cys Leu Gly Gly Asp Ala
305                 310                 315                 320

Ser Phe His Ala Val Leu Arg Pro Arg Ser Pro Glu Asp Val Cys Leu
                325                 330                 335

Met Thr Ala Ile Ala Glu Leu His Ala Gly Gly Thr Ala Ile Asp Trp
            340                 345                 350

Ala Lys Val Leu Ser Gly Gly Arg Ala Val Asp Leu Pro Val Tyr Pro
        355                 360                 365

Phe Gln His Gln Ser Tyr Trp Leu Ala Pro Ala Ala Pro Asp Ala Thr
    370                 375                 380

Ala Val Ala Pro Val Val Glu Glu Gly Gly Glu Tyr
385                 390                 395

<210> SEQ ID NO 78
<211> LENGTH: 390
<212> TYPE: PRT
<213> ORGANISM: Streptomyces cinnamonensis

<400> SEQUENCE: 78

Thr Gly Glu Pro His Ala Ala Leu Val Gly Pro Ala Cys Ser Gln Ala
1               5                   10                  15

Arg Val Gly Gly Asp Asp Val Val Trp Leu Phe Ser Gly Gln Gly Ser
            20                  25                  30

Gln Leu Val Gly Met Gly Ala Gly Leu Tyr Glu Arg Phe Pro Val Phe
        35                  40                  45

Ala Ala Ala Phe Asp Glu Val Cys Gly Leu Leu Glu Gly Pro Leu Gly
    50                  55                  60

Val Glu Ala Gly Gly Leu Arg Glu Val Phe Arg Gly Pro Arg Glu
65                  70                  75                  80

Arg Leu Asp His Thr Val Trp Ala Gln Ala Gly Leu Phe Ala Leu Gln
                85                  90                  95

Val Gly Leu Ala Arg Leu Trp Glu Ser Val Gly Val Arg Pro Asp Val
            100                 105                 110

Val Leu Gly His Ser Ile Gly Glu Ile Ala Ala His Val Ala Gly
        115                 120                 125

Val Phe Asp Leu Ala Asp Ala Cys Arg Val Val Gly Ala Arg Ala Arg
    130                 135                 140

Leu Met Gly Gly Leu Pro Glu Gly Gly Ala Met Cys Ala Val Gln Ala
145                 150                 155                 160

Thr Pro Ala Glu Leu Ala Ala Asp Val Asp Gly Ser Ala Val Ser Val
                165                 170                 175

Ala Ala Val Asn Thr Pro Asp Ser Thr Val Ile Ser Gly Pro Ser Asp
            180                 185                 190

Glu Val Asp Arg Ile Ala Gly Val Trp Arg Glu Arg Gly Arg Lys Thr
        195                 200                 205
```

-continued

```
Lys Ala Leu Ser Val Ser His Ala Phe His Ser Ala Leu Met Glu Pro
210                 215                 220

Met Leu Ala Glu Phe Thr Glu Ala Ile Arg Gly Val Lys Phe Arg Gln
225                 230                 235                 240

Pro Ser Ile Pro Leu Met Ser Asn Val Ser Gly Glu Arg Ala Gly Glu
                245                 250                 255

Glu Ile Thr Asp Pro Glu Tyr Trp Ala Arg His Val Arg Asn Ala Val
            260                 265                 270

Leu Phe Gln Pro Ala Ile Ala Gln Val Ala Asp Ser Ala Gly Val Phe
        275                 280                 285

Val Glu Leu Gly Pro Ala Pro Val Leu Thr Thr Ala Ala Gln His Thr
    290                 295                 300

Leu Asp Glu Ser Asp Ser Gln Glu Ser Val Leu Val Ala Ser Leu Ala
305                 310                 315                 320

Gly Glu Arg Pro Glu Glu Ser Ala Phe Val Glu Ala Met Ala Arg Leu
                325                 330                 335

His Thr Ala Gly Val Ala Val Asp Trp Ser Val Leu Phe Ala Gly Asp
            340                 345                 350

Arg Val Pro Gly Leu Val Glu Leu Pro Thr Tyr Ala Phe Gln Arg Glu
        355                 360                 365

Arg Phe Trp Leu Ser Gly Arg Ser Gly Gly Asp Ala Ala Thr Leu
    370                 375                 380

Gly Leu Val Ala Ala Gly
385                 390

<210> SEQ ID NO 79
<211> LENGTH: 395
<212> TYPE: PRT
<213> ORGANISM: Streptomyces cinnamonensis

<400> SEQUENCE: 79

Ala Gly Glu Glu His Pro Ala Val Thr Arg Ser Arg Glu Asp Gly Val
1               5                   10                  15

Ala Ala Ser Gly Ala Val Val Trp Leu Phe Ser Gly Gln Gly Ser Gln
                20                  25                  30

Leu Val Gly Met Gly Ala Gly Leu Tyr Glu Arg Phe Pro Val Phe Ala
            35                  40                  45

Ala Ala Phe Asp Glu Val Cys Gly Leu Leu Glu Gly Pro Leu Gly Val
        50                  55                  60

Glu Ala Gly Gly Leu Arg Glu Val Phe Arg Gly Pro Arg Glu Arg
65                  70                  75                  80

Leu Asp His Thr Met Trp Ala Gln Ala Gly Leu Phe Ala Leu Gln Val
                85                  90                  95

Gly Leu Ala Arg Leu Trp Glu Ser Val Gly Val Arg Pro Asp Val Val
            100                 105                 110

Leu Gly His Ser Ile Gly Glu Ile Ala Ala His Val Ala Gly Val
        115                 120                 125

Phe Asp Leu Ala Asp Ala Cys Arg Val Val Gly Ala Arg Ala Arg Leu
    130                 135                 140

Met Gly Gly Leu Pro Glu Gly Gly Ala Met Cys Ala Val Gln Ala Thr
145                 150                 155                 160

Pro Ala Glu Leu Ala Ala Asp Val Asp Asp Ser Gly Val Ser Val Ala
                165                 170                 175

Ala Val Asn Thr Pro Asp Ser Thr Val Ile Ser Gly Pro Ser Gly Glu
            180                 185                 190
```

```
Val Asp Arg Ile Ala Gly Val Trp Arg Glu Arg Gly Lys Thr Lys
    195                 200                 205

Ala Leu Ser Val Ser His Ala Phe His Ser Ala Leu Met Glu Pro Met
    210                 215                 220

Leu Ala Glu Phe Thr Glu Ala Ile Arg Glu Val Lys Phe Thr Arg Pro
225                 230                 235                 240

Lys Val Ser Leu Ile Ser Asn Val Ser Gly Leu Glu Ala Gly Glu Glu
                245                 250                 255

Ile Ala Ser Pro Glu Tyr Trp Ala Arg His Val Arg Gln Thr Val Leu
                260                 265                 270

Phe Gln Pro Gly Ile Ala Gln Val Ala Ser Thr Ala Gly Val Phe Val
            275                 280                 285

Glu Leu Gly Pro Gly Pro Val Leu Thr Thr Ala Ala Gln His Thr Leu
        290                 295                 300

Asp Asp Val Thr Asp Arg His Gly Pro Glu Pro Val Leu Val Ser Ser
305                 310                 315                 320

Leu Ala Gly Glu Arg Pro Glu Ser Ala Phe Val Glu Ala Met Ala
                325                 330                 335

Arg Leu His Thr Ala Gly Val Ala Val Asp Trp Ser Val Leu Phe Ala
                340                 345                 350

Gly Asp Arg Val Pro Gly Leu Val Glu Leu Pro Thr Tyr Ala Phe Gln
            355                 360                 365

Arg Glu Arg Phe Trp Leu Ser Gly Arg Ser Gly Gly Asp Ala Ala
        370                 375                 380

Thr Leu Gly Leu Val Ala Ala Gly His Pro Leu
385                 390                 395

<210> SEQ ID NO 80
<211> LENGTH: 391
<212> TYPE: PRT
<213> ORGANISM: Streptomyces cinnamonensis

<400> SEQUENCE: 80

Gly Glu Glu His Pro Ala Val Thr Arg Ser Arg Glu Glu Ala Val
1               5                   10                  15

Ala Ala Ser Gly Asp Val Val Trp Leu Phe Ser Gly Gln Gly Ser Gln
                20                  25                  30

Leu Val Gly Met Gly Ala Gly Leu Tyr Glu Arg Phe Pro Val Phe Ala
            35                  40                  45

Ala Ala Phe Asp Glu Val Cys Gly Leu Leu Glu Gly Glu Leu Gly Val
        50                  55                  60

Gly Ser Gly Gly Leu Arg Glu Val Val Phe Trp Gly Pro Arg Glu Arg
65                  70                  75                  80

Leu Asp His Thr Val Trp Ala Gln Ala Gly Leu Phe Ala Leu Gln Val
                85                  90                  95

Gly Leu Ala Arg Leu Trp Glu Ser Val Gly Val Arg Pro Asp Val Val
            100                 105                 110

Leu Gly His Ser Ile Gly Glu Ile Ala Ala His Val Ala Gly Val
            115                 120                 125

Phe Asp Leu Ala Asp Ala Cys Arg Val Val Gly Ala Arg Ala Arg Leu
        130                 135                 140

Met Gly Gly Leu Pro Glu Gly Gly Ala Met Cys Ala Val Gln Ala Thr
145                 150                 155                 160

Pro Ala Glu Leu Ala Ala Asp Val Asp Gly Ser Ser Val Ser Val Ala
                165                 170                 175
```

-continued

```
Ala Val Asn Thr Pro Asp Ser Thr Val Ile Ser Gly Pro Ser Gly Glu
            180                 185                 190

Val Asp Arg Ile Ala Gly Val Trp Arg Glu Arg Gly Arg Lys Thr Lys
        195                 200                 205

Ala Leu Ser Val Ser His Ala Phe His Ser Ala Leu Met Glu Pro Met
    210                 215                 220

Leu Gly Glu Phe Thr Glu Ala Ile Arg Gly Val Lys Phe Arg Gln Pro
225                 230                 235                 240

Ser Ile Pro Leu Met Ser Asn Val Ser Gly Glu Arg Ala Gly Glu Glu
                245                 250                 255

Ile Thr Ser Pro Glu Tyr Trp Ala Arg His Val Arg Gln Thr Val Leu
            260                 265                 270

Phe Gln Pro Gly Val Ala Gln Val Ala Ala Glu Ala Arg Ala Phe Val
        275                 280                 285

Glu Leu Gly Pro Gly Pro Val Leu Thr Ala Ala Ala Gln His Thr Leu
    290                 295                 300

Asp His Ile Thr Glu Pro Glu Gly Pro Glu Pro Val Val Thr Ala Ser
305                 310                 315                 320

Leu His Pro Asp Arg Pro Asp Asp Val Ala Phe Ala His Ala Met Ala
                325                 330                 335

Asp Leu His Val Ala Gly Ile Ser Val Asp Trp Ser Ala Tyr Phe Pro
            340                 345                 350

Asp Asp Pro Ala Pro Arg Thr Val Asp Leu Pro Thr Tyr Ala Phe Gln
        355                 360                 365

Gly Arg Arg Phe Trp Leu Ala Asp Ile Ala Ala Pro Glu Ala Val Ser
    370                 375                 380

Ser Thr Asp Gly Glu Glu Ala
385                 390

<210> SEQ ID NO 81
<211> LENGTH: 380
<212> TYPE: PRT
<213> ORGANISM: Sorangium cellulosum

<400> SEQUENCE: 81

Ala Ala Leu Ser Ala Val Ala Gln Gly Gln Thr Pro Ala Gly Ala Ala
1               5                   10                  15

Arg Cys Ile Ala Ser Ser Ser Arg Gly Lys Leu Ala Phe Leu Phe Thr
            20                  25                  30

Gly Gln Gly Ala Gln Thr Pro Gly Met Gly Arg Gly Leu Cys Ala Ala
        35                  40                  45

Trp Pro Ala Phe Arg Glu Ala Phe Asp Arg Cys Val Ala Leu Phe Asp
    50                  55                  60

Arg Glu Leu Asp Arg Pro Leu Arg Glu Val Met Trp Ala Glu Ala Gly
65                  70                  75                  80

Ser Ala Glu Ser Leu Leu Leu Asp Gln Thr Ala Phe Thr Gln Pro Ala
                85                  90                  95

Leu Phe Ala Val Glu Tyr Ala Leu Thr Ala Leu Trp Arg Ser Trp Gly
            100                 105                 110

Val Glu Pro Glu Leu Leu Val Gly His Ser Ile Gly Glu Leu Val Ala
        115                 120                 125

Ala Cys Val Ala Gly Val Phe Ser Leu Glu Asp Gly Val Arg Leu Val
    130                 135                 140

Ala Ala Arg Gly Arg Leu Met Gln Gly Leu Ser Ala Gly Gly Ala Met
145                 150                 155                 160
```

```
Val Ser Leu Gly Ala Pro Glu Ala Glu Val Ala Ala Val Ala Pro
            165                 170                 175

His Ala Ala Ser Val Ser Ile Ala Ala Val Asn Gly Pro Glu Gln Val
            180                 185                 190

Val Ile Ala Gly Val Glu Gln Ala Val Gln Ala Ile Ala Ala Gly Phe
            195                 200                 205

Ala Ala Arg Gly Ala Arg Thr Lys Arg Leu His Val Ser His Ala Phe
            210                 215                 220

His Ser Pro Leu Met Glu Pro Met Leu Glu Glu Phe Gly Arg Val Ala
225                 230                 235                 240

Ala Ser Val Thr Tyr Arg Arg Pro Ser Val Ser Leu Val Ser Asn Leu
                    245                 250                 255

Ser Gly Lys Val Val Thr Asp Glu Leu Ser Ala Pro Gly Tyr Trp Val
                260                 265                 270

Arg His Val Arg Glu Ala Val Arg Phe Ala Asp Gly Val Lys Ala Leu
            275                 280                 285

His Glu Ala Gly Ala Gly Thr Phe Val Glu Val Gly Pro Lys Pro Thr
            290                 295                 300

Leu Leu Gly Leu Leu Pro Ala Cys Leu Pro Glu Ala Glu Pro Thr Leu
305                 310                 315                 320

Leu Ala Ser Leu Arg Ala Gly Arg Glu Glu Ala Ala Gly Val Leu Glu
                    325                 330                 335

Ala Leu Gly Arg Leu Trp Ala Ala Gly Gly Ser Val Ser Trp Pro Gly
                340                 345                 350

Val Phe Pro Thr Ala Gly Arg Arg Val Pro Leu Pro Thr Tyr Pro Trp
            355                 360                 365

Gln Arg Gln Arg Tyr Trp Ile Glu Ala Pro Ala Glu
370                 375                 380

<210> SEQ ID NO 82
<211> LENGTH: 406
<212> TYPE: PRT
<213> ORGANISM: Sorangium cellulosum

<400> SEQUENCE: 82

Ala Val Ala Val Thr Ser Arg Glu Gly Leu Leu Ala Ala Leu Ser Ala
1               5                   10                  15

Val Ala Gln Gly Gln Thr Pro Pro Gly Ala Ala Arg Cys Ile Ala Ser
                20                  25                  30

Ser Ser Arg Gly Lys Leu Ala Phe Leu Phe Thr Gly Gln Gly Ala Gln
            35                  40                  45

Thr Pro Gly Met Gly Arg Gly Leu Cys Ala Ala Trp Pro Ala Phe Arg
    50                  55                  60

Glu Ala Phe Asp Arg Cys Val Ala Leu Phe Asp Arg Glu Leu Asp Arg
65                  70                  75                  80

Pro Leu Arg Glu Val Met Trp Ala Glu Pro Gly Ser Ala Glu Ser Leu
                85                  90                  95

Leu Leu Asp Gln Thr Ala Phe Thr Gln Pro Ala Leu Phe Thr Val Glu
            100                 105                 110

Tyr Ala Leu Thr Ala Leu Trp Arg Ser Trp Gly Val Glu Pro Glu Leu
            115                 120                 125

Val Ala Gly His Ser Ala Gly Glu Leu Val Ala Ala Cys Val Ala Gly
            130                 135                 140

Val Phe Ser Leu Glu Asp Gly Val Arg Leu Val Ala Ala Arg Gly Arg
145                 150                 155                 160
```

-continued

```
Leu Met Gln Gly Leu Ser Ala Gly Ala Met Val Ser Leu Gly Ala
            165                 170                 175

Pro Glu Ala Glu Val Ala Ala Val Ala Pro His Ala Ala Ser Val
        180                 185                 190

Ser Ile Ala Ala Val Asn Gly Pro Glu Gln Val Val Ile Ala Gly Val
        195                 200                 205

Glu Gln Ala Val Gln Ala Ile Ala Ala Gly Phe Ala Ala Arg Gly Ala
    210                 215                 220

Arg Thr Lys Arg Leu His Val Ser His Ala Ser His Ser Pro Leu Met
225                 230                 235                 240

Glu Pro Met Leu Glu Glu Phe Gly Arg Val Ala Ala Ser Val Thr Tyr
                245                 250                 255

Arg Arg Pro Ser Val Ser Leu Val Ser Asn Leu Ser Gly Lys Val Val
            260                 265                 270

Ala Asp Glu Leu Ser Ala Pro Gly Tyr Trp Val Arg His Val Arg Glu
        275                 280                 285

Ala Val Arg Phe Ala Asp Gly Val Lys Ala Leu His Glu Ala Gly Ala
    290                 295                 300

Gly Thr Phe Val Glu Val Gly Pro Lys Pro Thr Leu Leu Gly Leu Leu
305                 310                 315                 320

Pro Ala Cys Leu Pro Glu Ala Glu Pro Thr Leu Leu Ala Ser Leu Arg
                325                 330                 335

Ala Gly Arg Glu Glu Ala Ala Gly Val Leu Glu Ala Leu Gly Arg Leu
            340                 345                 350

Trp Ala Ala Gly Gly Ser Val Ser Trp Pro Gly Val Phe Pro Thr Ala
        355                 360                 365

Gly Arg Arg Val Pro Leu Pro Thr Tyr Pro Trp Gln Arg Gln Arg Tyr
    370                 375                 380

Trp Pro Asp Ile Glu Pro Asp Ser Arg Arg His Ala Ala Ala Asp Pro
385                 390                 395                 400

Thr Gln Gly Trp Phe Tyr
                405

<210> SEQ ID NO 83
<211> LENGTH: 383
<212> TYPE: PRT
<213> ORGANISM: Sorangium cellulosum

<400> SEQUENCE: 83

Val Ala Ala Gln Gly Gln Thr Pro Ala Gly Ala Ala Arg Gly Arg Ala
  1               5                  10                  15

Ala Ser Ser Pro Gly Lys Leu Ala Phe Leu Phe Ala Gly Gln Gly Ala
            20                  25                  30

Gln Val Pro Gly Met Gly Arg Gly Leu Trp Glu Ala Trp Pro Ala Phe
        35                  40                  45

Arg Glu Thr Phe Asp Arg Cys Val Thr Leu Phe Asp Arg Glu Leu His
    50                  55                  60

Gln Pro Leu Cys Glu Val Met Trp Ala Glu Pro Gly Ser Ser Arg Ser
65                  70                  75                  80

Ser Leu Leu Asp Gln Thr Ala Phe Thr Gln Pro Ala Leu Phe Ala Leu
                85                  90                  95

Glu Tyr Ala Leu Ala Ala Leu Phe Arg Ser Trp Gly Val Glu Pro Glu
            100                 105                 110

Leu Val Ala Gly His Ser Leu Gly Glu Leu Val Ala Ala Cys Val Ala
        115                 120                 125
```

Gly Val Phe Ser Leu Glu Asp Ala Val Arg Leu Val Ala Arg Gly
              130                 135                 140

Arg Leu Met Gln Ala Leu Pro Ala Gly Gly Ala Met Val Ser Ile Ala
145                 150                 155                 160

Ala Pro Glu Ala Asp Val Ala Ala Val Ala Pro His Ala Ala Leu
                165                 170                 175

Val Ser Ile Ala Ala Val Asn Gly Pro Glu Gln Val Val Ile Ala Gly
              180                 185                 190

Ala Glu Lys Phe Val Gln Gln Ile Ala Ala Phe Ala Ala Arg Gly
              195                 200                 205

Ala Arg Thr Lys Pro Leu His Val Ser His Ala Phe His Ser Pro Leu
              210                 215                 220

Met Asp Pro Met Leu Glu Ala Phe Arg Arg Val Thr Glu Ser Val Thr
225                 230                 235                 240

Tyr Arg Arg Pro Ser Ile Ala Leu Val Ser Asn Leu Ser Gly Lys Pro
                245                 250                 255

Cys Thr Asp Glu Val Ser Ala Pro Gly Tyr Trp Val Arg His Ala Arg
                260                 265                 270

Glu Ala Val Arg Phe Ala Asp Gly Val Lys Ala Leu His Ala Ala Gly
              275                 280                 285

Ala Gly Leu Phe Val Glu Val Gly Pro Lys Pro Thr Leu Leu Gly Leu
              290                 295                 300

Val Pro Ala Cys Leu Pro Asp Ala Arg Pro Val Leu Leu Pro Ala Ser
305                 310                 315                 320

Arg Ala Gly Arg Asp Glu Ala Ala Ser Ala Leu Glu Ala Leu Gly Gly
                325                 330                 335

Phe Trp Val Val Gly Ser Val Thr Trp Ser Gly Val Phe Pro Ser
              340                 345                 350

Gly Gly Arg Arg Val Pro Leu Pro Thr Tyr Pro Trp Gln Arg Glu Arg
                355                 360                 365

Tyr Trp Ile Glu Ala Pro Val Asp Arg Glu Ala Asp Gly Thr Gly
              370                 375                 380

<210> SEQ ID NO 84
<211> LENGTH: 403
<212> TYPE: PRT
<213> ORGANISM: Sorangium cellulosum

<400> SEQUENCE: 84

Ser Arg Glu Gly Leu Arg Ala Ala Leu Asp Ala Ala Gln Gly Gln
 1               5                  10                  15

Thr Ser Pro Gly Ala Val Arg Ser Ile Ala Asp Ser Ser Arg Gly Lys
                20                  25                  30

Leu Ala Phe Leu Phe Thr Gly Gln Gly Ala Gln Thr Leu Gly Met Gly
              35                  40                  45

Arg Gly Leu Tyr Asp Val Trp Ser Ala Phe Arg Glu Ala Phe Asp Leu
 50                  55                  60

Cys Val Arg Leu Phe Asn Gln Glu Leu Asp Arg Pro Leu Arg Glu Val
65                  70                  75                  80

Met Trp Ala Glu Pro Ala Ser Val Asp Ala Ala Leu Leu Asp Gln Thr
                85                  90                  95

Ala Phe Thr Gln Pro Ala Leu Phe Thr Phe Glu Tyr Ala Leu Ala Ala
              100                 105                 110

Leu Trp Arg Ser Trp Gly Val Glu Pro Glu Leu Val Ala Gly His Ser
              115                 120                 125

```
Ile Gly Glu Leu Val Ala Ala Cys Val Ala Gly Val Phe Ser Leu Glu
            130                 135                 140

Asp Ala Val Phe Leu Val Ala Arg Gly Arg Leu Met Gln Ala Leu
145                 150                 155                 160

Pro Ala Gly Gly Ala Met Val Ser Ile Glu Ala Pro Glu Ala Asp Val
                165                 170                 175

Ala Ala Ala Val Ala Pro His Ala Ala Ser Val Ser Ile Ala Ala Val
            180                 185                 190

Asn Ala Pro Asp Gln Val Val Ile Ala Gly Ala Gly Gln Pro Val His
            195                 200                 205

Ala Ile Ala Ala Ala Met Ala Ala Arg Gly Ala Arg Thr Lys Ala Leu
            210                 215                 220

His Val Ser His Ala Phe His Ser Pro Leu Met Ala Pro Met Leu Glu
225                 230                 235                 240

Ala Phe Gly Arg Val Ala Glu Ser Val Ser Tyr Arg Arg Pro Ser Ile
                245                 250                 255

Val Leu Val Ser Asn Leu Ser Gly Lys Ala Cys Thr Asp Glu Val Ser
                260                 265                 270

Ser Pro Gly Tyr Trp Val Arg His Ala Arg Glu Val Val Arg Phe Ala
            275                 280                 285

Asp Gly Val Lys Ala Leu His Ala Ala Gly Ala Gly Thr Phe Val Glu
            290                 295                 300

Val Gly Pro Lys Ser Thr Leu Leu Gly Leu Val Pro Ala Cys Met Pro
305                 310                 315                 320

Asp Ala Arg Pro Ala Leu Leu Ala Ser Ser Arg Ala Gly Arg Asp Glu
                325                 330                 335

Pro Ala Thr Val Leu Glu Ala Leu Gly Gly Leu Trp Ala Val Gly Gly
                340                 345                 350

Leu Val Ser Trp Ala Gly Leu Phe Pro Ser Gly Gly Arg Arg Val Pro
            355                 360                 365

Leu Pro Thr Tyr Pro Trp Gln Arg Glu Arg Tyr Trp Ile Asp Thr Lys
            370                 375                 380

Ala Asp Asp Ala Ala Arg Gly Asp Arg Arg Ala Pro Gly Ala Gly His
385                 390                 395                 400

Asp Glu Val

<210> SEQ ID NO 85
<211> LENGTH: 399
<212> TYPE: PRT
<213> ORGANISM: Sorangium cellulosum

<400> SEQUENCE: 85

Leu Arg Gly Ala Leu Asp Ala Ala Ala Gln Gln Lys Thr Pro Gln Gly
  1               5                  10                  15

Ala Val Arg Gly Lys Ala Val Ser Ser Arg Gly Lys Leu Ala Phe Leu
                 20                  25                  30

Phe Thr Gly Gln Gly Ala Gln Met Pro Gly Met Gly Arg Gly Leu Tyr
             35                  40                  45

Glu Thr Trp Pro Ala Phe Arg Glu Ala Phe Asp Arg Cys Val Ala Leu
         50                  55                  60

Phe Asp Arg Glu Ile Asp Gln Pro Leu Arg Glu Val Met Trp Ala Ala
 65                  70                  75                  80

Pro Gly Leu Ala Gln Ala Ala Arg Leu Asp Gln Thr Ala Tyr Ala Gln
                 85                  90                  95
```

-continued

```
Pro Ala Leu Phe Ala Leu Glu Tyr Ala Leu Ala Ala Leu Trp Arg Ser
                100                 105                 110

Trp Gly Val Glu Pro His Val Leu Gly His Ser Ile Gly Glu Leu
            115                 120                 125

Val Ala Ala Cys Val Ala Gly Val Phe Ser Leu Glu Asp Ala Val Arg
130                 135                 140

Leu Val Ala Ala Arg Gly Arg Leu Met Gln Ala Leu Pro Ala Gly Gly
145                 150                 155                 160

Ala Met Val Ala Ile Ala Ala Ser Glu Ala Glu Val Ala Ala Ser Val
                165                 170                 175

Ala Pro His Ala Ala Thr Val Ser Ile Ala Ala Val Asn Gly Pro Asp
            180                 185                 190

Ala Val Val Ile Ala Gly Ala Glu Val Gln Val Leu Ala Leu Gly Ala
        195                 200                 205

Thr Phe Ala Ala Arg Gly Ile Arg Thr Lys Arg Leu Ala Val Ser His
    210                 215                 220

Ala Phe His Ser Pro Leu Met Asp Pro Met Leu Glu Asp Phe Gln Arg
225                 230                 235                 240

Val Ala Ala Thr Ile Ala Tyr Arg Ala Pro Asp Arg Pro Val Val Ser
                245                 250                 255

Asn Val Thr Gly His Val Ala Gly Pro Glu Ile Ala Thr Pro Glu Tyr
            260                 265                 270

Trp Val Arg His Val Arg Ser Ala Val Arg Phe Gly Asp Gly Ala Lys
        275                 280                 285

Ala Leu His Ala Ala Gly Ala Ala Thr Phe Val Glu Val Gly Pro Lys
    290                 295                 300

Pro Val Leu Leu Gly Leu Leu Pro Ala Cys Leu Gly Glu Ala Asp Ala
305                 310                 315                 320

Val Leu Val Pro Ser Leu Arg Ala Asp Arg Ser Glu Cys Glu Val Val
                325                 330                 335

Leu Ala Ala Leu Gly Ala Trp Tyr Ala Trp Gly Gly Ala Leu Asp Trp
            340                 345                 350

Lys Gly Val Phe Pro Asp Gly Ala Arg Arg Val Ala Leu Pro Met Tyr
        355                 360                 365

Pro Trp Gln Arg Glu Arg His Trp Met Asp Leu Thr Pro Arg Ser Ala
    370                 375                 380

Ala Pro Ala Gly Ile Ala Gly Arg Trp Pro Leu Ala Gly Val Gly
385                 390                 395

<210> SEQ ID NO 86
<211> LENGTH: 381
<212> TYPE: PRT
<213> ORGANISM: Streptomyces caelestis

<400> SEQUENCE: 86

Ala Ala Ala His Asp Ala Leu Leu Ala Val Ala Asp Gly Arg Pro Ser
1               5                   10                  15

Asp Ala Val Val Thr Gly Ile Ala Arg Arg Gly Arg Asp Val Ala Phe
                20                  25                  30

Leu Phe Ser Gly Gln Gly Ala Gln Arg Ala Gly Ala Gly Arg Glu Leu
            35                  40                  45

Tyr Ala Ser Phe Pro Val Phe Ala Gln Ala Leu Asp Glu Val Ala Gly
        50                  55                  60

Gly Phe Asp Ala His Leu Glu Arg Pro Leu Leu Gln Val Met Phe Ala
65                  70                  75                  80
```

```
Glu Pro Gly Thr Ala Asp Ala Ala Leu Leu Asp Arg Thr Ala Tyr Ala
                85                  90                  95

Gln Pro Ala Leu Phe Ala Val Glu Thr Ala Leu Phe Arg Leu Phe Glu
            100                 105                 110

Ser Trp Gly Leu Met Pro Asp Val Leu Leu Gly His Ser Ile Gly Gly
            115                 120                 125

Leu Ala Ala Ala Tyr Ala Ala Gly Val Phe Ser Ser Ala Asp Ala Val
        130                 135                 140

Arg Leu Val Ala Ala Arg Gly Arg Leu Met Gln Arg Leu Pro Glu Gly
145                 150                 155                 160

Gly Ala Met Val Ala Val Arg Ala Thr Glu Gln Val Ala Glu Leu
            165                 170                 175

Glu Trp Ile Ala Gly Gly Arg Ala Val Val Ala Ala Phe Asn Gly Pro
            180                 185                 190

Asp Ser Leu Val Leu Ser Gly Asp Glu Gln Ala Val Val Ser Ala Ala
            195                 200                 205

Gly Glu Leu Ala Ala Arg Gly Arg Arg Thr Lys Arg Leu Ser Val Ser
        210                 215                 220

His Ala Phe His Ser Pro His Met Asp Ala Met Leu Ala Asp Phe Arg
225                 230                 235                 240

Ala Val Ala Glu Ser Val Thr Tyr Arg Thr Pro Arg Leu Pro Ile Val
            245                 250                 255

Ser Glu Val Thr Gly Arg Pro Ala Ala Pro Ser Glu Leu Met Asp Pro
            260                 265                 270

Gly Tyr Trp Thr Arg Gln Ile Arg Glu Pro Val Arg Phe Ala Ala Ala
        275                 280                 285

Val Arg Ala Ala Arg Ala Ala Gly Ala Ala Thr Phe Val Glu Leu Gly
290                 295                 300

Pro Asp Ala Val Leu Ser Gly Met Ala Arg Glu Cys Ala Ala Gly Asp
305                 310                 315                 320

Thr Gly Thr Ala Phe Ala Ala Ala Leu Arg Arg Gly Arg Pro Glu Cys
            325                 330                 335

Ala Thr Val Leu Pro Ala Ala Thr Ala Phe Val Gln Gly Ala His
            340                 345                 350

Val Asp Trp Ala Ala Pro Tyr Glu Gly Ala Gly Ala Arg Arg Val Asp
        355                 360                 365

Leu Pro Thr Tyr Pro Phe Gln His Thr Arg Tyr Trp Leu
        370                 375                 380

<210> SEQ ID NO 87
<211> LENGTH: 432
<212> TYPE: PRT
<213> ORGANISM: Streptomyces fradiae

<400> SEQUENCE: 87

Leu Arg Asp His Leu Ser Arg Thr Pro Gly Ala Arg Pro Arg Asp Ile
  1               5                  10                  15

Ala Phe Ser Leu Ala Ala Thr Arg Ala Ala Phe Asp His Arg Ala Val
                20                  25                  30

Leu Ile Gly Ser Asp Gly Ala Glu Leu Ala Ala Ala Leu Asp Ala Leu
            35                  40                  45

Ala Glu Gly Arg Asp Gly Pro Ala Val Val Arg Gly Val Asp Arg
        50                  55                  60

Asp Gly Arg Met Ala Phe Leu Phe Thr Gly Gln Gly Ser Gln Arg Ala
65                  70                  75                  80
```

```
Gly Met Ala His Asp Leu His Ala Ala His Thr Phe Phe Ala Ser Ala
                 85                  90                  95

Leu Asp Glu Val Thr Asp Arg Leu Asp Pro Leu Leu Gly Arg Pro Leu
            100                 105                 110

Gly Ala Leu Leu Asp Ala Arg Pro Gly Ser Pro Glu Ala Ala Leu Leu
        115                 120                 125

Asp Arg Thr Glu Tyr Thr Gln Pro Ala Leu Phe Ala Val Glu Val Ala
130                 135                 140

Leu His Arg Leu Leu Glu His Trp Gly Met Arg Pro Asp Leu Leu Leu
145                 150                 155                 160

Gly His Ser Val Gly Glu Leu Ala Ala His Val Ala Gly Val Leu
                165                 170                 175

Asp Leu Asp Asp Ala Cys Ala Leu Val Ala Ala Arg Gly Arg Leu Met
            180                 185                 190

Gln Arg Leu Pro Pro Gly Gly Ala Met Val Ser Val Arg Ala Gly Glu
        195                 200                 205

Asp Glu Val Arg Ala Leu Leu Ala Gly Arg Glu Asp Ala Val Cys Val
210                 215                 220

Ala Ala Val Asn Gly Pro Arg Ser Val Val Ile Ser Gly Ala Glu Glu
225                 230                 235                 240

Ala Val Ala Glu Ala Ala Ala Gln Leu Ala Gly Arg Gly Arg Arg Thr
                245                 250                 255

Arg Arg Leu Arg Val Ala His Ala Phe His Ser Pro Leu Met Asp Gly
            260                 265                 270

Met Leu Ala Gly Phe Arg Glu Val Ala Ala Gly Leu Arg Tyr Arg Glu
        275                 280                 285

Pro Glu Leu Thr Val Val Ser Thr Val Thr Gly Arg Pro Ala Arg Pro
290                 295                 300

Gly Glu Leu Thr Gly Pro Asp Tyr Trp Val Ala Gln Val Arg Glu Pro
305                 310                 315                 320

Val Arg Phe Ala Asp Ala Val Arg Thr Ala His Arg Leu Gly Ala Arg
                325                 330                 335

Thr Phe Leu Glu Thr Gly Pro Asp Gly Val Leu Cys Gly Met Ala Glu
            340                 345                 350

Glu Cys Leu Glu Asp Asp Thr Val Ala Leu Leu Pro Ala Ile His Lys
        355                 360                 365

Pro Gly Thr Ala Pro His Gly Pro Ala Ala Pro Gly Ala Leu Arg Ala
370                 375                 380

Ala Ala Ala Ala Tyr Gly Arg Gly Ala Arg Val Asp Trp Ala Gly Met
385                 390                 395                 400

His Ala Asp Gly Pro Glu Gly Pro Ala Arg Arg Val Glu Leu Pro Val
                405                 410                 415

His Ala Phe Arg His Arg Arg Tyr Trp Leu Ala Pro Gly Arg Ala Ala
            420                 425                 430

<210> SEQ ID NO 88
<211> LENGTH: 338
<212> TYPE: PRT
<213> ORGANISM: Sorangium cellulosum

<400> SEQUENCE: 88

Ala Val Leu Phe Thr Gly Gln Gly Ser Gln Arg Pro Thr Met Gly Arg
  1               5                  10                  15

Ala Leu Tyr Asp Ala Phe Pro Val Phe Arg Asp Ala Leu Asp Thr Val
             20                  25                  30
```

```
Ala Ala His Leu Asp Arg Asp Leu Asp Arg Pro Leu Arg Asp Val Leu
         35                  40                  45

Phe Ala Pro Asp Gly Ser Glu Gln Ala Ala Arg Leu Asp Gln Thr Ala
 50                  55                  60

Phe Thr Gln Pro Ala Leu Phe Ala Leu Glu Val Ala Leu Phe Gln Leu
 65                  70                  75                  80

Leu Gln Ser Phe Gly Leu Lys Pro Ala Leu Leu Gly His Ser Ile
                 85                  90                  95

Gly Glu Leu Val Ala Ala His Val Ala Gly Val Leu Ser Leu Gln Asp
                100                 105                 110

Ala Cys Thr Leu Val Ala Ala Arg Ala Lys Leu Met Gln Ala Leu Pro
            115                 120                 125

Gln Gly Gly Ala Met Val Thr Leu Arg Ala Ser Glu Glu Val Arg
130                 135                 140

Asp Leu Leu Gln Pro Tyr Asp Gly Arg Ala Ser Leu Ala Ala Leu Asn
145                 150                 155                 160

Gly Pro Leu Ser Thr Val Val Ala Gly Asp Glu Asp Ala Val Val Glu
                165                 170                 175

Ile Ala Arg Gln Ala Glu Ala Leu Gly Arg Lys Thr Thr Arg Leu Arg
            180                 185                 190

Val Ser His Ala Phe His Ser Pro His Met Asp Gly Met Leu Asp Asp
            195                 200                 205

Phe Arg Arg Val Ala Gln Ser Leu Thr Tyr His Pro Ala Arg Ile Pro
210                 215                 220

Ile Ile Ser Asn Val Thr Gly Ala Arg Ala Thr Asp His Glu Leu Ala
225                 230                 235                 240

Ser Pro Asp Tyr Trp Val Arg His Val Arg His Thr Val Arg Phe Leu
                245                 250                 255

Asp Gly Val Arg Ala Leu His Ala Glu Gly Ala Arg Val Phe Leu Glu
            260                 265                 270

Leu Gly Pro His Ala Val Leu Ser Ala Leu Ala Gln Asp Ala Leu Gly
            275                 280                 285

Gln Asp Glu Gly Thr Ser Pro Cys Ala Phe Leu Pro Thr Leu Arg Lys
290                 295                 300

Gly Arg Asp Asp Ala Glu Ala Phe Thr Ala Ala Leu Gly Ala Leu His
305                 310                 315                 320

Ala Ala Gly Leu Thr Pro Asp Trp Ser Ala Phe Phe Ala Pro Phe Ala
                325                 330                 335

Pro Arg

<210> SEQ ID NO 89
<211> LENGTH: 347
<212> TYPE: PRT
<213> ORGANISM: Sorangium cellulosum

<400> SEQUENCE: 89

Ala Ile Leu Phe Thr Gly Gln Gly Ser Gln Arg Pro Thr Met Gly Arg
 1               5                  10                  15

Ala Leu Tyr Asp Ala Phe Pro Val Phe Arg Gly Ala Leu Asp Ala Ala
                 20                  25                  30

Ala Ala His Leu Asp Arg Asp Leu Asp Arg Pro Leu Arg Asp Val Leu
            35                  40                  45

Phe Ala Pro Asp Gly Ser Glu Gln Ala Ala Arg Leu Asp Gln Thr Ala
 50                  55                  60
```

```
Phe Thr Gln Pro Ala Leu Phe Ala Leu Glu Val Ala Leu Phe Glu Leu
 65                  70                  75                  80

Leu Gln Ser Phe Gly Leu Lys Pro Ala Leu Leu Gly His Ser Ile
             85                  90                  95

Gly Glu Leu Val Ala Ala His Val Ala Gly Val Leu Ser Leu Gln Asp
            100                 105                 110

Ala Cys Thr Leu Val Ala Arg Ala Lys Leu Met Gln Ala Leu Pro
            115                 120                 125

Gln Gly Gly Ala Met Val Thr Leu Gln Ala Ser Gln Glu Ala Arg
130                 135                 140

Asp Leu Leu Gln Ala Ala Glu Gly Arg Val Ser Leu Ala Ala Val Asn
145                 150                 155                 160

Gly His Leu Ser Thr Val Val Ala Gly Asp Glu Asp Ala Val Leu Lys
                165                 170                 175

Ile Ala Arg Gln Val Glu Ala Leu Gly Arg Lys Ala Thr Arg Leu Arg
            180                 185                 190

Val Ser His Ala Phe His Ser Pro His Met Asp Gly Met Leu Asp Asp
            195                 200                 205

Phe Arg Arg Val Ala Gln Gly Leu Thr Phe His Pro Ala Arg Ile Pro
210                 215                 220

Ile Ile Ser Asn Val Thr Gly Ala Arg Ala Thr Asp Gln Glu Leu Ala
225                 230                 235                 240

Ser Pro Glu Thr Trp Val Arg His Val Arg Asp Thr Val Arg Phe Leu
                245                 250                 255

Asp Gly Val Arg Thr Leu His Ala Glu Gly Ala Arg Ala Phe Leu Glu
            260                 265                 270

Leu Gly Pro His Pro Val Leu Ser Ala Leu Ala Gln Asp Ala Leu Gly
            275                 280                 285

His Asp Glu Gly Pro Ser Pro Cys Ala Phe Leu Pro Thr Leu Arg Lys
290                 295                 300

Gly Arg Asp Asp Ala Glu Ala Phe Thr Ala Ala Leu Gly Ala Leu His
305                 310                 315                 320

Ala Ala Gly Leu Thr Pro Asp Trp Asn Ala Phe Phe Ala Pro Phe Ala
                325                 330                 335

Pro Cys Lys Val Pro Leu Pro Thr Tyr Thr Phe
            340                 345

<210> SEQ ID NO 90
<211> LENGTH: 387
<212> TYPE: PRT
<213> ORGANISM: Streptomyces noursei

<400> SEQUENCE: 90

Ala Asp Asp Pro Ala Ala Pro Ala Trp Ile Thr Gly Thr Thr Arg
 1               5                  10                  15

Ala Glu Thr Arg Leu Ala Val Leu Phe Thr Gly Gln Gly Ala Gln Arg
                20                  25                  30

Leu Gly Ala Gly Arg Glu Leu Ala Ala Arg Phe Pro Ala Phe Ala Thr
            35                  40                  45

Ala Leu Asp Ala Ala Leu Asp Ala Phe Thr Pro His Leu Asp Arg Pro
        50                  55                  60

Leu Arg Glu Val Leu Trp Gly Thr Asp Ala Ala Leu Leu Asp Arg Thr
65                  70                  75                  80

Ala Tyr Ala Gln Pro Ala Leu Phe Ala Val Glu Val Ala Leu Tyr Arg
                85                  90                  95
```

```
Leu Ile Glu Ser Phe Gly Val Arg Pro Asp His Leu Ala Gly His Ser
                100                 105                 110

Val Gly Glu Ile Val Ala Ala His Leu Ala Gly Val Leu Ser Leu Ala
            115                 120                 125

Asp Ala Ala Thr Leu Val Ala Ala Arg Gly Arg Leu Met Gln Ala Leu
        130                 135                 140

Pro Asp Gly Gly Ala Met Ile Ala Val Gln Ala Ser Glu Ala Asp Val
145                 150                 155                 160

Ala Pro Leu Leu Ala Gly His Glu Asp Gln Val Ala Ile Ala Ala Val
                165                 170                 175

Asn Gly Pro Ser Ala Val Val Leu Ser Gly Ala Glu Ala Thr Val Thr
            180                 185                 190

Ala Leu Ala Glu Gln Leu Ala Ala Asp Gly Arg Lys Thr Arg Arg Leu
        195                 200                 205

Arg Val Ser His Ala Phe His Ser Pro Leu Met Glu Pro Met Leu Asp
210                 215                 220                 240

Ala Phe Arg Ala Val Val Glu Asp Leu Thr Leu Gln Pro Pro Leu Leu
225                 230                 235                 240

Pro Val Val Ser Asn Leu Thr Gly Lys Pro Ala Thr Val Ala Gln Leu
                245                 250                 255

Thr Ser Ala Asp Tyr Trp Val Asp His Val Arg His Ala Val Arg Phe
            260                 265                 270

Ala Asp Gly Ile Asp Trp Leu Ala Arg His Asp Thr Thr Ala Phe Leu
        275                 280                 285

Glu Leu Gly Pro Asp Gly Val Leu Ser Ala Met Ala Gln Asp Cys Leu
290                 295                 300

Asp Ala Ala Asp Ala Asp Ala Val Thr Leu Pro Ala Leu Arg Ala Gly
305                 310                 315                 320

Arg Pro Glu Glu His Thr Leu Thr Thr Ala Leu Ala Gly Leu His Val
                325                 330                 335

His Gly Ala Thr Leu Asp Trp Thr Gly Cys Phe Ala Gly Thr Gly Ala
            340                 345                 350

Arg Arg Thr Asp Leu Pro Thr Tyr Ala Phe Gln Arg Arg Tyr Trp
        355                 360                 365

Pro Lys Ala Leu Gln Ser Gly Thr Ala Asp Leu Arg Ser Val Gly Leu
370                 375                 380

Gly Ala Ala
385

<210> SEQ ID NO 91
<211> LENGTH: 391
<212> TYPE: PRT
<213> ORGANISM: Streptomyces noursei

<400> SEQUENCE: 91

Ser Asp Gly Arg Pro Asp Pro Gly Leu Val Gln Gly Thr Ala Gly Arg
1               5                   10                  15

Gly Arg Thr Ala Phe Leu Phe Thr Gly Gln Gly Ser Gln Arg Pro Gly
            20                  25                  30

Met Gly Arg Glu Leu His Asp Arg Tyr Pro Val Phe Ala Asp Ala Leu
        35                  40                  45

Asp Glu Val Leu Ala Arg Leu Asp Asp Gly Pro Asp Arg Pro Leu Arg
    50                  55                  60

Glu Val Leu Phe Ala Ala Pro Asp Ser Ala Glu Ala Ala Leu Leu Asp
65                  70                  75                  80
```

-continued

```
Arg Thr Gly Tyr Ala Gln Pro Ala Leu Phe Ala Val Glu Val Ala Leu
                 85                  90                  95

Phe Arg Leu Leu Thr Ser Trp Gly Leu Thr Pro Asp Tyr Leu Ala Gly
            100                 105                 110

His Ser Val Gly Glu Leu Ala Ala His Val Ala Gly Val Leu Ser
        115                 120                 125

Leu Asp Asp Ala Cys Thr Leu Val Ala Arg Gly Arg Leu Met Gln
130                 135                 140

Ala Leu Pro Glu Gly Gly Ala Met Val Ala Leu Glu Ala Ala Glu Asp
145                 150                 155                 160

Glu Val Leu Pro Leu Leu Glu Gly Leu Thr Asp Arg Val Ser Val Ala
                165                 170                 175

Ala Val Asn Gly Pro Arg Ser Val Val Val Ala Gly Val Glu Glu Asp
            180                 185                 190

Val Leu Leu Leu Ala Asp Leu Phe Ala Ala Asp Gly Arg Arg Thr Lys
        195                 200                 205

Arg Leu Arg Val Ser His Ala Phe His Ser Pro Leu Met Asp Ala Met
        210                 215                 220

Leu Asp Asp Phe Ala Ala Val Ala Arg Gly Leu Thr Tyr His Pro Pro
225                 230                 235                 240

Thr Ile Pro Phe Val Ser Asn Val Ser Gly Gly Leu Ala Thr Ala Glu
                245                 250                 255

Gln Val Arg Thr Pro Asp Tyr Trp Val Gly His Val Arg Ala Ala Val
            260                 265                 270

Arg Phe Ala Asp Gly Ile Asp Trp Leu Ala Thr Gln Gly Asp Val His
        275                 280                 285

Thr Phe Leu Glu Leu Gly Pro Asp Gly Val Leu Ser Ala Met Ala Arg
        290                 295                 300

Glu Ser Leu Thr Asp Pro Ser Arg Thr Ala Leu Leu Pro Thr Leu Arg
305                 310                 315                 320

Gly Asp Arg Pro Glu Glu Pro Ala Leu Val Thr Ala Val Ala Ala Ala
                325                 330                 335

His Ala His Gly Ala Arg Val Asp Trp Ser Gly Tyr Phe Ala Asp His
            340                 345                 350

Gly Ala Arg Arg Thr Thr Leu Pro Thr Tyr Ala Phe Gln Arg Glu Arg
        355                 360                 365

Tyr Trp Pro Asp Thr Thr Ala Ala Thr Ser Ala His Thr Pro Gly Ser
370                 375                 380

Ala Leu Asp Ala Glu Phe Trp
385                 390
```

<210> SEQ ID NO 92
<211> LENGTH: 380
<212> TYPE: PRT
<213> ORGANISM: Streptomyces noursei

<400> SEQUENCE: 92

```
Pro Asp Leu Pro Glu Val Ala Arg Gly Ala Ala Thr Pro His Arg Thr
1               5                  10                  15

Ala Phe Leu Phe Ser Gly Gln Gly Ala Gln Arg Ser Gly Met Gly Arg
            20                  25                  30

Glu Leu His Ala Ala Phe Pro Val Phe Ala Ala Ala Phe Asp Glu Val
        35                  40                  45

Val Ala Val Leu Asp Ala Glu Leu Gly Ser Asp Ala Asp Gly Gly Val
    50                  55                  60
```

```
Ser Leu Arg Glu Val Met Trp Gly Gly Ser Glu Leu Leu Asp Arg
 65                  70                  75                  80

Thr Arg Phe Thr Gln Pro Ala Leu Phe Ala Val Glu Val Ala Leu Phe
                 85                  90                  95

Arg Leu Val Ala Ser Trp Gly Val Gly Pro Glu Phe Val Ala Gly His
            100                 105                 110

Ser Val Gly Glu Ile Ala Ala His Val Ala Gly Val Phe Ser Leu
        115                 120                 125

Val Asp Ala Cys Arg Leu Val Val Ala Arg Ala Ser Leu Met Asp Ala
    130                 135                 140

Leu Pro Val Gly Gly Val Met Val Ala Val Glu Ala Ala Glu Ala Glu
145                 150                 155                 160

Val Val Pro Leu Leu Val Asp Gly Val Ala Ile Ala Ala Val Asn Gly
                165                 170                 175

Pro Val Ser Val Val Ser Gly Val Glu Ala Ala Val Gly Gln Val
            180                 185                 190

Val Asp Gln Leu Val Glu Arg Gly Arg Val Arg Arg Leu Ala Val
        195                 200                 205

Ser His Ala Phe His Ser Pro Leu Met Asp Pro Met Leu Asp Ala Phe
    210                 215                 220

Arg Ala Val Ala Glu Gly Leu Glu Tyr His Gln Pro Arg Ile Pro Val
225                 230                 235                 240

Val Ser Asn Val Thr Gly Glu Val Ala Ala Glu Glu Leu Cys Ala
                245                 250                 255

Ala Asp Tyr Trp Val Arg His Val Arg Ala Thr Val Arg Phe Ala Asp
            260                 265                 270

Gly Val Arg Thr Leu Ala Glu Arg Gly Ala Thr Ala Phe Leu Glu Ile
        275                 280                 285

Gly Pro Asp Gly Val Leu Ser Ala Leu Ala Arg Gly Val Leu Pro Ala
    290                 295                 300

Glu Ala Leu Val Thr Pro Thr Leu Arg Lys Asp Arg Asp Glu Glu Ser
305                 310                 315                 320

Ala Leu Leu Ala Gly Leu Ala Arg Leu His Val Ala Gly Val Thr Val
                325                 330                 335

Asp Trp Ser Ala Ala Leu Thr Gly Thr Gly Ala Arg Gly Thr Asp Leu
            340                 345                 350

Pro Thr Tyr Ala Phe Gln Arg Glu Arg Tyr Trp Pro Glu Leu Ala Ala
        355                 360                 365

Glu Pro Ala Gly Gly Gly Ala Asp Ala Ala Asp Ala
    370                 375                 380

<210> SEQ ID NO 93
<211> LENGTH: 379
<212> TYPE: PRT
<213> ORGANISM: Streptomyces noursei

<400> SEQUENCE: 93

Ala Pro Asp Gly Ile Thr Ala Ala Ala Arg Ala Glu Ala Arg Glu Arg
 1               5                  10                  15

Ser Thr Ala Phe Leu Phe Ser Gly Gln Gly Ala Gln Arg Ser Gly Met
                20                  25                  30

Gly Arg Glu Leu His Ala Ala Phe Pro Val Phe Ala Ala Ala Phe Asp
            35                  40                  45

Glu Val Val Ala Val Leu Asp Ala Glu Leu Ala Thr Gly Ser Gly Gly
        50                  55                  60
```

```
Gly Val Ser Leu Arg Glu Val Met Trp Gly Gly Ser Glu Leu Leu
 65                  70                  75                  80

Asp Arg Thr Arg Phe Thr Gln Pro Ala Leu Phe Ala Val Glu Val Ala
                 85                  90                  95

Leu Phe Arg Leu Val Ala Ser Trp Gly Val Gly Pro Glu Phe Val Ala
            100                 105                 110

Gly His Ser Val Gly Glu Ile Ala Ala Ala Tyr Val Ala Gly Val Phe
        115                 120                 125

Ser Leu Val Asp Ala Cys Arg Leu Val Val Ala Arg Ala Ser Leu Met
    130                 135                 140

Asp Ala Leu Pro Val Gly Val Met Val Ala Val Glu Ala Ala Glu
145                 150                 155                 160

Ala Glu Val Val Pro Leu Leu Val Asp Gly Val Ala Ile Ala Ala Val
                165                 170                 175

Asn Gly Pro Val Ser Val Val Ser Gly Val Glu Ala Ala Val Gly
            180                 185                 190

Gln Val Val Asp Gln Leu Val Glu Arg Gly Arg Val Arg Arg Leu
        195                 200                 205

Ala Val Ser His Ala Phe His Ser Pro Leu Met Asp Pro Met Leu Asp
    210                 215                 220

Ala Phe Arg Ala Val Ala Glu Gly Leu Glu Tyr His Gln Pro Arg Ile
225                 230                 235                 240

Pro Val Val Ser Asn Val Thr Gly Glu Val Ala Ala Ala Glu Glu Leu
                245                 250                 255

Cys Ala Ala Asp Tyr Trp Val Arg His Val Arg Ala Thr Val Arg Phe
            260                 265                 270

Ala Asp Gly Val Arg Thr Leu Ala Glu Arg Gly Ala Thr Ala Phe Leu
        275                 280                 285

Glu Ile Gly Pro Asp Gly Val Leu Ser Ala Leu Ala Ala Ala Cys Leu
    290                 295                 300

Phe Asp Thr Asp Ala Glu Val Val Pro Ala Leu Arg Lys Gly Arg Pro
305                 310                 315                 320

Glu Glu His Thr Ala Leu Thr Ala Ala Ala Gln Leu His Val Ala Gly
                325                 330                 335

Val Asp Ile Asp Trp Thr Ala Val Leu Ala Gly Thr Gly Arg Arg
            340                 345                 350

Ile Ala Leu Pro Thr Tyr Ala Phe Gln Arg Glu Arg Tyr Trp Pro Ser
        355                 360                 365

Leu Ala Ala Gln Ala Pro Gly Asp Ala Gly Gly
    370                 375

<210> SEQ ID NO 94
<211> LENGTH: 395
<212> TYPE: PRT
<213> ORGANISM: Streptomyces noursei

<400> SEQUENCE: 94

Gly Tyr Ala Leu Ala Asp Gly Arg Ala Thr Phe Glu His Arg Ala Val
 1               5                  10                  15

Leu Leu Pro Asp Gly Thr Glu Leu Ala His Gly Thr Ala Gly Glu Gly
                20                  25                  30

Pro Cys Ala Val Leu Phe Ser Gly Gln Gly Ser Gln Arg Pro Gly Met
            35                  40                  45

Gly Arg Glu Leu His Ala Arg Phe Pro Val Phe Ala Ala Ala Phe Asp
        50                  55                  60
```

```
Glu Ile Thr Ala Leu Leu Asp Thr His Leu Asp Arg Pro Leu Arg Glu
 65                  70                  75                  80

Val Val Trp Gly Thr Asp Ala Asp Leu Leu Asn Asp Thr Gly Trp Ala
                 85                  90                  95

Gln Pro Ala Leu Phe Ala Val Glu Val Ala Leu Tyr Arg Leu Val Ala
            100                 105                 110

Ser Leu Gly Val Thr Pro Asp Phe Val Gly Gly His Ser Ile Gly Glu
        115                 120                 125

Leu Ala Ala Ala His Val Ala Gly Val Leu Ser Leu Glu Asp Ala Cys
    130                 135                 140

Thr Leu Val Ala Ala Arg Ala Arg Leu Met Gln Ala Leu Pro Arg Gly
145                 150                 155                 160

Gly Ala Met Leu Ala Ile Arg Ala Thr Glu Asp Glu Val Thr Pro His
                165                 170                 175

Leu Thr Asp Asp Val Ser Ile Ala Ala Val Asn Gly Pro Thr Ser Val
            180                 185                 190

Val Val Ala Gly Thr Glu Glu Ala Val Ala Ala Ile Gly Ala Arg Phe
        195                 200                 205

Thr Ala Gln Asp Arg Lys Thr Thr Arg Leu Arg Val Ser His Ala Phe
    210                 215                 220

His Ser Pro Leu Met Asp Pro Met Leu Ala Glu Phe Arg Ala Val Ala
225                 230                 235                 240

Ala Gly Leu Thr Tyr His Glu Pro Arg Ile Pro Val Leu Ser Asn Leu
                245                 250                 255

Thr Gly Thr Val Ala Ala Val Ala Asp Leu Cys Ser Ala Asp Tyr Trp
            260                 265                 270

Val Arg His Val Arg Glu Ala Val Arg Phe Ala Asp Gly Val Thr Ala
        275                 280                 285

Leu Thr Asp Arg Gly Val Thr Thr Leu Val Glu Leu Gly Pro Asp Gly
    290                 295                 300

Val Leu Ser Ala Met Ala Gln Glu Ser Leu Pro Asp Gly Ala Ala Ala
305                 310                 315                 320

Val Pro Leu Leu Arg Lys Asp Arg Pro Glu Glu Leu Ser Ala Val Thr
                325                 330                 335

Gly Leu Ala Arg Ala His Val Arg Gly Val Thr Val Arg Trp Ala Gly
            340                 345                 350

Leu Phe Asp Gly Thr Gly Ala Arg Arg Ala Asp Leu Pro Thr Tyr Pro
        355                 360                 365

Phe Gln His Gln Arg Phe Trp Pro Thr Ala Ala Arg Ala Ala Gln Asp
    370                 375                 380

Val Thr Ala Ala Gly Leu Gly Ala Ala Asp His
385                 390                 395

<210> SEQ ID NO 95
<211> LENGTH: 367
<212> TYPE: PRT
<213> ORGANISM: Streptomyces noursei

<400> SEQUENCE: 95

Pro Asp Ala His Glu Gly His Ala Ala Gly Arg Thr Arg Cys Ala Ala
 1               5                  10                  15

Leu Phe Ser Gly Gln Gly Ala Gln Arg Leu Gly Met Gly Arg Glu Leu
                 20                  25                  30

His Ala Arg Phe Pro Val Phe Ala Arg Ala Leu Asp Thr Ala Val Asp
            35                  40                  45
```

```
Leu Leu Asp Ala Glu Leu Gly Gly Thr Leu Arg Glu Val Ile Trp Gly
 50                  55                  60
Thr Asp Asp Ala Pro Leu Asn Glu Thr Gly Phe Thr Gln Pro Ala Leu
 65                  70                  75                  80
Phe Ala Val Glu Val Ala Leu Tyr Arg Leu Ile Glu Ser Trp Gly Val
                 85                  90                  95
Ala Pro Asp Phe Val Ala Gly His Ser Ile Gly Glu Ile Ala Ala Ala
                100                 105                 110
His Val Ala Gly Val Phe Ser Leu Glu Asp Ala Cys Thr Leu Val Ala
                115                 120                 125
Ala Arg Ala Gly Leu Met Gln Ala Leu Pro Arg Gly Gly Ala Met Val
                130                 135                 140
Ala Val Glu Ala Thr Glu Asp Glu Val Ser Pro Leu Leu Thr Asp Gly
145                 150                 155                 160
Val Ala Ile Ala Ala Ile Asn Gly Pro Thr Ser Leu Val Val Ser Gly
                165                 170                 175
Asp Glu Thr Ala Thr Leu Ala Val Ala Ala Arg Leu Ala Glu Gln Gly
                180                 185                 190
Arg Arg Thr Thr Arg Leu Arg Val Ser His Ala Phe His Ser Pro Leu
                195                 200                 205
Met Asp Pro Met Leu Ala Glu Phe Arg Ala Val Ala Glu Gly Leu Ser
210                 215                 220
Tyr Gly Glu Pro Gln Ile Pro Val Val Ser Asn Leu Thr Gly Ala Val
225                 230                 235                 240
Ala Asp Gly Thr Leu Leu Gly Thr Ala Asp Tyr Trp Val Arg His Val
                245                 250                 255
Arg Glu Ala Val Arg Phe Ala Asp Gly Ile Arg Ala Leu Thr Asp Ala
                260                 265                 270
Gly Val Gly Ala Phe Leu Glu Leu Gly Pro Asp Gly Thr Leu Ala Ala
                275                 280                 285
Leu Ala Gln Gln Ser Ala Pro Asp Ala Val Ser Val Pro Val Leu Arg
                290                 295                 300
Lys Asp Arg Asp Glu Glu Pro Ala Ala Val Ala Ala Leu Ala Arg Leu
305                 310                 315                 320
His Thr Ala Gly Val Pro Val Asp Trp Thr Ala Phe Tyr Ala Gly Thr
                325                 330                 335
Gly Ala His Arg Thr Asp Leu Pro Thr Tyr Ala Phe Gln Tyr Glu Arg
                340                 345                 350
Tyr Trp Pro Lys Ala Thr Tyr Arg Pro Ala Asp Ala Thr Gly Leu
                355                 360                 365

<210> SEQ ID NO 96
<211> LENGTH: 374
<212> TYPE: PRT
<213> ORGANISM: Streptomyces noursei

<400> SEQUENCE: 96

Ile Ala Ala Asp Glu Ala Asp Ala Ala Ala Thr Gly Arg Val Gly
 1                   5                  10                  15
Ala Gly Arg His Ala Val Leu Phe Ser Gly Gln Gly Ala Gln Arg Leu
                 20                  25                  30
Gly Met Gly Arg Glu Leu Tyr Glu Arg Phe Pro Val Phe Ala Glu Ala
                 35                  40                  45
Leu Asp Val Val Val Asp His Leu Asp Ala Ala Leu Pro Ala Gln Ala
 50                  55                  60
```

```
Gly Leu Arg Glu Val Met Trp Gly Asp Asp Ala Glu Leu Leu Asn Glu
 65                  70                  75                  80

Thr Gly Trp Thr Gln Pro Ala Leu Phe Ala Ile Glu Val Ala Leu Phe
             85                  90                  95

Arg Leu Val Glu Ser Trp Gly Val Arg Pro Asp Phe Val Ala Gly His
            100                 105                 110

Ser Ile Gly Glu Ile Ala Ala His Val Ala Gly Val Phe Ser Leu
            115                 120                 125

Glu Asp Ala Cys Arg Leu Val Ala Ala Arg Ala Thr Leu Met Gln Ala
        130                 135                 140

Leu Pro Ala Gly Gly Ala Met Ile Ala Val Gln Ala Thr Glu Asp Glu
145                 150                 155                 160

Val Thr Pro His Leu Thr Asp Asp Val Ala Ile Ala Ala Ile Asn Gly
                165                 170                 175

Pro Asn Ala Leu Val Val Ser Gly Val Glu Asp Ala Ala Val Glu Ile
            180                 185                 190

Gly Ala Arg Phe Ala Ala Glu Gly Arg Arg Thr Thr Arg Leu His Val
        195                 200                 205

Ser His Ala Phe His Ser Pro Leu Met Asp Pro Met Leu Ala Glu Phe
    210                 215                 220

Arg Val Val Ala Glu Gly Leu Ser Tyr Ala Ala Pro Ser Leu Pro Val
225                 230                 235                 240

Val Ser Asn Leu Thr Gly Gln Val Ala Thr Ala Asp Glu Leu Cys Ser
                245                 250                 255

Ala Glu Tyr Trp Val Arg His Val Arg Glu Ala Val Arg Phe Ala Asp
            260                 265                 270

Gly Val Thr Ala Leu Glu Ala Glu Gly Val Arg Thr Phe Leu Glu Leu
        275                 280                 285

Gly Pro Asp Gly Val Leu Ala Ala Met Ala Gly Ala Ser Leu Thr Glu
    290                 295                 300

Ser Ser Leu Ala Val Pro Leu Leu Arg Lys Asp Arg Pro Glu Glu Pro
305                 310                 315                 320

Ala Ala Leu Ala Ala Leu Ala Gln Leu His Ile Ala Gly Ala Arg Val
                325                 330                 335

Asp Trp Pro Val Leu Phe Ala Gly Val Gly Ala Gly Arg Val Glu Leu
            340                 345                 350

Pro Thr Tyr Ala Phe Gln Arg Gly Trp Phe Trp Pro Val Gly Arg Val
        355                 360                 365

Gly Val Gly Gly Asp Val
    370
```

<210> SEQ ID NO 97
<211> LENGTH: 388
<212> TYPE: PRT
<213> ORGANISM: Streptomyces noursei

<400> SEQUENCE: 97

```
Ala Leu Ala Ala Leu Ser Gly Val Ala Asp Pro Ala Val Val Ser
  1               5                  10                  15

Asp Ala Val Ser Thr Gly Gly Ser Ala Val Leu Phe Thr Gly Gln Gly
             20                  25                  30

Ala Gln Arg Leu Gly Met Gly Arg Glu Leu Tyr Gly Arg Phe Pro Val
         35                  40                  45

Phe Ala Glu Ala Leu Asp Val Val Asp His Leu Asp Ala Ala Leu
     50                  55                  60
```

Pro Ala Gln Ala Gly Leu Arg Glu Val Met Trp Gly Asp Asp Val Glu
65                  70                  75                  80

Leu Leu Asn Glu Thr Gly Trp Thr Gln Pro Ala Leu Phe Ala Val Glu
            85                  90                  95

Val Ala Leu Phe Arg Leu Val Glu Arg Trp Gly Val Arg Pro Asp Phe
            100                 105                 110

Val Ala Gly His Ser Ile Gly Glu Ile Ala Ala His Val Ala Gly
            115                 120                 125

Val Phe Ser Leu Glu Asp Ala Cys Arg Leu Val Ala Ala Arg Ala Thr
        130                 135                 140

Leu Met Gln Ala Leu Pro Thr Gly Gly Ala Met Ile Ala Val Gln Ala
145                 150                 155                 160

Thr Glu Asp Glu Val Thr Pro His Leu Thr Asp Glu Val Ala Ile Ala
                165                 170                 175

Ala Val Asn Gly Pro Thr Ser Val Val Ile Ser Gly Ala Glu Glu Ala
            180                 185                 190

Thr Gln Thr Val Ala Gln His Phe Ala Asp Gln Gly Arg Arg Thr Thr
        195                 200                 205

Ala Leu Arg Val Ser His Ala Phe His Ser Pro Leu Met Asp Pro Met
210                 215                 220

Leu Ala Glu Phe Arg Ala Val Ala Glu Gly Leu Ser Tyr Ala Thr Pro
225                 230                 235                 240

Ser Leu Pro Val Val Ser Asn Leu Thr Gly Trp Leu Ala Thr Ala Asp
            245                 250                 255

Glu Leu Cys Ser Ala Glu Tyr Trp Val Arg His Val Arg Glu Ala Val
            260                 265                 270

Arg Phe Ala Asp Gly Ile Thr Thr Leu Glu Ala Glu Gly Val Arg Thr
        275                 280                 285

Phe Leu Glu Leu Gly Pro Asp Gly Ile Leu Ser Ala Leu Ala Gln Gln
        290                 295                 300

Ser Leu Ala Gly Glu Ala Val Thr Val Pro Val Leu Arg Lys Asp Arg
305                 310                 315                 320

Gly Glu Glu Ser Thr Ala Leu Thr Ala Arg Ala His Leu His Thr Arg
            325                 330                 335

Gly Leu Ile Glu Asp Trp Gln Asp Phe Phe Ala Gly Val Gly Ala Gly
            340                 345                 350

Arg Val Glu Leu Pro Thr Tyr Ala Phe Gln Arg Gly Trp Phe Trp Pro
            355                 360                 365

Val Gly Arg Val Gly Val Gly Asp Val Gly Ala Val Gly Leu Gly
            370                 375                 380

Ser Ala Gly His
385

<210> SEQ ID NO 98
<211> LENGTH: 385
<212> TYPE: PRT
<213> ORGANISM: Streptomyces noursei

<400> SEQUENCE: 98

Ala Val Arg Ala Leu Thr Ala Leu Ala Ala Asp Ala Asp Leu Ser
1               5                   10                  15

Ala Val Val Gly Asp Thr Arg Thr Gly Arg His Ala Val Leu Phe Ser
            20                  25                  30

Gly Gln Gly Ser Gln Arg Leu Gly Met Gly Arg Glu Leu Tyr Glu Arg
        35                  40                  45

Phe Pro Val Phe Ala Glu Ala Leu Asp Val Ala Ile Asp His Leu Asp
    50                  55                  60

Ala Ala Leu Pro Ala Gln Ala Ser Leu Arg Glu Val Met Trp Gly Asp
 65                  70                  75                  80

Asp Val Glu Leu Leu Asp Glu Thr Gly Trp Thr Gln Pro Ala Leu Phe
                 85                  90                  95

Ala Val Glu Val Ala Leu Phe Arg Leu Val Glu Ser Trp Gly Val Arg
                100                 105                 110

Pro Asp Phe Val Ala Gly His Ser Ile Gly Glu Ile Ala Ala Ala His
            115                 120                 125

Val Val Gly Val Phe Ser Leu Glu Asp Ala Cys Arg Leu Val Ala Ala
130                 135                 140

Arg Ala Thr Leu Met Gln Ala Leu Pro Thr Gly Gly Ala Met Ile Ala
145                 150                 155                 160

Ile Gln Ala Ala Glu Asp Glu Val Thr Gln His Leu Thr Asp Asp Val
                165                 170                 175

Ser Ile Ala Ala Val Asn Gly Pro Thr Ser Val Val Ser Gly Ala
            180                 185                 190

Glu Ser Ala Ala Arg Thr Val Ala Asp Arg Leu Ala Glu Asn Gly Arg
            195                 200                 205

Lys Thr Thr Arg Leu Arg Val Ser His Ala Phe His Ser Pro Leu Met
210                 215                 220

Asp Pro Met Leu Ala Glu Phe Arg Ala Val Ala Glu Gly Leu Ser Tyr
225                 230                 235                 240

Ala Thr Pro Thr Leu Pro Val Val Ser Asn Leu Thr Gly Arg Leu Ala
                245                 250                 255

Thr Ala Asp Asp Leu Cys Ser Ala Glu Tyr Trp Ala Arg His Val Arg
            260                 265                 270

Glu Ala Val Arg Phe Ala Asp Gly Val Ser Thr Leu Glu Asn Glu Gly
            275                 280                 285

Val Thr Thr Phe Leu Glu Leu Gly Pro Asp Gly Val Leu Ser Ala Met
290                 295                 300

Ala Gln Gln Ser Leu Thr Gly Asp Ala Ala Thr Val Pro Ala Leu Arg
305                 310                 315                 320

Lys Asp Arg Asp Glu Glu Thr Ser Ala Leu Thr Ala Leu Ala His Leu
                325                 330                 335

His Thr Ala Gly Leu Arg Val Asp Trp Ala Ala Phe Phe Ala Gly Ser
            340                 345                 350

Gly Ala Thr Arg Val Asp Leu Pro Thr Tyr Ala Phe Gln His Ala Thr
            355                 360                 365

Tyr Trp Pro Thr Gly Thr Leu Pro Thr Ala His Ala Ala Ala Val Gly
            370                 375                 380

Leu
385

<210> SEQ ID NO 99
<211> LENGTH: 389
<212> TYPE: PRT
<213> ORGANISM: Streptomyces noursei

<400> SEQUENCE: 99

Ala Thr Arg Ala Leu Ser Ala Leu Ala Thr Thr Ala Ala Ser Asp Pro
 1               5                  10                  15

Ser Ala Leu Thr Gly Thr Val Thr Met Gly Arg Cys Ala Val Leu Phe
                20                  25                  30

```
Ser Gly Gln Gly Ser Gln Arg Leu Gly Met Gly Arg Glu Leu Tyr Glu
         35                  40                  45

Arg Phe Pro Val Phe Ala Glu Ala Leu Asp Val Ile Asp His Leu
 50                  55                  60

Asp Ala Ala Leu Pro Ala Gln Ala Gly Leu Arg Glu Val Met Trp Gly
 65                  70                  75                  80

Asp Asp Val Glu Leu Leu Asn Glu Thr Gly Trp Thr Gln Pro Ala Leu
                 85                  90                  95

Phe Ala Ile Glu Val Ala Leu Phe Arg Leu Val Glu Ser Trp Gly Val
                100                 105                 110

Arg Pro Asp Phe Val Ala Gly His Ser Ile Gly Glu Ile Ala Ala Ala
            115                 120                 125

His Val Val Gly Val Phe Ser Leu Glu Asp Ala Cys Arg Leu Val Ala
        130                 135                 140

Ala Arg Ala Thr Leu Met Gln Ala Leu Pro Ala Gly Gly Ala Met Ile
145                 150                 155                 160

Ala Val Gln Ala Thr Glu Asp Glu Val Ile Pro His Leu Thr Asp Glu
                165                 170                 175

Val Ala Ile Ala Ala Val Asn Gly Pro Thr Ser Val Val Ile Ser Gly
            180                 185                 190

Ala Glu Glu Ala Thr Gln Thr Val Ala Gln His Phe Ala Asp Gln Gly
        195                 200                 205

Arg Arg Thr Thr Ala Leu Arg Val Ser His Ala Phe His Ser Pro Leu
210                 215                 220

Met Met Leu Ala Glu Phe Arg Ala Val Ala Glu Gly Leu Ser Tyr Ala
225                 230                 235                 240

Thr Pro Thr Leu Pro Val Val Ser Asn Leu Thr Gly Gln Val Ala Thr
                245                 250                 255

Ala Asp Glu Leu Cys Ser Ala Glu Tyr Trp Val Arg His Val Arg Glu
            260                 265                 270

Ala Val Arg Phe Ala Asp Gly Val Thr Ala Leu Glu Ala Glu Gly Val
        275                 280                 285

Arg Thr Phe Leu Glu Leu Gly Pro Asp Gly Val Leu Ala Ala Met Ala
290                 295                 300

Arg Glu Thr Val Ala Asp Asp Thr Val Thr Val Pro Val Leu Arg Arg
305                 310                 315                 320

Asn Met Pro Glu Glu Arg Thr Leu Leu Thr Ala Leu Gly Arg Leu His
                325                 330                 335

Thr Thr Gly Thr Pro Ile Asp Trp Ala Ala Leu Leu Ala Pro Thr Gly
            340                 345                 350

Ala Arg Pro Val Asp Leu Pro Thr Tyr Ala Phe Gln His Arg Pro Phe
        355                 360                 365

Trp Pro Ser Gly Pro Arg Asp Thr Ala Asp Ala Ala Val Gly Ile
370                 375                 380

Ala Gly Ala Ser His
385

<210> SEQ ID NO 100
<211> LENGTH: 399
<212> TYPE: PRT
<213> ORGANISM: Streptomyces noursei
```

```
<400> SEQUENCE: 100

His Arg Ala Val Val Leu Gly Thr Asp Arg Ala Glu Ala Leu Arg Ala
  1               5                  10                  15

Leu Thr Ala Leu Ala Ala Gly Glu Thr Asp Pro Ala Ala Leu Thr Gly
             20                  25                  30

Thr Val Arg Thr Gly Arg Thr Ala Phe Leu Phe Ser Gly Gln Gly Ser
         35                  40                  45

Gln Arg Leu Gly Met Gly Arg Val Leu Tyr Glu Arg Phe Pro Ala Phe
     50                  55                  60

Ala Glu Ala Leu Asp Thr Val Leu Thr Ala Leu Asp Ala Glu Leu Gly
 65                  70                  75                  80

His Pro Leu Arg Asp Ile Ile Trp Gly Glu Asp Ala Gln Leu Val Asp
                 85                  90                  95

Arg Thr Gly Tyr Thr Gln Pro Ala Leu Phe Ala Ile Glu Val Ala Leu
             100                 105                 110

Phe Arg Leu Leu Glu Ala Trp Gly Ile Thr Pro Asp Phe Val Ala Gly
         115                 120                 125

His Ser Ile Gly Glu Ile Ala Ala Ala His Val Ala Gly Val Leu Ser
     130                 135                 140

Leu Gly Asp Ala Cys Arg Leu Val Ala Arg Ala Val Leu Met Gln
145                 150                 155                 160

Ser Leu Pro Glu Gly Gly Ala Met Ile Ala Val Gln Ala Thr Glu Asp
                 165                 170                 175

Glu Val Leu Pro Leu Leu Thr Asp Asp Val Ser Ile Ala Ala Val Asn
             180                 185                 190

Ser Pro Thr Ser Val Val Val Ser Gly Tyr Glu Asn Ala Thr Leu Ala
         195                 200                 205

Val Ala Arg His Phe Ala Asp Gln Gly Arg Arg Thr Thr Arg Leu Arg
     210                 215                 220

Val Ser His Ala Phe His Ser Pro Leu Met Ala Pro Met Leu Asp Asp
225                 230                 235                 240

Phe Arg Ala Val Val Glu Ser Leu Thr Phe Thr Ala Pro Thr Thr Pro
                 245                 250                 255

Val Val Ser Asn Leu Thr Gly Glu Leu Ala Pro Ala Glu Ala Leu Cys
             260                 265                 270

Ser Ala Asp Tyr Trp Val Arg His Val Arg Glu Ala Val Arg Phe Ala
         275                 280                 285

Asp Gly Ile Arg Thr Leu Ala Asp Arg Gly Val Thr Thr Phe Val Glu
     290                 295                 300

Leu Gly Pro Asp Ser Val Leu Ser Ala Met Ala Gln Glu Ser Ala Pro
305                 310                 315                 320

Glu Gly Ala Gly Thr Ile Pro Leu Leu Arg Arg Asp Arg Pro Glu Glu
                 325                 330                 335

Gln Ala Val Leu Ala Ala Leu Cys His Leu Gln Val Leu Gly Val Glu
             340                 345                 350

Ala Asp Trp Ser Ala Thr Phe Arg Gly Leu Asp Pro Val Arg Val Asp
         355                 360                 365

Leu Pro Thr Tyr Ala Phe Gln His Arg Trp Phe Trp Pro Ala Ala Arg
     370                 375                 380

Pro Ala Arg Pro Asp Asp Val Arg Ala Ala Gly Leu Gly Ala Ala
385                 390                 395
```

<210> SEQ ID NO 101
<211> LENGTH: 388
<212> TYPE: PRT
<213> ORGANISM: Streptomyces noursei

<400> SEQUENCE: 101

Asp Gly Leu Arg Thr Gly Leu Thr Ala Val Ala Glu Gly Thr Thr Ala
1               5                   10                  15

Pro His Thr Ala Glu His His Leu Gln Gly Thr Gly Lys Arg Ala Val
            20                  25                  30

Leu Phe Ser Gly Gln Gly Ser Gln Arg Leu Gly Met Gly Arg Glu Leu
        35                  40                  45

His Glu Arg His Pro Val Phe Ala Glu Ala Phe Asp Ser Val Leu Ala
    50                  55                  60

Arg Leu Asp Asp Arg Leu Asp Thr Pro Leu Arg Asp Val Val Trp Gly
65                  70                  75                  80

Thr Asp Glu Glu Ala Leu His Ala Thr Gly Asn Thr Gln Pro Ala Leu
                85                  90                  95

Phe Ala Val Glu Val Ala Leu Tyr Arg Leu Ile Glu Ser Trp Gly Val
            100                 105                 110

Arg Pro Asp Phe Val Ala Gly His Ser Val Gly Glu Leu Ala Ala Ala
        115                 120                 125

His Val Ala Gly Val Leu Ser Leu Asp Asp Ala Cys Arg Leu Val Ala
    130                 135                 140

Ala Arg Ala Ala Leu Met Gln Arg Leu Pro Ala Gly Gly Ala Met Ile
145                 150                 155                 160

Ala Val Glu Ala Thr Glu Asp Glu Val Thr Pro Leu Leu Thr Asp Gly
                165                 170                 175

Val Ser Leu Ala Ala Val Asn Gly Pro Thr Ala Val Val Leu Ser Gly
            180                 185                 190

Ala Gly Asp Ala Val Thr Ala Leu Gly Gln Ala Leu Ala Glu Arg Gly
        195                 200                 205

His Arg Thr Thr Arg Leu Arg Val Ser His Ala Phe His Ser His Leu
    210                 215                 220

Met Asp Pro Met Leu Ala Asp Phe Arg Thr Val Ala Glu Gly Leu Glu
225                 230                 235                 240

Tyr His Pro Pro Arg Ile Pro Val Val Ser Asn Leu Thr Gly Asp Val
                245                 250                 255

Ala Asp Ala Ala Asp Leu Cys Ser Ala Asp Tyr Trp Val Arg His Val
            260                 265                 270

Arg Gly Thr Val Arg Phe Ala Asp Gly Val Arg Thr Met Ala Asp Arg
        275                 280                 285

Gly Val His Leu Phe Leu Glu Leu Gly Pro Asp Ala Val Leu Ser Ala
    290                 295                 300

Met Ala Arg Gln Cys Ala Pro Asp Ala Val Val Pro Ala Leu Arg
305                 310                 315                 320

Arg Asn Arg Asp Glu Asp Glu Thr Leu Val Gly Ala Val Ala Arg Leu
                325                 330                 335

His Val His Gly Ala Gly Pro Arg Trp Asp Ala Tyr Phe Ala Gly Arg
            340                 345                 350

Gly Ala Gln Trp Leu Asp Leu Pro Thr Tyr Pro Phe Gln Arg Gly Arg
        355                 360                 365

Phe Trp Pro Glu Ser Leu Pro Gly Ala Ala Ser Ala Ala Pro Ala Ala
        370                 375                 380

Gly Gln Pro Ala
385

<210> SEQ ID NO 102
<211> LENGTH: 378
<212> TYPE: PRT
<213> ORGANISM: Streptomyces noursei

<400> SEQUENCE: 102

Ala Asp Ala Val Glu His Ala Arg Gly Ala Ala His Gln Arg Arg Thr
  1               5                  10                  15

Ala Val Leu Phe Ser Gly Gln Gly Ser Gln Arg Pro Gly Met Gly Arg
             20                  25                  30

Glu Leu Ala Ala Arg Phe Pro Val Phe Ala Asp Ala Leu Asp Asp Ala
         35                  40                  45

Leu Arg Ala Leu Asp Arg His Leu Asp Gly Pro Val Arg Glu Val Met
 50                  55                  60

Trp Gly Thr Asp Ala Ala Leu Leu Asp Arg Thr Gly Trp Thr Gln Pro
 65                  70                  75                  80

Ala Leu Phe Ala Val Glu Val Ala Leu His Arg Leu Val Ala Ser Leu
                 85                  90                  95

Gly Val Thr Pro Asp Phe Val Gly Gly His Ser Val Gly Glu Ile Ala
            100                 105                 110

Ala Ala His Val Ala Gly Val Leu Ser Leu Glu Asp Ala Cys Arg Leu
        115                 120                 125

Val Ala Ala Arg Ala Thr Leu Met Gln Ala Leu Pro Ala Gly Gly Ala
130                 135                 140

Met Ala Ala Leu Glu Ala Thr Glu Asp Glu Val Ala Pro Leu Leu Gly
145                 150                 155                 160

Ala His Leu Ala Leu Ala Ala Val Asn Gly Pro Thr Ala Val Val Val
                165                 170                 175

Ala Gly Ala Glu Asp Ala Val Arg Gln Leu Thr Ala Arg Phe Ala Asp
            180                 185                 190

Arg Gly Arg Arg Thr Ser Arg Leu Ala Val Ser His Ala Phe His Ser
        195                 200                 205

Pro Leu Met Glu Pro Met Leu Asp Ala Phe Arg Asp Val Val Ser Arg
    210                 215                 220

Leu Thr Phe His Gln Pro Ser Ile Pro Leu Val Ser Asn Leu Thr Gly
225                 230                 235                 240

Glu Leu Ala Gly Ser Glu Ile Thr Ser Ala Glu Tyr Trp Val Arg His
                245                 250                 255

Val Arg Asp Thr Val Arg Phe Ala Asp Gly Ile Thr Ala Leu Ala Lys
            260                 265                 270

Ala Gly Ala Asp Val Leu Ile Glu Leu Gly Pro Gly Gly Val Leu Ser
        275                 280                 285

Ala Met Ala Arg Asp Thr Leu Gly Pro Asp Ser Thr Thr Asp Val Val
    290                 295                 300

Pro Ala Leu Ser Lys Gly Arg Pro Glu Glu Thr Ala Phe Ala Gly Ala
305                 310                 315                 320

Leu Gly Arg Leu His Thr Leu Gly Val Pro Val Asp Trp Pro Ala Phe
                325                 330                 335

Tyr Ala Gly Thr Gly Ala Arg Arg Val Glu Leu Pro Thr Tyr Ala Phe
            340                 345                 350

```
Gln His Val Arg His Trp Pro Thr Pro Pro Arg Pro Asn Gly Ala Gly
        355                 360                 365

Pro Gly Ala Leu Gly His Pro Leu Leu Gly
        370                 375

<210> SEQ ID NO 103
<211> LENGTH: 404
<212> TYPE: PRT
<213> ORGANISM: Streptomyces noursei

<400> SEQUENCE: 103

Val Val Ala Gln Asp Arg Asp Gln Leu Ile Ala Ser Leu Gly Ala Leu
  1               5                  10                  15

Ala Ala Asp Arg Pro Asp Pro Ala Val Val Glu Gly Glu Ala Ala Gly
             20                  25                  30

Arg Gly Arg Thr Ala Val Leu Phe Thr Gly Gln Gly Ser Gln Arg Ala
         35                  40                  45

Ala Met Gly Arg Glu Leu His Glu Val Gln Pro Glu Phe Ala Ala Ala
     50                  55                  60

Phe Asp Ala Val Cys Ala Val Phe Asp Pro Leu Leu Asp Arg Pro Leu
 65                  70                  75                  80

Arg Glu Val Val Phe Ala Glu Asp Gly Ser Asp Glu Ala Ala Leu Leu
                 85                  90                  95

Asp Glu Thr Gly Trp Thr Gln Pro Ala Leu Phe Ala Val Glu Val Ala
            100                 105                 110

Leu Phe Arg Leu Val Glu Ser Trp Gly Val Arg Pro Asp Phe Val Ala
        115                 120                 125

Gly His Ser Ile Gly Glu Ile Ala Ala Ala His Val Ala Gly Val Leu
    130                 135                 140

Thr Leu Glu Asp Ala Cys Arg Leu Val Ala Ala Arg Ala Thr Leu Met
145                 150                 155                 160

Gln Ala Leu Pro Thr Gly Gly Ala Met Ile Ala Ile Gln Ala Thr Glu
                165                 170                 175

Asp Glu Ile Ala Ala His Leu Asp Asp Thr Val Ala Ile Ala Ala Val
            180                 185                 190

Asn Gly Pro Gln Ser Val Val Ile Ser Gly Asp Glu Ala Ala Glu
        195                 200                 205

Thr Ile Ala Ala Thr Phe Ala Glu Arg Gly Arg Lys Thr Lys Arg Leu
    210                 215                 220

Arg Val Ser His Ala Phe His Ser Pro Arg Met Asp Gly Met Leu Asp
225                 230                 235                 240

Ala Phe Arg Ile Val Ala Glu Gly Leu Thr Tyr Arg Ala Pro Arg Ile
                245                 250                 255

Pro Leu Val Ser Asp Leu Thr Gly Arg Arg Ala Asp Asp Ala Glu Val
            260                 265                 270

Cys Thr Ala Glu Tyr Trp Val Arg His Val Arg Glu Ala Val Arg Phe
        275                 280                 285

Ala Asp Cys Val Arg Thr Leu Arg Asp Ala Gly Ala Thr Thr Phe Leu
    290                 295                 300

Glu Leu Gly Ser Asp Gly Leu Leu Thr Ala Met Ala Glu Asp Thr Leu
305                 310                 315                 320

Gly Asp Asp His Asp Ala Glu Leu Val Pro Met Leu Arg Ala Gly Arg
                325                 330                 335

Ala Glu Glu Leu Ala Ala Ala Thr Ala Leu Ala Arg Leu Gln Val Arg
            340                 345                 350
```

```
Gly Val Asp Val Asp Trp Ala Ala Tyr Leu Ala Gly Thr Gly Ala Arg
        355                 360                 365

Arg Thr Asp Leu Pro Thr Tyr Ala Phe Gln His Ala Tyr Tyr Trp Pro
        370                 375                 380

Gln Leu Pro Thr Pro Ala Ala Ala Leu Ala Ala Ala Asp Pro Ala Asp
385                 390                 395                 400

Gln Gln Leu Trp

<210> SEQ ID NO 104
<211> LENGTH: 380
<212> TYPE: PRT
<213> ORGANISM: Streptomyces noursei

<400> SEQUENCE: 104

Glu Gly Gly Ala Val Thr Glu Val Ala Arg Gly Ala Val Pro Thr Gly
  1               5                  10                  15

Asp Arg Gly Gly Leu Ala Val Leu Phe Ser Gly Gln Gly Ser Gln Arg
                 20                  25                  30

Pro Gly Met Gly Arg Glu Leu His Ala Arg Tyr Pro Val Phe Ala Ala
             35                  40                  45

Ala Phe Asp Glu Thr Val Ala Leu Leu Asp Ala Arg Leu Gly Thr Ser
         50                  55                  60

Leu Arg Asp Ile Val Trp Asp Gln Asp Arg Thr Arg Leu Asp Asp Thr
 65                  70                  75                  80

Arg His Thr Gln Pro Ala Leu Phe Ala Val Glu Val Ala Leu Tyr Arg
                 85                  90                  95

Leu Leu Ala Ser Trp Gly Ile Arg Pro Asp His Val Thr Gly His Ser
                100                 105                 110

Ile Gly Glu Ile Thr Ala Ala His Val Ala Gly Val Leu Thr Leu Ala
            115                 120                 125

Asp Ala Cys Thr Leu Val Ala Ala Arg Ala Thr Ala Met Ser Glu Leu
        130                 135                 140

Pro Pro Gly Gly Ala Met Val Ala Leu Glu Ala Thr Glu Asp Glu Val
145                 150                 155                 160

Arg Pro Leu Leu Thr Asp Asp Leu Ala Ile Ala Ala Val Asn Ala Pro
                165                 170                 175

Arg Ser Val Val Ala Gly Ala Glu Asp Ala Ala Leu Ala Val Arg
            180                 185                 190

Arg His Phe Asp Asp Leu Gly Arg Arg Thr Thr Arg Leu Pro Val Ser
        195                 200                 205

His Ala Phe His Ser Pro Leu Met Asp Pro Met Leu Asp Ala Phe Arg
    210                 215                 220

Thr Ala Leu Ala Pro Leu Thr Phe Ala Glu Pro Glu Ile Pro Val Val
225                 230                 235                 240

Ser Asn Leu Thr Gly Leu Pro Ala Thr Ala Glu Glu Leu Ala Thr Pro
                245                 250                 255

His Tyr Trp Val Cys His Val Arg Gln Ala Val Arg Phe Gly Asp Gly
            260                 265                 270

Val Arg Ala Leu Ala Asp Arg Gly Val Arg Thr Phe Leu Glu Leu Gly
        275                 280                 285

Pro Asp Gly Val Leu Ser Ala Leu Val Arg Glu Asn Leu Pro Glu Pro
    290                 295                 300

Gly Leu Val Ala Val Pro Val Leu Arg Lys Glu Arg Pro Glu Glu Thr
305                 310                 315                 320
```

```
Thr Val Leu Ala Ala Leu Gly Thr Leu Trp Ala His Gly Ala Asp Val
            325                 330                 335

Asp Trp Asp Ala Val Phe Ala Gly Thr Arg Thr Pro Gln Ala Asp Pro
            340                 345                 350

Val Glu Leu Pro Thr Tyr Ala Phe Gln Arg Ala Arg Tyr Trp Pro Thr
            355                 360                 365

Leu Gly Ala Arg His Gly Asp Pro Ala Asp Leu Gly
            370                 375                 380

<210> SEQ ID NO 105
<211> LENGTH: 389
<212> TYPE: PRT
<213> ORGANISM: Streptomyces noursei

<400> SEQUENCE: 105

Leu Leu Ala Gly Pro Asp Gly Val Arg Glu Ala Ala Arg Ala Ala Ala
  1               5                  10                  15

Pro Arg Thr Pro Gly Arg Thr Ala Phe Leu Phe Ser Gly Gln Gly Ala
             20                  25                  30

Gln His Ala Leu Met Gly His Asp Leu Tyr Gln Arg Phe Pro Val Tyr
         35                  40                  45

Ala Asp Ala Leu Asp Thr Val Leu Ala Gln Phe Asp Thr Val Leu Asp
     50                  55                  60

Val Pro Leu Arg Ala Ala Leu Phe Ala Ala Pro Gly Thr Pro Glu Ala
 65                  70                  75                  80

Ala Leu Leu Asp Gln Thr Gly Phe Thr Gln Pro Ala Leu Phe Ala Val
                 85                  90                  95

Glu Val Ala Leu Phe Arg Leu Ala Glu Ser Trp Arg Leu Thr Pro Asp
            100                 105                 110

Phe Val Ala Gly His Ser Ile Gly Glu Ile Ala Ala His Val Ala
            115                 120                 125

Gly Val Phe Ser Leu Glu Asp Ala Cys Thr Leu Val Ala Ala Arg Ala
        130                 135                 140

Ser Leu Met Gln Gln Leu Pro Arg Asp Gly Ala Met Val Ala Leu Glu
145                 150                 155                 160

Ala Thr Glu Asp Glu Val Ala Pro Leu Leu Thr Asp Gly Val Ala Leu
                165                 170                 175

Ala Ala Val Asn Gly Pro Arg Ser Val Val Ala Gly Ala Glu Asp
            180                 185                 190

Ala Val Arg Ala Val Ala Asp Arg Leu Ala Ala Asp Gly Arg Arg Thr
        195                 200                 205

Arg Arg Leu Thr Val Ser His Ala Phe His Ser Pro Leu Met Asp Pro
    210                 215                 220

Met Leu Thr Asp Phe Ala Arg Val Ala Glu Gly Leu Thr Tyr His Glu
225                 230                 235                 240

Pro Arg Ile Pro Leu Val Ser Thr Leu Leu Gly Ala Pro Ala Gly Ala
                245                 250                 255

Glu Leu Arg Thr Pro Asp Tyr Trp Val Arg His Val Arg Glu Thr Val
            260                 265                 270

Arg Phe Ala Asp Gly Val Arg Ala Leu His Asp Ala Gly Ala Gly Thr
        275                 280                 285

Phe Val Glu Ile Gly Pro Asp Gly Val Leu Thr Ala Leu Thr Gln Gln
    290                 295                 300

Thr Leu Asp Thr Val Glu Ala Gly Ala Pro Ala Val Val Val Pro Leu
305                 310                 315                 320
```

```
Gln Arg Arg Asp Arg Ala Gly Asp Leu Ala Leu Leu Glu Gly Leu Ala
                325                 330                 335
Thr Leu His Thr His Gly Thr Gly Pro Ser Trp Pro Ala Tyr Phe Glu
            340                 345                 350
Ala Thr Gly Gly His Arg Thr Asp Leu Pro Thr Tyr Ala Phe Gln Arg
        355                 360                 365
Glu Arg Tyr Trp Pro Glu Leu Gly Ala Pro Val Ala Thr Ala Pro Gln
    370                 375                 380
Asp Pro Ala Ala Trp
385

<210> SEQ ID NO 106
<211> LENGTH: 406
<212> TYPE: PRT
<213> ORGANISM: Streptomyces avermitilis

<400> SEQUENCE: 106

Leu His Ala Leu Asp Ala Leu Ala Gly Gly Arg Pro Val Pro Gly Val
  1               5                  10                  15
Val Glu Gly Arg Thr Thr Ser Gly Glu Leu Ala Val Leu Phe Ala Gly
                 20                  25                  30
Gln Gly Thr Gln Arg Ala Gly Met Gly Arg Glu Leu Tyr Glu Ala Tyr
             35                  40                  45
Pro Val Phe Ala Gln Ala Ile Asp Glu Ile Cys Ala Glu Ala Asp Thr
 50                  55                  60
Ala Arg Thr Asp Pro Gly Ala Pro Gly Leu Arg Asp Val Leu Phe Ala
 65                  70                  75                  80
Pro Gln Asp Ser Pro Glu Gly Arg Leu Ile Glu Asp Thr Gly Phe Ala
                 85                  90                  95
Gln Pro Ala Leu Phe Ala Phe Glu Val Ala Leu Phe Arg Leu Leu Glu
            100                 105                 110
Thr Trp Gly Leu Thr Pro Asp Tyr Val Leu Gly His Ser Val Gly Glu
        115                 120                 125
Leu Ala Ala Ala His Val Ala Gly Met Leu Cys Leu Ala Asp Ala Val
    130                 135                 140
Ala Leu Val Val Ala Arg Gly Arg Leu Met Gln Gly Leu Pro Ser Gly
145                 150                 155                 160
Gly Ala Met Val Ala Ile Glu Ala Ser Glu Asp Ile Leu Pro Leu
                165                 170                 175
Pro Asp Glu Tyr Ala Ser Arg Val Ala His Ala Val Asn Gly Pro
            180                 185                 190
Arg Ser Ile Val Leu Ser Gly Asp Glu Asp Ala Val Leu Asp Leu Ala
        195                 200                 205
Gln Gln Trp Ala Ala Arg Gly Arg Thr Arg Arg Leu Arg Thr Ser
    210                 215                 220
His Ala Phe His Ser Pro His Met Asp Ala Met Leu Gly Asp Phe Arg
225                 230                 235                 240
Arg Ala Ala Glu Gln Val Thr Phe Ser Ala Pro Arg Ile Pro Val Val
                245                 250                 255
Ser Asn Val Thr Gly Ala Pro Leu Pro Ala Glu Thr Met Cys Thr Pro
            260                 265                 270
Asp Tyr Trp Val Glu His Ala Arg Ser Thr Val Arg Phe Ala Asp Gly
        275                 280                 285
Ile Ser Trp Leu Gln Glu Gln Gly Val Thr Thr Cys Leu Glu Ile Gly
    290                 295                 300
```

```
Pro Asp Gly Thr Leu Ser Ala Leu Ala Gln Asp Ser Leu Ser Ala Pro
305                 310                 315                 320

Ala Arg Ala Ile Pro Ala Leu Arg Pro Asp Gln Pro Glu Ala Arg Ser
            325                 330                 335

Val Met Thr Ala Leu Ala Glu Leu Phe Val Ala Gly Thr Ala Val Glu
            340                 345                 350

Trp Ala Gly Val Phe Glu Gly Thr Ala Arg Glu Val Gly Asp Gly Cys
        355                 360                 365

Gly Val Glu Leu Pro Thr Tyr Ala Phe Glu Arg Glu Arg Phe Trp Leu
    370                 375                 380

Asp Val Glu Glu Gly Ser Ala Gly Gly Ser Gly Val Ser Gly Met Trp
385                 390                 395                 400

Gly Gly Pro Leu Trp Glu
            405

<210> SEQ ID NO 107
<211> LENGTH: 379
<212> TYPE: PRT
<213> ORGANISM: Amycolatopsis mediterranei

<400> SEQUENCE: 107

Arg Ala Val Val Leu Ala Ser Asp Arg Ala Gln Leu Cys Ala Asp Leu
1               5                   10                  15

Ala Ala Phe Gly Ser Gly Val Val Thr Gly Thr Pro Val Asp Gly Lys
            20                  25                  30

Leu Ala Val Leu Phe Thr Gly Gln Gly Ser Gln Trp Ala Gly Met Gly
        35                  40                  45

Arg Glu Leu Ala Glu Thr Phe Pro Val Phe Arg Asp Ala Phe Glu Ala
    50                  55                  60

Ala Cys Glu Ala Val Asp Thr His Leu Arg Glu Arg Pro Leu Arg Glu
65                  70                  75                  80

Val Val Phe Asp Asp Ser Ala Leu Leu Asp Gln Thr Met Tyr Thr Gln
                85                  90                  95

Gly Ala Leu Phe Ala Val Glu Thr Ala Leu Phe Arg Leu Phe Glu Ser
            100                 105                 110

Trp Gly Val Arg Pro Gly Leu Leu Ala Gly His Ser Ile Gly Glu Leu
        115                 120                 125

Ala Ala Ala His Val Ser Gly Val Leu Asp Leu Ala Asp Ala Gly Glu
    130                 135                 140

Leu Val Ala Ala Arg Gly Arg Leu Met Gln Ala Leu Pro Ala Gly Gly
145                 150                 155                 160

Ala Met Val Ala Val Gln Ala Thr Glu Asp Glu Val Ala Pro Leu Leu
                165                 170                 175

Asp Gly Thr Val Cys Val Ala Ala Val Asn Gly Pro Asp Ser Val Val
            180                 185                 190

Leu Ser Gly Thr Glu Ala Ala Val Leu Ala Val Ala Asp Glu Leu Ala
        195                 200                 205

Gly Arg Gly Arg Lys Thr Arg Arg Leu Ala Val Ser His Ala Phe His
    210                 215                 220

Ser Pro Leu Met Glu Pro Met Leu Asp Asp Phe Arg Ala Val Ala Glu
225                 230                 235                 240

Arg Leu Thr Tyr Arg Ala Gly Ser Leu Pro Val Val Ser Thr Leu Thr
                245                 250                 255

Gly Glu Leu Ala Ala Leu Asp Ser Pro Asp Tyr Trp Val Gly Gln Val
            260                 265                 270
```

```
Arg Asn Ala Val Arg Phe Ser Asp Ala Val Thr Ala Leu Gly Ala Gln
            275                 280                 285

Gly Ala Ser Thr Phe Leu Glu Leu Gly Pro Gly Gly Ala Leu Ala Ala
        290                 295                 300

Met Ala Leu Gly Thr Leu Gly Gly Pro Glu Gln Ser Cys Val Ala Thr
305                 310                 315                 320

Leu Arg Lys Asn Gly Ala Glu Val Pro Asp Val Leu Thr Ala Leu Ala
                325                 330                 335

Glu Leu His Val Arg Gly Val Gly Val Asp Trp Thr Thr Val Leu Asp
            340                 345                 350

Glu Pro Ala Thr Ala Val Gly Thr Val Leu Pro Thr Tyr Ala Phe Gln
        355                 360                 365

His Gln Arg Phe Trp Val Asp Val Asp Glu Thr
        370                 375

<210> SEQ ID NO 108
<211> LENGTH: 393
<212> TYPE: PRT
<213> ORGANISM: Streptomyces cinnamonensis

<400> SEQUENCE: 108

Ala Leu Ala Ala Gly Arg Ala His Pro Ala Leu Thr Arg Ala Ala Gly
1               5                  10                  15

Pro Ala Arg Asn Gly Gly Thr Ala Phe Leu Phe Thr Gly Gln Gly Ser
                20                  25                  30

Gln Arg Pro Gly Met Gly Arg Gln Leu Tyr Asp Thr Phe Asp Val Phe
            35                  40                  45

Ala Glu Ser Leu Asp Glu Thr Cys Ala Arg Leu Asp Pro Leu Leu Glu
        50                  55                  60

Gln Pro Leu Lys Pro Val Leu Phe Ala Pro Ala Asp Thr Ala Gln Ala
65                  70                  75                  80

Ala Val Leu His Gly Thr Gly Met Thr Gln Ala Ala Leu Phe Ala Leu
                85                  90                  95

Glu Val Ala Leu Tyr Arg Gln Val Thr Ser Phe Gly Ile Ala Pro Ser
            100                 105                 110

His Leu Thr Gly His Ser Val Gly Glu Ile Ala Ala His Val Ala
        115                 120                 125

Gly Val Phe Ser Leu Ala Asp Ala Cys Thr Leu Val Ala Ala Arg Gly
    130                 135                 140

Arg Leu Met Gln Ala Leu Pro Ala Gly Gly Ala Met Leu Ala Val Gln
145                 150                 155                 160

Ala Ala Glu Asp Asp Val Leu Pro Leu Leu Ala Gly Gln Glu Glu Arg
                165                 170                 175

Leu Ser Leu Ala Ala Val Asn Gly Pro Thr Ala Val Val Val Ser Gly
            180                 185                 190

Glu Ala Ala Ala Val Gly Glu Val Glu Lys Ala Leu Arg Gly Arg Gly
        195                 200                 205

Leu Lys Thr Lys Arg Leu Asn Val Ser His Ala Phe His Ser Pro Leu
    210                 215                 220

Ile Glu Pro Met Leu Asp Asp Phe Arg Glu Val Ala Arg Gly Leu Thr
225                 230                 235                 240

Phe His Ala Pro Thr Leu Pro Val Val Ser Asn Leu Thr Gly Arg Leu
                245                 250                 255

Ala Asp Ala Glu Leu Met Ala Asp Ala Glu Tyr Trp Val Arg His Val
            260                 265                 270
```

-continued

```
Arg Arg Pro Val Arg Phe His Asp Gly Leu Arg Ala Leu Ser Glu Gln
        275                 280                 285

Gly Val Val Arg Tyr Leu Glu Leu Gly Pro Asp Pro Val Leu Ala Thr
    290                 295                 300

Met Val Gln Asp Gly Leu Pro Ala Pro Ala Glu Gly Glu Pro Glu
305                 310                 315                 320

Pro Val Val Ala Ala Leu Arg Ser Lys His Asp Glu Gly Arg Thr
                325                 330                 335

Leu Leu Gly Ala Val Ala Ala Leu His Thr Asp Gly Gln Pro Ala Asp
                340                 345                 350

Leu Thr Ala Leu Phe Pro Ala Asp Ala Gly Gln Val Pro Leu Pro Thr
                355                 360                 365

Tyr Arg Phe Gln Arg Arg Tyr Trp Arg Val Ala Pro Asp Ala Ala
            370                 375                 380

Ala Pro Ala Arg Ala Ala Gly Leu Gln
385                 390

<210> SEQ ID NO 109
<211> LENGTH: 421
<212> TYPE: PRT
<213> ORGANISM: Streptomyces avermitilis

<400> SEQUENCE: 109

Gln Ala Leu Asp Ala Leu Ala Glu Gly Arg Ser Ala Asp Gly Leu Ile
  1               5                   10                  15

Glu Gly Ser Val Gly Pro Arg Gly Gly His Ser Gly Arg Arg Gly
            20                  25                  30

Lys Thr Ala Met Leu Phe Ala Gly Gln Gly Thr Gln Arg Val Gly Met
        35                  40                  45

Gly Arg Gln Leu Tyr Ala Ala His Pro Ala Tyr Ala Asp Ala Leu Asp
    50                  55                  60

Gln Val Leu Ala Glu Leu Asp Gly His Leu Asp Gln Pro Leu Arg Pro
 65                  70                  75                  80

Leu Ile His Ala Ser Ala Asp Leu Ala Asp Val Ala Asp Ala Ala Asp
                85                  90                  95

Val Leu Asp Arg Thr Arg Tyr Ala Gln Pro Ala Leu Phe Ala Val Gln
                100                 105                 110

Val Ala Leu Phe Arg His Leu Glu Arg Leu Gly Val Arg Ala Asp Phe
            115                 120                 125

Val Ala Gly His Ser Ile Gly Glu Leu Ala Ala His Val Ala Gly
    130                 135                 140

Val Leu Pro Leu Ala Ala Ala Cys Arg Leu Val Ala Ala Arg Gly Arg
145                 150                 155                 160

Leu Met Glu Gln Leu Ala Pro Gly Ala Met Val Ala Val Arg Ala
                165                 170                 175

Ser Glu Ala Glu Ala Arg Gln Ala Leu Asp Gly Arg Glu Ala Arg Val
            180                 185                 190

Ser Val Ala Ala Val Asn Gly Pro Ala Ser Val Phe Ser Gly Ala
    195                 200                 205

Glu Asp Glu Val Gly Asn Met Ala Asp Trp Phe Ala Glu Arg Gly Arg
    210                 215                 220

Arg Val Lys Arg Leu Arg Thr Gly His Ala Phe His Ser Pro Leu Met
225                 230                 235                 240

Asp Pro Met Leu Glu Glu Phe Gln Gln Val Ala Ala Ser Leu Thr Tyr
                245                 250                 255
```

```
Ser Glu Pro Ala Ile Pro Met Val Ser Thr Leu Thr Gly Asp Ile Val
            260                 265                 270

Ala Ala Gly Glu Leu Ser Asp Pro Glu Tyr Trp Val Arg Gln Val Arg
        275                 280                 285

Arg Thr Val Arg Phe Gly Asp Ala Ile Ser Arg Leu His Thr Asp Gly
    290                 295                 300

Val Arg Thr Phe Met Glu Leu Gly Pro Asp Gly Thr Leu Ser Ala Leu
305                 310                 315                 320

Ala Glu Glu Cys Leu Glu Ala Thr Ala Asp Ser His Pro Ala Asp Asp
            325                 330                 335

Asp Thr Gly Thr Pro Gln Glu Asn Leu Leu Ile Pro Leu Leu Arg Pro
        340                 345                 350

Asp Ser Pro Glu Pro Gly Thr Leu Leu Thr Gly Leu Ala Arg Leu His
    355                 360                 365

Thr His Gly Ala Ala Ala Val Asn Trp Pro Ala Ala Leu Pro Glu Arg
370                 375                 380

Asp Arg Ala Arg His Leu Asp Leu Pro Thr Tyr Ala Phe Asp His His
385                 390                 395                 400

Arg Tyr Trp Val Asp Thr Ser Ala Gly His Pro Gly Asp Leu Ser Ala
            405                 410                 415

Ala Gly Leu Gly Thr
            420

<210> SEQ ID NO 110
<211> LENGTH: 406
<212> TYPE: PRT
<213> ORGANISM: Amycolatopsis mediterranei

<400> SEQUENCE: 110

Gly Arg Ala Leu Leu Gly Asp Arg Ala Val Val Ala Gly Thr Asp
  1               5                  10                  15

Glu Asp Ala Val Ala Gly Leu Arg Ala Leu Ala Arg Gly Asp Arg Ala
                20                  25                  30

Pro Gly Val Leu Thr Gly Ser Ala Lys His Gly Lys Val Val Tyr Val
            35                  40                  45

Phe Pro Gly Gln Gly Ser Gln Arg Leu Gly Met Gly Arg Glu Leu Tyr
        50                  55                  60

Asp Arg Tyr Pro Val Phe Ala Thr Ala Phe Asp Glu Ala Cys Glu Gln
65                  70                  75                  80

Leu Asp Val Cys Leu Ala Gly Arg Ala Gly His Arg Val Arg Asp Val
                85                  90                  95

Val Leu Gly Glu Val Pro Ala Glu Thr Gly Leu Leu Asn Gln Thr Val
            100                 105                 110

Phe Thr Gln Ala Gly Leu Phe Ala Val Glu Ser Ala Leu Phe Arg Leu
        115                 120                 125

Ala Glu Ser Trp Gly Val Arg Pro Asp Val Val Leu Gly His Ser Ile
    130                 135                 140

Gly Glu Ile Thr Ala Ala Tyr Ala Ala Gly Val Phe Ser Leu Pro Asp
145                 150                 155                 160

Ala Ala Arg Ile Val Ala Ala Arg Gly Arg Leu Met Gln Ala Leu Ala
                165                 170                 175

Pro Gly Gly Ala Met Val Ala Val Ala Ser Glu Ala Glu Val Ala
            180                 185                 190

Glu Leu Leu Gly Asp Gly Val Glu Leu Ala Ala Val Asn Gly Pro Ser
        195                 200                 205
```

```
Ala Val Val Leu Ser Gly Asp Ala Asp Ala Val Val Ala Ala Ala
    210                 215                 220

Arg Met Arg Glu Arg Gly His Lys Thr Lys Gln Leu Lys Val Ser His
225                 230                 235                 240

Ala Phe His Ser Ala Arg Met Ala Pro Met Leu Ala Glu Phe Ala Ala
                245                 250                 255

Glu Leu Ala Gly Val Thr Trp Arg Glu Pro Glu Ile Pro Val Val Ser
                260                 265                 270

Asn Val Thr Gly Arg Phe Ala Glu Pro Gly Glu Leu Thr Glu Pro Gly
                275                 280                 285

Tyr Trp Ala Glu His Val Arg Arg Pro Val Arg Phe Ala Glu Gly Val
    290                 295                 300

Ala Ala Ala Thr Glu Ser Gly Gly Ser Leu Phe Val Glu Leu Gly Pro
305                 310                 315                 320

Gly Ala Ala Leu Thr Ala Leu Val Glu Glu Thr Ala Glu Val Thr Cys
                325                 330                 335

Val Ala Ala Leu Arg Asp Asp Arg Pro Glu Val Thr Ala Leu Ile Thr
                340                 345                 350

Ala Val Ala Glu Leu Phe Val Arg Gly Val Ala Val Asp Trp Pro Ala
            355                 360                 365

Leu Leu Pro Pro Val Thr Gly Phe Val Asp Leu Pro Lys Tyr Ala Phe
370                 375                 380

Asp Gln Gln His Tyr Trp Leu Gln Pro Ala Ala Gln Ala Thr Asp Ala
385                 390                 395                 400

Ala Ser Leu Gly Gln Val
                405

<210> SEQ ID NO 111
<211> LENGTH: 412
<212> TYPE: PRT
<213> ORGANISM: Streptomyces cinnamonensis

<400> SEQUENCE: 111

Leu Ala Glu Gly Ala Glu Thr Ala Ser Ile Val Arg Gly Glu Ala Tyr
  1               5                  10                  15

Thr Glu Gly Arg Thr Ala Phe Leu Phe Ser Gly Gln Gly Ala Gln Arg
                20                  25                  30

Leu Gly Met Gly Arg Glu Leu Tyr Ala Val Phe Pro Val Phe Ala Asp
            35                  40                  45

Ala Leu Asp Glu Ala Phe Ala Ala Leu Asp Val His Leu Asp Arg Pro
 50                  55                  60

Leu Arg Glu Ile Val Leu Gly Glu Thr Asp Ser Gly Gly Asn Val Ser
 65                  70                  75                  80

Gly Glu Asn Val Ile Gly Glu Gly Ala Asp His Gln Ala Leu Leu Asp
                85                  90                  95

Gln Thr Ala Tyr Thr Gln Pro Ala Leu Phe Ala Ile Glu Thr Ser Leu
            100                 105                 110

Tyr Arg Leu Ala Ala Ser Phe Gly Leu Lys Pro Asp Tyr Val Leu Gly
        115                 120                 125

His Ser Val Gly Glu Ile Ala Ala Ala His Val Ala Gly Val Leu Ser
    130                 135                 140

Leu Pro Asp Ala Ser Ala Leu Val Ala Thr Arg Gly Arg Leu Met Gln
145                 150                 155                 160

Ala Val Arg Ala Pro Gly Ala Met Ala Ala Trp Gln Ala Thr Ala Asp
                165                 170                 175
```

-continued

Glu Ala Ala Glu Gln Leu Ala Gly His Glu Arg His Val Thr Val Ala
                180                 185                 190

Ala Val Asn Gly Pro Asp Ser Val Val Ser Gly Asp Arg Ala Thr
        195                 200                 205

Val Asp Glu Leu Thr Ala Ala Trp Arg Gly Arg Gly Arg Lys Ala His
    210                 215                 220

His Leu Lys Val Ser His Ala Phe His Ser Pro His Met Asp Pro Ile
225                 230                 235                 240

Leu Asp Glu Leu Arg Ala Val Ala Ala Gly Leu Thr Phe His Glu Pro
                245                 250                 255

Val Ile Pro Val Val Ser Asn Val Thr Gly Glu Leu Val Thr Ala Thr
            260                 265                 270

Ala Thr Gly Ser Gly Ala Gly Gln Ala Asp Pro Glu Tyr Trp Ala Arg
        275                 280                 285

His Ala Arg Glu Pro Val Arg Phe Leu Ser Gly Val Arg Gly Leu Cys
    290                 295                 300

Glu Arg Gly Val Thr Thr Phe Val Glu Leu Gly Pro Asp Ala Pro Leu
305                 310                 315                 320

Ser Ala Met Ala Arg Asp Cys Phe Pro Ala Pro Ala Asp Arg Ser Arg
                325                 330                 335

Pro Arg Pro Ala Ala Ile Ala Thr Cys Arg Arg Gly Arg Asp Glu Val
            340                 345                 350

Ala Thr Phe Leu Arg Ser Leu Ala Gln Ala Tyr Val Arg Gly Ala Asp
        355                 360                 365

Val Asp Phe Thr Arg Ala Tyr Gly Ala Thr Ala Thr Arg Arg Phe Pro
    370                 375                 380

Leu Pro Thr Tyr Pro Phe Gln Arg Glu Arg His Trp Pro Ala Ala Ala
385                 390                 395                 400

Gly Val Gly Gln Gln Pro Glu Thr Pro Glu Leu Pro
                405                 410

<210> SEQ ID NO 112
<211> LENGTH: 512
<212> TYPE: PRT
<213> ORGANISM: Streptomyces fradiae

<400> SEQUENCE: 112

Ser Val Pro Ala Gly Glu Pro Pro Ala Ala Gly Arg Pro Glu Asp Thr
1               5                   10                  15

Gly Gly Ala Trp Thr Val Ser Gly Arg Gly Pro Ala Ala Leu Arg Ala
            20                  25                  30

Gln Ala Ala Arg Leu Tyr Asp Ala Leu Thr Gly Thr Gly Thr Gly Thr
        35                  40                  45

Gly Gln Gly Ala Gly Gln Gly Ala Gly Pro Gly Thr Ala Glu Val Ala
    50                  55                  60

Gly Ala Leu Ala His Ala Arg Thr Ala Phe Arg His Arg Ala Val Val
65                  70                  75                  80

Leu Gly Gly Asn Arg Ala Glu Leu Leu Ala Gly Leu Arg Glu Leu Ala
                85                  90                  95

Glu Glu Glu His Pro Gly Pro Arg Val Val Thr Gly Thr Ala Pro Ala
            100                 105                 110

Thr Glu Arg Arg Thr Ala Phe Leu Phe Ser Gly Gln Gly Ser Gln Arg
        115                 120                 125

Ala Gly Ser Gly Arg Gly Leu Tyr Arg Arg His Pro Val Phe Ala Arg
    130                 135                 140

```
Ala Leu Asp Glu Val Cys Ala Ala Leu Glu Pro His Leu His Arg Pro
145                 150                 155                 160

Leu Arg Asp Leu Met Phe Ala Glu Pro Gly Ser Pro Glu Ala Glu Pro
            165                 170                 175

Leu Asp Arg Thr Glu Phe Thr Gln Pro Ala Leu Phe Ala Leu Gln Thr
            180                 185                 190

Ala Leu Phe Arg Leu Ala Glu His His Gly Leu Arg Ala Glu Ala Leu
        195                 200                 205

Cys Gly His Ser Val Gly Glu Ile Ala Ala His Ala Ala Gly Val
    210                 215                 220

Leu Thr Leu Pro Asp Ala Ala Arg Leu Val Ala Arg Gly Arg Leu
225                 230                 235                 240

Met Gln Ala Leu Pro Ala Gly Gly Ala Met Ala Ala Leu Arg Ala Thr
                245                 250                 255

Ala Glu Glu Ile Ala Pro Leu Leu Glu Arg Arg Ala Gly Glu Leu Ala
            260                 265                 270

Leu Ala Ala Val Asn Gly Pro Ser Ser Val Val Ser Gly Asp Glu
        275                 280                 285

Ala Ala Val Leu Glu Leu Leu Glu Gln Trp Arg Ala Glu Gly Arg Glu
    290                 295                 300

Ala Arg Arg Leu Ala Val Ser His Ala Phe His Ser Pro Arg Met Asp
305                 310                 315                 320

Gly Met Leu Thr Gln Phe Asp Arg Val Ala Arg Thr Leu Thr Phe Ala
                325                 330                 335

Pro Pro Thr Ile Pro Leu Val Ser Thr Leu Thr Gly Thr Pro Val Thr
                340                 345                 350

Glu Glu Thr Leu Cys Thr Ala Asp His Trp Val Arg Gln Ala Arg Glu
            355                 360                 365

Pro Val Arg Phe Leu Asp Ala Met Arg Thr Leu Arg Ala Asp Gly Ile
    370                 375                 380

Asp Thr Phe Val Glu Leu Gly Pro Asp Gly Val Leu Ser Ala Met Ala
385                 390                 395                 400

Arg Asp Cys Ala Asp Asp Arg Pro Asp Gly Asp Thr Thr Gly Ala Gly
                405                 410                 415

Asp Gly Glu Thr Pro Asp Pro Leu Leu Thr Leu Pro Leu Leu Arg Arg
            420                 425                 430

Ser Val Pro Glu Thr Gly Asp Ala Glu His Pro Gly Gly Phe Glu Arg
        435                 440                 445

Ala Leu Ala Thr Ala Tyr Ala His Gly Val Pro Leu Arg Leu Ala Pro
    450                 455                 460

Ala Pro Asp Ala Ala Ser Leu Ala Val Ala Ala Glu Leu Pro Thr Tyr
465                 470                 475                 480

Ala Phe Gln Arg Thr His Tyr Trp Leu Asp Ala Pro Ala Ala Pro Ala
                485                 490                 495

Ala Leu Pro Ala Gly Leu Asp Asp Ala Gly His Pro Leu Leu Ser Ala
            500                 505                 510

<210> SEQ ID NO 113
<211> LENGTH: 1871
<212> TYPE: DNA
<213> ORGANISM: Streptomyces cinnamonensis
```

<400> SEQUENCE: 113

```
ggtggtgccg acgccatggc ccgtgagcgc tcacagcgct tccgcgctgc gcgcgcaggc        60
cggtcgcctg cggacgcacc tcgccgccca ccgccccacc cccgacgccg cgcgggtcgg       120
ccacgcgctc gccaccaccc gtgcgcccct cgcccaccgc gcggtcctgc tcggcggcga       180
caccgccgaa ctgctgggct ccctggacgc gctggccgag ggcgcggaga ccgcgtccat       240
cgtgcgcggc gaggcgtaca ccgagggcag gacggccttc ctcttcagtg ggcagggagc       300
gcaacgcctc ggcatggggc gggagttgta tgccgtgttc cccgtcttcg ccgacgctct       360
cgacgaggcg ttcgccgccc tggacgtaca tctggaccgc ccactgcgcg agatcgtctt       420
gggcgagacc gactcgggtg ggaacgtctc gggtgagaat gtcatcggcg agggtgccga       480
ccatcaggca ctcctcgacc agaccgccta cacccagccc gcgctcttcg cgatcgagac       540
gagcctgtac cggctggcag cctccttcgg cctgaagccg gactacgtcc tcggccactc       600
ggtcggcgag atcgccgccg cgcacgtcgc cggtgtcctc tcgttgccgg acgcgagcgc       660
tctggtggcc acgcggggac ggctcatgca ggcggttcgc gcgcccggcg cgatggccgc       720
gtggcaggcc acggcggacg aggcggccga acagctcgcc gggcacgagc ggcacgtcac       780
cgtggccgcc gtcaacggcc ccgactccgt ggtcgtctcc ggcgaccgcg ccaccgtcga       840
cgaactgacc gccgcctggc ggggacgcgg ccgcaaggcc caccacctga aggtcagcca       900
cgccttccac tccccgcaca tggaccccat cctcgacgag ctgcgcgcgg tcgccgccgg       960
cctgaccttc cacgagccgg tcattcccgt cgtctccaac gtcaccggtg aactggtgac      1020
cgcgaccgcg accgggagcg gcgccgggca ggccgacccc gagtactggg cgcggcatgc      1080
gcgcgagccc gtgcggttcc tgtccggggt gcgggggctg tgcgagcgcg gggtgaccac      1140
gttcgtcgag ctcggcccgg acgcaccgct gtccgcgatg gcccgcgact gcttccccgc      1200
ccccgcggac cggagccgtc cgcgccccgc cgccatcgcc acatgccgcc gcgggcgcga      1260
cgaggtggcc acgttcctga ggtcgctggc ccaggcgtac gtccgcggcg ccgatgtcga      1320
cttcaccccgg gcctacggcg ccaccgccac gcgccgcttc ccctccccca cgtatccctt      1380
ccagcgcgag cgccattggc ctgccgctgc cggggtgggg cagcagccgg agaccccgga      1440
acttccggaa tcctcggagt cctcggagca ggcagggcat gagcgggagg aggggcgcg       1500
cgcgtggggc gggcctgaag gcggcttgc cgggctctcc gtgaacgacc aggagcgggt      1560
cctcctcggc ctggtcacca agcacgtggc cgtcgtgctc ggggacgcct cgggcacggt      1620
acaagccgcc cgcaccttca agcagttggg cttcgactcg atggccgccg ccgagctgag      1680
cgaacggctc ggcacggaga cgggcctgcc gttgccgcc accctcacct tcgactaccc       1740
gaccctctg gccgtcgccg cgcacctgcg gcggagctc accggtacgc ccgccccggc       1800
cggctccgcg cccgccacgg gcgccctcgg cgcgggtgac ctcggcacgg acgaggaccc       1860
ggtcgccatc g                                                          1871
```

<210> SEQ ID NO 114
<211> LENGTH: 4
<212> TYPE: PRT
<213> ORGANISM: Artificial Sequence
<220> FEATURE:
<223> OTHER INFORMATION: Description of Artificial Sequence: Motif

<400> SEQUENCE: 114

Tyr Ala Ser His
 1

```
<210> SEQ ID NO 115
<211> LENGTH: 4
<212> TYPE: PRT
<213> ORGANISM: Artificial Sequence
<220> FEATURE:
<223> OTHER INFORMATION: Description of Artificial Sequence: Motif

<400> SEQUENCE: 115

Leu Pro Thr Tyr
  1

<210> SEQ ID NO 116
<211> LENGTH: 4
<212> TYPE: PRT
<213> ORGANISM: Artificial Sequence
<220> FEATURE:
<223> OTHER INFORMATION: Description of Artificial Sequence: Motif
<220> FEATURE:
<221> NAME/KEY: SITE
<222> LOCATION: (1)
<223> OTHER INFORMATION: Xaa is most frequently but not limited to Phe,
      Thr, Val or His

<400> SEQUENCE: 116

Xaa Ala Gly His
  1

<210> SEQ ID NO 117
<211> LENGTH: 4
<212> TYPE: PRT
<213> ORGANISM: Artificial Sequence
<220> FEATURE:
<223> OTHER INFORMATION: Description of Artificial Sequence: Motif

<400> SEQUENCE: 117

His Ala Phe His
  1

<210> SEQ ID NO 118
<211> LENGTH: 4
<212> TYPE: PRT
<213> ORGANISM: Artificial Sequence
<220> FEATURE:
<223> OTHER INFORMATION: Description of Artificial Sequence: Motif

<400> SEQUENCE: 118

Thr Ala Gly His
  1

<210> SEQ ID NO 119
<211> LENGTH: 4
<212> TYPE: PRT
<213> ORGANISM: Artificial Sequence
<220> FEATURE:
<223> OTHER INFORMATION: Description of Artificial Sequence: Motif

<400> SEQUENCE: 119

His Ala Gly His
  1

<210> SEQ ID NO 120
<211> LENGTH: 4
<212> TYPE: PRT
<213> ORGANISM: Artificial Sequence
<220> FEATURE:
<223> OTHER INFORMATION: Description of Artificial Sequence: Motif
```

```
<400> SEQUENCE: 120

Cys Pro Thr His
  1

<210> SEQ ID NO 121
<211> LENGTH: 4
<212> TYPE: PRT
<213> ORGANISM: Artificial Sequence
<220> FEATURE:
<223> OTHER INFORMATION: Description of Artificial Sequence: Motif

<400> SEQUENCE: 121

His Ala Ser His
  1

<210> SEQ ID NO 122
<211> LENGTH: 4
<212> TYPE: PRT
<213> ORGANISM: Artificial Sequence
<220> FEATURE:
<223> OTHER INFORMATION: Description of Artificial Sequence: Motif

<400> SEQUENCE: 122

Val Ala Gly His
  1

<210> SEQ ID NO 123
<211> LENGTH: 5
<212> TYPE: PRT
<213> ORGANISM: Artificial Sequence
<220> FEATURE:
<223> OTHER INFORMATION: Description of Artificial Sequence: Motif

<400> SEQUENCE: 123

His Ala Phe His Ser
  1               5

<210> SEQ ID NO 124
<211> LENGTH: 4
<212> TYPE: PRT
<213> ORGANISM: Artificial Sequence
<220> FEATURE:
<223> OTHER INFORMATION: Description of Artificial Sequence: Motif

<400> SEQUENCE: 124

Gly His Ser Gln
  1

<210> SEQ ID NO 125
<211> LENGTH: 6
<212> TYPE: PRT
<213> ORGANISM: Artificial Sequence
<220> FEATURE:
<223> OTHER INFORMATION: Description of Artificial Sequence: Motif
<220> FEATURE:
<221> NAME/KEY: SITE
<222> LOCATION: (4)..(5)
<223> OTHER INFORMATION: Xaa is unspecified

<400> SEQUENCE: 125

Gly Gln Gly Xaa Xaa Trp
  1               5

<210> SEQ ID NO 126
<211> LENGTH: 6
<212> TYPE: PRT
<213> ORGANISM: Artificial Sequence
```

```
<220> FEATURE:
<223> OTHER INFORMATION: Description of Artificial Sequence: Motif
<220> FEATURE:
<221> NAME/KEY: SITE
<222> LOCATION: (2)..(4)
<223> OTHER INFORMATION: Xaa is unspecified

<400> SEQUENCE: 126

Arg Xaa Xaa Xaa Met Gln
 1               5

<210> SEQ ID NO 127
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 127
tttttttggc cagggttggc agtgggcggg ca                          32

<210> SEQ ID NO 128
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 128
tttttacggc cagccgcttg gcgcggat                               28

<210> SEQ ID NO 129
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 129
cggtgcctag gtgcaccgac tcccagtcc                              29

<210> SEQ ID NO 130
<211> LENGTH: 57
<212> TYPE: DNA
<213> ORGANISM: Artificial Sequence
<220> FEATURE:
<223> OTHER INFORMATION: Description of Artificial Sequence: Primer

<400> SEQUENCE: 130
tttttccaag cggctggccg tggaccacgc gttccactcc tcgcacgtcg agacgat  57

<210> SEQ ID NO 131
<211> LENGTH: 57
<212> TYPE: DNA
<213> ORGANISM: Artificial Sequence
<220> FEATURE:
<223> OTHER INFORMATION: Description of Artificial Sequence: Primer

<400> SEQUENCE: 131
tttttccaag cggctggccg tggaccacgc gtcgcactcc tcgcacgtcg agacgat  57

<210> SEQ ID NO 132
<211> LENGTH: 57
<212> TYPE: DNA
<213> ORGANISM: Artificial Sequence
<220> FEATURE:
<223> OTHER INFORMATION: Description of Artificial Sequence: Primer
```

```
<400> SEQUENCE: 132
tttttccaag cggctggccg tggacgtcgc ggggcactcc tcgcacgtcg agacgat        57

<210> SEQ ID NO 133
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 133
ggcaaacata tgaaggaaat cctggacgcg                                      30

<210> SEQ ID NO 134
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 134
tccgcggatc ctcagtgcgt tcagatcagt gc                                   32

<210> SEQ ID NO 135
<211> LENGTH: 70
<212> TYPE: DNA
<213> ORGANISM: Artificial Sequence
<220> FEATURE:
<223> OTHER INFORMATION: Description of Artificial Sequence: Primer

<400> SEQUENCE: 135
ggggacgcgg ccgcaaggcc caccacctga aggtcagcta cgcctcccac tccccgcaca     60
tggaccccat                                                            70

<210> SEQ ID NO 136
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 136
ggctagcggg tcctcgtccg tgccgaggtc a                                    31

<210> SEQ ID NO 137
<211> LENGTH: 4
<212> TYPE: PRT
<213> ORGANISM: Artificial Sequence
<220> FEATURE:
<223> OTHER INFORMATION: Description of Artificial Sequence: Motif
<220> FEATURE:
<221> NAME/KEY: SITE
<222> LOCATION: (1)
<223> OTHER INFORMATION: Xaa is unspecified

<400> SEQUENCE: 137

Xaa Ala Phe His
  1

<210> SEQ ID NO 138
<211> LENGTH: 4
<212> TYPE: PRT
<213> ORGANISM: Artificial Sequence
<220> FEATURE:
<223> OTHER INFORMATION: Description of Artificial Sequence: Motif
```

```
-continued
<220> FEATURE:
<221> NAME/KEY: SITE
<222> LOCATION: (1)
<223> OTHER INFORMATION: In claim 7 as filed, Xaa is unspecified. In
      claim 10 as filed, Xaa is selected from Tyr, His, Trp
      and Val

<400> SEQUENCE: 138

Xaa Ala Ser His
 1
```